US012668562B2

(12) United States Patent
Schneebeli et al.

(10) Patent No.: US 12,668,562 B2
(45) Date of Patent: Jun. 30, 2026

(54) MOLECULAR TETRAHEDRON NANOCAGE, ITS PREPARATION, AND USES THEREOF

(71) Applicant: Purdue Research Foundation, West Lafayette, IN (US)

(72) Inventors: Severin T. Schneebeli, West Lafayette, IN (US); Jianing Li, West Lafayette, IN (US); Mona Sharafi, Winooski, VT (US)

(73) Assignee: Purdue Research Foundation, West Lafayette, IN (US)

( * ) Notice: Subject to any disclaimer, the term of this patent is extended or adjusted under 35 U.S.C. 154(b) by 647 days.

(21) Appl. No.: 18/007,639

(22) PCT Filed: Jun. 1, 2021

(86) PCT No.: PCT/US2021/035238
§ 371 (c)(1),
(2) Date: Dec. 1, 2022

(87) PCT Pub. No.: WO2021/247566
PCT Pub. Date: Dec. 9, 2021

(65) Prior Publication Data

US 2023/0303472 A1 Sep. 28, 2023

Related U.S. Application Data

(60) Provisional application No. 63/033,764, filed on Jun. 2, 2020.

(51) Int. Cl.
*C07C 45/46* (2006.01)
*C07C 241/04* (2006.01)
*C08K 5/25* (2006.01)

(52) U.S. Cl.
CPC ............ *C07C 45/46* (2013.01); *C07C 241/04* (2013.01); *C08K 5/25* (2013.01); *C08K 2201/011* (2013.01)

(58) Field of Classification Search
None
See application file for complete search history.

(56) References Cited

U.S. PATENT DOCUMENTS

| | | | |
|---|---|---|---|
| 6,764,776 | B2 | 7/2004 | Seo |
| 2005/0124819 | A1 | 6/2005 | Yaghi et al. |

(Continued)

FOREIGN PATENT DOCUMENTS

| | | | |
|---|---|---|---|
| WO | WO 2021247566 | * | 12/2021 |
| WO | WO2021247566 | A1 | 12/2021 |

(Continued)

OTHER PUBLICATIONS

Zhang et al. (Inorg. Chem. Comm., 2014, 49, 140) (Year: 2014).*

(Continued)

*Primary Examiner* — Renee Claytor
*Assistant Examiner* — Jennifer C Sawyer
(74) *Attorney, Agent, or Firm* — Purdue Research Foundation

(57) ABSTRACT

The present application is directed to a nanocage of Formula (I): wherein A and R are as described herein. The present application is also directed to a process for preparation of a nanocage of Formula (I). Methods of utilizing the nanocage for detecting an analyte in a fluid and for functionalizing a polymer are also described.

18 Claims, 58 Drawing Sheets

(56) References Cited

U.S. PATENT DOCUMENTS

2009/0143596 A1 6/2009 Eddaoudi et al.
2016/0362359 A1 12/2016 Kitagawa et al.

FOREIGN PATENT DOCUMENTS

WO WO 2024015528 * 1/2024
WO WO2024015528 A1 1/2024

OTHER PUBLICATIONS

International Search Report and Written Opinion for corresponding Application No. PCT/US2021/035238 (mailed Sep. 1, 2021).
Sharafi et al., "Application of Nanotechnology in Creation of Low-Cost Test Strips for Assessing Saffron Quality," 3rd Annual Workshop on Saffron Production and Marketing, Mar. 15, 2019, Burlington, VT.
International Preliminary Report on Patentability for PCT/US2021/035238 (Dec. 6, 2022).
Sharafi et al., "Size-Selective Catalytic Polymer Acylation with a Molecular Tetrahedron," Chem 6:1469-1494 (2020).
Greenaway, R.L. et al., High-Throughput Discovery of Organic Cages and Catenanes Using Computational Screening Fused with Robotic Synthesis, Nature Communication, 2018, vol. 9 (2849), 1-11 pages.
Rahman, Md. Ataur et al., A direct and Convenient Synthesis of Periodoarenes Using Molecular Iodine, Synthesis, 2010, 27-29 pages.
Sharafi, Mona et al., Crystal-Packing-Driven Enrichment of Atropoisomers, Angewandte Chemie, 2017, vol. 56, 7097-7101 pages.
International Search Report and Written Opinion, PCT Application No. PCT/US2023/027664, mailed Oct. 11, 2023, 11 pages.
International Preliminary Report on Patentability, PCT Application No. PCT/US2023/027664, mailed Dec. 18, 2024, 9 pages.

* cited by examiner

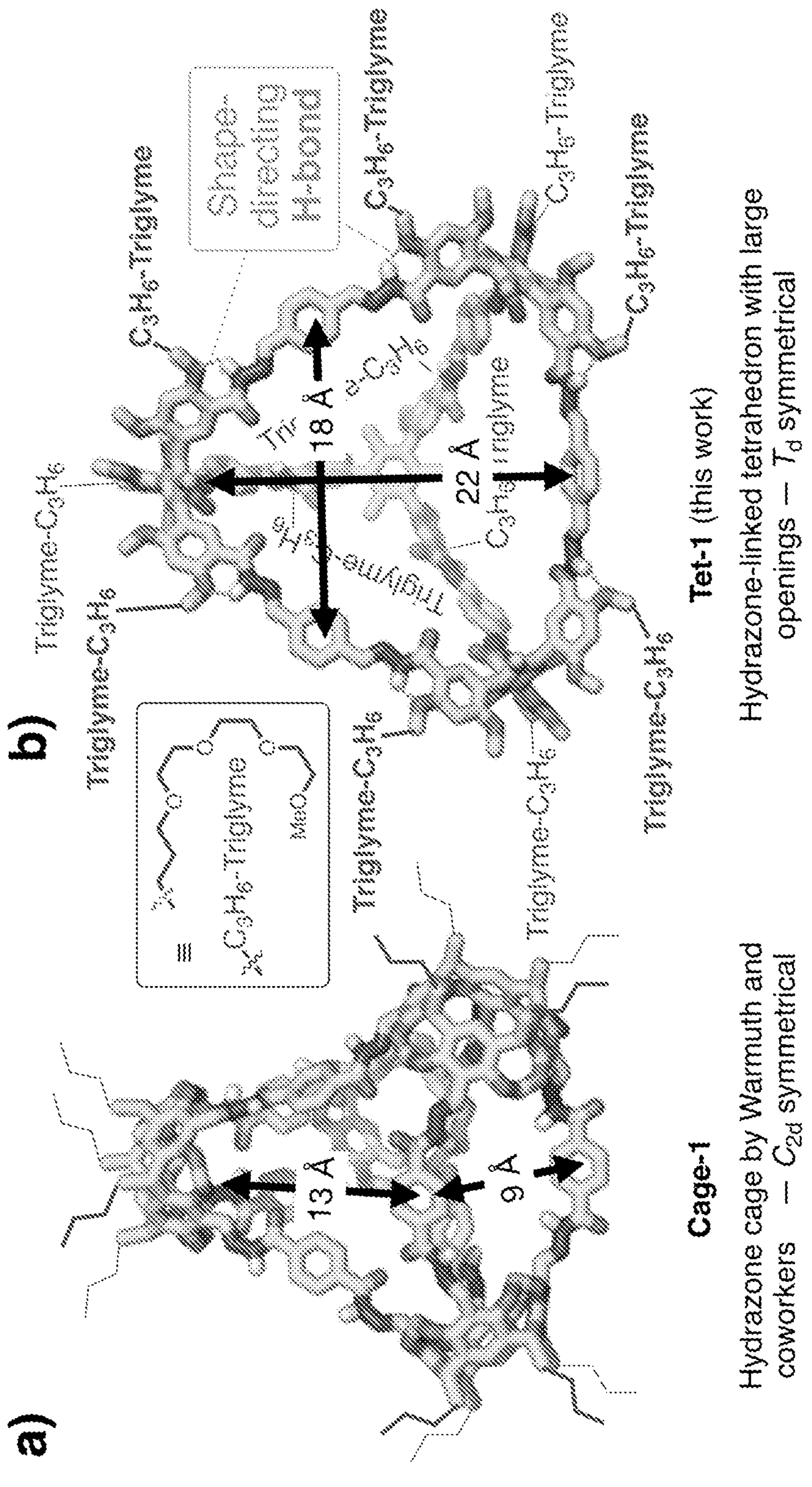
FIGURES 2A-B

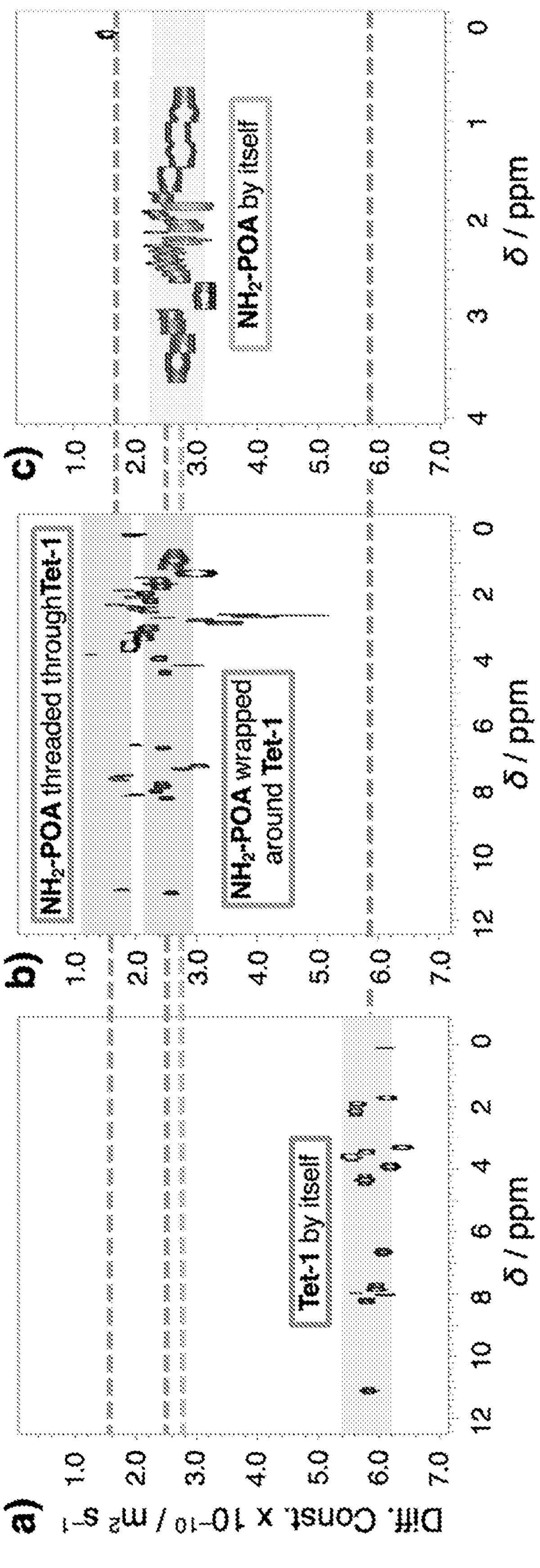
FIGURES 3A-C

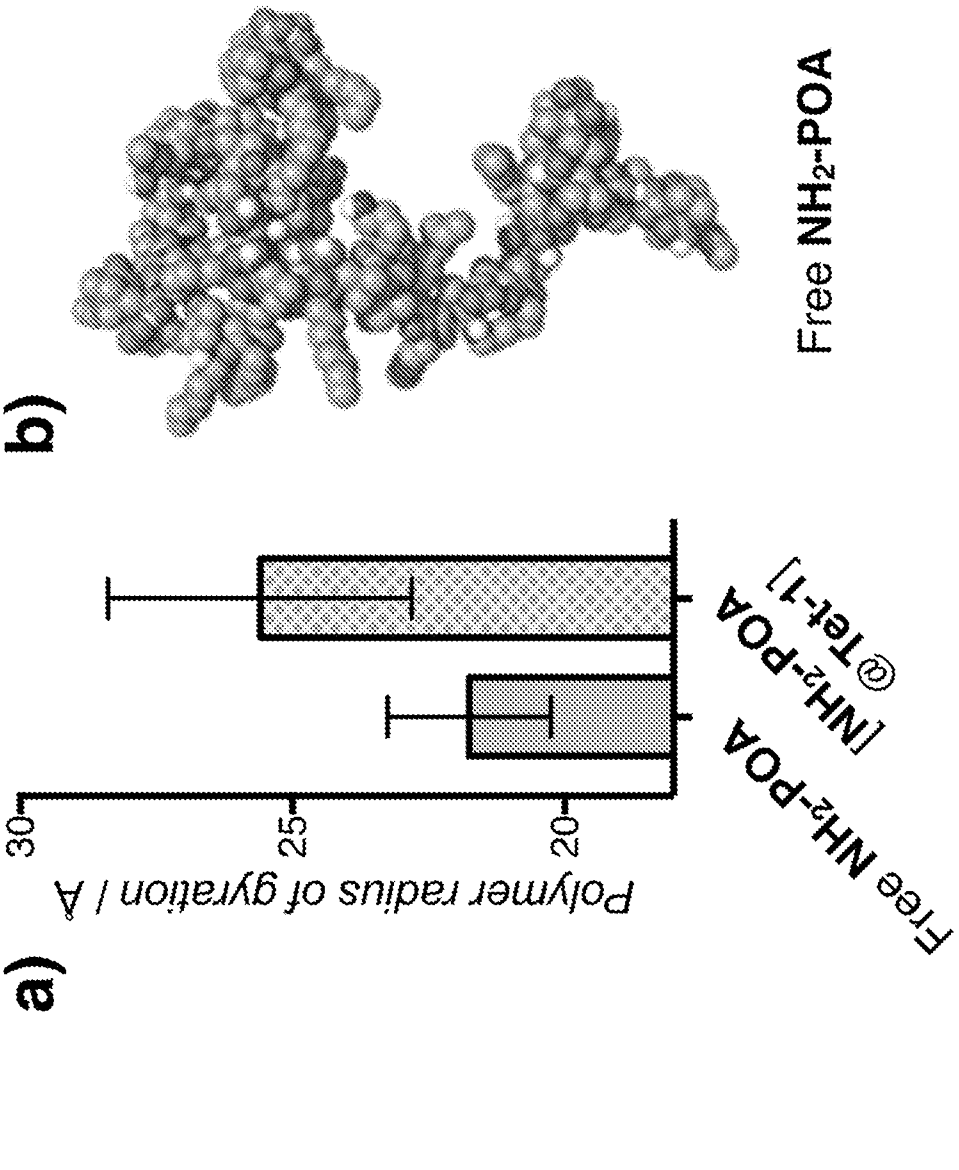
FIGURES 4A-B

[$NH_2$-POA@Tet-1]

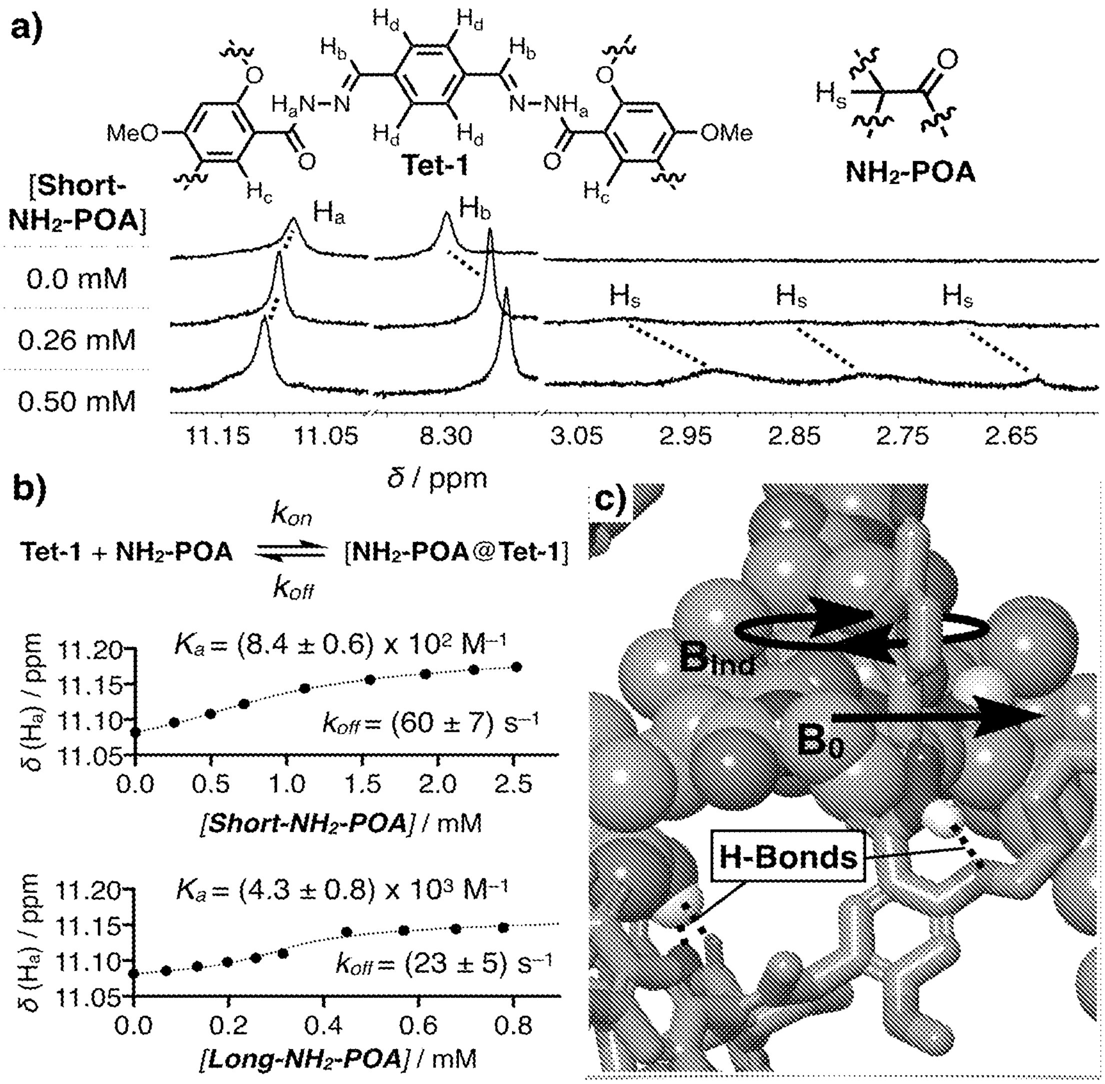
FIGURES 5A-C

| Organocatalyst | $k_{obs}$ | Average # of acylated amines per polymer chain after 48 hrs ( $\overline{\overline{m}}$ ) |
|---|---|---|
| **Tet-1** (0.28 mM) | $(8.3 \pm 0.9) \times 10^8\ M^{-3}\ hr^{-1}$ | $3.0 \pm 0.2$ |
| **Edge-model** (1.7 mM) | $(7.8 \pm 0.6) \times 10^3\ M^{-2}\ hr^{-1}$ | $2.0 \pm 0.1$ |
| **Control + Triglyme** (3.4 mM each) | $(3.6 \pm 0.3) \times 10^3\ M^{-2}\ hr^{-1}$ | $2.0 \pm 0.1$ |
| **Triglyme** (3.4 mM)* | $(3.8 \pm 0.3) \times 10^3\ M^{-2}\ hr^{-1}$ | $1.9 \pm 0.1$ |
| No Organocatalyst | $(7.9 \pm 0.9) \times 10^0\ M^{-1}\ hr^{-1}$ | $1.5 \pm 0.1$ |

FIGURE 6C

* 0.28 mM Tet-1 was added to measure the solvodynamic diameter of the dissolved $NH_2$-POA starting material to obtain a more accurate size-comparison with the product samples, which also contained Tet-1 in the same concentration.

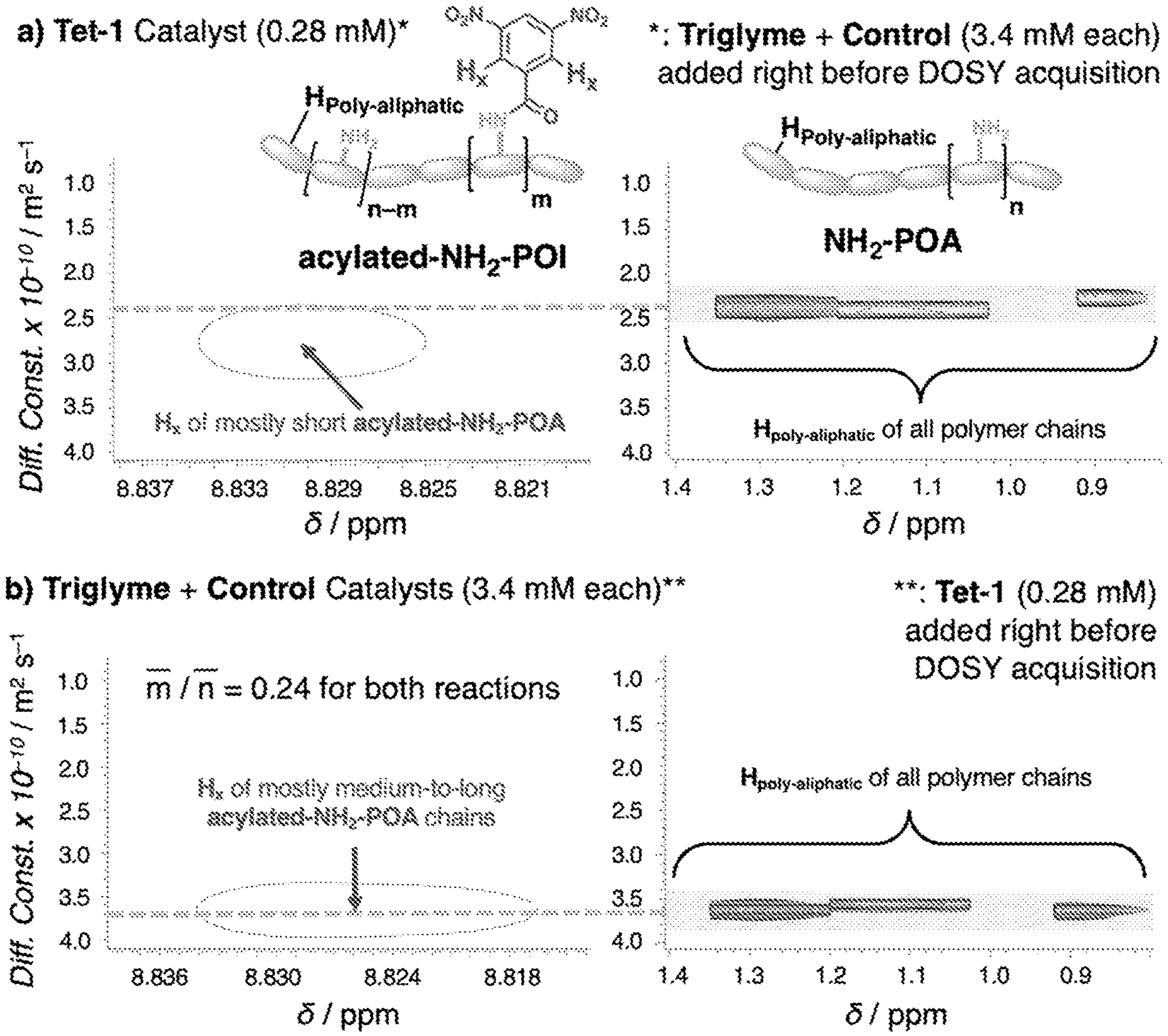
FIGURES 8A-B

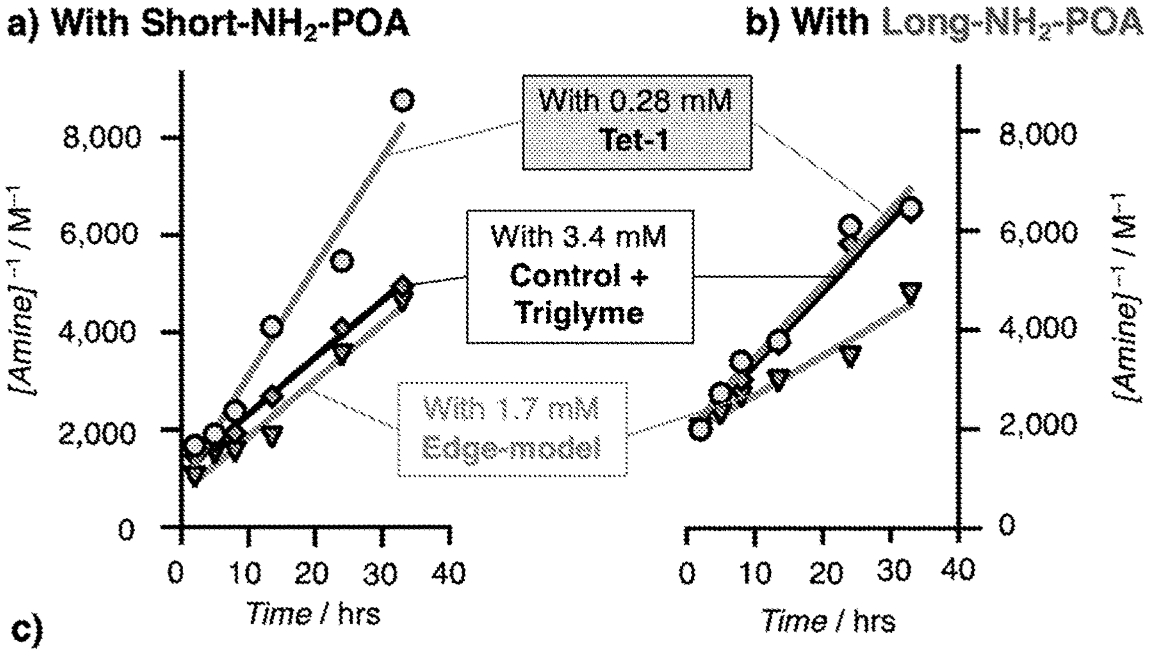

c)

| Organocatalyst | $k_{obs}$ with Short-$NH_2$-POA | $k_{obs}$ with Long-$NH_2$-POA |
|---|---|---|
| Tet-1 | $(2.9 \pm 0.4) \times 10^9\ M^{-3}\ hr^{-1}$ | $(1.9 \pm 0.3) \times 10^9\ M^{-3}\ hr^{-1}$ |
| Edge-model | $(6.8 \pm 0.6) \times 10^4\ M^{-2}\ hr^{-1}$ | $(4.6 \pm 0.6) \times 10^4\ M^{-2}\ hr^{-1}$ |
| Control + Triglyme | $(3.4 \pm 0.2) \times 10^4\ M^{-2}\ hr^{-1}$ | $(4.3 \pm 0.4) \times 10^4\ M^{-2}\ hr^{-1}$ |

d)

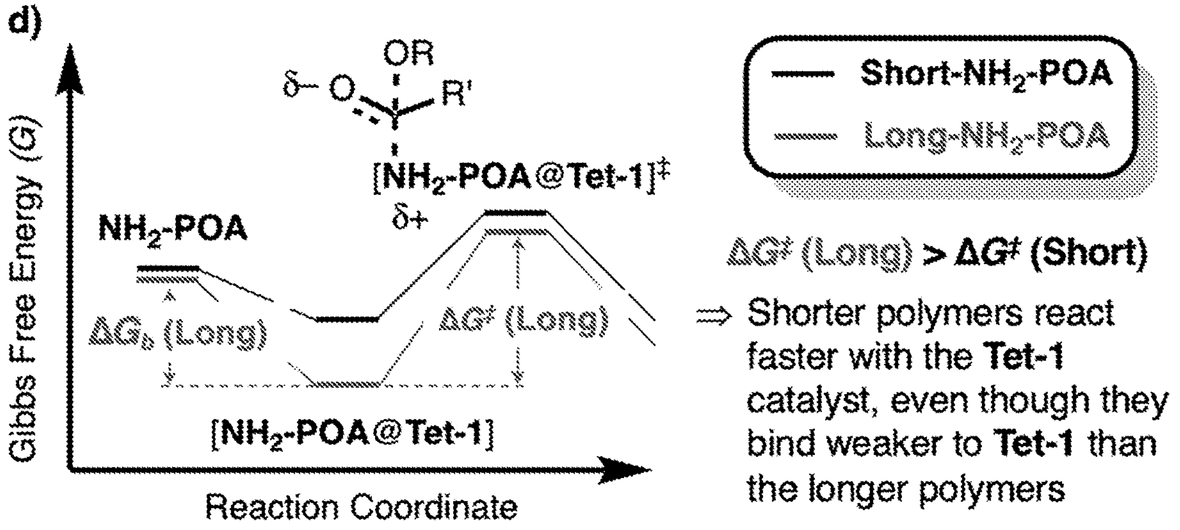

ΔG‡ (Long) > ΔG‡ (Short)

⇒ Shorter polymers react faster with the Tet-1 catalyst, even though they bind weaker to Tet-1 than the longer polymers

FIGURES 9A-D

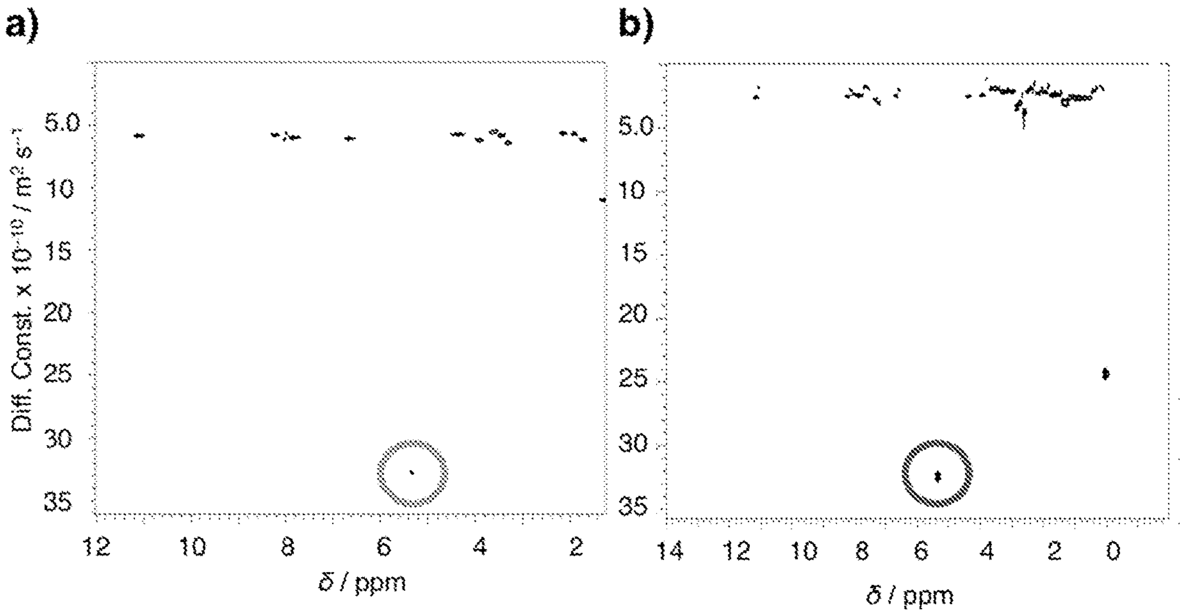
FIGURES 15A-B
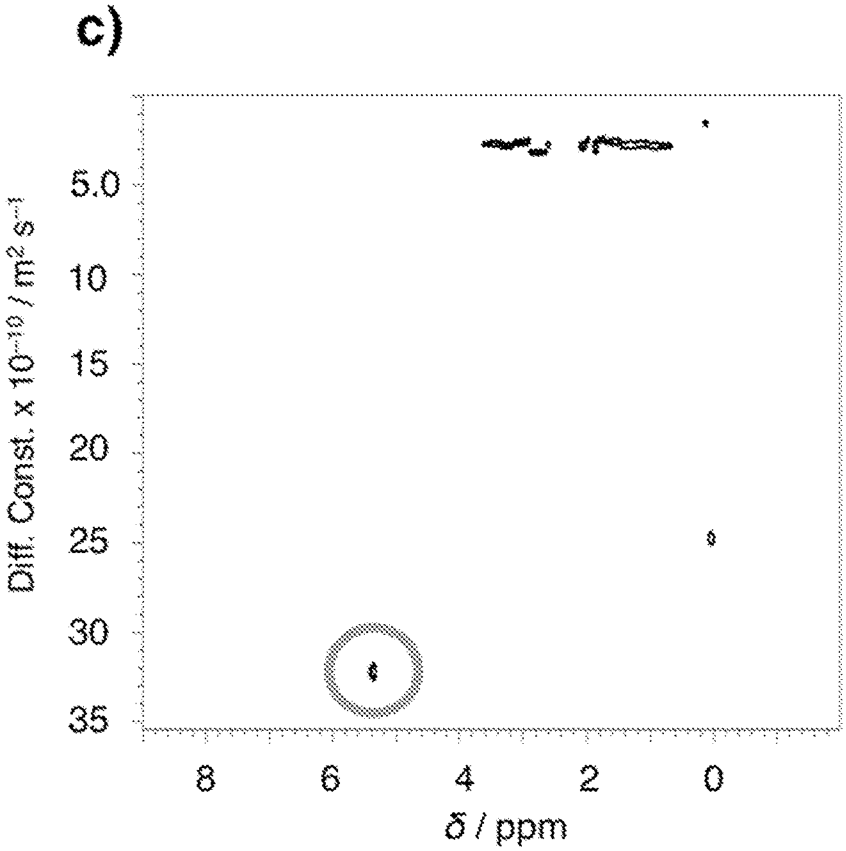
FIGURE 15C

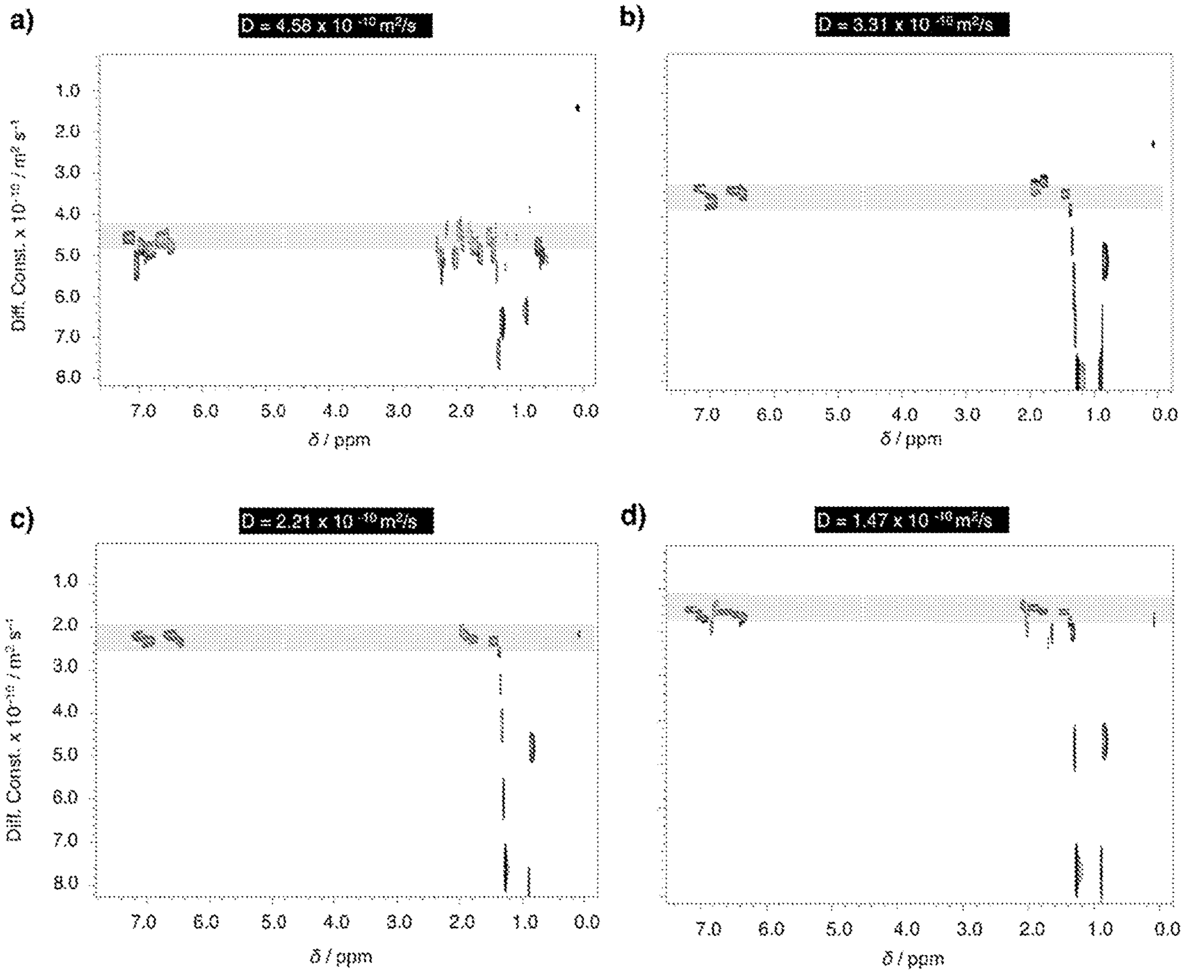
FIGURES 16A-D

FIGURES 18A-C

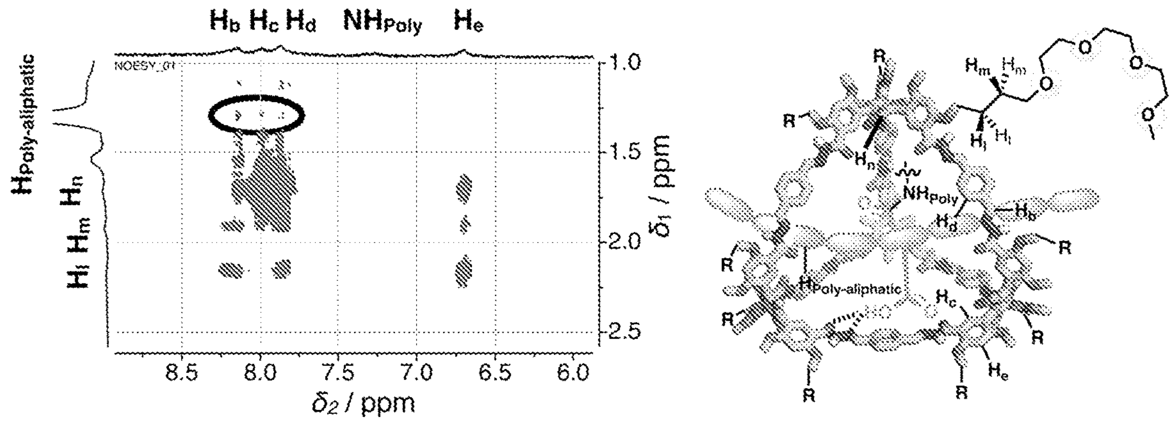
FIGURE 19
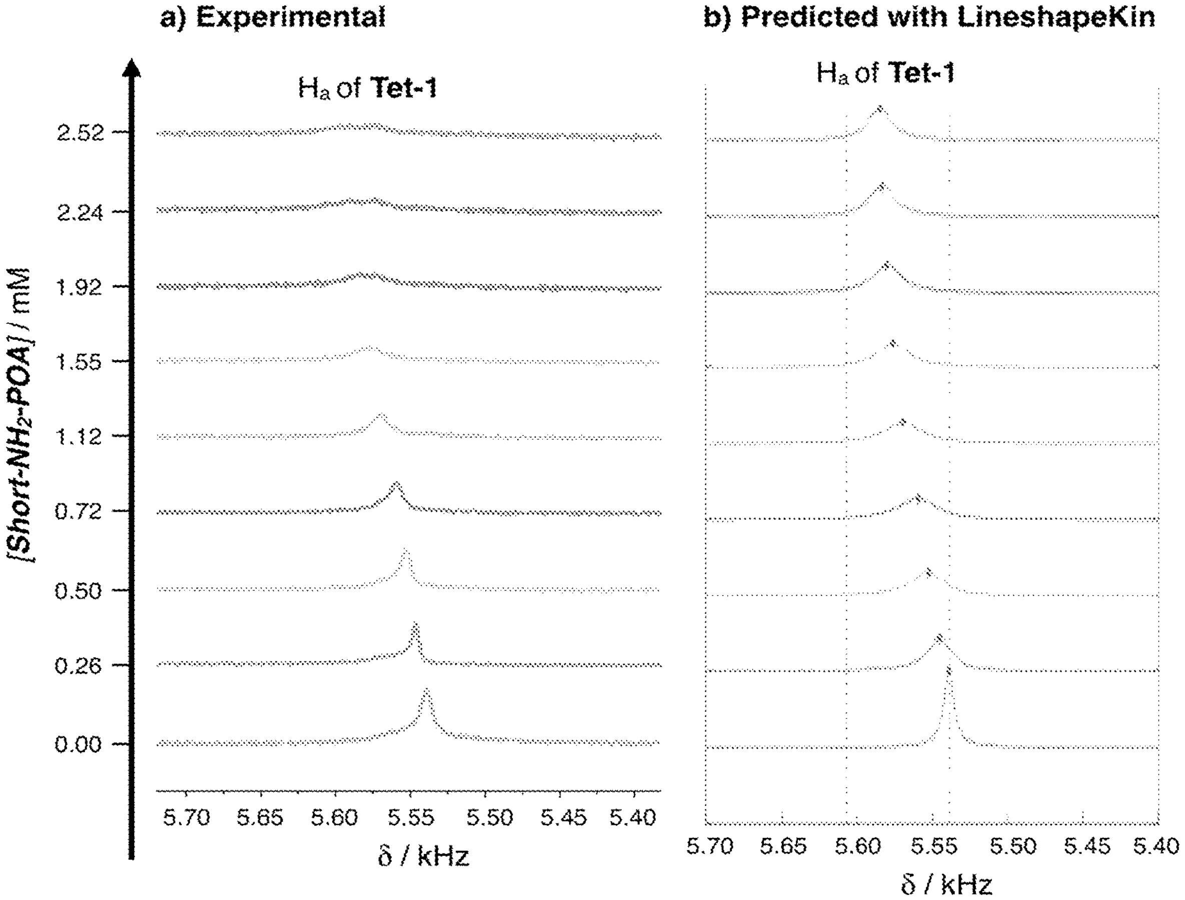
FIGURES 20A-B

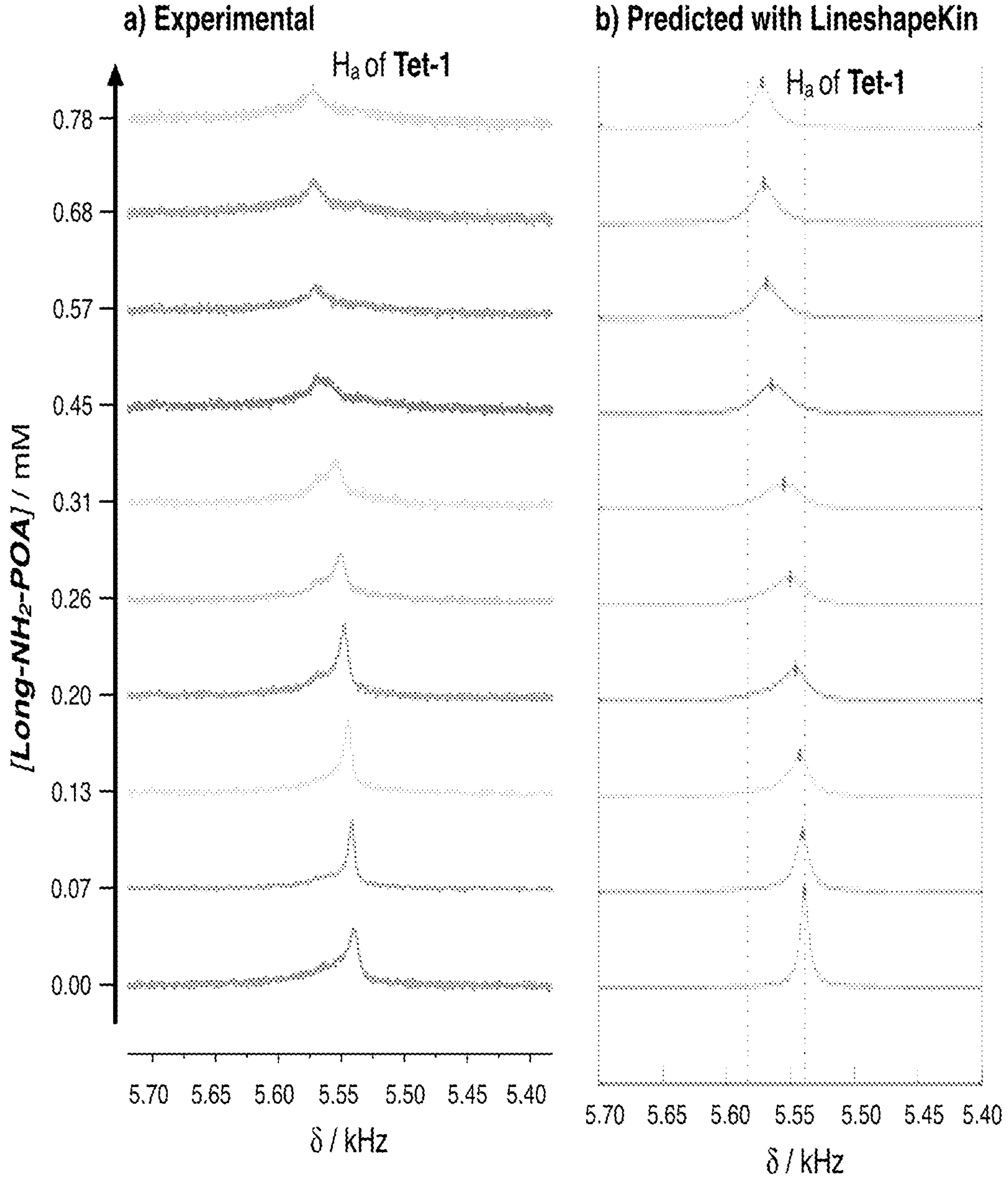
FIGURES 21A-B

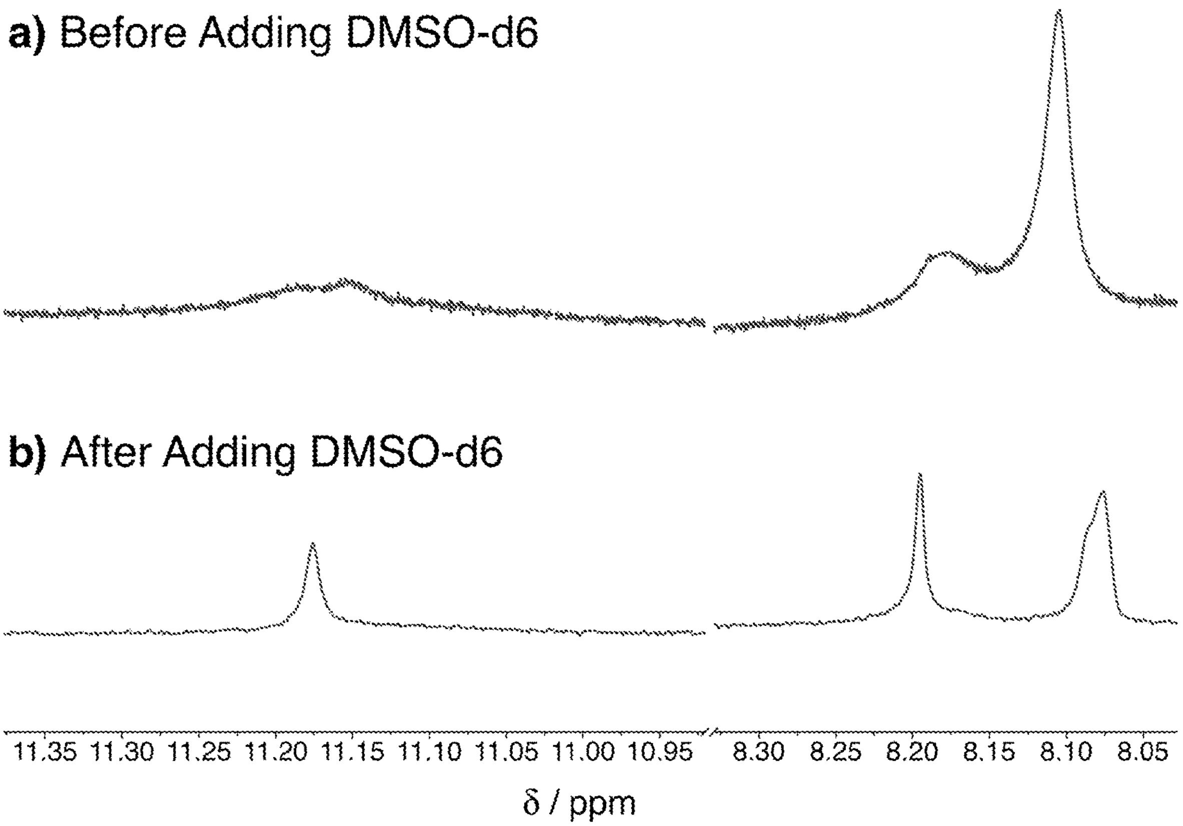
FIGURES 22A-B

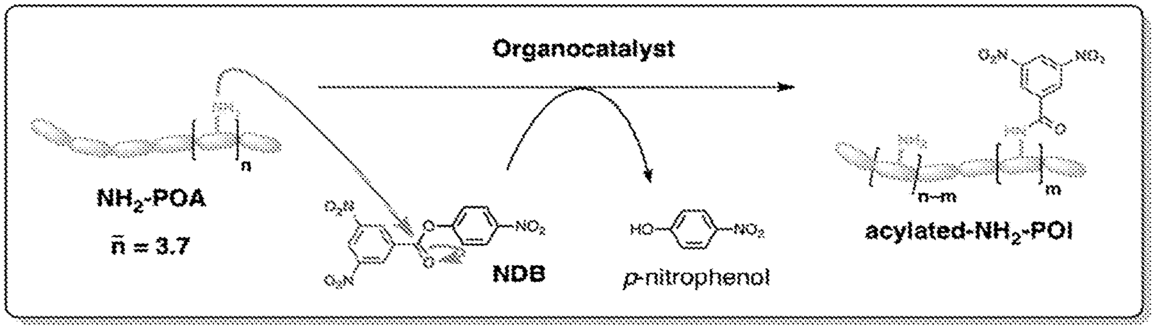
FIGURE 39A
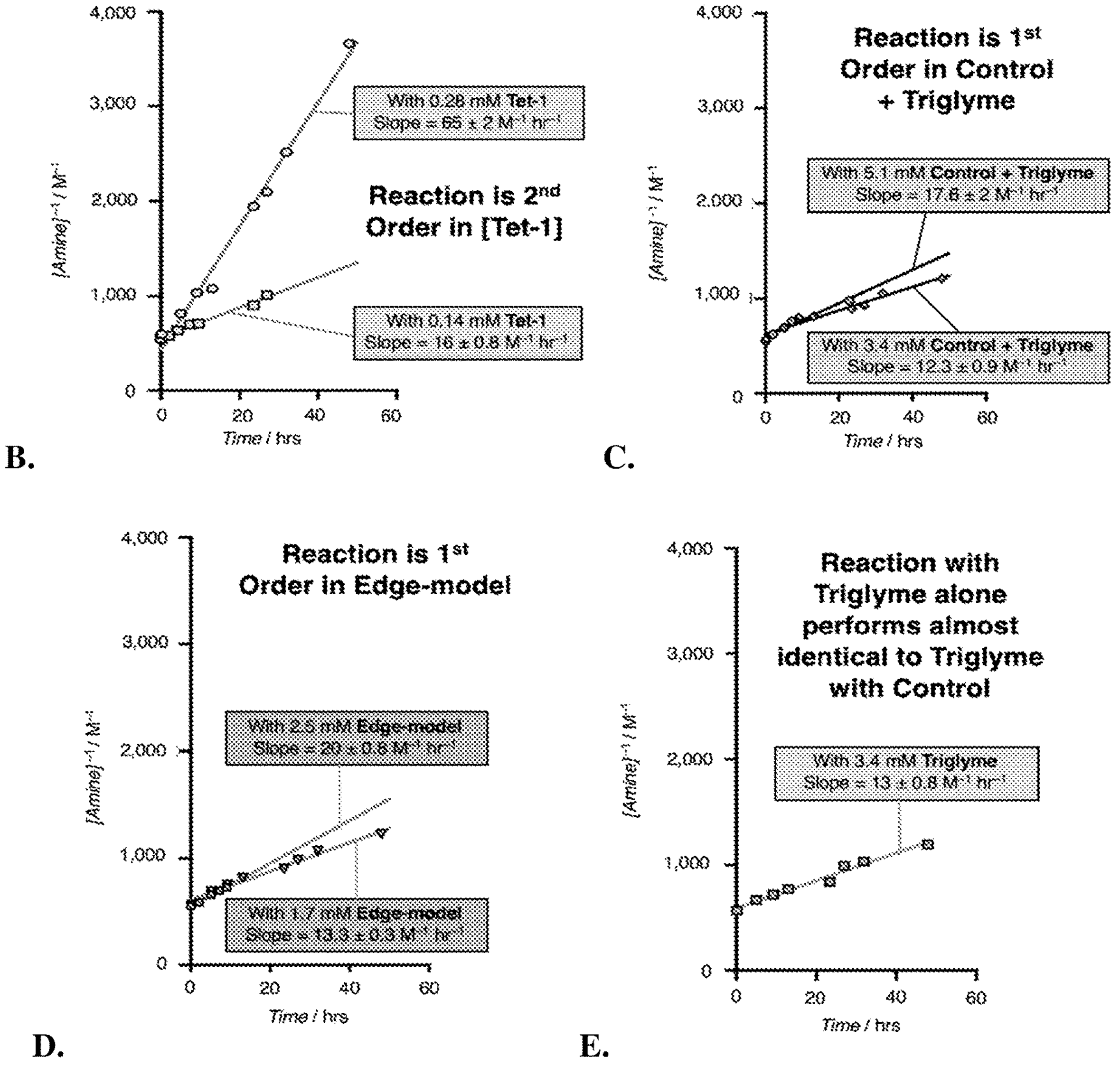
FIGURES 39B-E

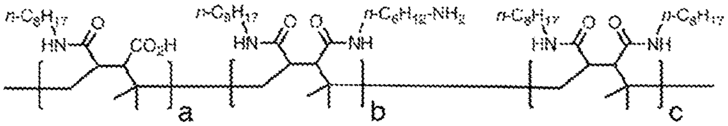
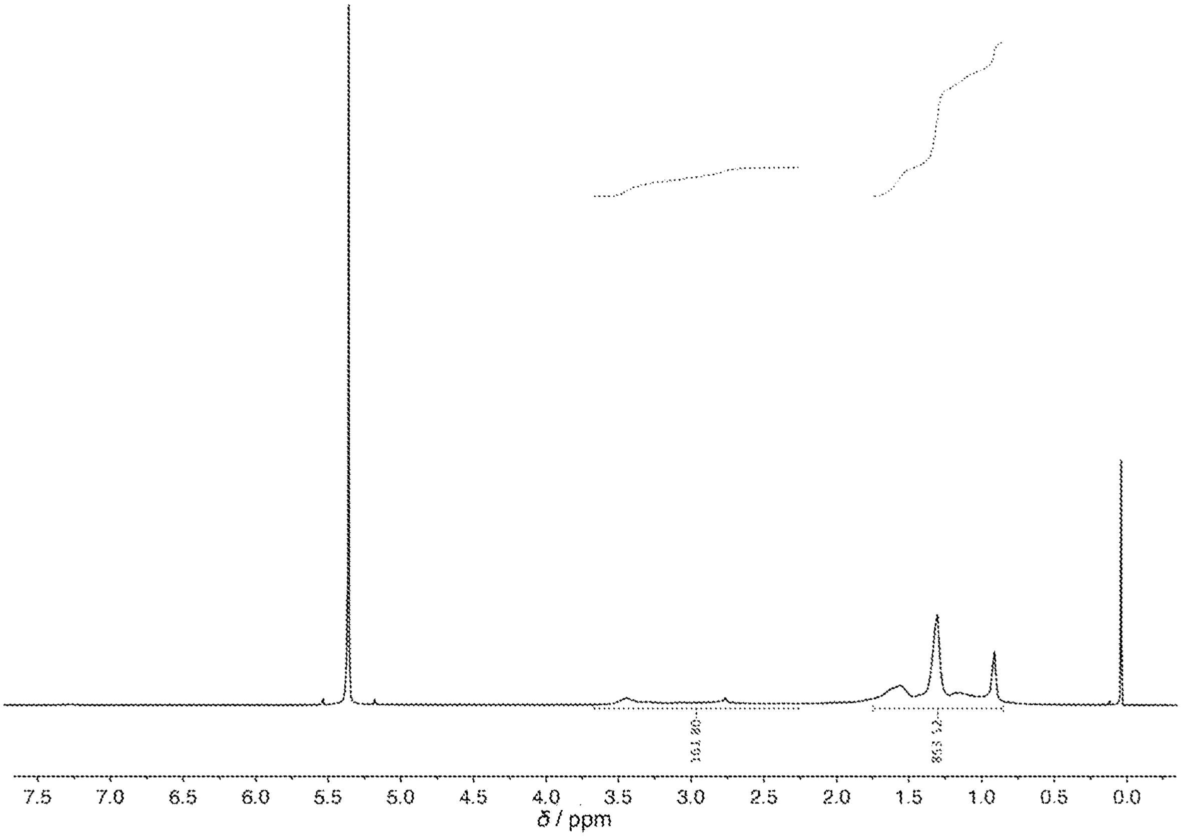
FIGURE 44

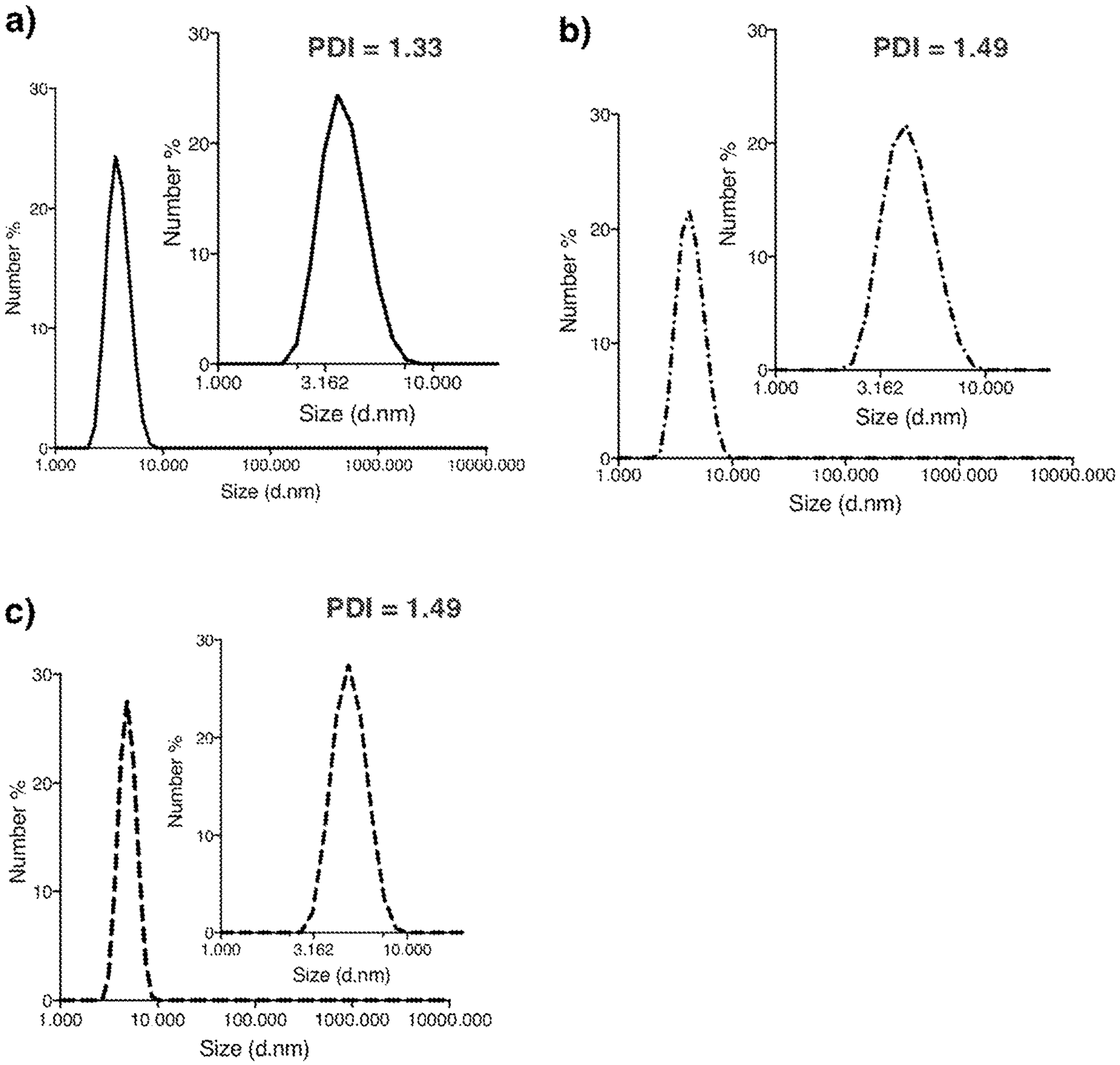
FIGURES 46A-C

```
# This script automatically fits thermodynamic and kinetic parameters with Lineshapekin
# It calls Lineshapekin from matlab, then calculates the RMSD of the fit and then minimizes the RMSD of the fit with curve_fit
# RMSDs are calculated in the end from the covariance matrix obtained from the curve_fit

import math
import matlab.engine
#import matplotlib
import sys
from itertools import permutations
import numpy as np
import random
#from scipy.optimize import minimize
from scipy.optimize import curve_fit
from scipy.spatial.distance import cdist

def read_in_experimental_shifts():
    # This function reads in the experimental shifts for each L/R ratio
    # It stores this data in the dictionary exp_data_dict: keys are the L/R ratios; values are
    # the corresponding experimental shifts

    # First, read in the file
    f = open('experimental_titration_points.txt', 'r')
    exp_data_dict = {}
    for line in f.readlines()[1:]:
        larr = line.split()

        # Convert to floats
        for i in range(len(larr)):
            if larr[i] == 'N/A':
                pass
            else:
                larr[i] = float(larr[i])

        # Now, add the first peak:
        exp_data_dict[larr[0]] = larr[1]
    f.close()
    return exp_data_dict


def read_shifts_from_lineshapekin():
    # This function reads in the predicted shifts for each L/R ratio from lineshapekin (version 4)
    # It stores this data in the dictionary lsk_data_dict: keys are the L/R ratios; values are arrays with corresponding experimental chemical shifts (in Hz)

    # First, read in the file
    f = open('Example_2/U_RL_Af_Bs/U_RL_Af_Bs_titration_curve.txt', 'r')
    lsk_data_dict = {}
    for line in f.readlines():
        larr = line.split()

        # Convert to floats
        for i in range(len(larr)):
            larr[i] = float(larr[i])


        if lsk_data_dict.has_key(larr[0]):
            lsk_data_dict[larr[0]].append(larr[1])
        else:
            # Now, add the peak:
            lsk_data_dict[larr[0]] = [larr[1]]

    f.close()
    return lsk_data_dict



def remove_duplicates(in_list):
    final_list = []
    for el in in_list:
        if el not in final_list:
            final_list.append(el)
    return final_list
```

FIGURE 47

```
def calculate_RMSD(experimental, predicted):
    # Calculates the RMSD of the experimental and predicted shifts (in Hz)

    for L_to_R_ratio in experimental.keys():
        if not predicted.has_key(L_to_R_ratio):
            predicted[L_to_R_ratio] = []

        n_exp = len(experimental[L_to_R_ratio])
        n_predicted = len(predicted[L_to_R_ratio])
        n_max = max([n_exp, n_predicted])

        # Now, if either the experimental or the predicted spectrum has more peaks than the other, fill
        # in 'N/A' into the one with fewer peaks
        diff_in_number_of_peaks = n_exp - n_predicted
        if diff_in_number_of_peaks > 0:
            for i in range(diff_in_number_of_peaks):
                predicted[L_to_R_ratio].append('N/A')

        if diff_in_number_of_peaks < 0:
            for i in range(fabs(diff_in_number_of_peaks)):
                experimental[L_to_R_ratio].append('N/A')


        # Now, we keep the order of the elements in experimental[L_to_R_ratio] constant
        # At the same time, we check for all permutations of the elements in predicted[L_to_R_ratio]
        # to find out which permutation of elements fits the best (judged by the smallest sum of squares)...
        permutation_options = list(permutations(predicted[L_to_R_ratio]))
        permutation_options = remove_duplicates(permutation_options)

        soqs = []
        for permut_option in permutation_options:
            soq = 0.0
            for j in range(len(permut_option)):
                if experimental[L_to_R_ratio][j] == 'N/A' and permut_option[j] != 'N/A':
                    soq += 10000 # Penalty for 'N/A' missmatch...
                    continue
                if experimental[L_to_R_ratio][j] != 'N/A' and permut_option[j] == 'N/A':
                    soq += 10000 # Penalty for 'N/A' missmatch...
                    continue
                if permut_option[j] == 'N/A' and experimental[L_to_R_ratio][j] == 'N/A':
                    continue

                diff = permut_option[j] - experimental[L_to_R_ratio][j]
                soq += diff*diff
            soqs.append(soq)
        min_ind = np.argmin(soqs)

        # Finally, assign the permutation with the smallest soq
        predicted[L_to_R_ratio] = permutation_options[min_ind]
        #print L_to_R_ratio, experimental[L_to_R_ratio], predicted[L_to_R_ratio]

    # Now, calculate the final rmsd
    rmsd = 0.0
    n = 0
    for L_to_R_ratio in experimental.keys():
        for i in range(len(experimental[L_to_R_ratio])):
            if experimental[L_to_R_ratio][i] == 'N/A':
                continue
            if predicted[L_to_R_ratio][i] == 'N/A':
                continue
            diff = experimental[L_to_R_ratio][i] - predicted[L_to_R_ratio][i]
            rmsd += diff*diff
            n += 1

    rmsd /= n
    rmsd = math.sqrt(rmsd)
    return rmsd
```

FIGURE 47(cont)

```
def write_lineshapekin_input_file(Ka=None, ka=None, omega=None):
    # Writes a lineshapekin input file with the parameters params
    # x is the parameter array, defined below...

    print 'writing lineshapekin input with the following parameters: Ka = %f, ka = %f, omega = %f' %(Ka, ka, omega)


    txt = '#  Unique model identifier\n'
    txt += 'Model_code     U\n\n'

    txt += '# Model description\n'
    txt += 'Description Simple 1:1\n\n'

    txt += '# Association constants\n'
    txt += 'Ka_names   A\n'
    txt += 'Ka        %f\n\n'%(Ka)

    txt += '# Rate constants of REVERSE reactions\n'
    txt += 'k_names     A\n'
    txt += 'k2          %f\n\n'%(ka)

    txt += '# Names of NMR-active species\n'
    txt += 'Species_names      R   RL\n\n'

    txt += '# Names of NMR unobservable species\n'
    txt += 'NMR_invisible_species_names     L\n\n'

    txt += '# Chemical shifts of pure species, 1/s\n'
    txt += 'w0      5539  %f\n\n' %(omega)

    txt += '# Relaxation rates of pure species, 1/s\n'
    txt += 'R2      1      1\n\n'

    txt += '# Heat of formation of the species, relative units\n'
    txt += '# The original species is a standard state with dH=0 !\n'
    txt += 'dH     0    -2\n\n'


    f = open('U_RL_Af_Bs.txt', 'w')
    f.write(txt)
    f.close()

def closest(lst, K):

    return lst[min(range(len(lst)), key = lambda i: abs(lst[i]-K))]



def func(x, Ka, ka, omega):

    # This function runs lineshapekin with the following parameters:
    # x = L/R ratio
    # Ka = Equilibrium constant
    # ka = rate constant (reverse reaction)
    # omega = chemical shift of RL in Hz

    # It returns the calculated (with lineshapekin) chemical shift at the given L/R ratio with the given parameters...

    write_lineshapekin_input_file(Ka=Ka, ka=ka, omega=omega)
    eng.Simulate('setup', 'U_RL_Af_Bs', nargout=0)
    lsk_shift_dict = read_shifts_from_lineshapekin()
    #print 'experimental shifts: ', exp_shifts
    yout = []
    for key in x:
        yout.append(closest(lsk_shift_dict[key], exp_shifts[key]))

    print lsk_shift_dict, yout
    #print x, lsk_shifts
#    print 'current distance = %f'%cdist(x,yout,'sqeuclidean')
    return np.array(yout)
```

FIGURE 47(cont)

```
# Main Program

#Define initial parameters
x0 = [ 4000, # Ka_A parameter
      #  2, # Ka_B parameter
       150, # k2_A parameter
     #    4, # k2_B parameter
      5594, # w0_RL parameter
      #4038, # w0_R*L parameter
   ]



# Setup things used all the time...
exp_shifts = read_in_experimental_shifts()
eng = matlab.engine.start_matlab()
eng.addpath('~/software/LineShapeKin_Simulation_4.1/Matlab_code/Models', nargout=0)
eng.addpath('~/software/LineShapeKin_Simulation_4.1/Matlab_code', nargout=0)


# Now, define the data to be fit
xdata = []
ydata = []
for key in exp_shifts.keys():
    xdata.append(key)
    ydata.append(exp_shifts[key])

# Define initial guess
p0 = [2000, 10, 5570]

# Now, fit the curve...
#popt, pconv = curve_fit(func, xdata, ydata, p0=p0, epsfcn=0.01)
popt, pconv = curve_fit(func, xdata, ydata, p0=p0, method='trf', bounds=([100, 5, 5560],[10000, 80, 5650]), diff_step=[0.01, 0.01, 0.001])
print popt
print pconv
perr = np.sqrt(np.diag(pconv))
print perr


print ('done')
```

FIGURE 47(cont)

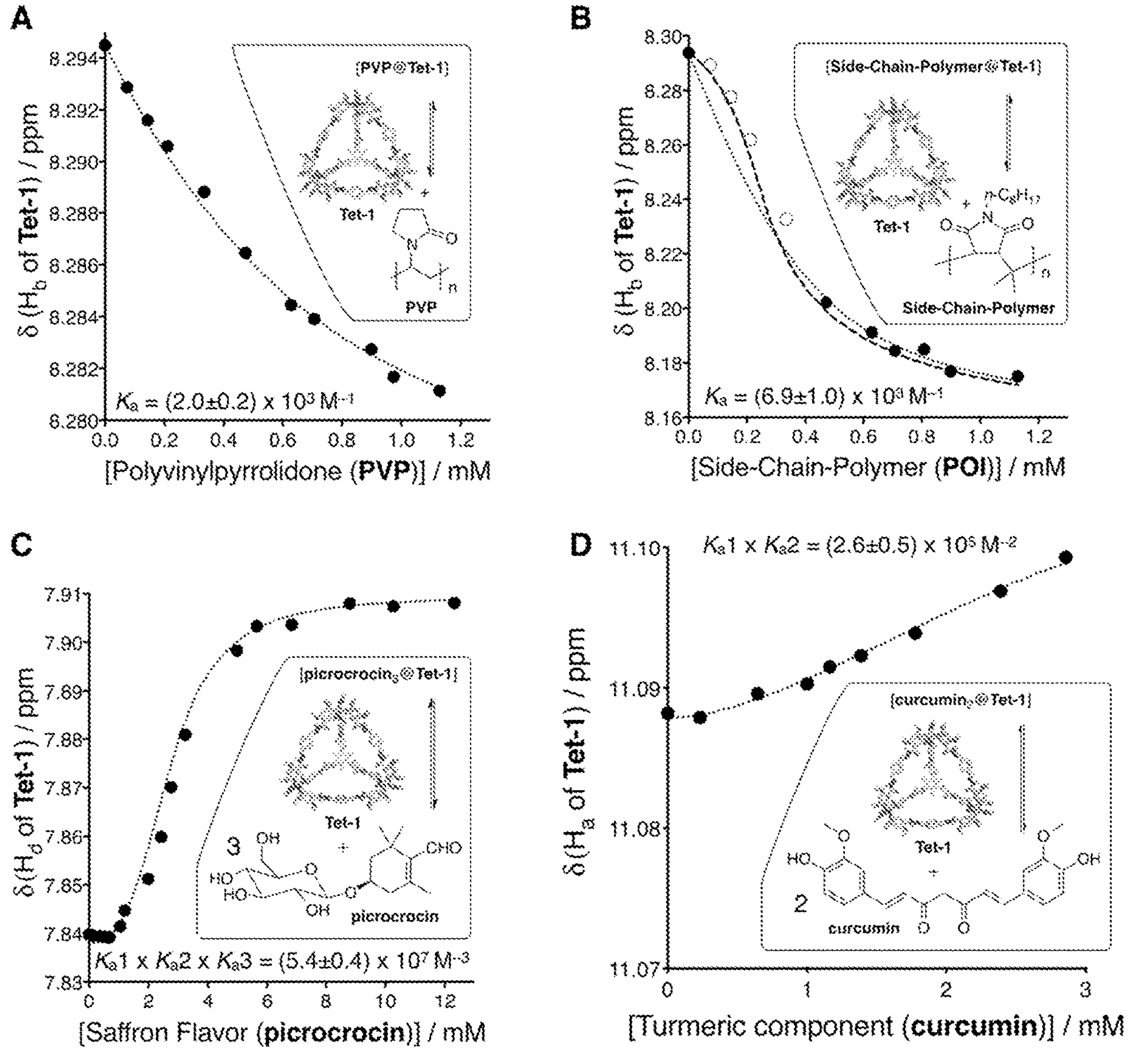
FIGURES 48A-D

MOLECULAR TETRAHEDRON NANOCAGE, ITS PREPARATION, AND USES THEREOF

This application is a national stage application under 35 U.S.C. § 371 of International Application No. PCT/US2021/035238, filed Jun. 1, 2021, which claims the priority benefit of U.S. Provisional Patent Application Ser. No. 63/033,764, filed, Jun. 2, 2020, which is are hereby incorporated by reference in their entirety.

This invention was made with government support under CHE-1609137 and CHE-1848444 awarded by the National Science Foundation. The government has certain rights in the invention.

FIELD

The present application relates to a molecular tetrahedron nanocage, its preparation, and uses thereof.

BACKGROUND

Nature creates macromolecules to regulate macromolecules (Li et al., "Peptide Mimics by Linear Arylamides: A Structural and Functional Diversity Test," *Acc. Chem. Res.* 41:1343-1353 (2008); Simons et al., "Lipid Rafts and Signal Transduction," *Nat. Rev. Mol. Cell Biol.* 1:31-39 (2000)) with diverse and selective multivalent interactions. While these interactions between proteins, nucleic acids, and glycosides are essential for life, not much is known yet about how synthetic macromolecular hosts for glycoside natural products (Sun et al., "Glucose Sensing in Supramolecular Chemistry," *Chem. Rev.* 115:8001-8037 (2015); Ke et al., "A Simple and Accessible Synthetic Lectin for Glucose Recognition and Sensing," *Nat. Chem.* 4:718-723 (2012)) and other oligomers/polymers with side-chains can be created. To efficiently recognize such compounds, synthetic hosts should possess C-shaped (Sharafi et al., "Controlled Self-Assembly Inside C-Shaped Polyaromatic Strips," *Synlett* 27:2145-2149 (2016); Liu et al., "Regulating Molecular Recognition With C-Shaped Strips Attained by Chirality-Assisted Synthesis," *Angew. Chem., Int. Ed.* 54:12772-12776 (2015)) or cage-like structures with large openings and selective microenvironments (Trinh et al., "DNA-Imprinted Polymer Nanoparticles With Monodispersity and Prescribed DNA-Strand Patterns," *Nat. Chem.* 10:184-192 (2018); Ueda et al., "Permeable Self-Assembled Molecular Containers for Catalyst Isolation Enabling Two-Step Cascade Reactions," *J. Am. Chem. Soc.* 139:6090-6093 (2017)). Macrocycles, on the other hand, have commonly been employed to bind to side-chain-less polymers (Cantekin et al., "Allosterically Controlled Threading of Polymers Through Macrocyclic Dimers," *J. Am. Chem. Soc.* 137:3915-3923 (2015); del Barrio et al., "Photocontrol Over Cucurbit [8]uril Complexes: Stoichiometry and Supramolecular Polymers," *J. Am. Chem. Soc.* 135:11760-11763 (2013); Harada et al., "The Molecular Necklace: a Rotaxane Containing Many Threaded α-Cyclodextrins," *Nature* 356:325-327 (1992)).

Although many molecular cages are known (Ronson et al., "Design Principles for the Optimization of Guest Binding in Aromatic-Paneled FeII4L6 Cages," *J. Am. Chem. Soc.* 139:9698-9707 (2017); Moneypenny et al., "Impact of Shape Persistence on the Porosity of Molecular Cages," *J. Am. Chem. Soc.* 139:3259-3264 (2017); Wang et al., "Dynamic Covalent Synthesis of Aryleneethynylene Cages Through Alkyne Metathesis: Dimer, Tetramer, or Interlocked complex?," *Chem. Sci.* 7:3370-3376 (2016); Yan et al., "Highly Emissive Platinum (II) Metallacages," *Nat. Chem.* 7:342-348 (2015); Zhang et al., "A Shape-Persistent Quadruply Interlocked Giant Cage Catenane With two Distinct Pores in the Solid State," *Angew. Chem., Int. Ed.* 53:5126-5130 (2014); Schneider et al., "Exo-Functionalized Shape-Persistent [2+3] Cage Compounds: Influence of Molecular Rigidity on Formation and Permanent Porosity," *Chem. Eur. J.* 18:4156-4160 (2012)), only a few examples (mostly metal-linked molecular flasks encapsulating small proteins) of cages binding to polymers with side-chains have been revealed (Mosquera et al., "Sequence-selective Encapsulation and Protection of Long Peptides by a Self-Assembled FeII8L6 Cubic Cage, *Nat. Commun.* 8:14882 (2017); Fujita et al., "Protein Encapsulation Within Synthetic Molecular Hosts.," *Nat. Commun.* 3:1093 (2012)) to date.

Selective catalytic chemical modification after synthesis represents (Breslow, R. "Artificial Enzymes," *Science* 218:532-537 (1982); Trinh et al., "DNA-Imprinted Polymer Nanoparticles with Monodispersity and Prescribed DNA-Strand Patterns," *Nat. Chem.* 10:184-192 (2018)) an effective means to diversify the structures and functions of small molecules and polymers. Yet, despite various examples of protein posttranslational modifications (PTMs) catalyzed by enzymes, it remains a daunting task to create catalysts that can selectively recognize and modify man-made polymers. Thus, it has been a major goal of synthetic chemists to create supramolecular catalysts. For a review on supramolecular catalysis with metalated hosts see: Brown et al., "Supramolecular Catalysis in Metal-Ligand Cluster Hosts," *Chem. Rev.* 115:3012-3035 (2015); Mahata et al., "Giant Electroactive $M_4L6$ Tetrahedral Host Self-Assembled with Fe(II) Vertices and Perylene Bisimide Dye Edges," *J. Am. Chem. Soc.* 135:15656-15661 (2013); For a review on artificial enzyme mimetics see: Raynal et al., "*Supramolecular Catalysis. Part* 2: Artificial Enzyme Mimics," *Chem. Soc. Rev.* 43:1734-1787 (2014); Fang et al., "Catalytic Reactions Within the Cavity of Coordination Cages," *Chem. Soc. Rev.* 4:4707-4730 (2019); Pappalardo et al., "Catalysis Inside Supramolecular Capsules: Recent Developments," Catalysts 9:630 (2019)), which can operate selectively on man-made polymers (Lewandowski et al., "Sequence-Specific Peptide Synthesis by an Artificial Small-Molecule Machine," *Science* 339:189-193 (2013); Deutman et al., "Designing Processive Catalytic Systems. Threading Polymers Through a Flexible Macrocycle Ring," *J. Am. Chem. Soc.* 136:9165-9172 (2014). These efforts have led to the successful application of selective supramolecular catalysts for small-molecule transformations (Gianneschi et al., "Reversibly Addressing an Allosteric Catalyst in Situ: Catalytic Molecular Tweezers," *Angew. Chem. Int. Ed.* 43:5503-5507 (2004); Yoshizawa et al., "Diels-Alder in Aqueous Molecular Hosts: Unusual Regioselectivity and Efficient Catalysis," *Science* 312:251-254 (2006); Pluth et al., "Acid Catalysis in Basic Solution: A Supramolecular Host Promotes Orthoformate Hydrolysis," *Science* 316:85-88 (2007); Han et al., "Chiral Covalent Organic Frameworks with High Chemical Stability for Heterogeneous Asymmetric Catalysis," *J. Am. Chem. Soc.* 139:8693-8697 (2017); Jiao et al., "Design and Self-Assembly of Hexahedral Coordination Cages for Cascade Reactions," *Nat. Commun.* 9:4423 (2018); Takezawa et al., "Site-Selective Functionalization of Linear Diterpenoids Through U-Shaped Folding in a Confined Artificial Cavity," *J. Am. Chem. Soc.* 141:5112-5115 (2019); Zhang et al., "Hexameric Resorcinarene Capsule is a Bronsted Acid: Investigation and Application to Synthesis and Catalysis," *J. Am. Chem. Soc.* 135:16213-16219 (2013). For a recent review on the topic of substrate-selective catalysis see: Otte, M. "Size-Selective Molecular Flasks," *ACS. Catal.* 6:6491-6510 (2016); Wang et al., "Self-Assembled Nanospheres with Multiple Endohedral Binding Sites Pre-Organize Catalysts and Substrates for Highly Efficient Reactions," *Nat. Chem.* 8:225-230 (2016) as well as for growth (Lewandowski et al., "Sequence-Specific Peptide Synthesis by an Artificial Small-Molecule Machine," *Science* 339:189-193 (2013); Osaki et al., "An Artificial Molecular Chaperone: Poly-Pseudo-Rotaxane with an Extensible Axle," *J. Am. Chem. Soc.* 129:14452-14457 (2007); del Barrio et al., "Photocontrol Over Cucurbit [8]uril Complexes: Stoichiometry and Supramolecular Polymers," *J. Am. Chem. Soc.* 135:11760-11763 (2013) and functionalization (Deutman et al., "Designing Processive Catalytic Systems. Threading Polymers Through a Flexible Macrocycle Ring," *J. Am. Chem. Soc.* 136:9165-9172 (2014); Thordarson et al., "Epoxidation of Polybutadiene by a Topologically Linked Catalyst," *Nature* 424:915-918 (2003)) of linear polymers in a processive manner. However, selective post-synthetic polymer modification (PSPM) by supramolecular organocatalysts has, to the best of applicant's knowledge, not yet been reported.

The present application is directed to overcoming these and other deficiencies in the art.

SUMMARY

One aspect of the present application relates to a nanocage of Formula (I):

(I)

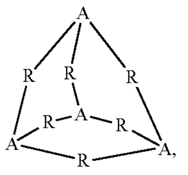

wherein each A is independently selected and has the formula

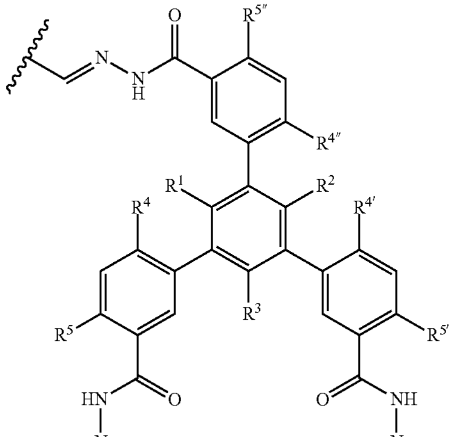

is the point of attachment of A to R;

each R is independently selected and has the formula

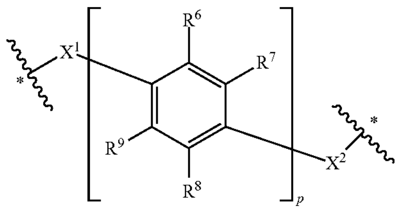

indicates the point of attachment of R to A;

$R^1$, $R^2$, and $R^3$ are each independently selected from the group consisting of H, halogen, OH, $C_{1-20}$ alkyl, $C_{2-20}$ alkenyl, $C_{2-20}$ alkynyl, perfluorinated $C_{1-20}$ alkyl, aryl, hereroaryl, heterocyclyl, —$OC_{1-20}$ alkyl, —$OC_{2-20}$ alkenyl, —$OC_{2-20}$ alkynyl, —O-perfluorinated $C_{1-20}$ alkyl, —Oaryl, —$COOC_{1-20}$ alkyl, —COO perfluorinated $C_{1-20}$ alkyl, —COOaryl, —$CONHC_{1-20}$ alkyl, —$CONHC_{2-20}$ alkenyl, —$CONHC_{2-20}$ alkynyl, —CONH perfluorinated $C_{1-20}$ alkyl, —CONH-aryl, —CONH-heteroaryl, and —CONH-heterocyclyl, wherein each $C_{1-20}$ alkyl, $C_{2-20}$ alkenyl, alkenyl, —$OC_{2-20}$ alkynyl, —O-perfluorinated $C_{1-20}$ alkyl, —Oaryl, —$COOC_{1-20}$ alkyl, —COO perfluorinated $C_{1-20}$ alkyl, —COOaryl, —$CONHC_{1-20}$ alkyl, —$CONHC_{2-20}$ alkenyl, —$CONHC_{2-20}$ alkynyl, —CONH perfluorinated $C_{1-20}$ alkyl, —CONH-aryl, —CONH-heteroaryl, and —CONH-heterocyclyl can be optionally substituted from 1 to 3 times with a substituent selected from the group consisting of H, halogen, OH, $C_{1-6}$ alkyl, aryl, and arylalkyl;

$R^4$, $R^{4'}$, and $R^{4''}$ are each independently selected from the group consisting of H, halogen, $C_{1-20}$ alkyl, $C_{2-20}$ alkenyl, $C_{2-20}$ alkynyl, perfluorinated $C_{1-20}$ alkyl, aryl, hereroaryl, heterocyclyl, OH, —$OC_{1-20}$ alkyl, —$OC_{2-20}$ alkenyl, —$OC_{2-20}$ alkynyl, —O-perfluorinated $C_{1-20}$ alkyl, —Oaryl, —$COOC_{1-20}$ alkyl, —COO perfluorinated $C_{1-20}$ alkyl, —COOaryl, —$CONHC_{1-20}$ alkyl, —$CONHC_{2-20}$ alkenyl, —$CONHC_{2-20}$ alkynyl, —CONH perfluorinated $C_{1-20}$ alkyl, —CONH-aryl, —CONH-heteroaryl, and —CONH-heterocyclyl, wherein each $C_{1-20}$ alkyl, $C_{2-20}$ alkenyl, $C_{2-20}$ alkynyl, perfluorinated $C_{1-20}$ alkyl, aryl, hereroaryl, heterocyclyl, —$OC_{1-20}$ alkyl, —$OC_{2-20}$ alkenyl, —$OC_{2-20}$ alkynyl, —O-perfluorinated $C_{1-20}$ alkyl, —Oaryl, —$COOC_{1-20}$ alkyl, —COO perfluorinated $C_{1-20}$ alkyl, —COOaryl, —$CONHC_{1-20}$ alkyl, —$CONHC_{2-20}$ alkenyl, —$CONHC_{2-20}$ alkynyl, —CONH perfluorinated $C_{1-20}$ alkyl, —CONH-aryl, —CONH-heteroaryl, and —CONH-heterocyclyl can be optionally substituted from 1 to 3 times with a substituent selected from the group consisting of H, halogen, OH, $C_{1-6}$ alkyl, aryl, and arylalkyl;

$R^5$, $R^{5'}$, and $R^{5''}$ are each independently selected from the group consisting of H, halogen, OH, —$O(CH_2)_n$—$(OCH_2CH_2)_m$—$OC_{1-6}$ alkyl, aryl, hereroaryl, heterocyclyl, —$OC_{1-20}$ alkyl, —O-perfluorinated $C_{1-20}$ alkyl, —Oaryl, and —$NR^{10}R^{11}$;

$R^6$, $R^7$, $R^8$, and $R^9$ are each independently selected at each occurrence from the group consisting of H, halogen, $C_{1-20}$ alkyl, $C_{2-20}$ alkenyl, $C_{2-20}$ alkynyl, perfluorinated $C_{1-20}$ alkyl, aryl, hereroaryl, heterocyclyl, OH, —$OC_{1-20}$ alkyl, —$OC_{2-20}$ alkenyl, —O-perfluorinated $C_{1-20}$ alkyl, —$OC_{2-20}$ alkynyl, aryl, heteroaryl, heterocyclyl, and —$COOC_{1-20}$ alkyl, —COO perfluorinated $C_{1-20}$ alkyl, —COOaryl, —$CONHC_{1-20}$ alkyl, —$CONHC_{2-20}$ alkenyl, —$CONHC_{2-20}$ alkynyl, —CONH perfluorinated $C_{1-20}$ alkyl, —CONH-aryl, —CONH-heteroaryl, and —CONH-heterocyclyl, wherein each $C_{1-20}$ alkyl, $C_{2-20}$ alkenyl, $C_{2-20}$ alkynyl, perfluorinated $C_{1-20}$ alkyl, aryl, hereroaryl, heterocyclyl, —$OC_{1-20}$ alkyl, —$OC_{2-20}$ alkenyl, —$OC_{2-20}$ alkynyl, —O-perfluorinated $C_{1-20}$ alkyl, —Oaryl, —$COOC_{1-20}$ alkyl, —COO perfluorinated $C_{1-20}$ alkyl, —COOaryl, —$CONHC_{1-20}$ alkyl, —$CONHC_{2-20}$ alkenyl, —$CONHC_{2-20}$ alkynyl, —CONH perfluorinated $C_{1-20}$ alkyl, —CONH-aryl, —CONH-heteroaryl, and —CONH-heterocyclyl can be optionally substituted from 1 to 3 times with a substituent selected from the group consisting of H, halogen, OH, $C_{1-6}$ alkyl, aryl, and arylalkyl;

$R^{10}$ and $R^{11}$ are each independently selected from the group consisting of H, $C_{1-6}$ alkyl, $C_{2-6}$ alkenyl, $C_{2-6}$ alkynyl, aryl, heteroarylalkyl, heterocyclylalkyl, and arylalkyl, wherein each $C_{1-6}$ alkyl, $C_{2-6}$ alkenyl, $C_{2-6}$ alkynyl, aryl, heteroarylalkyl, heterocyclylalkyl, and arylalkyl can be optionally substituted from 1 to 3 times with a substituent selected from the group consisting of H, $C_{1-6}$ alkyl, heteroarylalkyl, heterocyclylalkyl, and arylalkyl;

$X^1$ and $X^2$ are absent or are independently selected from the group consisting of $C_{1-6}$ alkylene, $C_{3-8}$ cycloalkylene, and arylene, wherein $C_{1-6}$ alkylene, $C_{3-8}$ cycloalkylene, and arylene can be optionally substituted from 1 to 3 times with H or $C_{1-6}$ alkyl;

p is 1 to 3;

n is 1 to 10; and m is 1 to 10.

Another aspect of the present application relates to a process for preparation of a nanocage of Formula (I):

(I)

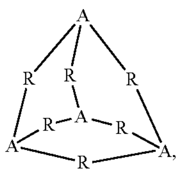

wherein each A is independently selected and has the formula

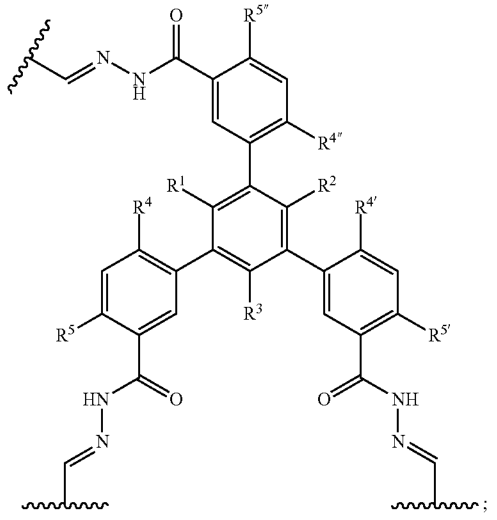

is the point of attachment of A to R;

each R is independently selected and has the formula

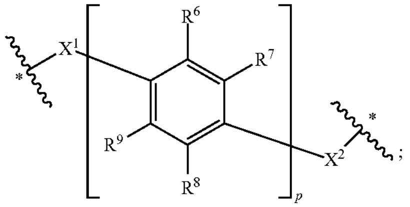

indicates the point of attachment of R to A;

$R^1$, $R^2$, and $R^3$ are each independently selected from the group consisting of H, halogen, OH, $C_{1-20}$ alkyl, $C_{2-20}$ alkenyl, $C_{2-20}$ alkynyl, perfluorinated $C_{1-20}$ alkyl, aryl, hereroaryl, heterocyclyl, —$OC_{1-20}$ alkyl, —$OC_{2-20}$ alkenyl, —$OC_{2-20}$ alkynyl, —O-perfluorinated $C_{1-20}$ alkyl, —Oaryl, —$COOC_{1-20}$ alkyl, —COO perfluorinated $C_{1-20}$ alkyl, —COOaryl, —$CONHC_{1-20}$ alkyl, —$CONHC_{2-20}$ alkenyl, —$CONHC_{2-20}$ alkynyl, —CONH perfluorinated $C_{1-20}$ alkyl, —CONH-aryl, —CONH-heteroaryl, and —CONH-heterocyclyl, wherein each $C_{1-20}$ alkyl, $C_{2-20}$ alkenyl, $C_{2-20}$ alkynyl, perfluorinated $C_{1-20}$ alkyl, aryl, hereroaryl, heterocyclyl, —$OC_{1-20}$ alkyl, —$OC_{2-20}$ alkenyl, —$OC_{2-20}$ alkynyl, —O-perfluorinated $C_{1-20}$ alkyl, —Oaryl, —$COOC_{1-20}$ alkyl, —COO perfluorinated $C_{1-20}$ alkyl, —COOaryl, —$CONHC_{1-20}$ alkyl, —$CONHC_{2-20}$ alkenyl, —$CONHC_{2-20}$ alkynyl, —CONH perfluorinated $C_{1-20}$ alkyl, —CONH-aryl, —CONH-heteroaryl, and —CONH-heterocyclyl can be optionally substituted from 1 to 3 times with a substituent selected from the group consisting of H, halogen, OH, $C_{1-6}$ alkyl, aryl, and arylalkyl;

$R^4$, $R^{4'}$, and $R^{4''}$ are each independently selected from the group consisting of H, halogen, $C_{1-20}$ alkyl, $C_{2-20}$ alkenyl, $C_{2-20}$ alkynyl, perfluorinated $C_{1-20}$ alkyl, aryl, hereroaryl, heterocyclyl, OH, —$OC_{1-20}$ alkyl, —$OC_{2-20}$ alkenyl, —$OC_{2-20}$ alkynyl, —O-perfluorinated $C_{1-20}$ alkyl, —Oaryl, —$COOC_{1-20}$ alkyl, —COO perfluorinated $C_{1-20}$ alkyl, —COOaryl, —$CONHC_{1-20}$ alkyl, —$CONHC_{2-20}$ alkenyl, —$CONHC_{2-20}$ alkynyl, —CONH perfluorinated $C_{1-20}$ alkyl, —CONH-aryl, —CONH-heteroaryl, and —CONH-heterocyclyl, wherein each $C_{1-20}$ alkyl, $C_{2-20}$ alkenyl, $C_{2-20}$ alkynyl, perfluorinated $C_{1-20}$ alkyl, aryl, hereroaryl, heterocyclyl, —$OC_{1-20}$ alkyl, —$OC_{2-20}$ alkenyl, —$OC_{2-20}$ alkynyl, —O-perfluorinated $C_{1-20}$ alkyl, —Oaryl, —$COOC_{1-20}$ alkyl, —COO perfluorinated $C_{1-20}$ alkyl, —COOaryl, —$CONHC_{1-20}$ alkyl, —$CONHC_{2-20}$ alkenyl, —$CONHC_{2-20}$ alkynyl, —CONH perfluorinated $C_{1-20}$ alkyl, —CONH-aryl, —CONH-heteroaryl, and —CONH-heterocyclyl can be optionally substituted from 1 to 3 times with a substituent selected from the group consisting of H, halogen, OH, $C_{1-6}$ alkyl, aryl, and arylalkyl;

$R^5$, $R^{5'}$, and $R^{5''}$ are each independently selected from the group consisting of H, halogen, OH, —$O(CH_2)_n$—$(OCH_2CH_2)_m$—$OC_{1-6}$ alkyl, aryl, hereroaryl, heterocyclyl, —$OC_{1-20}$ alkyl, —O-perfluorinated $C_{1-20}$ alkyl, —Oaryl, and —$NR^{10}R^{11}$;

$R^6$, $R^7$, $R^8$, and $R^9$ are each independently selected at each occurrence from the group hereroaryl, heterocyclyl, OH, —$OC_{1-20}$ alkyl, —$OC_{2-20}$ alkenyl, —O-perfluorinated $C_{1-20}$ alkyl, —$OC_{2-20}$ alkynyl, aryl, heteroaryl, heterocyclyl, and —$COOC_{1-20}$ alkyl, —COO perfluorinated $C_{1-20}$ alkyl, —COOaryl, —$CONHC_{1-20}$ alkyl, —$CONHC_{2-20}$ alkenyl, —$CONHC_{2-20}$ alkynyl, —CONH perfluorinated $C_{1-20}$ alkyl, —CONH-aryl, —CONH-heteroaryl, and —CONH-heterocyclyl, wherein each $C_{1-20}$ alkyl, $C_{2-20}$ alkenyl, $C_{2-20}$ alkynyl, perfluorinated $C_{1-20}$ alkyl, aryl, hereroaryl, heterocyclyl, —$OC_{1-20}$ alkyl, —$OC_{2-20}$ alkenyl, —$OC_{2-20}$ alkynyl, —O-perfluorinated $C_{1-20}$ alkyl, —Oaryl, —$COOC_{1-20}$ alkyl, —COO perfluorinated $C_{1-20}$ alkyl, —COOaryl, —$CONHC_{1-20}$ alkyl, —$CONHC_{2-20}$ alkenyl, —$CONHC_{2-20}$ alkynyl, —CONH perfluorinated $C_{1-20}$ alkyl, —CONH-aryl, —CONH-heteroaryl, and —CONH-heterocyclyl can be optionally substituted from 1 to 3 times with a substituent selected from the group consisting of H, halogen, OH, $C_{1-6}$ alkyl, aryl, and arylalkyl;

$R^{10}$ and $R^{11}$ are each independently selected from the group consisting of H, $C_{1-6}$ alkyl, $C_{2-6}$ alkenyl, $C_{2-6}$ alkynyl, aryl, heteroarylalkyl, heterocyclylalkyl, and arylalkyl, wherein each $C_{1-6}$ alkyl, $C_{2-6}$ alkenyl, $C_{2-6}$ alkynyl, aryl, heteroarylalkyl, heterocyclylalkyl, and arylalkyl can be optionally substituted from 1 to 3 times with a substituent selected from the group consisting of H, $C_{1-6}$ alkyl, heteroarylalkyl, heterocyclylalkyl, and arylalkyl;

$X^1$ and $X^2$ are absent or are independently selected from the group consisting of $C_{1-6}$ alkylene, $C_{3-8}$ cycloalkylene, and arylene, wherein $C_{1-6}$ alkylene, $C_{3-8}$ cycloalkylene, and arylene can be optionally substituted from 1 to 3 times with H or $C_{1-6}$ alkyl;

p is 1 to 3;

n is 1 to 10; and m is 1 to 10, said process comprising:

providing one or more compounds of Formula (II) having the structure:

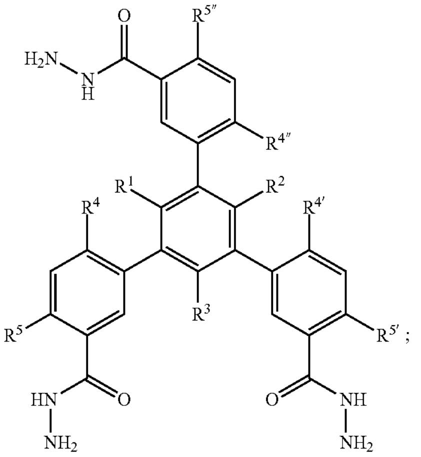

and and forming the nanocage of Formula (I) from the one or more compounds of Formula (II).

Another aspect of the present application relates to a method for detecting an analyte in a fluid. This method includes:

providing a sensor comprising a nanocage of Formula (I):

(I)

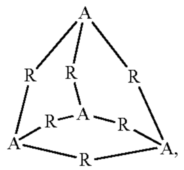

wherein each A is independently selected and has the formula

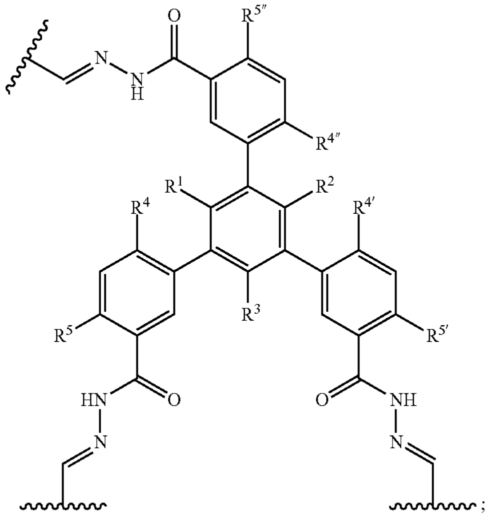

is the point of attachment of A to R;

each R is independently selected and has the formula

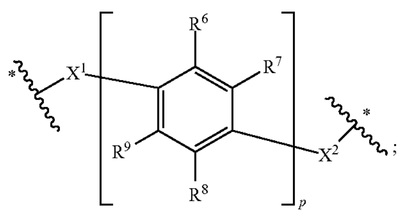

indicates the point of attachment of R to A;

$R^1$, $R^2$, and $R^3$ are each independently selected from the group consisting of H, halogen, OH, $C_{1-20}$ alkyl, $C_{2-20}$ alkenyl, $C_{2-20}$ alkynyl, perfluorinated $C_{1-20}$ alkyl, aryl, hereroaryl, heterocyclyl, —$OC_{1-20}$ alkyl, —$OC_{2-20}$ alkenyl, —$OC_{2-20}$ alkynyl, —O-perfluorinated $C_{1-20}$ alkyl, —Oaryl, —$COOC_{1-20}$ alkyl, —COO perfluorinated $C_{1-20}$ alkyl, —COOaryl, —$CONHC_{1-20}$ alkyl, —$CONHC_{2-20}$ alkenyl, —$CONHC_{2-20}$ alkynyl, —CONH perfluorinated $C_{1-20}$ alkyl, —CONH-aryl, —CONH-heteroaryl, and —CONH-heterocyclyl, wherein each $C_{1-20}$ alkyl, $C_{2-20}$ alkenyl, alkenyl, —$OC_{2-20}$ alkynyl, —O-perfluorinated $C_{1-20}$ alkyl, —Oaryl, —$COOC_{1-20}$ alkyl, —COO perfluorinated $C_{1-20}$ alkyl, —COOaryl, —$CONHC_{1-20}$ alkyl, —$CONHC_{2-20}$ alkenyl, —$CONHC_{2-20}$ alkynyl, —CONH perfluorinated $C_{1-20}$ alkyl, —CONH-aryl, —CONH-heteroaryl, and —CONH-heterocyclyl can be optionally substituted from 1 to 3 times with a substituent selected from the group consisting of H, halogen, OH, $C_{1-6}$ alkyl, aryl, and arylalkyl;

$R^4$, $R^{4'}$, and $R^{4''}$ are each independently selected from the group consisting of H, halogen, $C_{1-20}$ alkyl, $C_{2-20}$ alkenyl, $C_{2-20}$ alkynyl, perfluorinated $C_{1-20}$ alkyl, aryl, hereroaryl, heterocyclyl, OH, —$OC_{1-20}$ alkyl, —$OC_{2-20}$ alkenyl, —$OC_{2-20}$ alkynyl, —O-perfluorinated $C_{1-20}$ alkyl, —Oaryl, —$COOC_{1-20}$ alkyl, —COO perfluorinated $C_{1-20}$ alkyl, —COOaryl, —$CONHC_{1-20}$ alkyl, —$CONHC_{2-20}$ alkenyl, —$CONHC_{2-20}$ alkynyl, —CONH perfluorinated $C_{1-20}$ alkyl, —CONH-aryl, —CONH-heteroaryl, and —CONH-heterocyclyl, wherein each $C_{1-20}$ alkyl, $C_{2-20}$ alkenyl, $Cl_{2-20}$ alkynyl, perfluorinated $C_{1-20}$ alkyl, aryl, hereroaryl, heterocyclyl, —$OC_{1-20}$ alkyl, —$OC_{2-20}$ alkenyl, —$OC_{2-20}$ alkynyl, —O-perfluorinated $C_{1-20}$ alkyl, —Oaryl, —$COOC_{1-20}$ alkyl, —COO perfluorinated $C_{1-20}$ alkyl, —COOaryl, —$CONHC_{1-20}$ alkyl, —$CONHC_{2-20}$ alkenyl, —$CONHC_{2-20}$ alkynyl, —CONH perfluorinated $C_{1-20}$ alkyl, —CONH-aryl, —CONH-heteroaryl, and —CONH-heterocyclyl can be optionally substituted from 1 to 3 times with a substituent selected from the group consisting of H, halogen, OH, $C_{1-6}$ alkyl, aryl, and arylalkyl;

$R^5$, $R^{5'}$, and $R^{5''}$ are each independently selected from the group consisting of H, halogen, OH, —$O(CH_2)_n$—$(OCH_2CH_2)_m$—$OC_{1-6}$ alkyl, aryl, hereroaryl, heterocyclyl, —$OC_{1-20}$ alkyl, —O-perfluorinated $C_{1-20}$ alkyl, —Oaryl, and —$NR^{10}R^{11}$; $R^6$, $R^7$, $R^8$, and $R^9$ are each independently selected at each occurrence from the group consisting of H, halogen, $C_{1-20}$ alkyl, $C_{2-20}$ alkenyl, $C_{2-20}$ alkynyl, perfluorinated $C_{1-20}$ alkyl, aryl, hereroaryl, heterocyclyl, OH, —$OC_{1-20}$ alkyl, —$OC_{2-20}$ alkenyl, —O-perfluorinated $C_{1-20}$ alkyl, —$OC_{2-20}$ alkynyl, aryl, heteroaryl, heterocyclyl, and —$COOC_{1-20}$ alkyl, —COO perfluorinated $C_{1-20}$ alkyl, —COOaryl, —$CONHC_{1-20}$ alkyl, —$CONHC_{2-20}$ alkenyl, —$CONHC_{2-20}$ alkynyl, —CONH perfluorinated $C_{1-20}$ alkyl, —CONH-aryl, —CONH-heteroaryl, and —CONH-heterocyclyl, wherein each $C_{1-20}$ alkyl, $C_{2-20}$ alkenyl, $C_{2-20}$ alkynyl, perfluorinated $C_{1-20}$ alkyl, aryl, hereroaryl, heterocyclyl, —$OC_{1-20}$ alkyl, —$OC_{2-20}$ alkenyl, —$OC_{2-20}$ alkynyl, —O-perfluorinated $C_{1-20}$ alkyl, —Oaryl, —$COOC_{1-20}$ alkyl, —COO perfluorinated $C_{1-20}$ alkyl, —COOaryl, —$CONHC_{1-20}$ alkyl, —$CONHC_{2-20}$ alkenyl, —$CONHC_{2-20}$ alkynyl, —CONH perfluorinated $C_{1-20}$ alkyl, —CONH-aryl, —CONH-heteroaryl, and —CONH-heterocyclyl can be optionally substituted from 1 to 3 times with a substituent selected from the group consisting of H, halogen, OH, $C_{1-6}$ alkyl, aryl, and arylalkyl;

$R^{10}$ and $R^{11}$ are each independently selected from the group consisting of H, $C_{1-6}$ alkyl, $C_{2-6}$ alkenyl, $C_{2-6}$ alkynyl, aryl, heteroarylalkyl, heterocyclylalkyl, and arylalkyl, wherein each $C_{2-6}$ alkyl, $C_{2-6}$ alkenyl, $C_{2-6}$ alkynyl, aryl, heteroarylalkyl, heterocyclylalkyl, and arylalkyl can be optionally substituted from 1 to 3 times with a substituent selected from the group consisting of H, $C_{1-6}$ alkyl, heteroarylalkyl, heterocyclylalkyl, and arylalkyl;

$X^1$ and $X^2$ are absent or are independently selected from the group consisting of $C_{1-6}$ alkylene, $C_{3-8}$ cycloalkylene, and arylene, wherein $C_{1-6}$ alkylene, $C_{3-8}$ cycloalkylene, and arylene can be optionally substituted from 1 to 3 times with H or $C_{1-6}$ alkyl;

p is 1 to 3;

n is 1 to 10; and m is 1 to 10;

providing a fluid containing an analyte; and contacting a fluid containing the analyte with the sensor to capture the analyte in the nanocage and detect the analyte in the fluid.

Another aspect of the present application relates to a method of functionalizing a polymer. This method includes:

providing a polymer;

providing a nanocage of Formula (I):

(I)

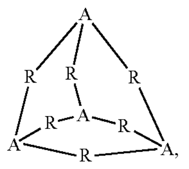

wherein each A is independently selected and has the formula

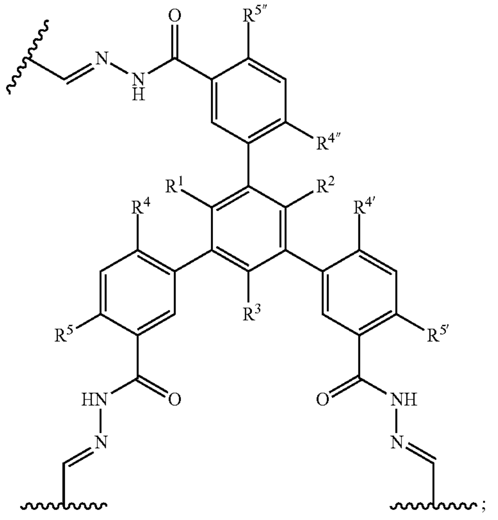

is the point of attachment of A to R;

each R is independently selected and has the formula

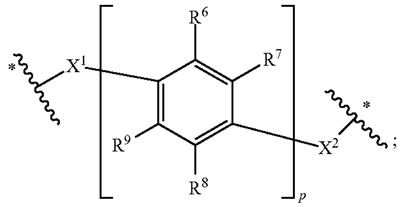

indicates the point of attachment of R to A;

$R^1$, $R^2$, and $R^3$ are each independently selected from the group consisting of H, halogen, OH, $C_{1-20}$ alkyl, $C_{2-20}$ alkenyl, $C_{2-20}$ alkynyl, perfluorinated $C_{1-20}$ alkyl, aryl, hereroaryl, heterocyclyl, —$OC_{1-20}$ alkyl, —$OC_{2-20}$ alkenyl, —$OC_{2-20}$ alkynyl, —O-perfluorinated $C_{1-20}$ alkyl, —Oaryl, —$COOC_{1-20}$ alkyl, —COO perfluorinated $C_{1-20}$ alkyl, —COOaryl, —$CONHC_{1-20}$ alkyl, —$CONHC_{2-20}$ alkenyl, —$CONHC_{2-20}$ alkynyl, —CONH perfluorinated $C_{1-20}$ alkyl, —CONH-aryl, —CONH-heteroaryl, and —CONH-heterocyclyl, wherein each $C_{1-20}$ alkyl, $C_{2-20}$ alkenyl, $C_{2-20}$ alkynyl, perfluorinated $C_{1-20}$ alkyl, aryl, hereroaryl, heterocyclyl, —$OC_{1-20}$ alkyl, —$OC_{2-20}$ alkenyl, —$OC_{2-20}$ alkynyl, —O-perfluorinated $C_{1-20}$ alkyl, —Oaryl, —$COOC_{1-20}$ alkyl, —COO perfluorinated $C_{1-20}$ alkyl, —COOaryl, —$CONHC_{1-20}$ alkyl, —$CONHC_{2-20}$ alkenyl, —$CONHC_{2-20}$ alkynyl, —CONH perfluorinated $C_{1-20}$ alkyl, —CONH-aryl, —CONH-heteroaryl, and —CONH-heterocyclyl can be optionally substituted from 1 to 3 times with a substituent selected from the group consisting of H, halogen, OH, $C_{1-6}$ alkyl, aryl, and arylalkyl;

$R^4$, $R^{4'}$, and $R^{4''}$ are each independently selected from the group consisting of H, halogen, $C_{1-20}$ alkyl, $C_{2-20}$ alkenyl, $C_{2-20}$ alkynyl, perfluorinated $C_{1-20}$ alkyl, aryl, hereroaryl, heterocyclyl, OH, —$OC_{1-20}$ alkyl, —$OC_{2-20}$ alkenyl, —$OC_{2-20}$ alkynyl, —O-perfluorinated $C_{1-20}$ alkyl, —Oaryl, —$COOC_{1-20}$ alkyl, —COO perfluorinated $C_{1-20}$ alkyl, —COOaryl, —$CONHC_{1-20}$ alkyl, —$CONHC_{2-20}$ alkenyl, —$CONHC_{2-20}$ alkynyl, —CONH perfluorinated $C_{1-20}$ alkyl, —CONH-aryl, —CONH-heteroaryl, and —CONH-heterocyclyl, wherein each $C_{1-20}$ alkyl, $C_{2-20}$ alkenyl, alkenyl, —$OC_{2-20}$ alkynyl, —O-perfluorinated $C_{1-20}$ alkyl, —Oaryl, —$COOC_{1-20}$ alkyl, —COO perfluorinated $C_{1-20}$ alkyl, —COOaryl, —$CONHC_{1-20}$ alkyl, —$CONHC_{2-20}$ alkenyl, —$CONHC_{2-20}$ alkynyl, —CONH perfluorinated $C_{1-20}$ alkyl, —CONH-aryl, —CONH-heteroaryl, and —CONH-heterocyclyl can be optionally substituted from 1 to 3 times with a substituent selected from the group consisting of H, halogen, OH, $C_{1-6}$ alkyl, aryl, and arylalkyl;

$R^5$, $R^{5'}$, and $R^{5''}$ are each independently selected from the group consisting of H, halogen, OH, —$O(CH_2)_n$—$(OCH_2CH_2)_m$—$OC_{1-6}$ alkyl, aryl, hereroaryl, heterocyclyl, —$OC_{1-20}$ alkyl, —O-perfluorinated $C_{1-20}$ alkyl, —Oaryl, and —$NR^{10}R^{11}$;

$R^6$, $R^7$, $R^8$, and $R^9$ are each independently selected at each occurrence from the group consisting of H, halogen, $C_{1-20}$ alkyl, $C_{2-20}$ alkenyl, $C_{2-20}$ alkynyl, perfluorinated $C_{1-20}$ alkyl, aryl, hereroaryl, heterocyclyl, OH, —$OC_{1-20}$ alkyl, —$OC_{2-20}$ alkenyl, —O-perfluorinated $C_{1-20}$ alkyl, —$OC_{2-20}$ alkynyl, aryl, heteroaryl, heterocyclyl, and —$COOC_{1-20}$ alkyl, —COO perfluorinated $C_{1-20}$ alkyl, —COOaryl, —$CONHC_{1-20}$ alkyl, —$CONHC_{2-20}$ alkenyl, —$CONHC_{2-20}$ alkynyl, —CONH perfluorinated $C_{1-20}$ alkyl, —CONH-aryl, —CONH-heteroaryl, and —CONH-heterocyclyl, wherein each $C_{1-20}$ alkyl, $C_{2-20}$ alkenyl, $C_{2-20}$ alkynyl, perfluorinated $C_{1-20}$ alkyl, aryl, hereroaryl, heterocyclyl, —$OC_{1-20}$ alkyl, —$OC_{2-20}$ alkenyl, —$OC_{2-20}$ alkynyl, —O-perfluorinated $C_{1-20}$ alkyl, —Oaryl, —$COOC_{1-20}$ alkyl, —COO perfluorinated $C_{1-20}$ alkyl, —COOaryl, —$CONHC_{1-20}$ alkyl, —$CONHC_{2-20}$ alkenyl, —$CONHC_{1-20}$ alkynyl, —CONH perfluorinated $C_{1-20}$ alkyl, —CONH-aryl, —CONH-heteroaryl, and —CONH-heterocyclyl can be optionally substituted from 1 to 3 times with a substituent selected from the group consisting of H, halogen, OH, $C_{1-6}$ alkyl, aryl, and arylalkyl;

$R^{10}$ and $R^{11}$ are each independently selected from the group consisting of H, $C_{1-6}$ alkyl, $C_{2-6}$ alkenyl, $C_{2-6}$ alkynyl, aryl, heteroarylalkyl, heterocyclylalkyl, and arylalkyl, wherein each $C_{1-6}$ alkyl, $C_{2-6}$ alkenyl, $C_{2-6}$ alkynyl, aryl, heteroarylalkyl, heterocyclylalkyl, and arylalkyl can be optionally substituted from 1 to 3 times with a substituent selected from the group consisting of H, $C_{1-6}$ alkyl, heteroarylalkyl, heterocyclylalkyl, and arylalkyl;

$X^1$ and $X^2$ are absent or are independently selected from the group consisting of $C_{1-6}$ alkylene, $C_{3-8}$ cycloalkylene, and arylene, wherein $C_{1-6}$ alkylene, $C_{3-8}$ cycloalkylene, and arylene can be optionally substituted from 1 to 3 times with H or $C_{1-6}$ alkyl;

p is 1 to 3;

n is 1 to 10; and m is 1 to 10;

providing a functionalizing reagent;

reacting the polymer with the functionalizing reagent within the nanocage having a Formula (I) to produce a functionalized polymer.

The present application describes the synthesis of a metal-free $T_d$-symmetrical hydrazone-linked tetrahedron (Tet-1), which binds to polyvinylpyrrolidone (PVP) and poly (isobutylene-alt-n-octyl maleimide) (POI) as well as to picrocrocin—a monoterpene glycoside, which is primarily responsible for the distinct taste of saffron. In terms of surface area per face, a tetrahedral geometry provides the largest openings of all possible regular polyhedra. For instance, the surface area per face of a tetrahedron is 1.8 times larger than the corresponding surface area per face for a cube with an identical volume. Therefore, tetrahedral geometries are well suited to allow polymers with voluminous side chains to thread through their openings while also permitting multiple copies of small molecules like glycosides to bind cooperatively.

Picrocrocin binds to Tet-1 selectively. Most importantly, only picrocrocin and no other abundant species like safranal in saffron was recognized by the first-generation nanocage, which allowed to selectively detect picrocrocin with Tet-1. The structures of the cages can be adjusted by simply modifying the linkers, which will allow rational design and creation of cages that can detect other key saffron components (like crocin or safranal) in the future. The observed titration data showed cooperative behavior, with multiple picrocrocin molecules binding inside of a single cage. Such cooperative binding effects are advantageous for sensing as they lead to sigmoidal binding curves.

Selective catalysis at the molecular level represents a cornerstone of chemical synthesis. However, it still remains an open question how to elevate tunable catalysis to larger length scales to functionalize whole polymer chains in a selective manner. The present application describes a hydrazone-linked tetrahedron with wide openings, which acts as a catalyst to size-selectively functionalize polydisperse polymer mixtures. Experimental and computational evidence described in the present application supports a dual role of the hydrazone-linked tetrahedron. To accelerate functionalization of the polymer substrates, the tetrahedron (i) unfolds the polymer substrates and/or breaks the polymer aggregates as well as (ii) enables target sites (amino groups) on the polymers to coordinate with catalytic units (triglyme) attached to the tetrahedron. With the tetrahedron as the catalyst, it was found that the reactivity of the shorter polymers increases selectively. These findings enable the possibility to engineer hydrolytically stable molecular polyhedra as organocatalysts for size-selective polymer modification.

A hydrazone-linked tetrahedron with large openings described in the present application can size-selectively functionalize (FIG. 1B) complex polymeric mixtures. Analogous to previously-reported catalytic transport systems operating with polymeric tracks (Thordarson et al., "Epoxidation of Polybutadiene by a Topologically Linked Catalyst," *Nature* 424:915-918 (2003); Zheng et al., "Catalytic Transport of Molecular Cargo using Diffusive Binding Along a Polymer Track," *Nat. Chem.* 11:359-366 (2019), which are hereby incorporated by reference in their entirety) the catalyst described in the present application is designed to slide along the polymeric substrates during the reaction, which leads to efficient (FIGS. 6A-B) catalytic functionalization of side-chain functional groups. This process is enabled-like in the seminal system of Nolte and coworkers (Osaki et al., "An Artificial Molecular Chaperone: Poly-Pseudo-Rotaxane with an Extensible Axle," *J. Am. Chem. Soc.* 129:14452-14457 (2007); del Barrio et al., "Photocontrol Over Cucurbit [8]uril Complexes: Stoichiometry and Supramolecular Polymers," *J. Am. Chem. Soc.* 135:11760-11763 (2013); Thordarson et al., "Epoxidation of Polybutadiene by a Topologically Linked Catalyst," *Nature* 424:915-918 (2003), which are hereby incorporated by reference in their entirety)—by threading of the polymer chains through the cavity of the catalyst. Yet, in contrast to Nolte's catalyst, which was optimized for linear polymers, threading and size-selective functionalization of side-chains polymers also becomes possible with the organocatalytic tetrahedron. In regards to prior work in the field of size-selective catalysis (which has recently been reviewed by Otte, M. "Size-Selective Molecular Flasks," *ACS. Catal.* 6:6491-6510 (2016), which is hereby incorporated by reference in its entirety) the present system is unique in that it acts on a polydisperse mixture of polymer chains in a size-selective manner, while mostly pairs of small-molecules were used as the substrates for size-selective catalysis in prior work (FIG. 1A).

The work described in the present application provides the foundation to bring selective catalysis to polymeric substrates. Results described in the present application show that man-made catalysts with large openings were able to distinguish between polymer chains of different lengths in a polydisperse mixture, while functionalizing them selectively. These findings will likely advance the fundamental understanding of the thermodynamic and kinetic phenomena controlling the interactions between molecular cages and synthetic polymers. In addition, it might reform one's ability to create complex polymeric materials in the future in a catalytic manner in general. For instance, tailored, size-selective catalysts could eventually be utilized to create otherwise difficult-to-access size distributions of linear, branched, and crosslinked polymers in a more efficient manner. These results also pave the way to better understand future site-selective, post-synthetic polymer modification (inspired by post-translational protein modification).

BRIEF DESCRIPTION OF THE DRAWINGS

FIG. 1A shows examples of prior work in the size-selective catalysis arena with small-molecule substrates. FIG. 1B shows how the concept of size-selective catalysis was extended to larger substrates in the present application with a hydrazone-linked molecular tetrahedron as the organocatalyst, which can size-selectively modify a polydisperse mixture of polymer chains. Catalysts, reactive substrates and products, unreactive substrates, and reagents are all shown. All structures are shown approximately on the same scale and the polymer chains are illustrated schematically in their fully extended conformations. The longer polymer chains have a tendency to not only fold, but also aggregate more than the shorter ones, which can explain the catalyst's selectivity towards the shorter polymer chains.

FIGS. 2A-B show a comparison of tetrameric hydrazone-linked molecular cages. FIG. 2A shows a $C_{2d}$-symmetrical hydrazone cage reported by Lin et al., "Multicomponent Assembly of Cavitand-Based Polyacylhydrazone Nanocapsules," *Chem. Eur. J.* 17:9395-9405 (2011), which is hereby incorporated by reference in its entirety. FIG. 2B shows the $T_d$-symmetrical hydrazone tetrahedron reported in the present application. Its wide openings allow it to act as a size-selective catalyst for post-synthetic polymer modification (PSPM). Molecular models of both cages were minimized with the OPLS3 (Harder et al., "OPLS3: A Force Field Providing Broad Coverage of Drug-Like Small Molecules and Proteins," *J. Chem. Theory. Comput.* 12:281-296 (2016), which is hereby incorporated by reference in its entirety) force field.

FIGS. 3A-D are $^1$H-DOSY and $^1$H-$^1$H-NOESY NMR spectra demonstrating complex formation and threading of the polymers through the cavity of the Tet-1 catalyst. Partial DOSY $^1$H-NMR spectra (500 MHZ, $CD_2Cl_2$, 298 K) of Tet-1 (0.28 mM) (FIG. 3A), a mixture of Tet-1 (0.28 mM) and $NH_2$-POA (3.0 mg $mL^{-1}$; 0.45 mM) (FIG. 3B), as well as pure $NH_2$-POA (3.0 mg $mL^{-1}$; 0.45 mM) (FIG. 3C). The spectra show a decrease of the diffusion constants for both $NH_2$-POA and Tet-1 upon mixing. This finding establishes complex formation between the two compounds. The diffusion constant of the solvent ($CHDCl_2$) resonance at 5.32 ppm remained constant ($32.5\times10^{-10}$ $m^2$ $s^{-1}$ in all cases, see FIGS. 15A-C), indicating that the viscosities of the NMR solutions were not affected significantly by the presence of the polymers at the low concentrations employed. FIG. 3D shows partial $^1$H-$^1$H-NOESY NMR spectrum (500 MHZ, $CD_2Cl_2$, 298 K) of Short-$NH_2$-POA (3.0 mg $mL^{-1}$) in complex with Tet-1 (0.28 mM). Short-$NH_2$-POA represents the shorter chains ($\overline{M}_w$=2.6 kDa) of the $NH_2$-POA polymer sample, which were isolated by running an additional size-exclusion column on parts of the original $NH_2$-POA sample. NOE cross peaks between the aliphatic polymer resonances ($H_{Poly-aliphatic}$) and signals corresponding to Tet-1 are circled. Notably, a NOE cross peak between $H_{Poly-aliphatic}$ and the $H_c$ protons on Tet-1 (pointing inward) was observed, which is consistent with the $NH_2$-POA polymers threading through the cavity of Tet-1. An analogous NOESY spectrum has been obtained (see FIG. 19) for the longer chains in $NH_2$-POA, i.e. Long-$NH_2$-POA ($\overline{M}_w$=9.9 kDa), which shows similar (although slightly weaker) NOE cross peaks.

FIGS. 4A-C are molecular dynamics (MD) simulations showing an $NH_2$-POA polymer chain unfolding when binding to Tet-1. The MD simulations helped explain the increase of the polymer's solvodynamic diameter, which was observed (FIG. 3B) upon complexation with Tet-1 by DOSY $^1$H-NMR spectroscopy. FIG. 4A is a time-average bar-charts showing the radius of gyration (rgyr) of the $NH_2$-POA polymer chain by itself (pattern-free bar) and in complex (patterned bar) with Tet-1. Error bars represent standard deviations. The time-averages and standard deviations were calculated from the last 400 ns of 800-ns MD simulations in explicit solvent. FIG. 4B is a final snapshot of an 800-ns MD simulation of $NH_2$-POA by itself. The solvent ($CH_2Cl_2$) is hidden for clarity. FIG. 4C is a final snapshot of an analogous MD simulation with $NH_2$-POA threaded through the cavity of Tet-1.

FIGS. 5A-C show that Long-$NH_2$-POA binds stronger to Tet-1 than Short-$NH_2$-POA but the short polymers decomplex faster. FIG. 5A is a partial $^1$H-NMR spectra (500 MHz, $CD_2Cl_2$, 298 K) demonstrating how Tet-1 and polymer resonances change upon titration of Short-$NH_2$-POA into a 0.28 mM solution of Tet-1. FIG. 5B shows titration curves fitted to a 1:1 binding model in the intermediate-slow NMR exchange regime for threading of both Short- and Long-$NH_2$-POA into the cavity of Tet-1. While the longer polymer chains bind stronger to Tet-1 (which leads to weaker catalysis with the longer chains as illustrated in FIG. 9D), the shorter polymer chains de-thread faster (with an off-rate, $k_{off}$, nearly three-times as fast as for the longer polymers). $K_a$=Complex association constants. The titration curves were fit with a custom python script, making use of the LineshapeKin 4.0 NMR simulation software (Kovrigin, E. L., "NMR Line Shapes and Multi-State Binding Equilibria," *J. Biomol. NMR* 53:257-270 (2012), which is hereby incorporated by reference in its entirety) in combination with the curve-fit algorithm implemented in the SciPy 0.18 package (Virtanen et al., "SciPy 1.0—Fundamental Algorithms for Scientific Computing in Python," *arXiv* 1907:10121 (2019), which is hereby incorporated by reference in its entirety) with the trust region reflective (TRF) algorithm. Error bars represent standard deviations calculated from the covariance matrix of the best fit obtained with the SciPy curve-fit algorithm. See FIGS. 20A-B and 21A-B for a full comparison of the experimental and predicted spectra. FIG. 5C is a zoomed-in snapshot (at 800-ns) of the MD simulation of the [$NH_2$-POA@Tet-1] complex (see FIG. 4C for a zoomed-out view). The snapshot shows that the threaded polymer chains preferentially pass by the side of the aromatic linkers in Tet-1. It was hypothesized that classical (Wannere et al., "How do Ring Currents Affect $^1$H NMR Chemical Shifts?," *Org. Lett.* 5:605-608 (2003), which is hereby incorporated by reference in its entirety) aromatic ring-current effects operating in this binding geometry are primarily responsible for the observed downfield (the percentage of polymer chains complexed to Tet-1 is highest at the titration point with [Short-$NH_2$-POA]=0.26 mM and [Tet-1]=0.28 mM. A smaller percentage of the polymers are complexed to the Tet-1 receptor at the titration point with [Short-$NH_2$-POA]=0.50 mM. Thus, based on the data shown in FIG. 5A, the resonances of $NH_2$-POA clearly shift downfield upon complexation to Tet-1, which was observed (FIG. 5A) for the polymer resonances in the range of 3.05-2.55 ppm upon complexation with Tet-1.

FIGS. 6A-C show evidence of Tet-1's catalytic activity for functionalizing $NH_2$-POA polymers. FIG. 6A shows a schematic for acylation of the $NH_2$-POA polymer. FIG. 6B shows plots of the inverse total amine concentration ($[amine]^{-1}$) vs. time. The fact that these plots are linear demonstrates that the reactions are all 2$^{nd}$ order in the amine concentration. The kinetic experiments were carried out in 600 μL of $CD_2Cl_2$ at 298 K using an initial amine concentration of 1.8 mM, with an excess (5.1 mM) of the active ester nitrophenyl-3,5-dinitrobenzoate (NDB) in the presence of one of the following catalysts: 0.28 mM Tet-1 (circles); 1.7 mM Edge-Model (triangles); 3.4 mM Triglyme+Control (squares); no catalytic additives (triangles). FIG. 6C is a table showing observed rate constants, $k_{obs}$ (defined in Eqs. 1-3) and average number of functionalized amine units after 48 hours of reaction time. Error bars represent standard errors.

FIGS. 8A-B show additional evidence for size-selectivity in the polymer mixture based on a direct comparison of the relative diffusion constants for the functionalized polymers with the average diffusion constants of all the polymer chains (both functionalized and unfunctionalized) with Tet-1 as the catalyst (FIG. 8A) and control reaction with Triglyme+Control as the catalysts (FIG. 8B). The average diffusion constant of the functionalized polymers was measured via the diffusion constant of the distinct $^1$H-NMR resonance at 8.82 ppm, which corresponds to the ortho-protons ($H_x$) of the 3,5-dinitrobenzamide units attached to the functionalized polymers. The average diffusion constant of all polymer chains was determined from the diffusion constant of the broad $^1$H-NMR resonances between 0.8 to 1.4 ppm, which correspond to the aliphatic protons of the polymer chains. All reactions were run to 24% conversion and all DOSY $^1$H-NMR spectra were obtained for reaction mixtures "equalized" in the following manner: for the functionalization reaction catalyzed by Tet-1 (0.28 mM), Triglyme (3.4 mM) and Control (3.4 mM) were added just before recording the DOSY $^1$H-NMR spectrum (FIG. 8A) and for the control reaction catalyzed by Triglyme (3.4 mM)+Control (3.4 mM), Tet-1 (0.28 mM) was added, again just before recording the DOSY $^1$H-NMR spectrum (FIG. 8B).

FIGS. 9A-D show that the rate constants ($k_{obs}$) obtained for isolated short and long polymer samples confirm that Tet-1 is a more active catalyst for shorter polymer chains. FIGS. 9A-B are plots of the inverse total amine concentration ($[amine]^{-1}$) vs. time for Short-$NH_2$-POA (FIG. 9A) and Long-$NH_2$-POA (FIG. 9B). The kinetic experiments were carried out in 600 μL of $CD_2Cl_2$ at 298 K using an initial amine concentration of 1.2 mM for Short-$NH_2$-POA and 0.5 mM for Long-$NH_2$-POA with an excess (5.1 mM) of the active ester nitrophenyl-3,5-dinitrobenzoate (NDB) in the presence of one of the following catalysts: 0.28 mM Tet-1 (circles); 1.7 mM Edge-Model (triangles); 3.4 mM Triglyme+Control (squares). FIG. 9C is a table of observed rate constants, $k_{obs}$ (defined in Eqs. 1-3). Error bars represent standard errors. FIG. 9D is a schematic showing proposed model explaining why the Tet-1 catalyst reacts faster with the shorter polymer chains, while it binds stronger to the substrates (but not the transition states) with longer chains. $\Delta G^{\ddagger}$ (Long)=Activation Gibbs free energy with Long-$NH_2$-POA; $\Delta G^{\ddagger}$ (Short)=Activation Gibbs free energy with Short-$NH_2$-POA; $\Delta G_b$ (Long)=Binding Gibbs free energy with Long-$NH_2$-POA; $\Delta G_b$ (Short)=Binding Gibbs free energy with Short-$NH_2$-POA.

FIGS. 15A-C are full DOSY $^1$H-NMR spectra (500 MHZ, $CD_2Cl_2$) of Tet-1 (FIG. 15A), [$NH_2$-POA@Tet-1] (FIG. 15B) and $NH_2$-POA (FIG. 15C). These spectra show that the viscosity of the solution doesn't change upon complex formation.

FIGS. 16A-D are DOSY $^1$H-NMR spectra (500 MHz, $CDCl_3$) of PS standards used to calibrate the molecular weight measurements: PS ($\overline{M}_w$=1,220 Da) (FIG. 16A), PS ($\overline{M}_w$=3,510 Da) (FIG. 16B), PS ($\overline{M}_w$=8,560 Da) (FIG. 16C), and PS ($\overline{M}_w$=17,300 Da) (FIG. 16D).

FIG. 19 is a $^1$H-$^1$H-NOESY NMR (500 MHZ, $CD_2Cl_2$, 298 K) spectrum of the [Long-$NH_2$-POA@Tet-1] complex. NOE cross-peaks observed between aliphatic polymer ($H_{Poly\text{-}aliphatic}$) and Tet-1 resonances are circled.

FIGS. 20A-B show partial $^1$H-NMR (500 MHZ, $CD_2Cl_2$, 298 K) spectra for the titration of Tet-1 with Short-$NH_2$-POA (FIG. 20A) and LineshapeKin 4.0-predicted spectra (FIG. 20B) for the titration series in panel a with a simple 1:1 binding model (FIG. 5B) with the following parameters: $K_a$ (complex association constant)=(8.4±0.6)×$10^2$ $M^{-1}$; $K_{off}$= (decomplexation rate constant)=(60±7) $s^{-1}$; chemical shift of Tet-1=5,539 Hz; chemical shift of the [Long-$NH_2$-POA@Tet-1] complex=(5,607±7) Hz; relaxation rate of Tet-1=4 $s^{-1}$; relaxation rate of the [Long-$NH_2$-POA@Tet-1] complex=4 $s^{-1}$.

FIGS. 21A-B show partial $^1$H-NMR (500 MHZ, $CD_2Cl_2$, 298 K) spectra for the titration of Tet-1 with Long-$NH_2$-

POA (FIG. 21A) and LineshapeKin 4.0-predicted spectra (FIG. 21B) for the titration series in panel a with a simple 1:1 binding model (FIG. 5B) with the following parameters: $K_a$ (complex association constant)=(4.3±0.8)×$10^3$ $M^{-1}$; $k_{off}$= (decomplexation rate constant)=(23±5) $s^{-1}$; chemical shift of Tet-1=5,539 Hz; chemical shift of the [Long-$NH_2$-POA@Tet-1] complex=(5,584±8) Hz; relaxation rate of Tet-1=4 $s^{-1}$; relaxation rate of the [Long-$NH_2$-POA@Tet-1] complex=4 $s^{-1}$.

FIGS. 22A-B are partial $^1$H-NMR (500 MHZ, $CD_2Cl_2$, 298 K) spectra for a mixture of Short-$NH_2$-POA (1.2 mM) and Tet-1 (0.23 mM) before (FIG. 22A) and after (FIG. 22B) addition of DMSO-d6 (60 μL).

Figure 23:
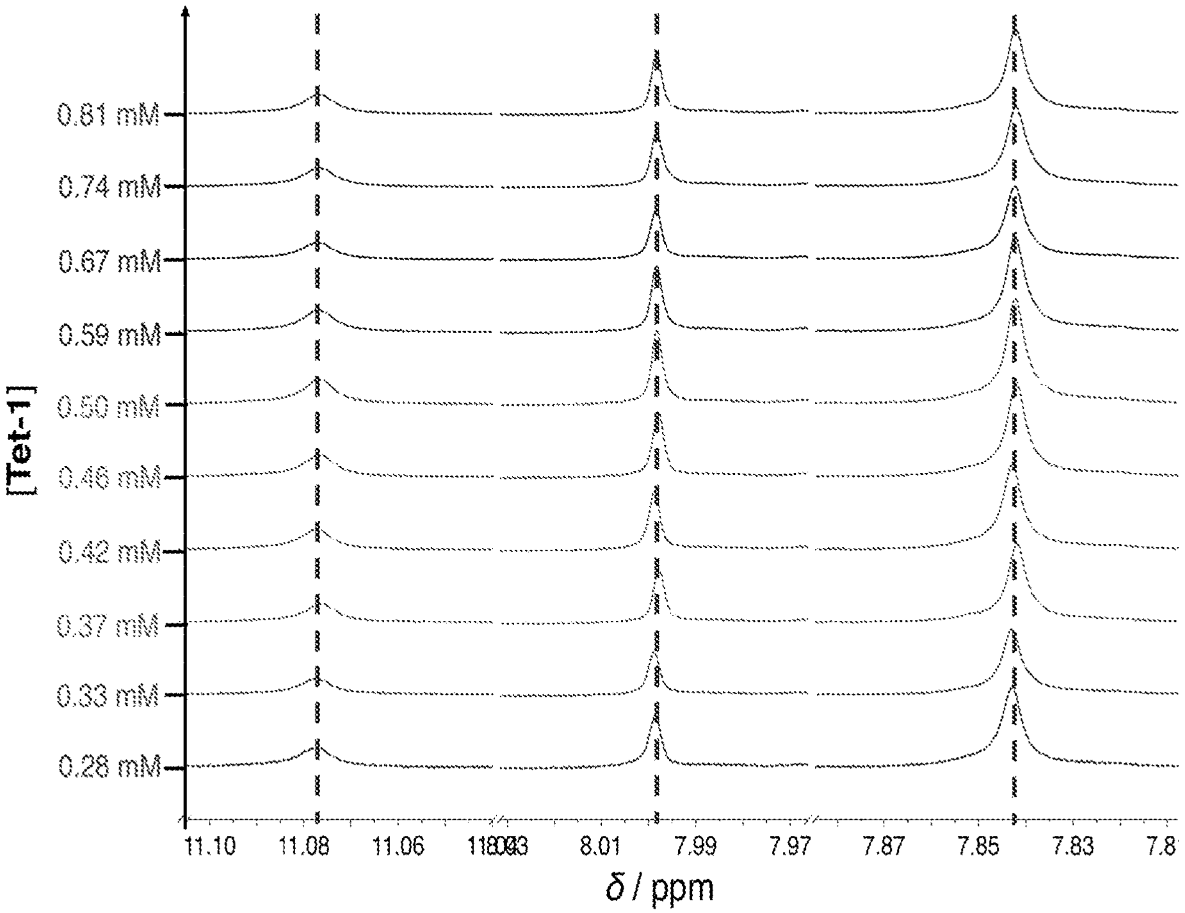

FIG. 23 shows partial $^1$H-NMR (500 MHZ, $CD_2Cl_2$, 298 K) spectra for the titration of Tet-1 with itself.

Figure 24:
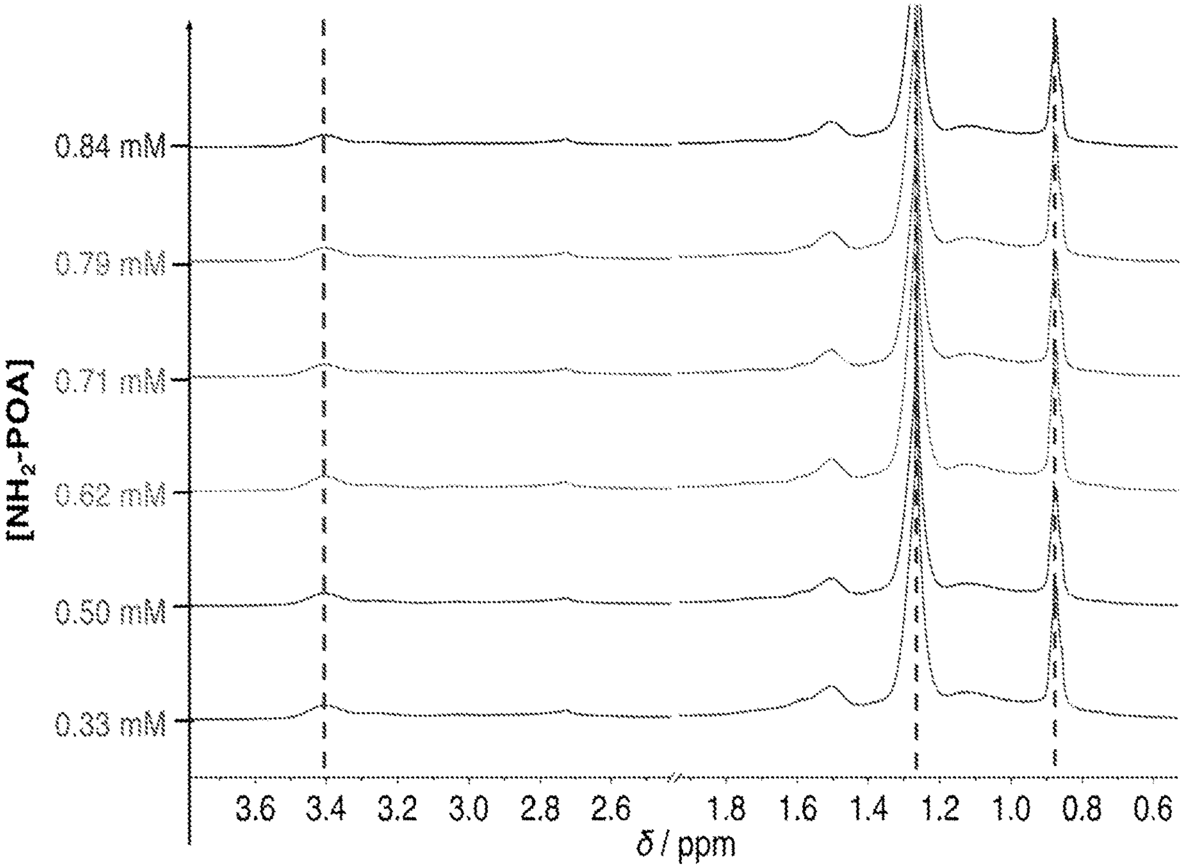

FIG. 24 shows partial $^1$H-NMR (500 MHZ, $CD_2Cl_2$, 298 K) spectra for the titration of $NH_2$-POA with itself.

Figure 25:
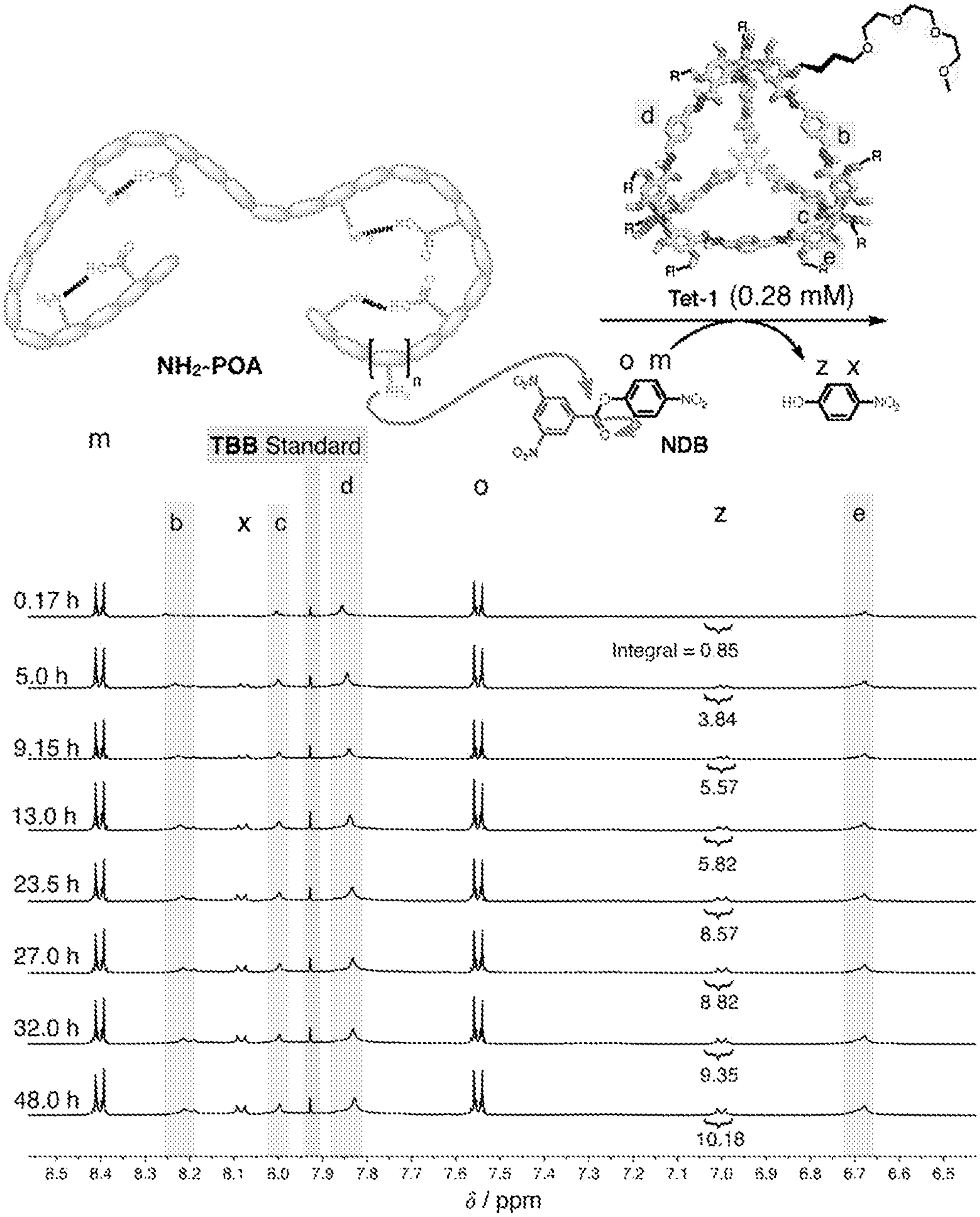

FIG. 25 shows stacked $^1$H-NMR spectra (500 MHZ, $CD_2Cl_2$, 298 K) showing reaction progress for the Tet-1-catalyzed acylation of $NH_2$-POA with nitrophenyl-3,5-dinitrobenzoate (NDB). All integrals of the internal standard (1,2,4,5-tetrabromobenzene, TBB) were set to 2.00.

Figure 26:
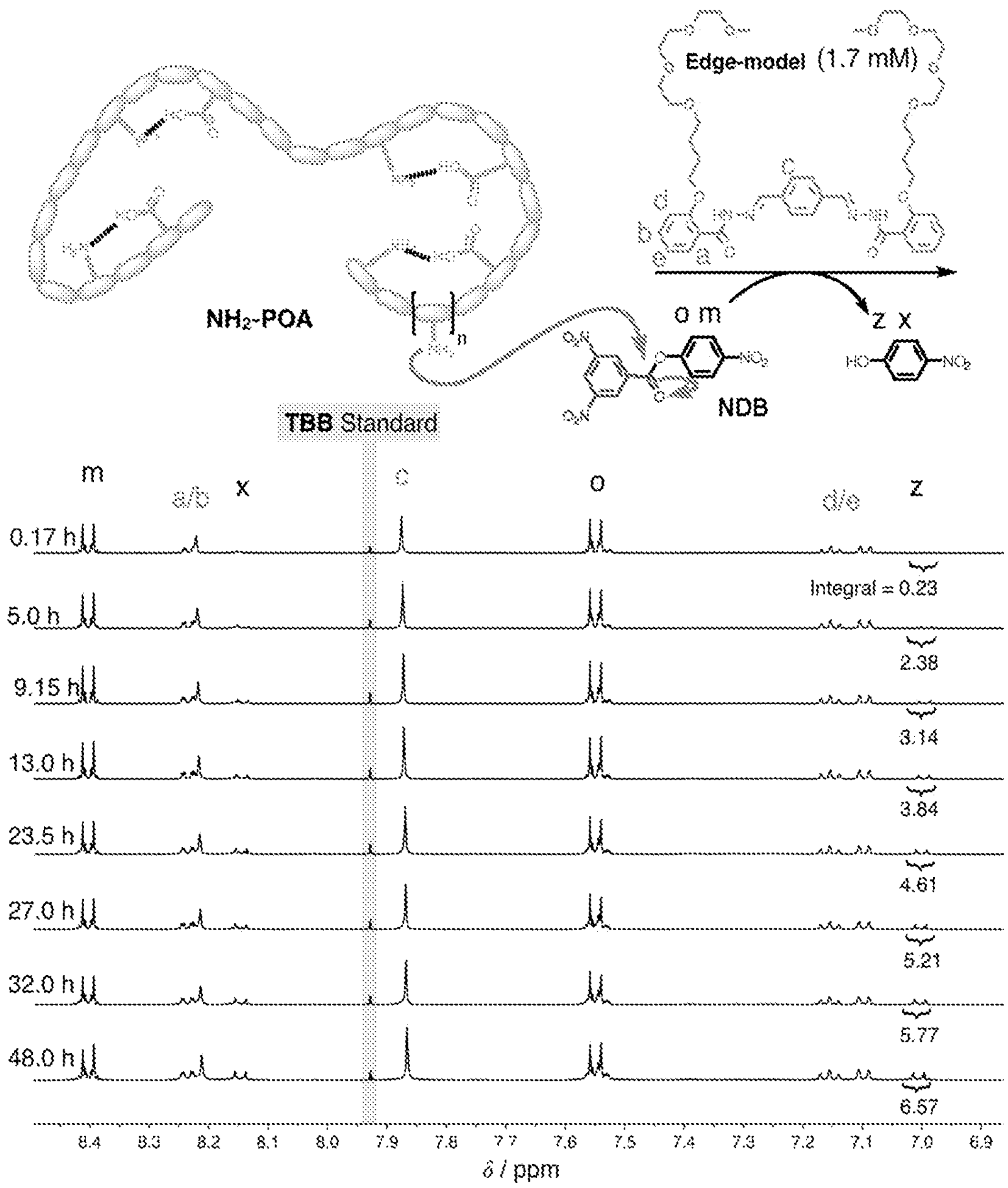

FIG. 26 shows stacked $^1$H-NMR spectra (500 MHZ, $CD_2Cl_2$, 298 K) showing reaction progress for the Edge-model-catalyzed acylation of $NH_2$-POA with nitrophenyl-3,5-dinitrobenzoate (NDB). All integrals of the internal standard (1,2,4,5-tetrabromobenzene, TBB) were set to 2.00.

Figure 27:
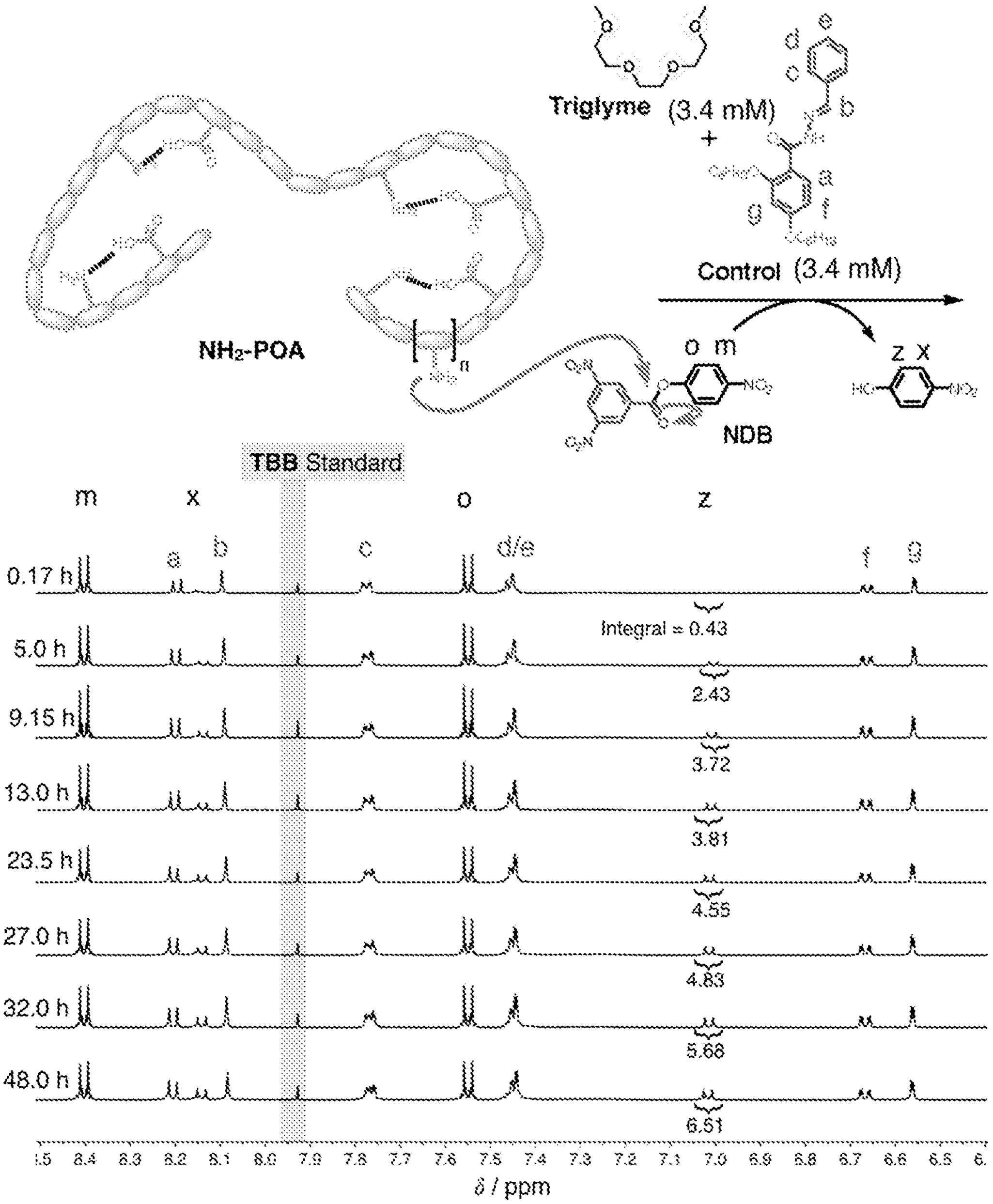

FIG. 27 shows stacked $^1$H-NMR spectra (500 MHZ, $CD_2Cl_2$, 298 K) showing reaction progress for the Control-catalyzed acylation of $NH_2$-POA with nitrophenyl-3,5-dinitrobenzoate (NDB). All integrals of the internal standard (1,2,4,5-tetrabromobenzene, TBB) were set to 2.00.

Figure 28:
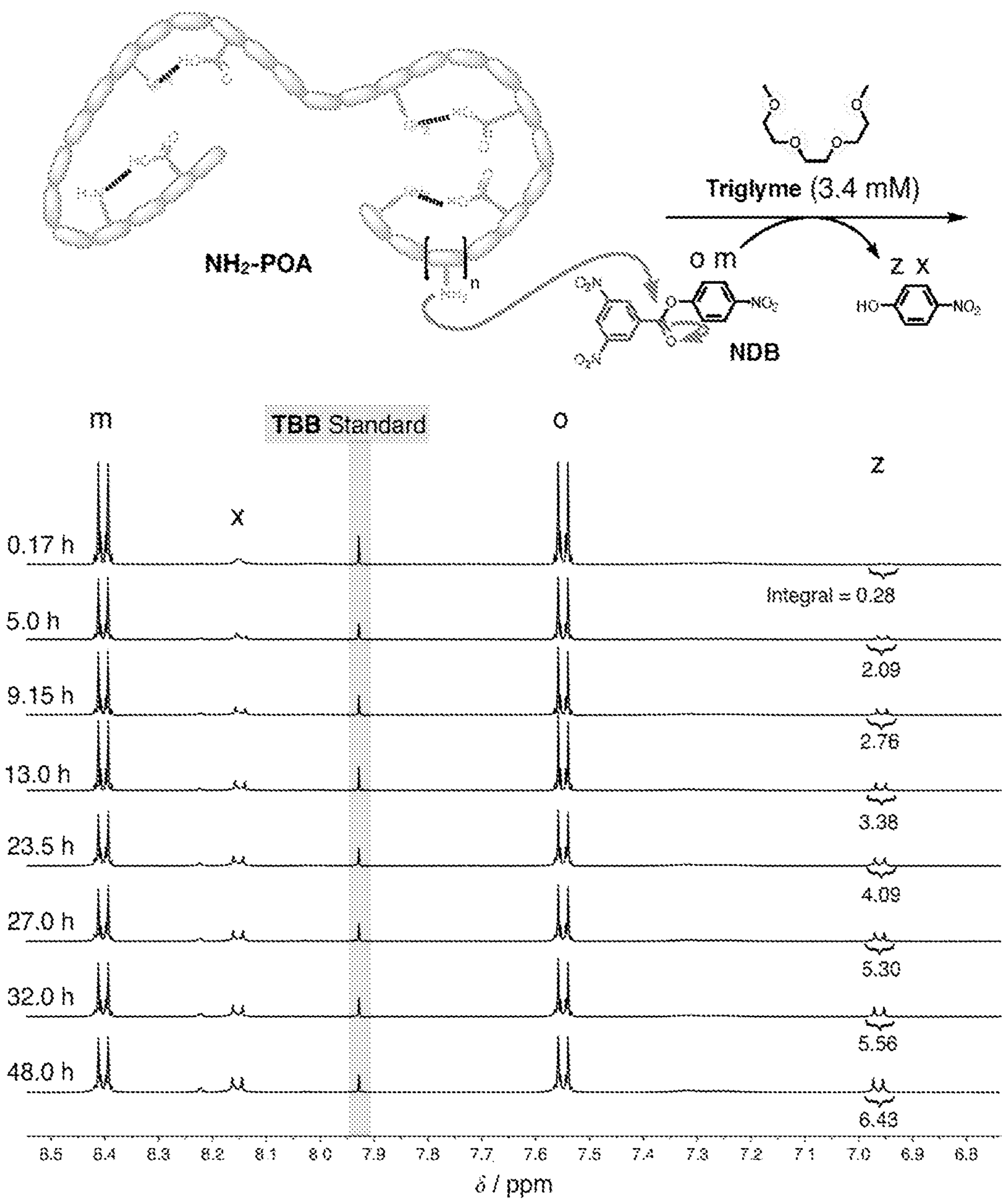

FIG. 28 shows stacked $^1$H-NMR spectra (500 MHz, $CD_2Cl_2$, 298 K) showing reaction progress for the Triglyme-catalyzed acylation of $NH_2$-POA with nitrophenyl-3,5-dinitrobenzoate (NDB). All integrals of the internal standard (1,2,4,5-tetrabromobenzene, TBB) were set to 2.00.

Figure 29:
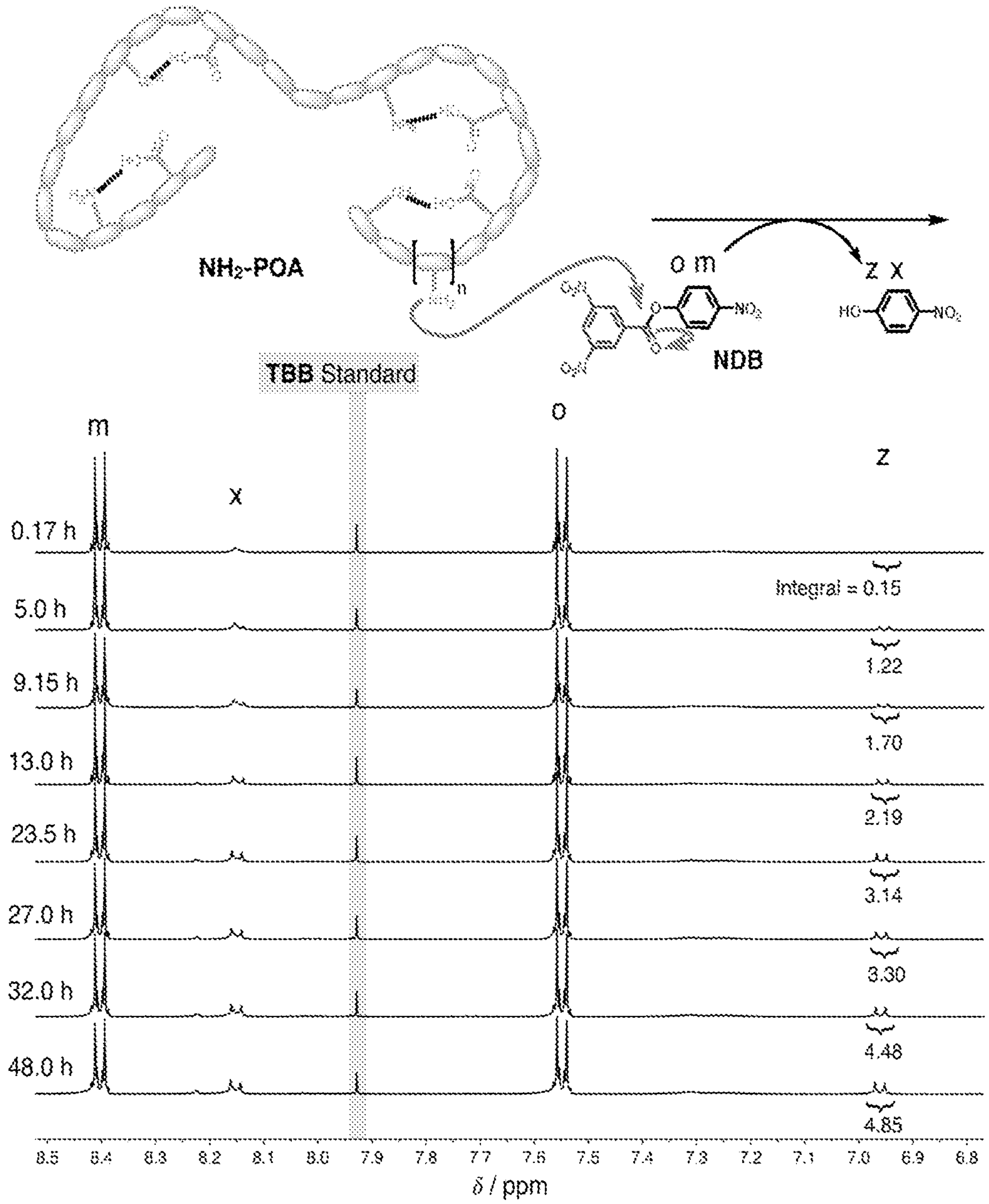

FIG. 29 shows stacked $^1$H-NMR spectra (500 MHz, $CD_2Cl_2$, 298 K) showing reaction progress for the uncatalyzed acylation of $NH_2$-POA with nitrophenyl-3,5-dinitrobenzoate (NDB). All integrals of the internal standard (1,2,4,5-tetrabromobenzene, TBB) were set to 2.00.

Figure 30:
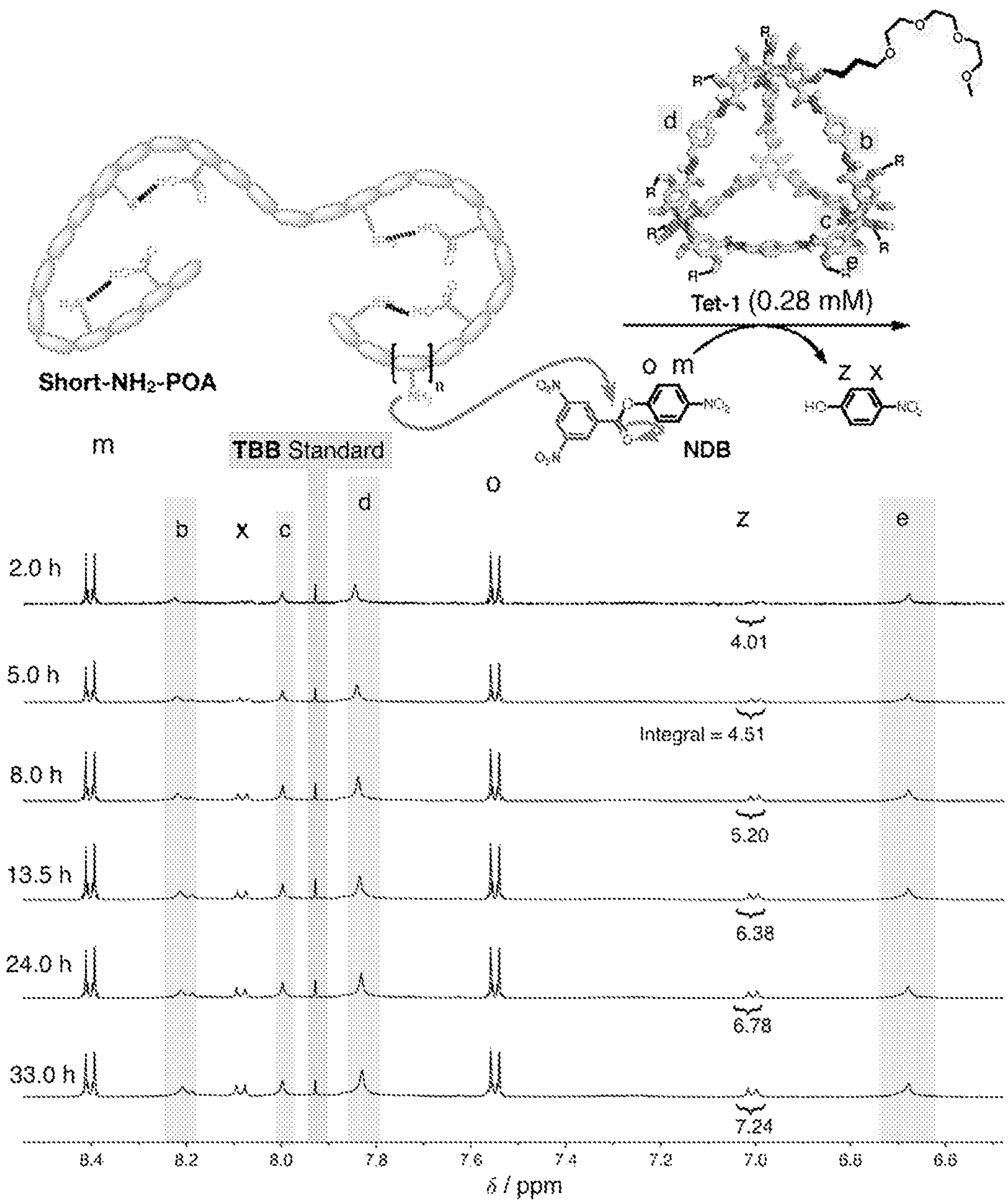

FIG. 30 shows stacked $^1$H-NMR spectra (500 MHZ, $CD_2Cl_2$, 298 K) showing reaction progress for the Tet-1-catalyzed acylation of Short-$NH_2$-POA with nitrophenyl-3,5-dinitrobenzoate (NDB). All integrals of the internal standard (1,2,4,5-tetrabromobenzene, TBB) were set to 2.00.

Figure 31:
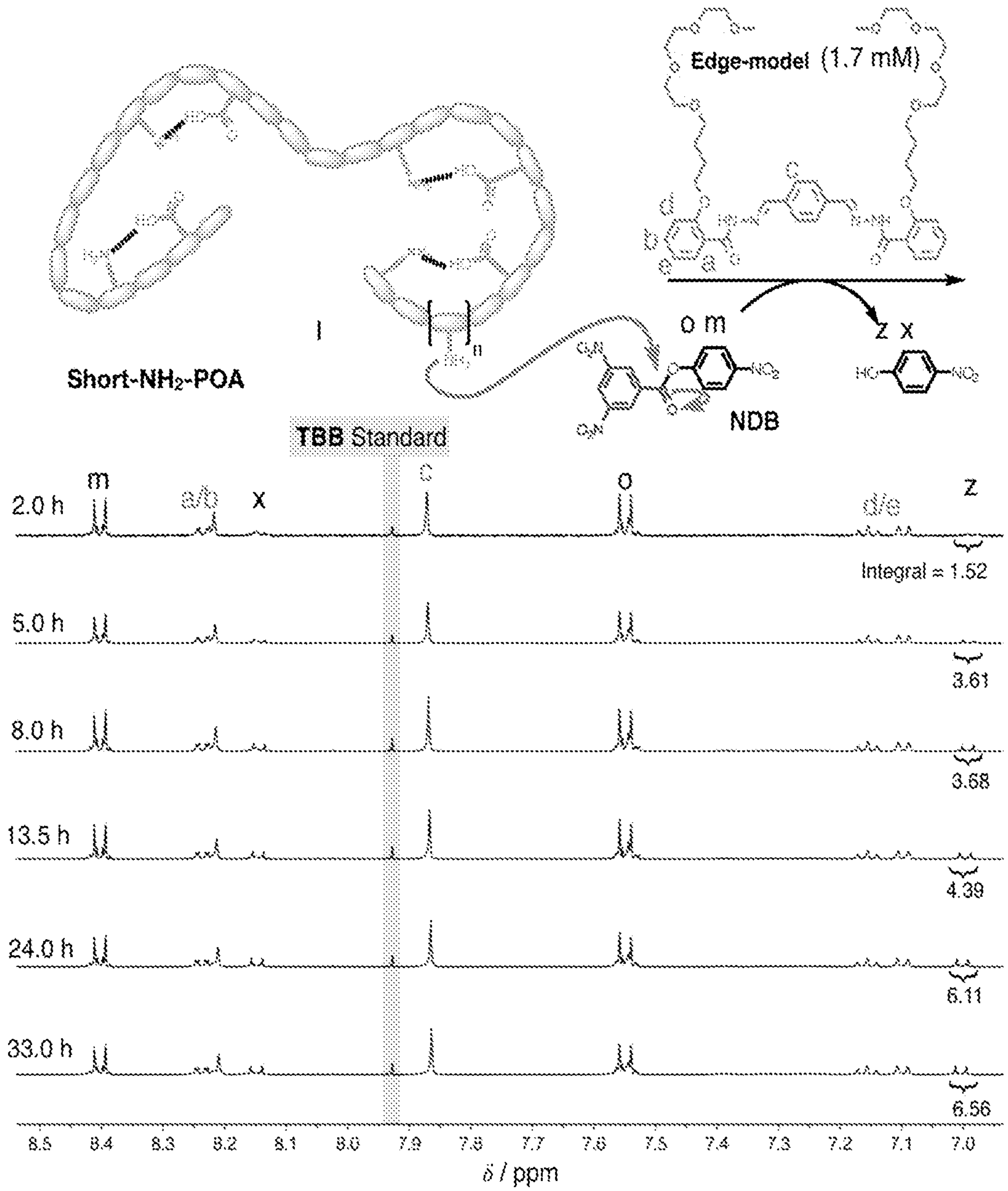

FIG. 31 shows stacked $^1$H-NMR spectra (500 MHZ, $CD_2Cl_2$, 298 K) showing reaction progress for the Edge-model-catalyzed acylation of Short-$NH_2$-POA with nitrophenyl-3,5-dinitrobenzoate (NDB). All integrals of the internal standard (1,2,4,5-tetrabromobenzene, TBB) were set to 2.00.

Figure 32:
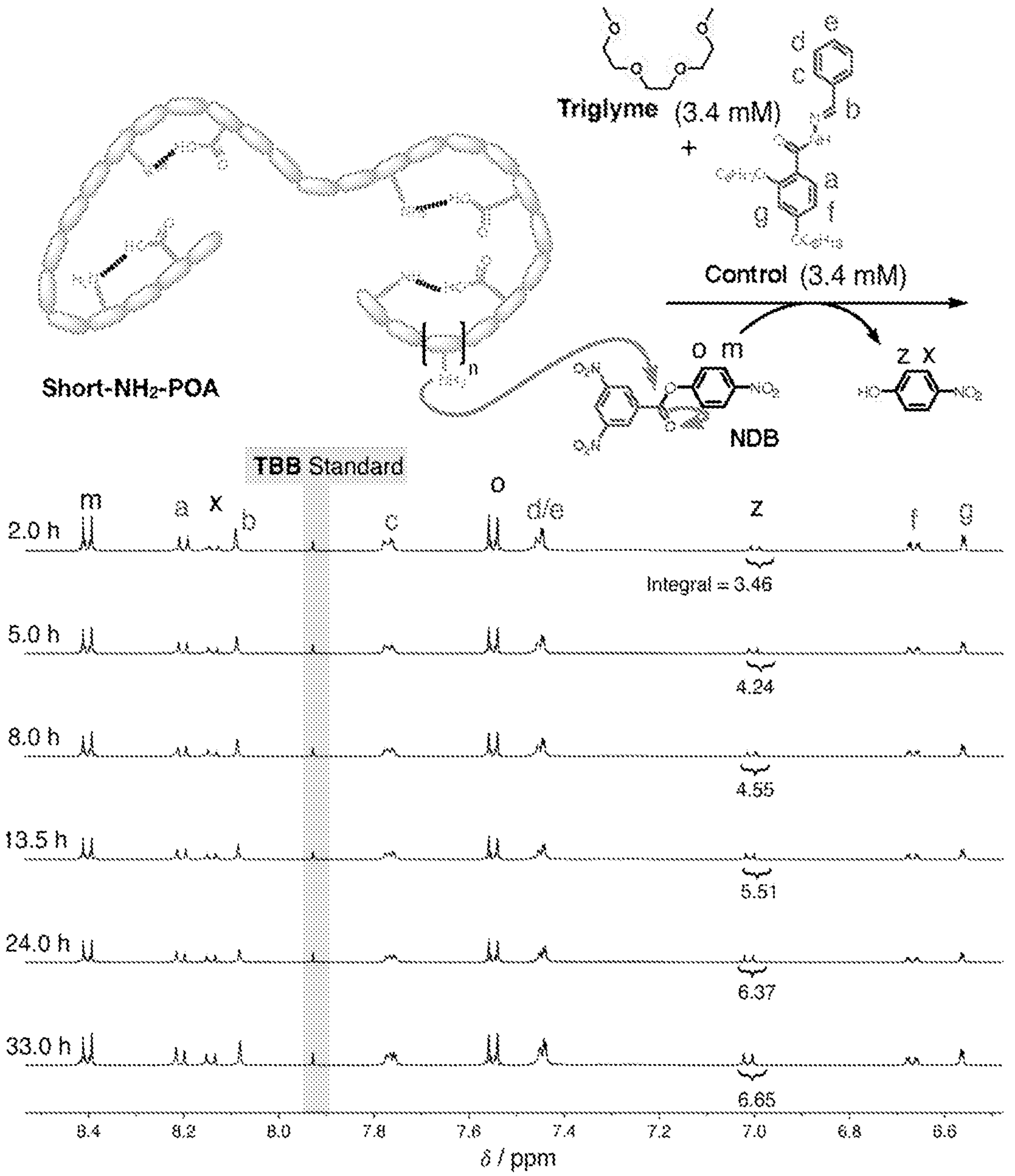

FIG. 32 shows stacked $^1$H-NMR spectra (500 MHz, $CD_2Cl_2$, 298 K) showing reaction progress for the Control+Triglyme-catalyzed acylation of Short-$NH_2$-POA with nitrophenyl-3,5-dinitrobenzoate (NDB). All integrals of the internal standard (1,2,4,5-tetrabromobenzene, TBB) were set to 2.00.

Figure 33:
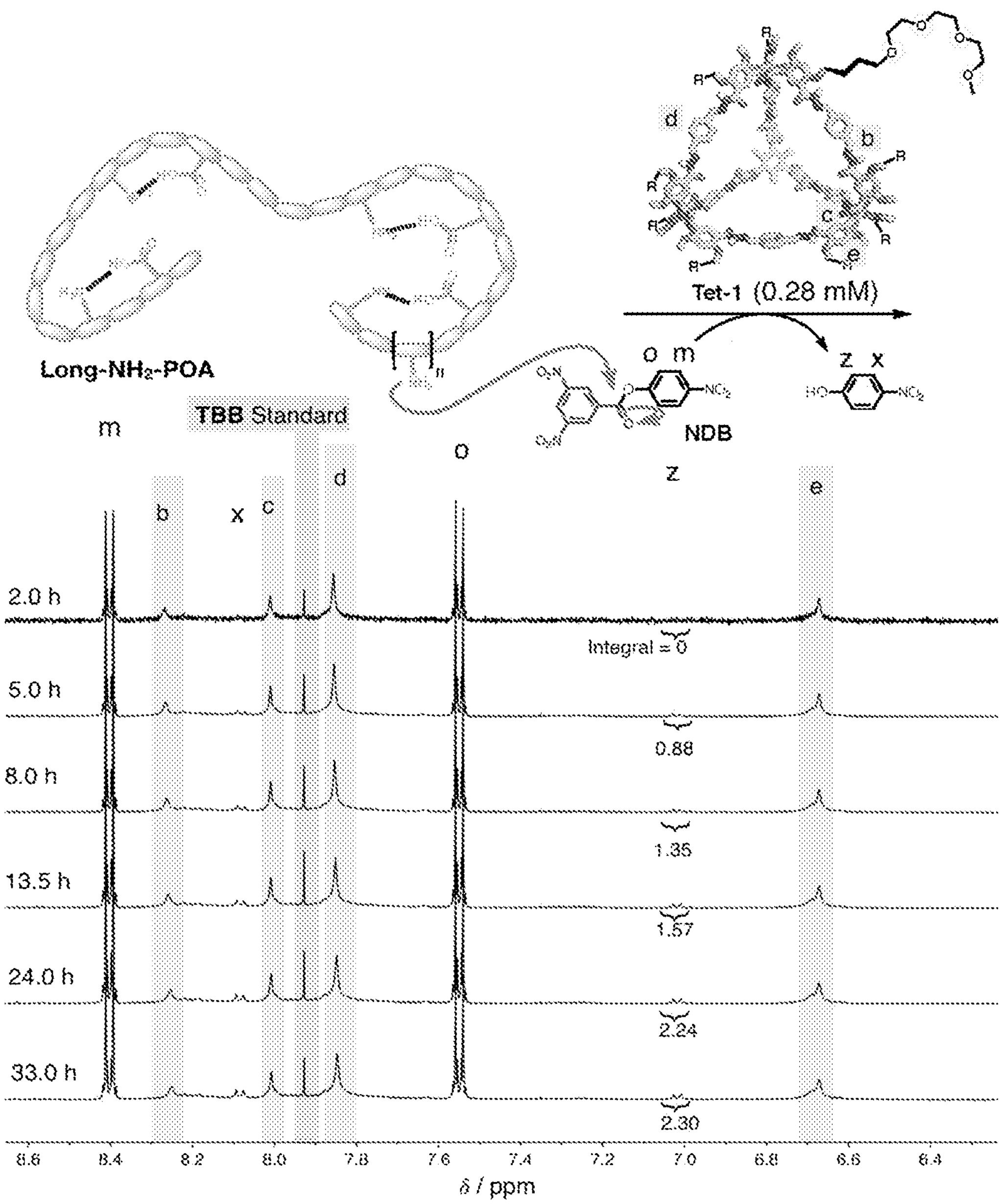

FIG. 33 shows stacked $^1$H-NMR spectra (500 MHz, $CD_2Cl_2$, 298 K) showing reaction progress for the Tet-1-catalyzed acylation of Long-$NH_2$-POA with nitrophenyl-3,5-dinitrobenzoate (NDB). All integrals of the internal standard (1,2,4,5-tetrabromobenzene, TBB) were set to 2.00.

Figure 34:
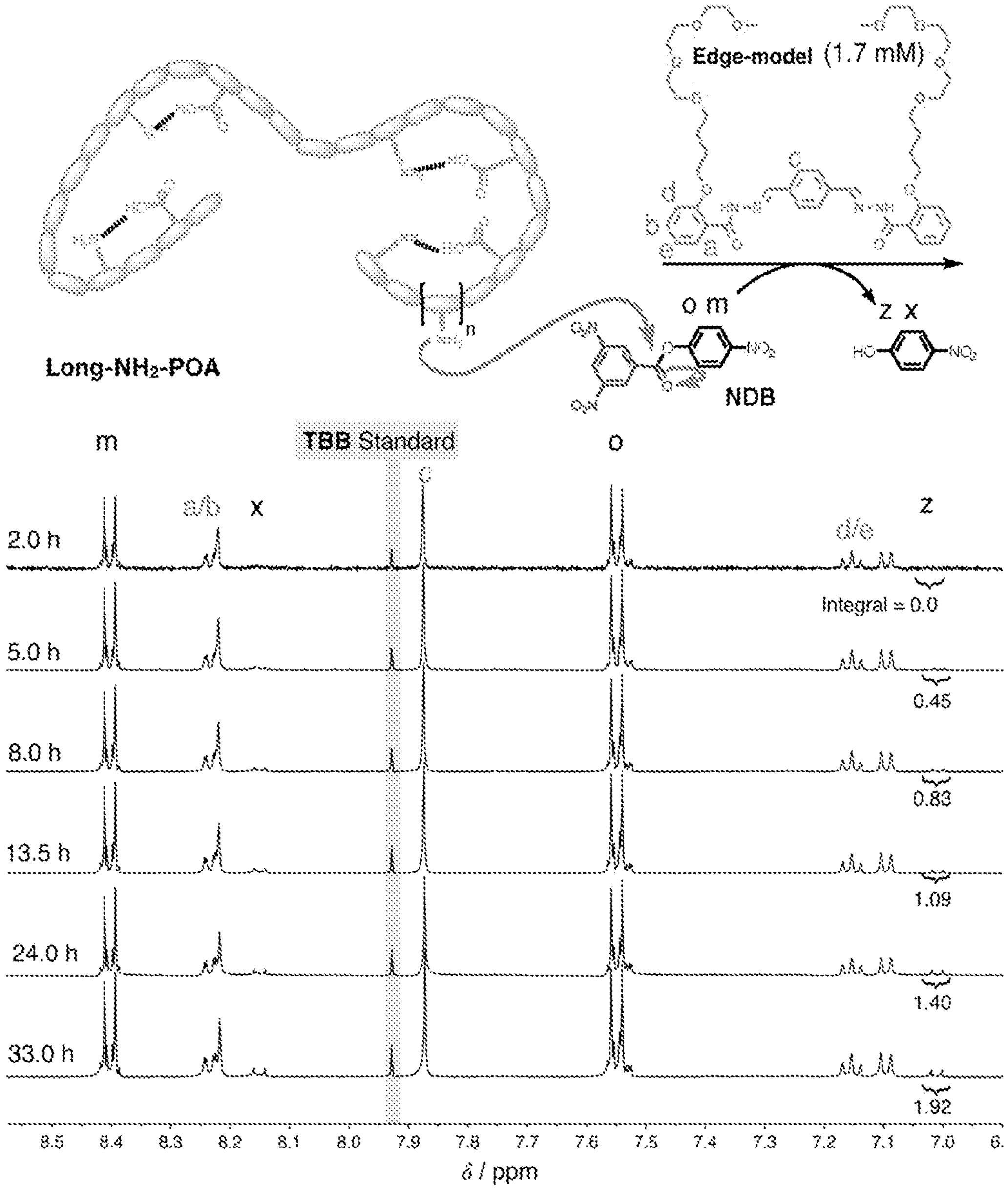

FIG. 34 shows stacked $^1$H-NMR spectra (500 MHZ, $CD_2Cl_2$, 298 K) showing reaction progress for the Edge-model-catalyzed acylation of Long-$NH_2$-POA with nitrophenyl-3,5-dinitrobenzoate (NDB). All integrals of the internal standard (1,2,4,5-tetrabromobenzene, TBB) were set to 2.00.

Figure 35:
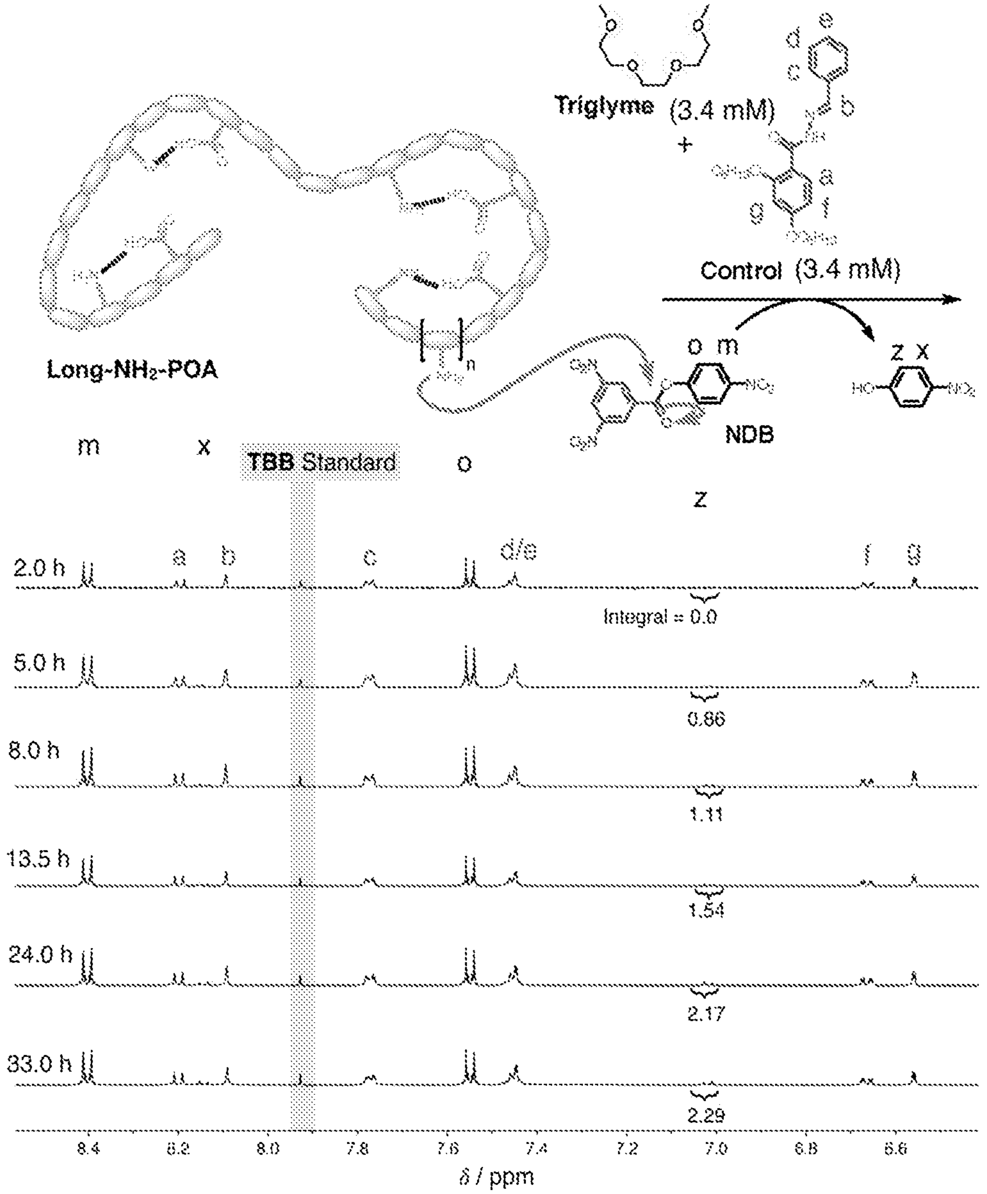

FIG. 35 shows stacked $^1$H-NMR spectra (500 MHZ, $CD_2Cl_2$, 298 K) showing reaction progress for the Control+Triglyme-catalyzed acylation of Long-$NH_2$-POA with nitrophenyl-3,5-dinitrobenzoate (NDB). All integrals of the internal standard (1,2,4,5-tetrabromobenzene, TBB) were set to 2.00.

Figure 36:
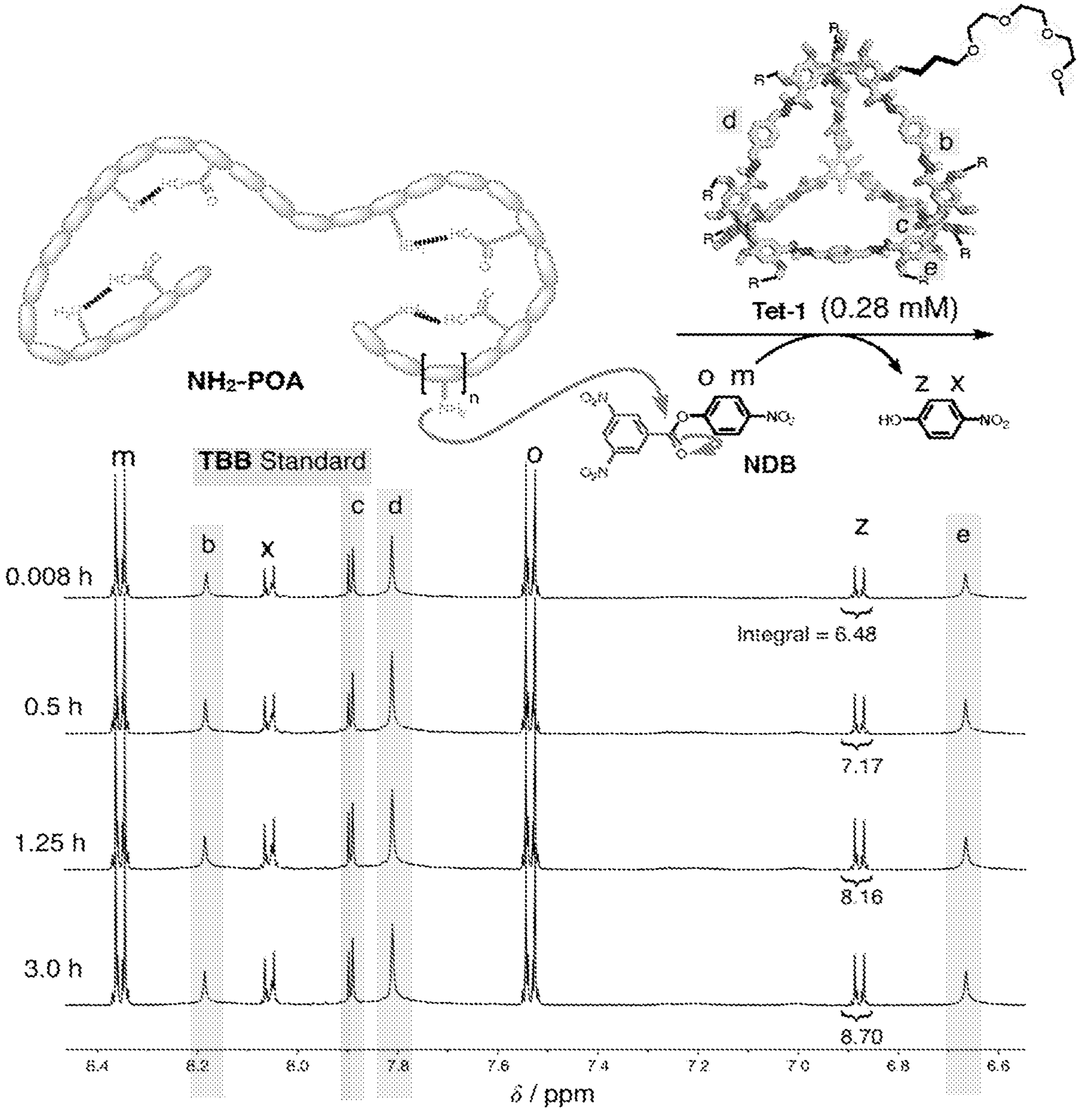

FIG. 36 shows stacked $^1$H-NMR spectra (500 MHz, 90:10 vol % $CD_2Cl_2$:DMSO-d6, 298 K) showing reaction progress for the Tet-1-catalyzed acylation of $NH_2$-POA with nitrophenyl-3,5-dinitrobenzoate (NDB). All integrals of the internal standard (1,2,4,5-tetrabromobenzene, TBB) were set to 2.00.

Figure 37:
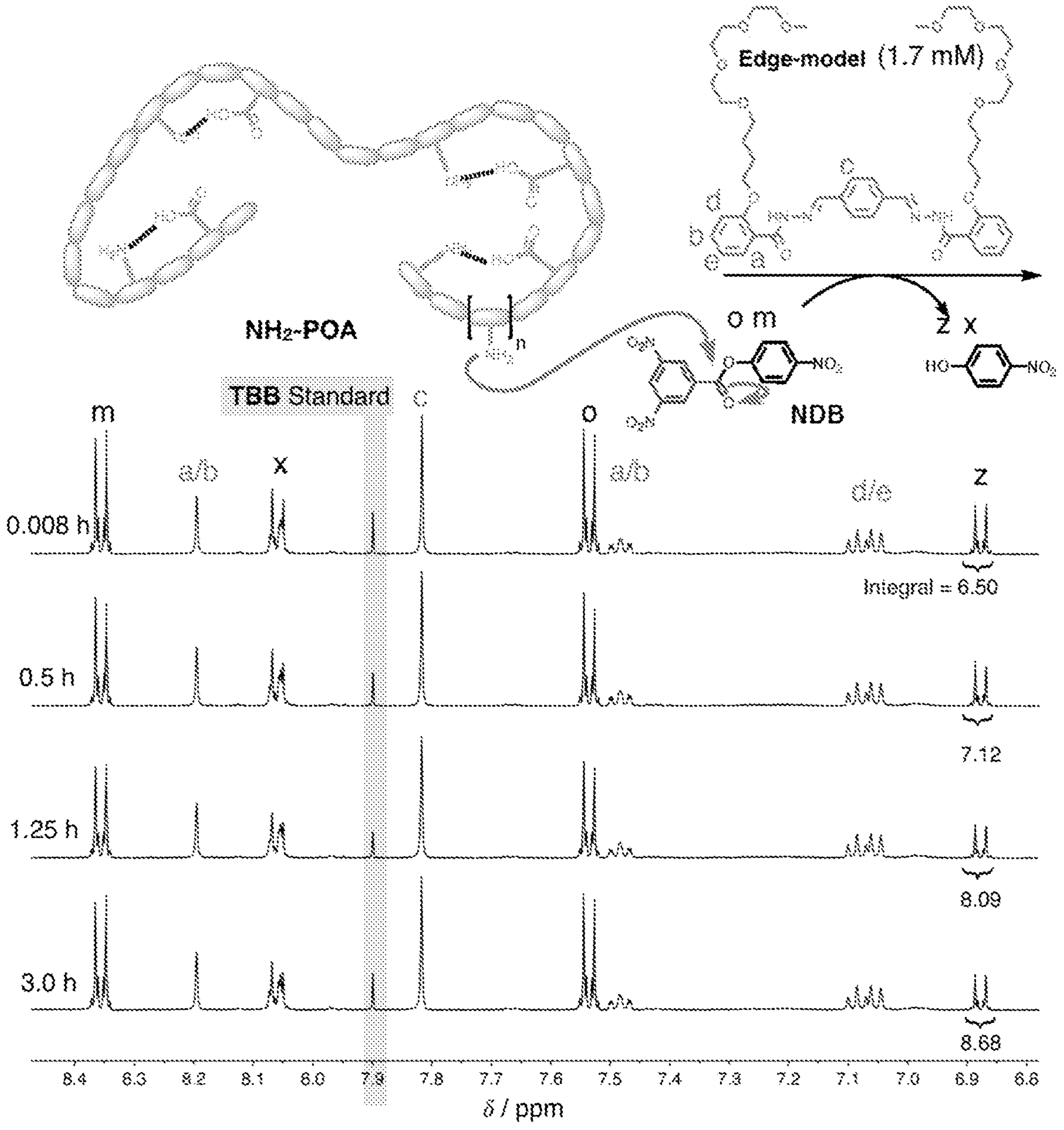

FIG. 37 shows stacked $^1$H-NMR spectra (500 MHZ, 90:10 vol % $CD_2Cl_2$:DMSO-d6, 298 K) showing reaction progress for the Edge-model-catalyzed acylation of $NH_2$-POA with nitrophenyl-3,5-dinitrobenzoate (NDB). All integrals of the internal standard (1,2,4,5-tetrabromobenzene, TBB) were set to 2.00.

Figure 38:
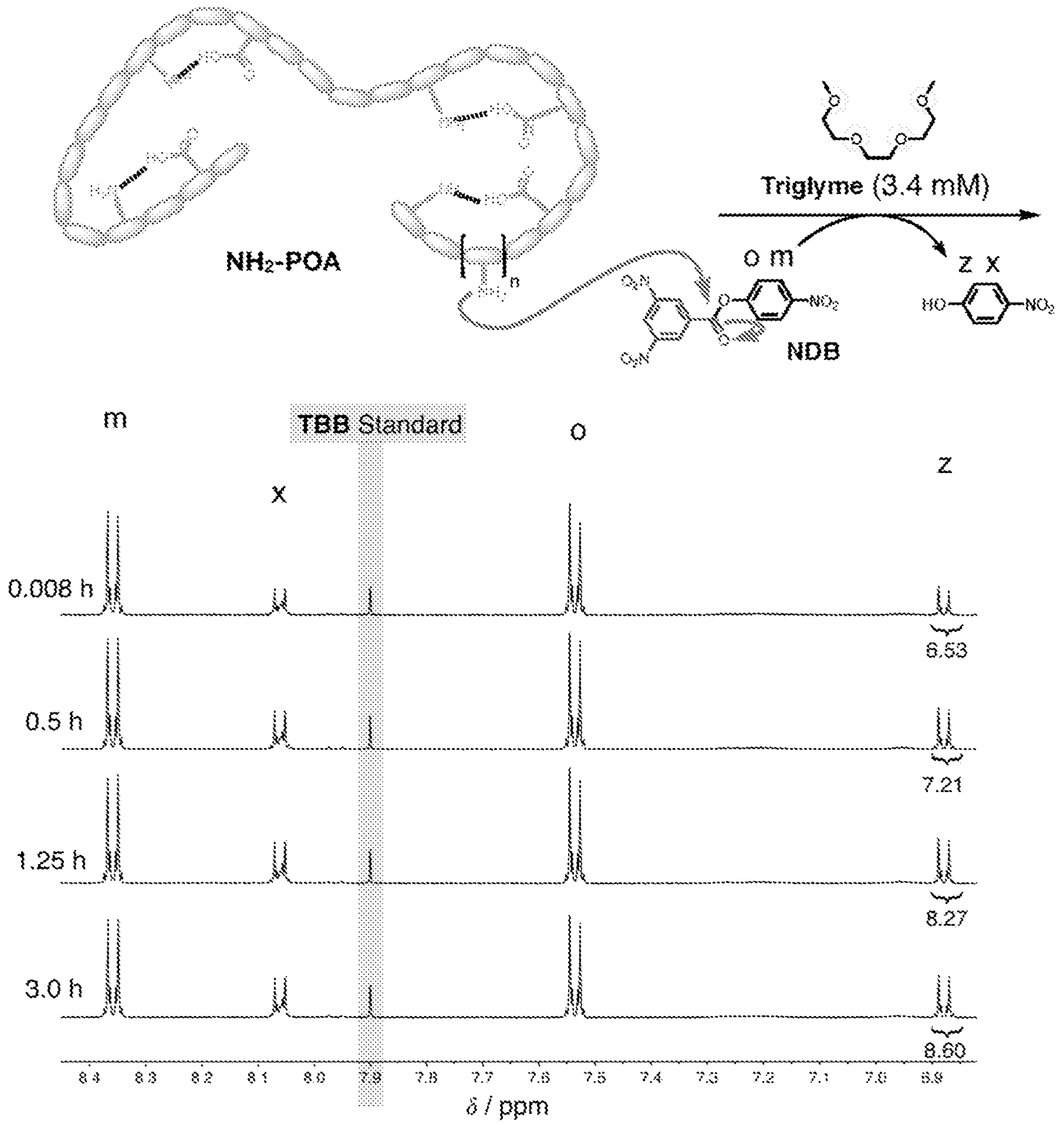

FIG. 38 shows stacked $^1$H-NMR spectra (500 MHZ, 90:10 vol % $CD_2Cl_2$:DMSO-d6, 298 K) showing reaction progress for the Triglyme-catalyzed acylation of $NH_2$-POA with nitrophenyl-3,5-dinitrobenzoate (NDB). All integrals of the internal standard (1,2,4,5-tetrabromobenzene, TBB) were set to 2.00.

FIGS. 39A-E show a schematic for acylation of the $NH_2$-POA polymer (FIG. 39A) plots of the inverse total amine concentration ($[amine]^{-1}$) vs. time with different organocatalyst concentrations (FIGS. 39B-E). The reaction conditions were identical to the ones described in FIG. 6A. The plots show that the reaction is second order with respect to [Tet-1], but first order in the catalyst concentration for the other two simpler organocatalysts (Triglyme and Edge-model).

Figure 40:
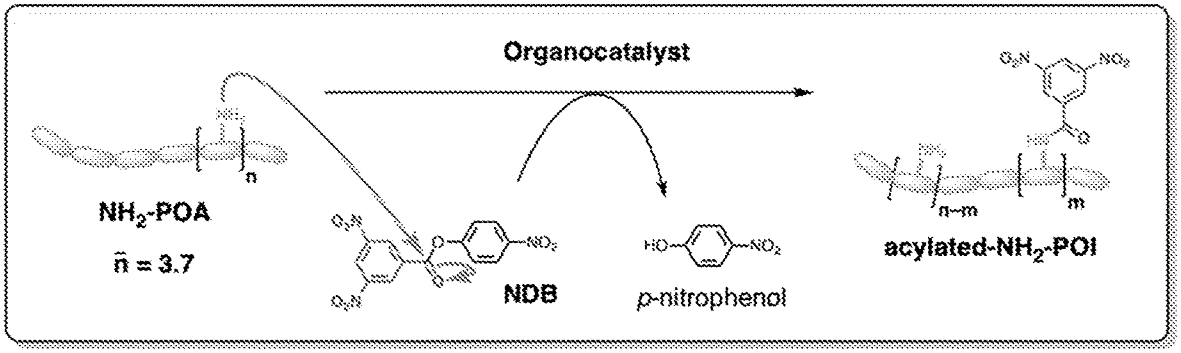
Figure 40:
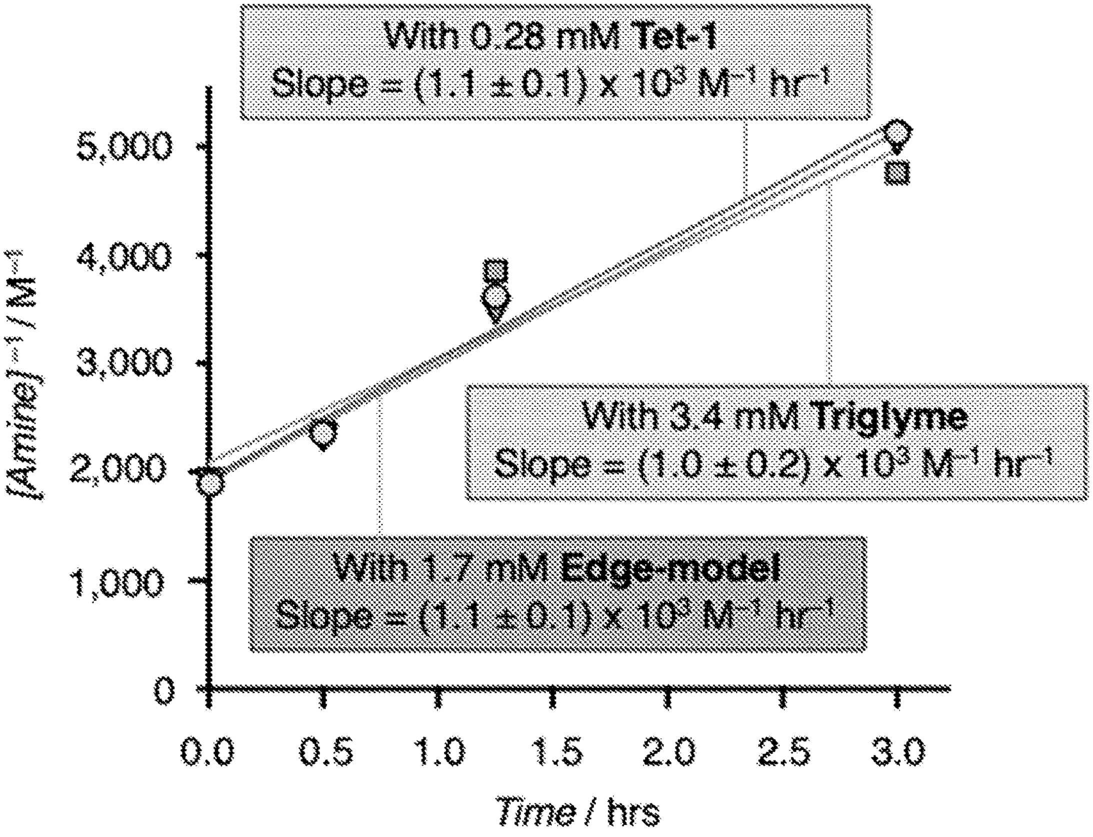

FIGS. 40A-B show a schematic for acylation of the $NH_2$-POA polymer (FIG. 40A) and plots of the inverse total amine concentration ($[amine]^{-1}$) vs. time for the different organocatalysts with $CD_2Cl_2$:DMSO-d6 (90:10 vol %) as the reaction solvent (FIG. 40B). These results indicate that in the presence of a polar solvent like DMSO (which disrupts hydrogen bonding between the Tet-1 catalyst and the $NH_2$-POA polymer substrates) Tet-1 is no longer able to selectively accelerate the acylation reactions since it can no longer effectively bind to the substrates via hydrogen-bonding. See FIGS. 22A-B for additional evidence in this regard.

Figure 41:
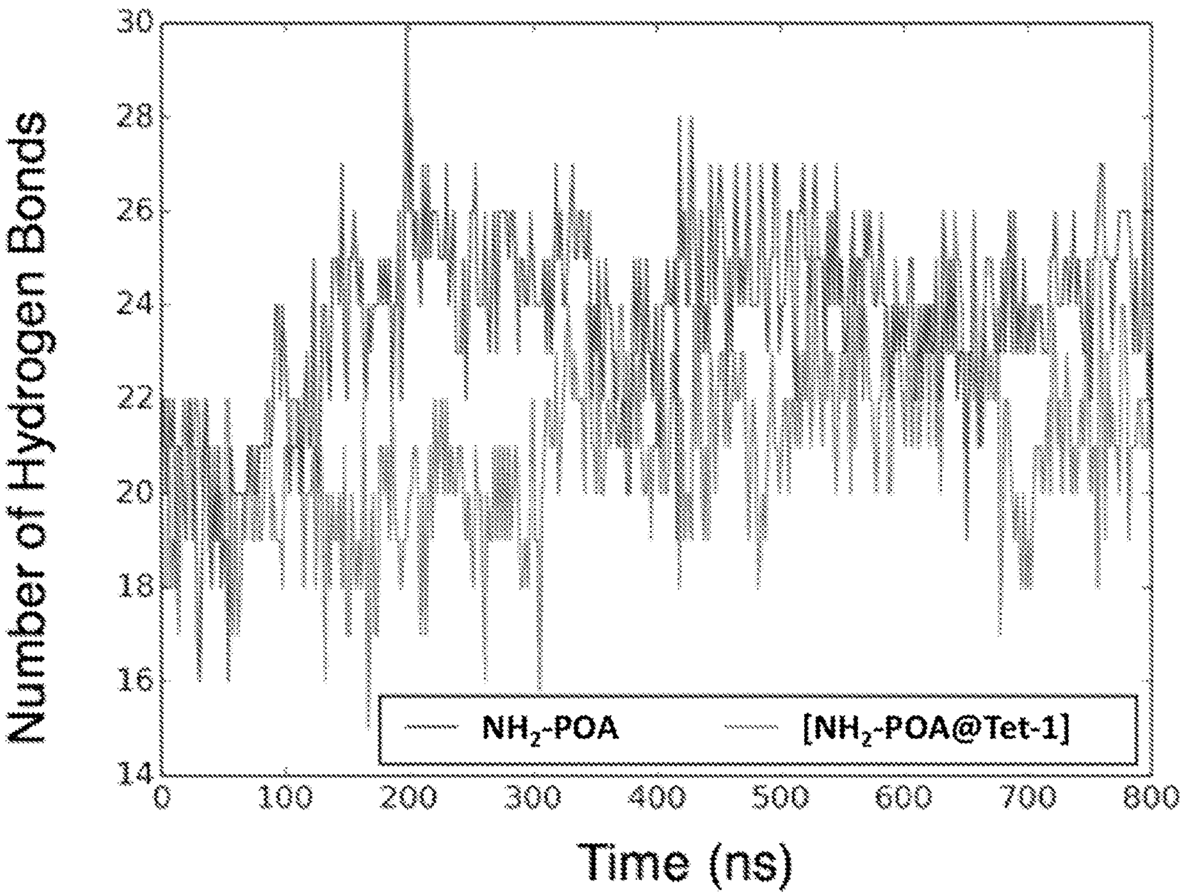

FIG. 41 shows plots of the overall number of intramolecular hydrogen bonds in a prototypical $NH_2$-POA polymer chain as a function of time plotted with and without Tet-1. The plots were generated from trajectories of 800 ns-long all-atom molecular dynamics (MD) simulations in explicit solvent. This figure clearly shows that the overall numbers of intramolecular hydrogen bonds of $NH_2$-POA reduced when bound to Tet-1, which is in agreement with the rgyr simulation results shown in FIG. 4. The observed increase in size shown in FIG. 4 was mostly caused by the formation of hydrogen bonds between the polymer and Tet-1, which helped to unfold the polymer.

Figure 42:
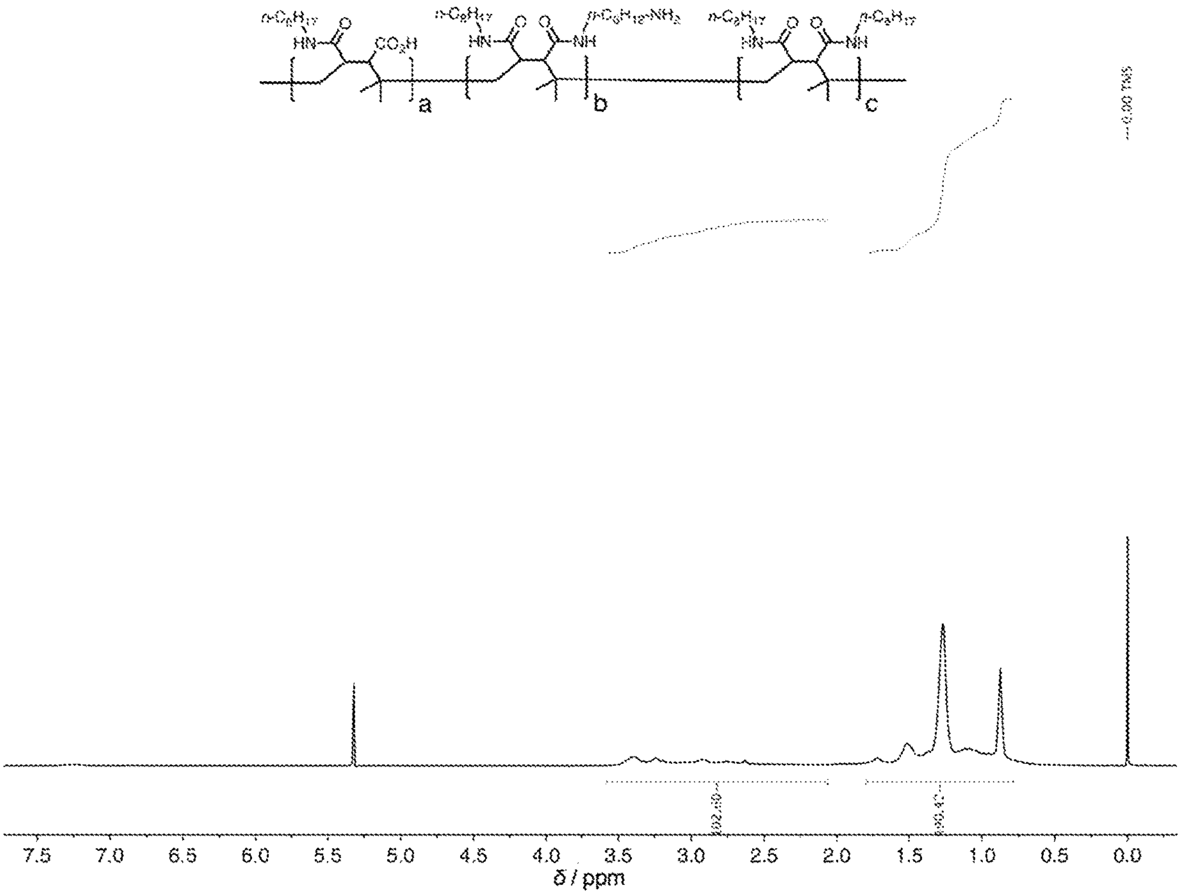

FIG. 42 shows the $^1$H-NMR spectrum (500 MHZ, $CD_2Cl_2$ 298 K) of $NH_2$-POA.

Figure 43:
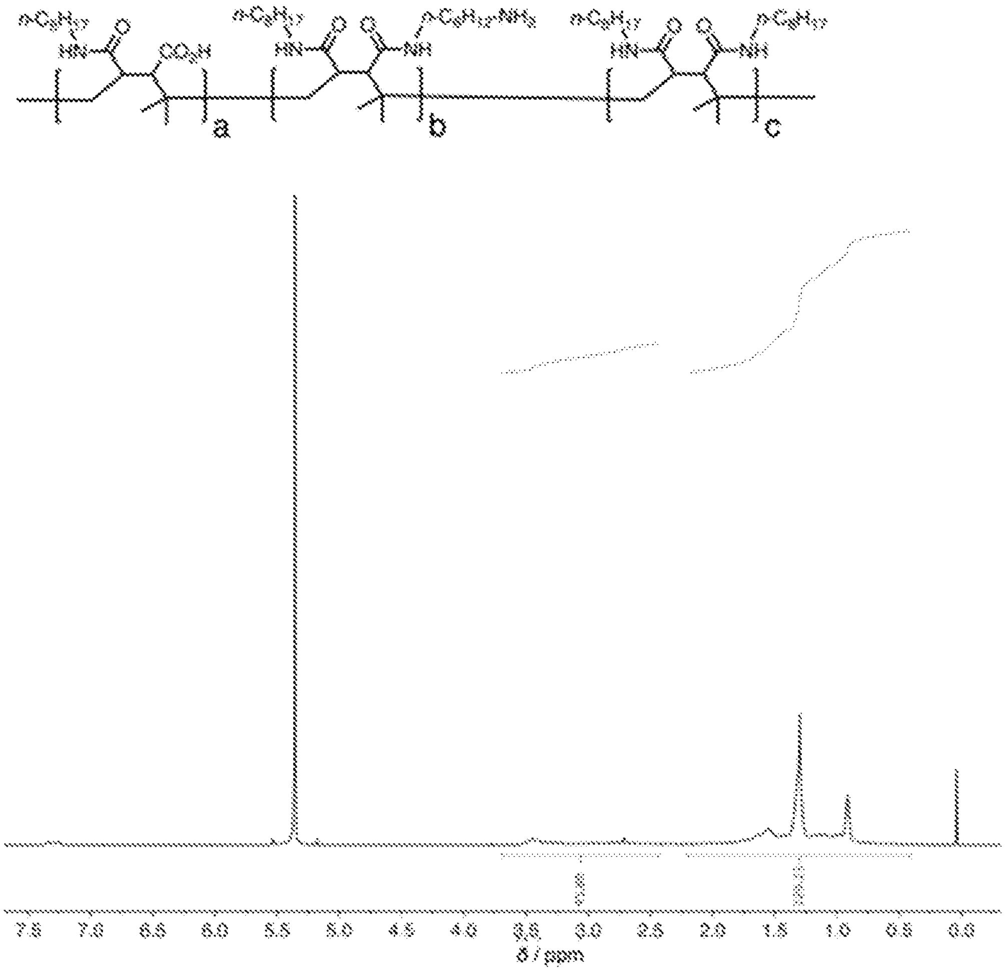

FIG. 43 shows the $^1$H-NMR spectrum (500 MHZ, $CD_2Cl_2$, 298 K) of Short-$NH_2$-POA.

FIG. 44 shows the $^1$H-NMR spectrum (500 MHZ, $CD_2Cl_2$, 298 K) of Long-$NH_2$-POA.

Figure 45:
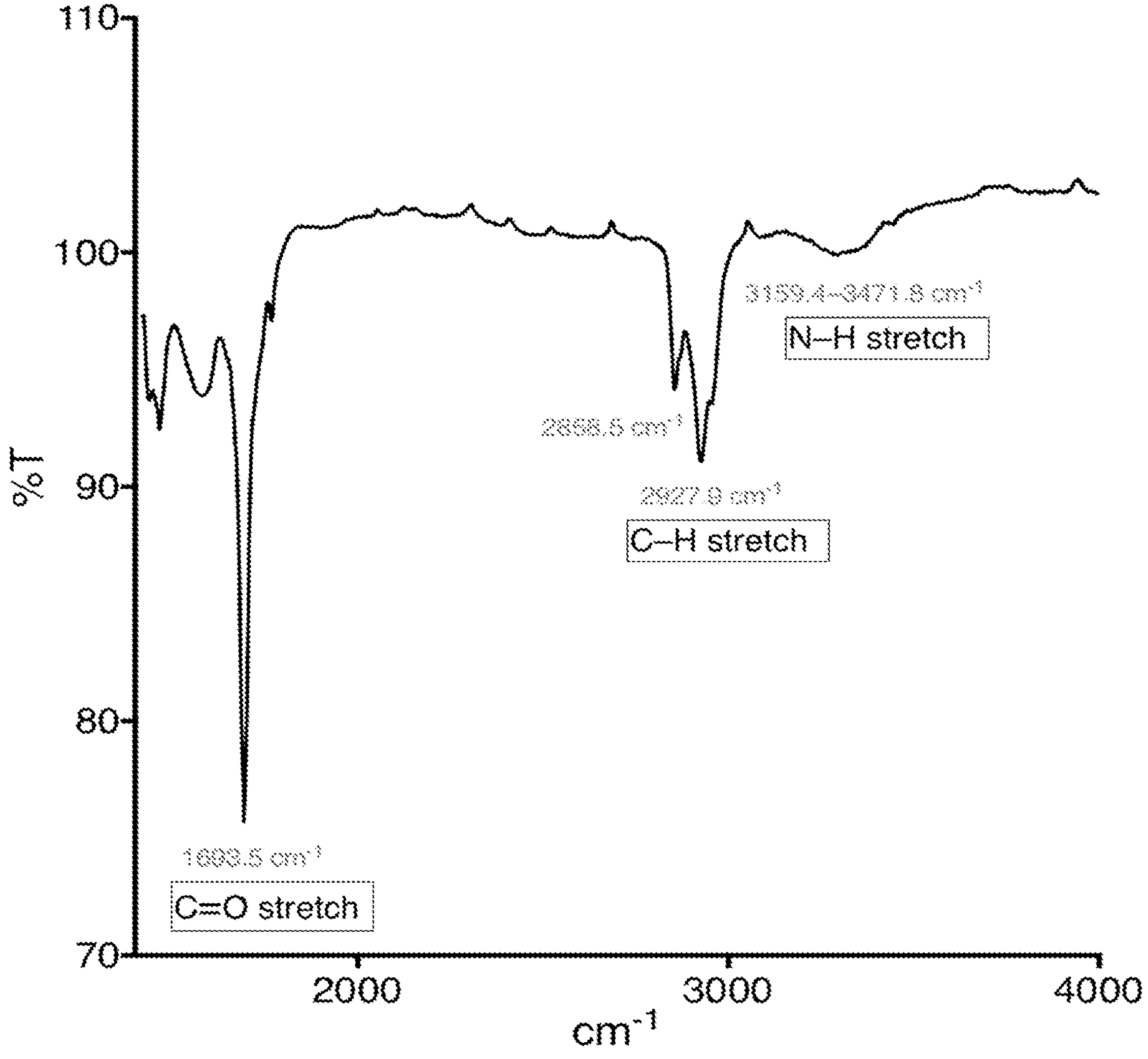

FIG. 45 shows the IR spectrum (KBr) of $NH_2$-POA.

FIGS. 46A-C show the DLS spectra ($CH_2Cl_2$, 2.5 mg $mL^{-1}$, 298 K) of the $NH_2$-POA polymer samples: Short-$NH_2$-POA (FIG. 46A), Long-$NH_2$-POA (FIG. 46B), and $NH_2$-POA (FIG. 46C).

FIG. 47 shows the custom python script, which runs the software LineshapeKin 4.0.

FIGS. 48A-D show $^1$H-NMR (500 MHZ, $CD_2Cl_2$, 298 K) titration data (filled and empty circles) for polymers (FIGS. 48A-B) as well as picrocrocin (FIG. 48C) and curcumin (FIG. 48D) binding to Tet-1. All filled circles were used to fit (dotted lines) the indicated binding models with Dynafit (Kuzmic, P., "Program DYNAFIT for the Analysis of Enzyme Kinetic Data: Application to HIV Proteinase," Anal. Biochem. 237:260-273 (1996), which is hereby incorporated by reference in its entirety). Error bars reported for the complex association constants $K_a$ represent the standard errors of the non-linear least-squares regression analyses. The following proton resonances of Tet-1 were used for the fits simultaneously: $H_a$, $H_b$, $H_c$, $H_a$, and $H_e$ for PVP, $H_a$, $H_b$, $H_c$, and $H_a$ for POI, $H_a$, $H_b$, and $H_a$ for picrocrocin, as well as $H_a$ and Hp for curcumin. In FIG. 48B, the titration curves with POI appear sigmoidal due to intermediate-slow host-guest exchange at the $^1$H-NMR timescale. A titration curve (dashed line) which incorporates the kinetics of host-guest exchange was computed with LineShapeKin (Kovrigin, E. L., "NMR Line Shapes and Multi-State Binding Equilibria," *J. Biomol. NMR* 53:257-270 (2012), which is hereby incorporated by reference in its entirety) for a 1:1 binding model with the following parameters: $K_a$ (obtained from the dynafit fit)=6,932 $M^{-1}$; $k_{off}$ (complex dissociation rate constant)=40 $s^{-1}$; $\delta_0$'s (chemical shifts of the pure species, obtained from the dynafit fits)=4148 $s^{-1}$ (receptor) and 4078 $s^{-1}$ (ligand-receptor complex); as well as $R_2$'s (relaxation rates of the pure species, measured for the pure receptor from the average $^1$H-NMR linewidth)=10 $s^{-1}$ for both the receptor and the ligand-receptor complex. In FIG. 48C, binding of picrocrocin is cooperative with a 3:1 ligand (L) to receptor (R) stoichiometry in the complex. The hill coefficient for the binding process ($n_h$~3.0) was calculated from the picrocrocin concentration at the half-saturation point ($[L]_{half\text{-}saturation}$=2.7 mM) and the product of the binding constants $K_a1 \times K_a2 \times K_a3$ (obtained from the Dynafit fit) with the following standard relationship: $[L]_{half\text{-}saturation} = \sqrt[n_h]{(K_a1 \times K_a2 \times K_a3)^{-1}}$.

Figure 49:
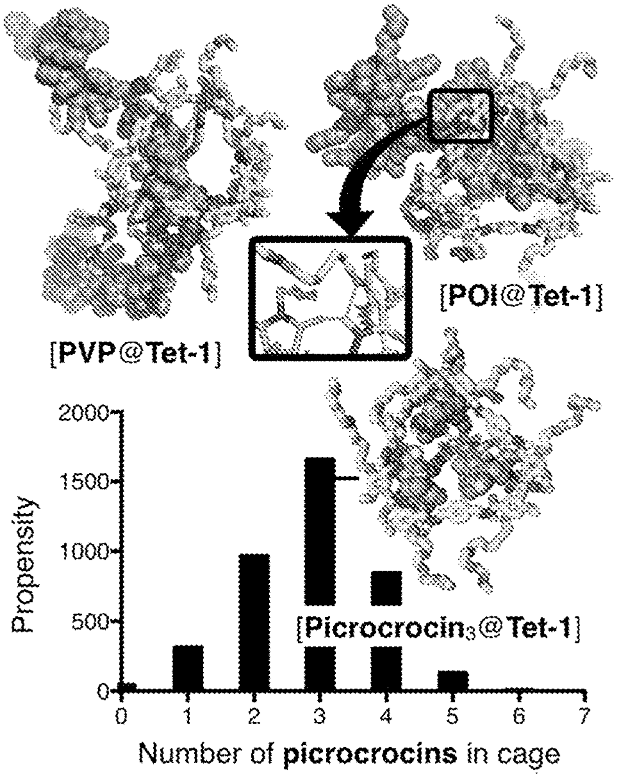

FIG. 49 shows snapshots of MD simulations. Ligands are illustrated in space-filling mode, with C atoms shown. The histogram shows that Tet-1 has the highest propensity to bind three picrocrocins concurrently, which is consistent with the experimentally observed (FIG. 48C) cooperative binding of picrocrocin to Tet-1. The histogram was constructed by analyzing all frames of the trajectory from 20 to 100 ns. A picrocrocin molecule was considered inside of the cage, if its center of mass was located within a sphere (radius=10 Å) placed at the center of the cage.

Figure 50:
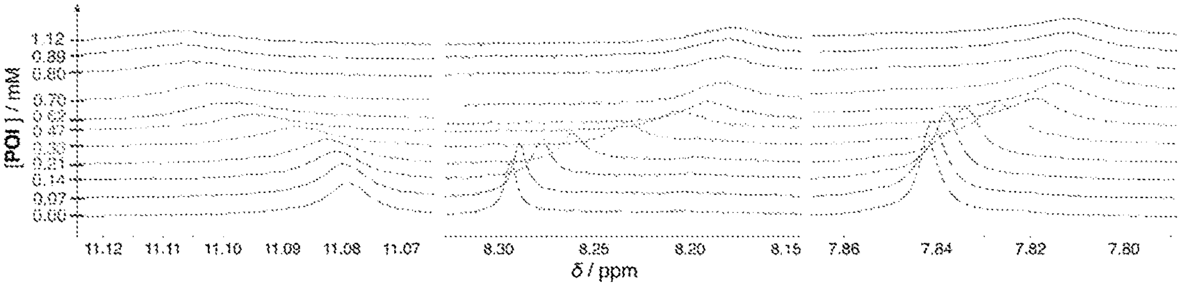

FIG. 50 shows partial $^1$H-NMR (500 MHZ, $CD_2Cl_2$, 298 K) spectra for the titration of Tet-1 with POI.

Figure 51:
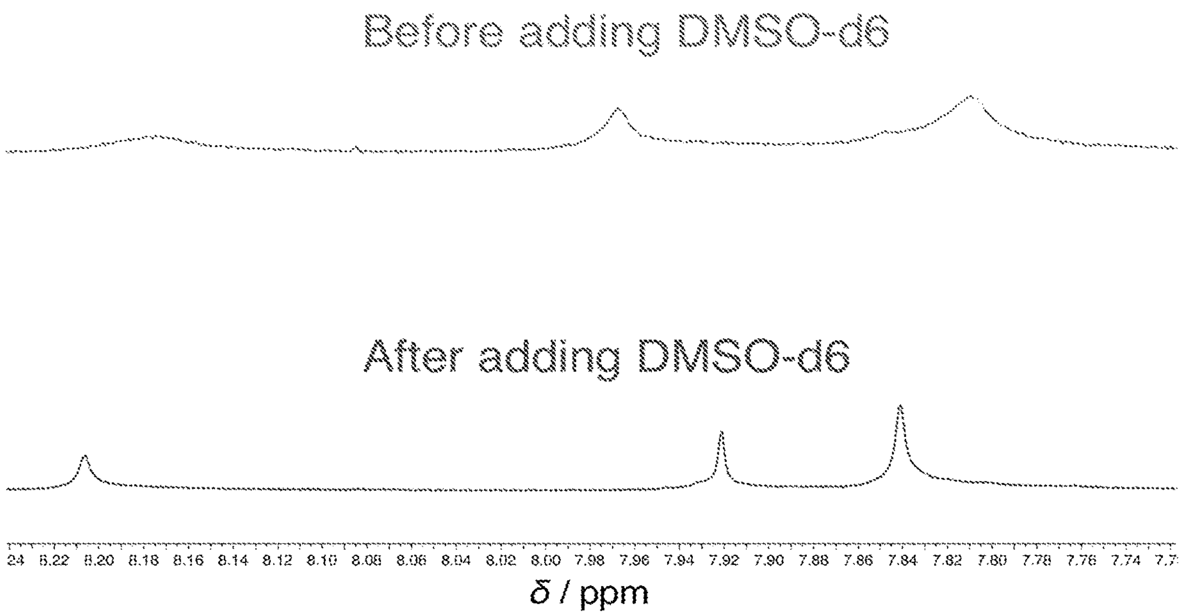

FIG. 51 shows partial $^1$H-NMR (500 MHZ, $CD_2Cl_2$, 298 K) spectra for a mixture of POI (1.13 mM) and Tet-1 (0.22 mM) before and after addition of DMSO-d6 (10 μL)

Figure 52:
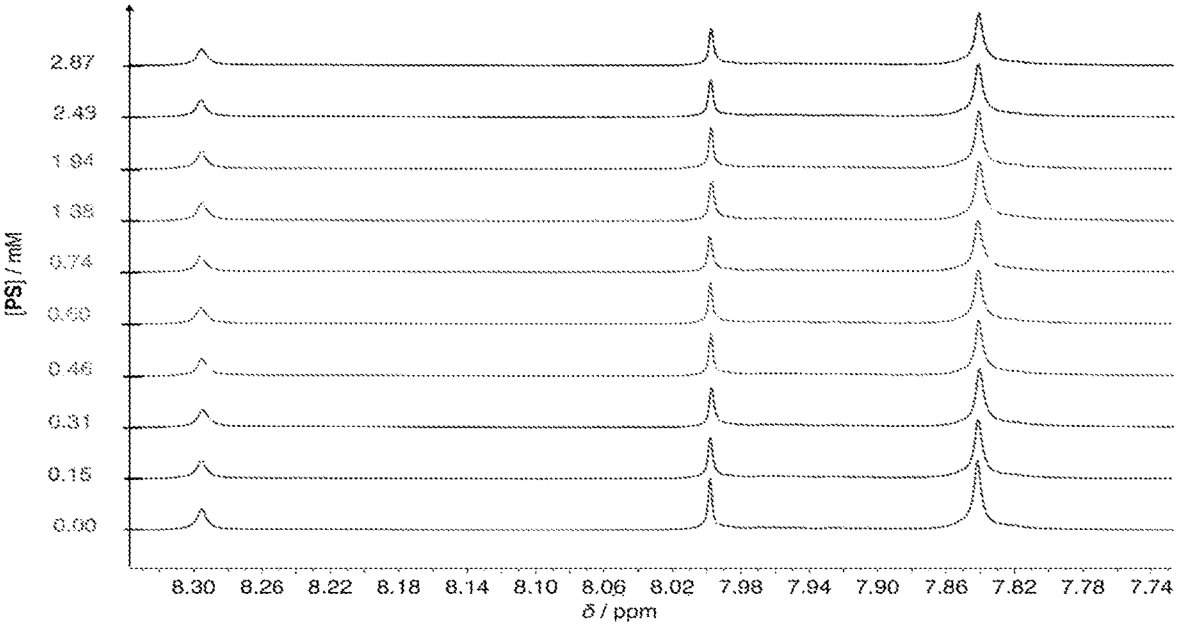

FIG. 52 shows partial $^1$H-NMR (500 MHZ, $CD_2Cl_2$, 298 K) spectra for the titration of Tet-1 with PS.

Figure 53:
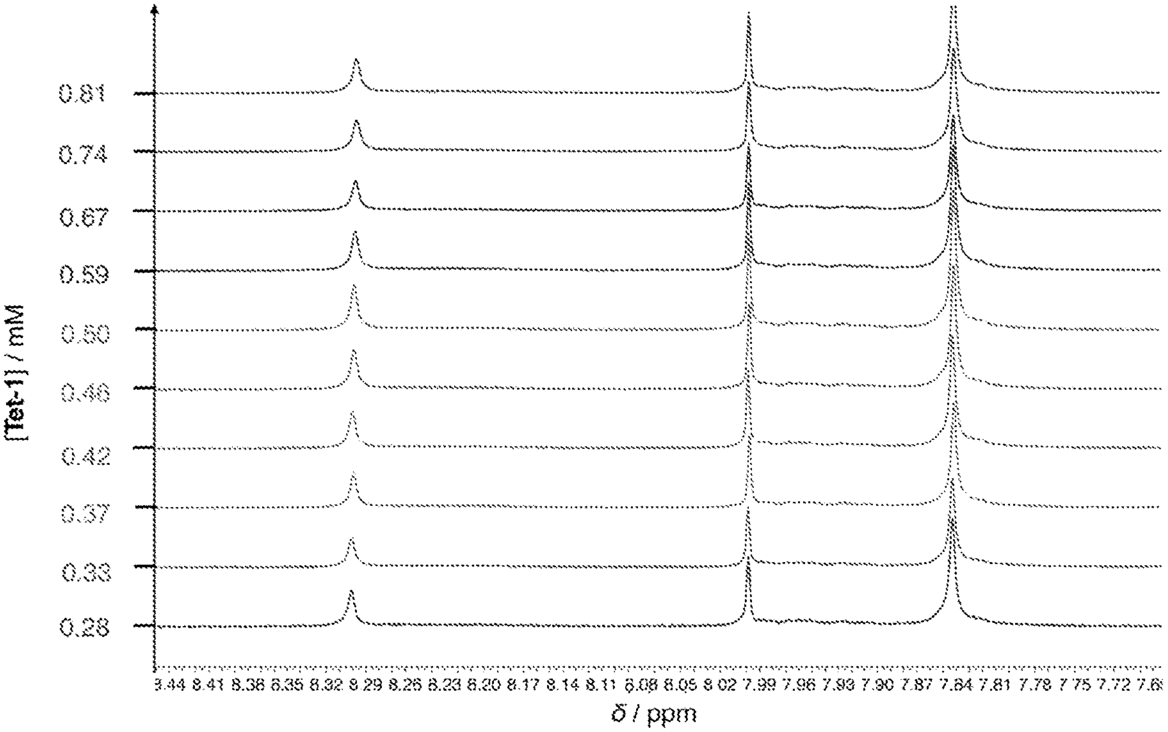

FIG. 53 shows partial $^1$H-NMR (500 MHZ, $CD_2Cl_2$, 298 K) spectra for the titration of Tet-1 with itself.

Figure 54:
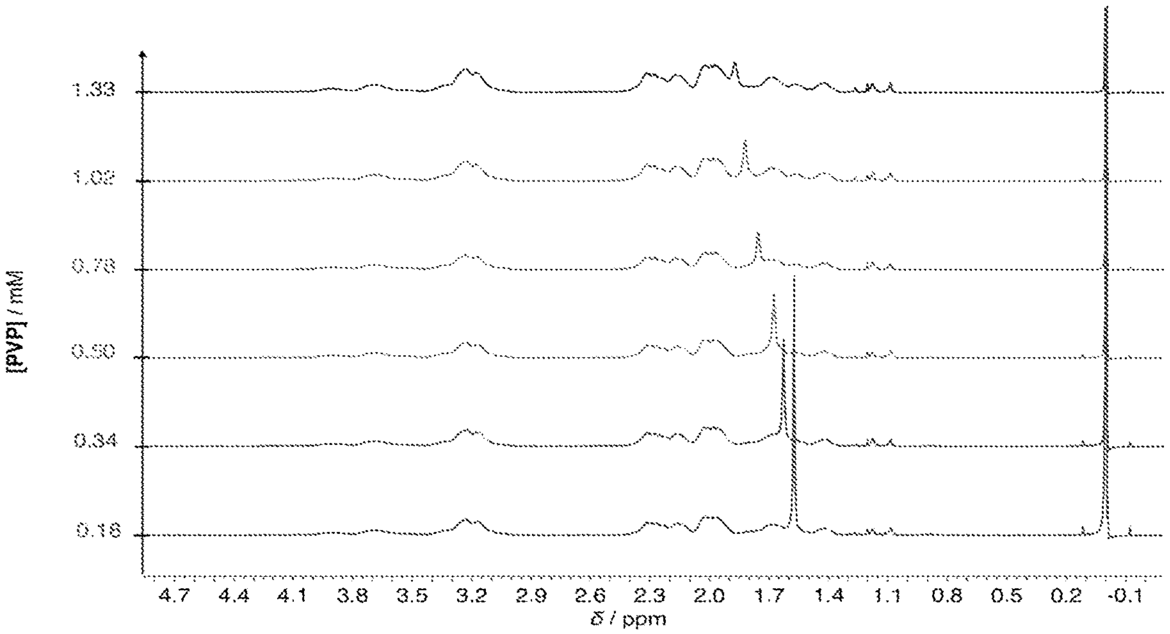

FIG. 54 shows partial $^1$H-NMR (500 MHZ, $CD_2Cl_2$, 298 K) spectra for the titration of PVP with itself.

Figure 55:
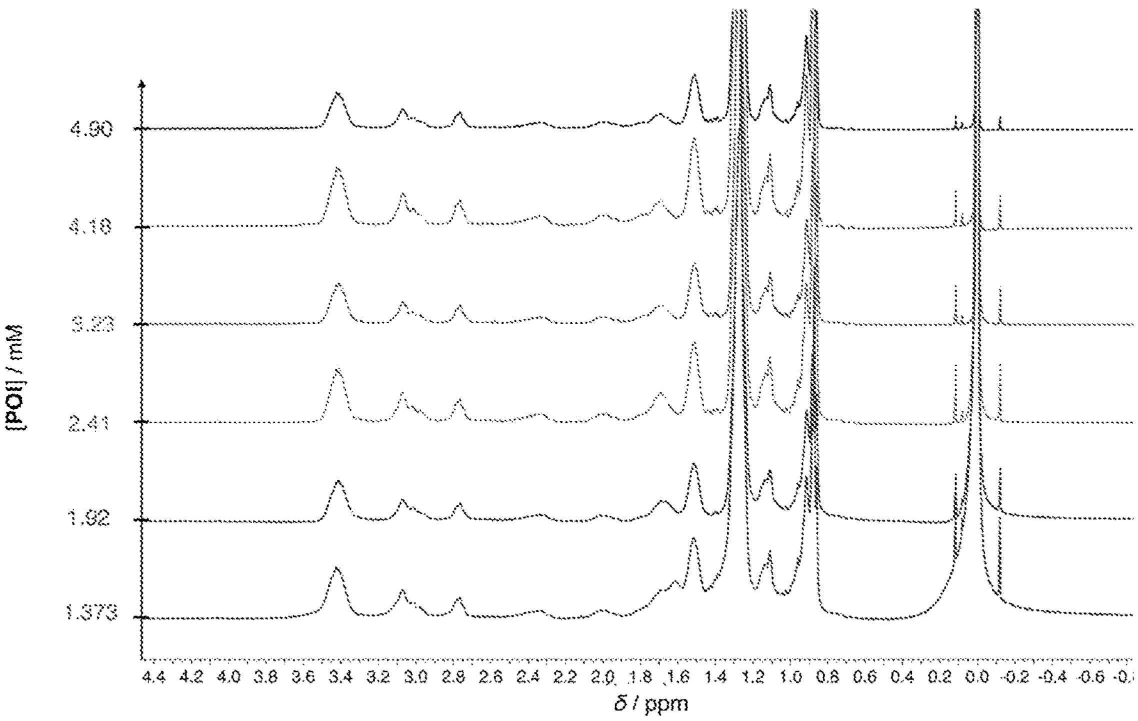

FIG. 55 shows partial $^1$H-NMR (500 MHZ, $CD_2Cl_2$, 298 K) spectra for the titration of POI with itself.

Figure 56:
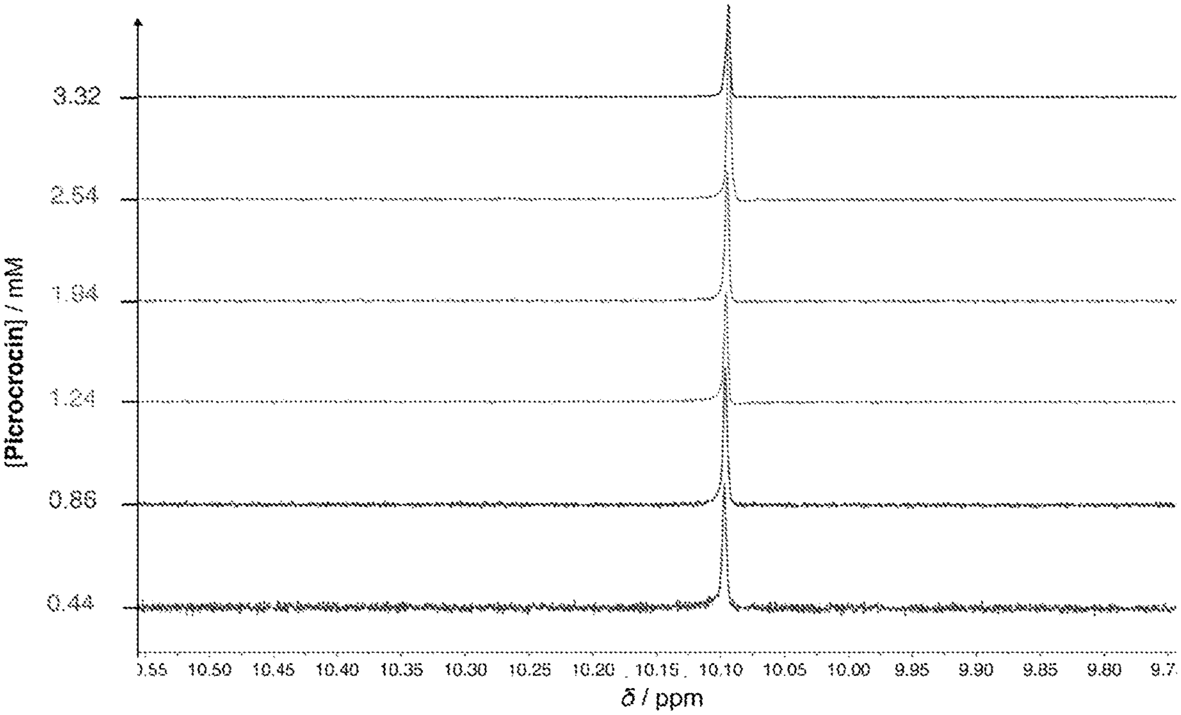

FIG. 56 shows partial $^1$H-NMR (500 MHz, $CD_2Cl_2$, 298 K) spectra for the titration of picrocrocin with itself.

Figure 57:
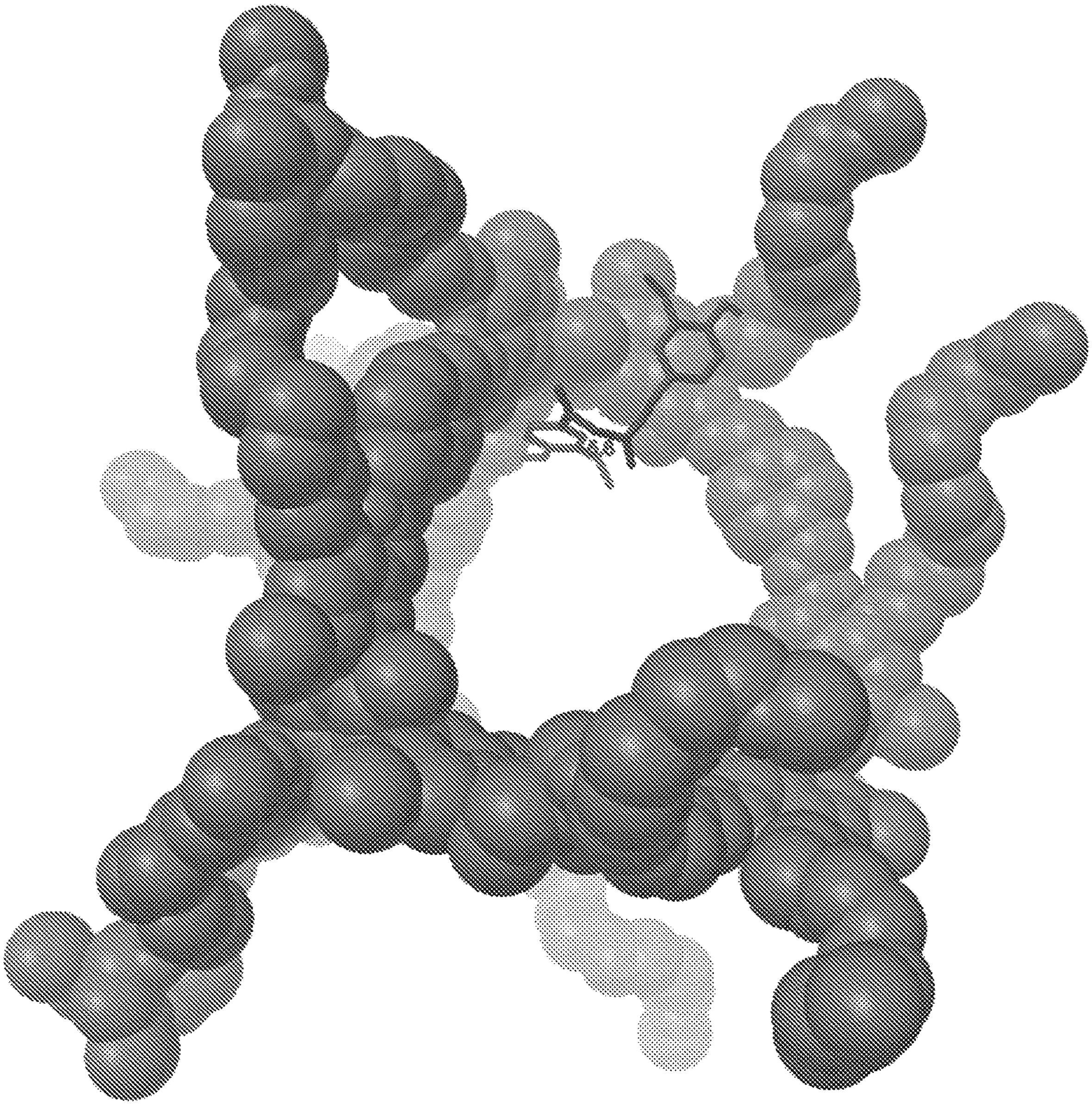

FIG. 57 shows a favorable docking pose of curcumin (FIG. 48D) binding to Tet-1. Tet-1 is shown in space-filling mode and curcumin is shown in stick mode.

DETAILED DESCRIPTION

One aspect of the present application relates to a nanocage of Formula (I):

(I)

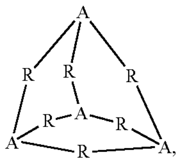

wherein each A is independently selected and has the formula

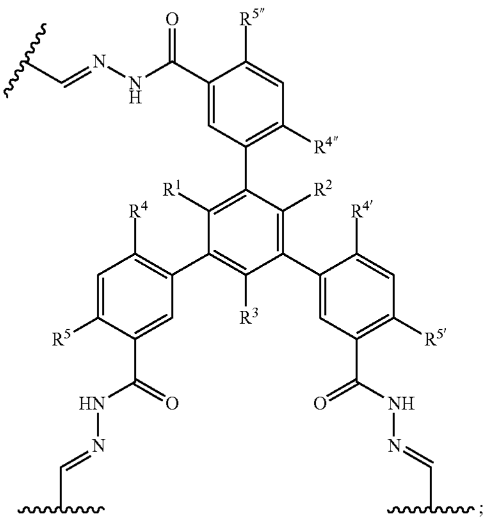

is the point of attachment of A to R;

each R is independently selected and has the formula

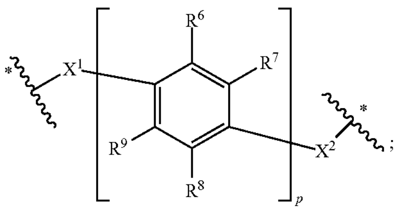

indicates the point of attachment of R to A;

$R^1$, $R^2$, and $R^3$ are each independently selected from the group consisting of H, halogen, OH, $C_{1-20}$ alkyl, $C_{2-20}$ alkenyl, $C_{2-20}$ alkynyl, perfluorinated $C_{1-20}$ alkyl, aryl, hereroaryl, heterocyclyl, —O$C_{1-20}$ alkyl, —O$C_{2-20}$ alkenyl, —O$C_{2-20}$ alkynyl, —O-perfluorinated $C_{1-20}$ alkyl, —Oaryl, —COO$C_{1-20}$ alkyl, —COO perfluorinated $C_{1-20}$ alkyl, —COOaryl, —CONH$C_{1-20}$ alkyl, CONH$C_{2-20}$ alkenyl, —CONH$C_{2-20}$ alkynyl, —CONH perfluorinated $C_{1-20}$ alkyl, —CONH-aryl, —CONH-heteroaryl, and —CONH-heterocyclyl, wherein each $C_{1-20}$ alkyl, $C_{2-20}$ alkenyl, alkenyl, —O$C_{2-20}$ alkynyl, —O-perfluorinated $C_{1-20}$ alkyl, —Oaryl, —COO$C_{1-20}$ alkyl, —COO perfluorinated $C_{1-20}$ alkyl, —COOaryl, —CONH$C_{1-20}$ alkyl, —CONH$C_{2-20}$ alkenyl, —CONH$C_{2-20}$ alkynyl, —CONH perfluorinated $C_{1-20}$ alkyl, —CONH-aryl, —CONH-heteroaryl, and —CONH-heterocyclyl can be optionally substituted from 1 to 3 times with a substituent selected from the group consisting of H, halogen, OH, $C_{1-6}$ alkyl, aryl, and arylalkyl;

$R^4$, $R^{4'}$, and $R^{4''}$ are each independently selected from the group consisting of H, halogen, $C_{1-20}$ alkyl, $C_{2-20}$ alkenyl, $C_{2-20}$ alkynyl, perfluorinated $C_{1-20}$ alkyl, aryl, hereroaryl, heterocyclyl, OH, —O$C_{1-20}$ alkyl, —O$C_{2-20}$ alkenyl, —O$C_{2-20}$ alkynyl, —O-perfluorinated $C_{1-20}$ alkyl, —Oaryl, —COO$C_{1-20}$ alkyl, —COO perfluorinated $C_{1-20}$ alkyl, —COOaryl, —CONH$C_{1-20}$ alkyl, —CONH$C_{2-20}$ alkenyl, —CONH$C_{2-20}$ alkynyl, —CONH perfluorinated $C_{1-20}$ alkyl, —CONH-aryl, —CONH-heteroaryl, and —CONH-heterocyclyl, wherein each $C_{1-20}$ alkyl, $C_{2-20}$ alkenyl, $C_{2-20}$ alkynyl, perfluorinated $C_{1-20}$ alkyl, aryl, hereroaryl, heterocyclyl, —O$C_{1-20}$ alkyl, —O$C_{2-20}$ alkenyl, —O$C_{2-20}$ alkynyl, —O-perfluorinated $C_{1-20}$ alkyl, —Oaryl, —COO$C_{1-20}$ alkyl, —COO perfluorinated $C_{1-20}$ alkyl, —COOaryl, —CONH$C_{1-20}$ alkyl, —CONH$C_{2-20}$ alkenyl, —CONH$C_{2-20}$ alkynyl, —CONH perfluorinated $C_{1-20}$ alkyl, —CONH-aryl, —CONH-heteroaryl, and —CONH-heterocyclyl can be optionally substituted from 1 to 3 times with a substituent selected from the group consisting of H, halogen, OH, $C_{1-6}$ alkyl, aryl, and arylalkyl;

$R^5$, $R^{5'}$, and $R^{5''}$ are each independently selected from the group consisting of H, halogen, OH, $—O(CH_2)_n—(OCH_2CH_2)_m—OC_{1-6}$ alkyl, aryl, hereroaryl, heterocyclyl, —O$C_{1-20}$ alkyl, —O-perfluorinated $C_{1-20}$ alkyl, —Oaryl, and —$NR^{10}R^{11}$;

$R^6$, $R^7$, $R^8$, and $R^9$ are each independently selected at each occurrence from the group consisting of H, halogen, $C_{1-20}$ alkyl, $C_{2-20}$ alkenyl, $C_{2-20}$ alkynyl, perfluorinated $C_{1-20}$ alkyl, aryl, hereroaryl, heterocyclyl, OH, —O$C_{1-20}$ alkyl, —O$C_{2-20}$ alkenyl, —O-perfluorinated $C_{1-20}$ alkyl, —O$C_{2-20}$ alkynyl, aryl, heteroaryl, heterocyclyl, and —COO$C_{1-20}$ alkyl, —COO perfluorinated $C_{1-20}$ alkyl, —COOaryl, —CONH$C_{1-20}$ alkyl, —CONH$C_{2-20}$ alkenyl, —CONH$C_{2-20}$ alkynyl, —CONH perfluorinated $C_{1-20}$ alkyl, —CONH-aryl, —CONH-heteroaryl, and —CONH-heterocyclyl, wherein each $C_{1-20}$ alkyl, $C_{2-20}$ alkenyl, $C_{2-20}$ alkynyl, perfluorinated $C_{1-20}$ alkyl, aryl, hereroaryl, heterocyclyl, —O$C_{1-20}$ alkyl, —O$C_{2-20}$ alkenyl, —O$C_{2-20}$ alkynyl, —O-perfluorinated $C_{1-20}$ alkyl, —Oaryl, —COO$C_{1-20}$ alkyl, —COO perfluorinated $C_{1-20}$ alkyl, —COOaryl, —CONH$C_{1-20}$ alkyl, —CONH$C_{2-20}$ alkenyl, —CONH$C_{2-20}$ alkynyl, —CONH perfluorinated $C_{1-20}$ alkyl, —CONH-aryl, —CONH-heteroaryl, and —CONH-heterocyclyl can be optionally substituted from 1 to 3 times with a substituent selected from the group consisting of H, halogen, OH, $C_{1-6}$ alkyl, aryl, and arylalkyl;

$R^{10}$ and $R^{11}$ are each independently selected from the group consisting of H, $C_{1-6}$ alkyl, $C_{2-6}$ alkenyl, $C_{2-6}$ alkynyl, aryl, heteroarylalkyl, heterocyclylalkyl, and arylalkyl, wherein each $C_{1-6}$ alkyl, $C_{2-6}$ alkenyl, $C_{2-6}$ alkynyl, aryl, heteroarylalkyl, heterocyclylalkyl, and arylalkyl can be optionally substituted from 1 to 3 times with a substituent selected from the group consisting of H, $C_{1-6}$ alkyl, heteroarylalkyl, heterocyclylalkyl, and arylalkyl;

$X^1$ and $X^2$ are absent or are independently selected from the group consisting of $C_{1-6}$ alkylene, $C_{3-8}$ cycloalkylene, and arylene, wherein $C_{1-6}$ alkylene, $C_{3-8}$ cycloalkylene, and arylene can be optionally substituted from 1 to 3 times with H or $C_{1-6}$ alkyl;

p is 1 to 3;

n is 1 to 10; and m is 1 to 10.

As used above, and throughout the description herein, the following terms, unless otherwise indicated, shall be understood to have the following meanings. If not defined otherwise herein, all technical and scientific terms used herein have the same meaning as is commonly understood by one of ordinary skill in the art to which this technology belongs. In the event that there is a plurality of definitions for a term herein, those in this section prevail unless stated otherwise.

The term "alkyl" means an aliphatic hydrocarbon group which may be straight or branched. When not otherwise restricted, the term refers to an alkyl of 20 or fewer carbons. Lower alkyl refers to alkyl groups having about 1 to about 6 carbon atoms in the chain. Branched means that one or more lower alkyl groups such as methyl, ethyl, or propyl are attached to a linear alkyl chain. Exemplary alkyl groups include methyl, ethyl, n-propyl, i-propyl, n-butyl, t-butyl, n-pentyl, 3-pentyl, and the like.

The term "alkenyl" means an aliphatic hydrocarbon group containing a carbon-carbon double bond and which may be straight or branched having about 2 to about 20 carbon atoms in the chain. Particular alkenyl groups have 2 to about 10 carbon atoms in the chain. Branched means that one or more lower alkyl groups such as methyl, ethyl, or propyl are attached to a linear alkenyl chain. Exemplary alkenyl groups include ethenyl, propenyl, n-butenyl, and i-butenyl. The term "alkenyl" may also refer to a hydrocarbon chain having 2 to 6 carbons containing at least one double bond and at least one triple bond.

The term "alkynyl" means an aliphatic hydrocarbon group containing a carbon-carbon triple bond and which may be straight or branched having about 2 to about 20 carbon atoms in the chain. Particular alkynyl groups have 2 to about 10 carbon atoms in the chain. Branched means that one or more lower alkyl groups such as methyl, ethyl, or propyl are attached to a linear alkynyl chain. Exemplary alkynyl groups include ethynyl, propynyl, n-butynyl, 2-butynyl, 3-methylbutynyl, and n-pentynyl.

As used herein, the term "alkane" refers to aliphatic hydrocarbons of formula $C_nH_{2n+2}$, which may be straight or branched having about 1 to about 40 (e.g., 1-2, 1-3, 1-4, 1-5, 1-6, 1-7, 1-8) carbon atoms in the chain. Branched means that one or more lower alkyl groups such as methyl, ethyl, or propyl are attached to a linear alkyl chain. Exemplary alkanes include methane, ethane, n-propane, i-propane, n-butane, t-butane, n-pentane, and 3-pentane. The term "alkylene" refers to a divalent group formed from an alkane by removal of two hydrogen atoms. Exemplary alkylene groups include, but are not limited to, divalent groups derived from the alkanes described above.

As used herein, the term "cycloalkane" refers to aliphatic hydrocarbons of formula $C_nH_{2n}$, which may be straight or branched having about 3 to about 8 carbon atoms in the chain. Exemplary cycloalkanes include cyclopropane, cyclobutane, cyclopentane, cyclohexane, and cycloheptane. The term "cycloalkylene" refers to a divalent group formed from a cycloalkane by removal of two hydrogen atoms. Exemplary cycloalkylene groups include, but are not limited to, divalent groups derived from the cycloalkanes described above.

As used herein, "heterocyclyl" or "heterocycle" refers to a stable 3- to 18-membered ring (radical) which consists of carbon atoms and from one to five heteroatoms selected from the group consisting of nitrogen, oxygen, and sulfur. For purposes of this application, the heterocycle may be a monocyclic, or a polycyclic ring system, which may include fused, bridged, or spiro ring systems; and the nitrogen, carbon, or sulfur atoms in the heterocycle may be optionally oxidized; the nitrogen atom may be optionally quaternized; and the ring may be partially or fully saturated. Examples of such heterocycles include, without limitation, azepinyl, azocanyl, pyranyl dioxanyl, dithianyl, 1,3-dioxolanyl, tetrahydrofuryl, dihydropyrrolidinyl, decahydroisoquinolyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, 2-oxoazepinyl, oxazolidinyl, oxiranyl, piperidinyl, piperazinyl, 4-piperidonyl, pyrrolidinyl, pyrazolidinyl, thiazolidinyl, tetrahydropyranyl, thiamorpholinyl, thiamorpholinyl sulfoxide, and thiamorpholinyl sulfone. Further heterocycles and heteroaryls are described in Katritzky et al., eds., Comprehensive Heterocyclic Chemistry: The Structure, Reactions, Synthesis and Use of Heterocyclic Compounds, Vol. 1-8, Pergamon Press, N.Y. (1984), which is hereby incorporated by reference in its entirety.

The term "monocyclic" used herein indicates a molecular structure having one ring.

The term "polycyclic" or "multi-cyclic" used herein indicates a molecular structure having two or more rings, including, but not limited to, fused, bridged, or spiro rings.

The term "aryl" means an aromatic monocyclic or multi-cyclic (polycyclic) ring system of 6 to about 19 carbon atoms, or of 6 to about 10 carbon atoms, and includes arylalkyl groups. The ring system of the aryl group may be optionally substituted. Representative aryl groups include, but are not limited to, groups such as phenyl, naphthyl, azulenyl, phenanthrenyl, anthracenyl, fluorenyl, pyrenyl, triphenylenyl, chrysenyl, and naphthacenyl.

The term "heteroaryl" means an aromatic monocyclic or multi-cyclic ring system of about 5 to about 19 ring atoms, or about 5 to about 10 ring atoms, in which one or more of the atoms in the ring system is/are element(s) other than carbon, for example, nitrogen, oxygen, or sulfur. In the case of multi-cyclic ring system, only one of the rings needs to be aromatic for the ring system to be defined as "heteroaryl". Particular heteroaryls contain about 5 to 6 ring atoms. The prefix aza, oxa, thia, or thio before heteroaryl means that at least a nitrogen, oxygen, or sulfur atom, respectively, is present as a ring atom. A nitrogen, carbon, or sulfur atom in the heteroaryl ring may be optionally oxidized; the nitrogen may optionally be quaternized. Representative heteroaryls include pyridyl, 2-oxo-pyridinyl, pyrimidinyl, pyridazinyl, pyrazinyl, triazinyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, indolyl, isoindolyl, benzofuranyl, benzothiophenyl, indolinyl, 2-oxoindolinyl, dihydrobenzofuranyl, dihydrobenzothiophenyl, indazolyl, benzimidazolyl, benzooxazolyl, benzothiazolyl, benzoisoxazolyl, benzoisothiazolyl, benzotriazolyl, benzo[1,3]dioxolyl, quinolinyl, isoquinolinyl, quinazolinyl, cinnolinyl, pthalazinyl, quinoxalinyl, 2,3-dihydro-benzo[1,4]dioxinyl, benzo[1,2,3]triazinyl, benzo[1,2,4]triazinyl, 4H-chromenyl, indolizinyl, quinolizinyl, 6aH-thieno[2,3-d]imidazolyl, $^1$H-pyrrolo[2,3-b]pyridinyl, imidazo[1,2-a]pyridinyl, pyrazolo[1,5-a]pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, imidazo[1,2-a]pyrazinyl, 5,6,7,8-tetrahydroimidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-$^1$H-pyrrolo[2,3-b]pyridinyl, benzo[c][1,2,5]oxadiazolyl, benzo[c][1,2,5]thiadiazolyl, 3,4-dihydro-2H-benzo[b][1,4]oxazinyl, 5,6,7,8-tetrahydro-[1,2,4]triazolo[4,3-a]pyrazinyl, [1,2,4]triazolo[4,3-a]pyrazinyl, 3-oxo-[1,2,4]triazolo[4,3-a]pyridin-2 (3H)-yl, and the like.

The terms "arylalkyl" and "heteroarylalkyl" mean an alkyl substituted with one or more aryl or heteroaryl groups, wherein the alkyl, aryl, and heteroaryl groups are as herein described. One particular example is an arylmethyl or heteroarylmethyl group, in which a single carbon spacer unit is attached to an aryl or heteroaryl group, where the carbon spacer and the aryl or heteroaryl group can be optionally substituted as described herein.

The term "heterocyclylalkyl" mean an alkyl substituted with one or more heterocyclyl groups, wherein the alkyl and heterocyclyl groups are as herein described.

The term "arylene" means a group obtained by removal of a hydrogen atom from an aryl group. Non-limiting examples of arylene include phenylene and naphthylene.

The term "halogen" means fluoro, chloro, bromo, or iodo.

The term "perfluorinated $C_{1-20}$ alkyl" means both branched and straight-chain alkyl substituted with one or more fluorine atoms, wherein the alkyl group is as herein described.

The term "optionally substituted" is used to indicate that a group may have a substituent at each substitutable atom of the group (including more than one substituent on a single atom), provided that the designated atom's normal valency is not exceeded, and the identity of each substituent is independent of the others. Up to three H atoms in each residue are replaced with alkyl, halogen, haloalkyl, hydroxy, loweralkoxy, carboxy, carboalkoxy (also referred to as alkoxycarbonyl), carboxamido (also referred to as alkylaminocarbonyl), cyano, carbonyl, nitro, amino, alkylamino, dialkylamino, mercapto, alkylthio, sulfoxide, sulfone, acylamino, amidino, phenyl, benzyl, heteroaryl, phenoxy, benzyloxy, or heteroaryloxy.

"Unsubstituted" atoms bear all of the hydrogen atoms dictated by their valency. When a substituent is keto (i.e., =0), then two hydrogens on the atom are replaced. Combinations of substituents and/or variables are permissible only if such combinations result in stable compounds; by "stable compound" or "stable structure" is meant a compound that is sufficiently robust to survive isolation to a useful degree of purity from a reaction mixture, and formulation into an efficacious therapeutic agent.

The term "a derivative thereof" refers to a salt thereof, an ester thereof, a free acid form thereof, a free base form thereof, a solvate thereof, a deuterated derivative thereof, a hydrate thereof, an N-oxide thereof, a polymorph thereof, a stereoisomer thereof, a geometric isomer thereof, a tautomer thereof, a mixture of tautomers thereof, an enantiomer thereof, a diastereomer thereof, a racemate thereof, a mixture of stereoisomers thereof, an isotope thereof (e.g., tritium, deuterium), or a combination thereof.

Compounds described herein may contain one or more asymmetric centers and may thus give rise to enantiomers, diastereomers, and other stereoisomeric forms. Each chiral center may be defined, in terms of absolute stereochemistry, as (R)- or(S)—. This technology is meant to include all such possible isomers, as well as mixtures thereof, including racemic and optically pure forms. Optically active (R)- and(S)—, (−)- and (+)—, or (D)- and (L)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both (E)- and (Z)-geometric isomers. Likewise, all tautomeric forms are also intended to be included.

Compounds described herein contain hydrazone bonds. All possible cis/trans/s-cis/s-trans isomers of the hydrazone bonds are intended to be encompassed within the scope of the present application. This technology is meant to include all such possible isomers, as well as mixtures thereof.

Compounds described herein may also contain isotopes at one or more of the atoms that constitute such compounds. For example, the compounds may be radiolabeled with radioactive isotopes, such as for example tritium ($^{3}$H), iodine-125 ($^{12}$I), carbon-14 ($^{14}$C), carbon-11 ($^{11}$C), or fluorine-18 ($^{18}$F). All isotopic variations of the compounds of the present application, whether radioactive or not, are intended to be encompassed within the scope of the present application.

In one embodiment, at least one A in the nanocage of Formula (I) is different from the other A.

In another embodiment, all R in the nanocage of Formula (I) are the same.

In another embodiment, all R in the nanocage of Formula (I) are different.

In yet another embodiment, at least one R in the nanocage of Formula (I) is different from the other R.

In a further embodiment, the nanocage is $T_d$-symmetric.

The height of the nanocage can be determined with standard molecular modeling tools with the "measure distance" application programming interfaces (APIs) (Humphrey et al., "VMD—Visual Molecular Dynamics," *J. Molec. Graphics.* 14:33-38 (1996); Hanwell et al., "Avogadro: An Advanced Semantic Chemical Editor, Visualization, and Analysis Platform," *J. Cheminform.* 4:17 (2012); Guex et al., "SWISS-MODEL and the Swiss-PDB Viewer: An Environment for Comparative Protein Modeling," *Electrophoresis* 18:2714-2723 (1997); Pirhadi et al., "Open Source Molecular Modeling," *J. Mol. Graphics Modell.* 69:127-143 (2016), which are hereby incorporated by reference in their entirety).

According to the present application, the nanocage has a height from 15 Å to 40 Å. Preferably, the nanocage has a height from 15 Å to 39 Å, from 15 Å to 38 Å, from 15 Å to 37 Å, from 15 Å to 36 Å, from 16 Å to 35 Å, from 17 Å to 34 Å, from 18 Å to 33 Å, from 19 Å to 32 Å, from 20 Å to 31 Å, from 20 Å to 30 Å, from 20 Å to 29 Å, from 20 Å to 28 Å, from 20 Å to 27 Å, from 20 Å to 26 Å, from 20 Å to 25 Å. More preferably, the nanocage has a height from 21 Å to 25 Å, from 22 Å to 25 Å, from 23 Å to 25 Å, from 24 Å to 25 Å, 21 Å to 24 Å, from 22 Å to 24 Å, from 23 Å to 24 Å, from 24 Å to 25 Å, 21 Å to 23 Å, from 21 Å to 22 Å, from 22 Å to 23 Å.

One embodiment relates to the nanocage of Formula (I), wherein $R^1$, $R^2$, and $R^3$ are Me, $R^4$ is —OMe, $R^5$ is —$O(CH_2)_4$—$(OCH_2CH_2)_3$—OMe.

In one embodiment, the nanocage of Formula (I) is stable in water.

In another embodiment, the nanocage of Formula (I) is stable in water at elevated temperatures. For example, the nanocage of Formula (I) is stable in water at 30° C., 40° C., 50° C., 60° C., 70° C., 80° C., 90° C., or 100° C.

Another aspect of the present application relates to a process for preparation of a nanocage of Formula (I):

(I)

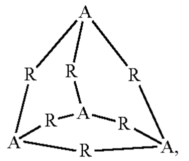

wherein each A is independently selected and has the formula

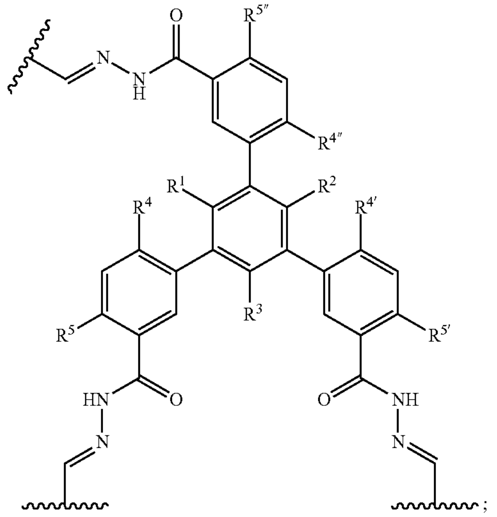

is the point of attachment of A to R;

each R is independently selected and has the formula

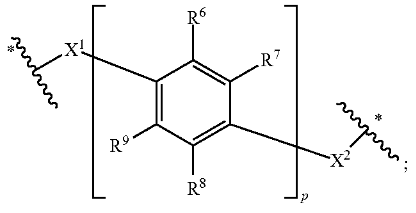

indicates the point of attachment of R to A;

$R^1$, $R^2$, and $R^3$ are each independently selected from the group consisting of H, halogen, OH, $C_{1-20}$ alkyl, $C_{2-20}$ alkenyl, $C_{2-20}$ alkynyl, perfluorinated $C_{1-20}$ alkyl, aryl, hereroaryl, heterocyclyl, —$OC_{1-20}$ alkyl, —$OC_{2-20}$ alkenyl, —$OC_{2-20}$ alkynyl, —O-perfluorinated $C_{1-20}$ alkyl, —Oaryl, —$COOC_{1-20}$ alkyl, —COO perfluorinated $C_{1-20}$ alkyl, —COOaryl, —$CONHC_{1-20}$ alkyl, —$CONHC_{2-20}$ alkenyl, —$CONHC_{2-20}$ alkynyl, —CONH perfluorinated $C_{1-20}$ alkyl, —CONH-aryl, —CONH-heteroaryl, and —CONH-heterocyclyl, wherein each $C_{1-20}$ alkyl, $C_{2-20}$ alkenyl, $C_{2-20}$ alkynyl, perfluorinated $C_{1-20}$ alkyl, aryl, hereroaryl, heterocyclyl, —$OC_{1-20}$ alkyl, —$OC_{2-20}$ alkenyl, —$OC_{2-20}$ alkynyl, —O-perfluorinated $C_{1-20}$ alkyl, —Oaryl, —$COOC_{1-20}$ alkyl, —COO perfluorinated $C_{1-20}$ alkyl, —COOaryl, —$CONHC_{1-20}$ alkyl, —$CONHC_{2-20}$ alkenyl, —$CONHC_{2-20}$ alkynyl, —CONH perfluorinated $C_{1-20}$ alkyl, —CONH-aryl, —CONH-heteroaryl, and —CONH-heterocyclyl can be optionally substituted from 1 to 3 times with a substituent selected from the group consisting of H, halogen, OH, $C_{1-6}$ alkyl, aryl, and arylalkyl;

$R^4$, $R^{4'}$, and $R^{4''}$ are each independently selected from the group consisting of H, halogen, $C_{1-20}$ alkyl, $C_{2-20}$ alkenyl, $C_{2-20}$ alkynyl, perfluorinated $C_{1-20}$ alkyl, aryl, hereroaryl, heterocyclyl, OH, —$OC_{1-20}$ alkyl, —$OC_{2-20}$ alkenyl, —$OC_{2-20}$ alkynyl, —O-perfluorinated $C_{1-20}$ alkyl, —Oaryl, —$COOC_{1-20}$ alkyl, —COO perfluorinated $C_{1-20}$ alkyl, —COOaryl, —$CONHC_{1-20}$ alkyl, —$CONHC_{2-20}$ alkenyl, —$CONHC_{2-20}$ alkynyl, —CONH perfluorinated $C_{1-20}$ alkyl, —CONH-aryl, —CONH-heteroaryl, and —CONH-heterocyclyl, wherein each $C_{1-20}$ alkyl, $C_{2-20}$ alkenyl, $C_{2-20}$ alkynyl, perfluorinated $C_{1-20}$ alkyl, aryl, hereroaryl, heterocyclyl, —$OC_{1-20}$ alkyl, —$OC_{2-20}$ alkenyl, —$OC_{2-20}$ alkynyl, —O-perfluorinated $C_{1-20}$ alkyl, —Oaryl, —$COOC_{1-20}$ alkyl, —COO perfluorinated $C_{1-20}$ alkyl, —COOaryl, —$CONHC_{1-20}$ alkyl, —$CONHC_{2-20}$ alkenyl, —$CONHC_{2-20}$ alkynyl, —CONH perfluorinated $C_{1-20}$ alkyl, —CONH-aryl, —CONH-heteroaryl, and —CONH-heterocyclyl can be optionally substituted from 1 to 3 times with a substituent selected from the group consisting of H, halogen, OH, $C_{1-6}$ alkyl, aryl, and arylalkyl;

$R^5$, $R^{5'}$, and $R^{5''}$ are each independently selected from the group consisting of H, halogen, OH, —$O(CH_2)_n$—$(OCH_2CH_2)_m$—$OC_{1-6}$ alkyl, aryl, hereroaryl, heterocyclyl, —$OC_{1-20}$ alkyl, —O-perfluorinated $C_{1-20}$ alkyl, —Oaryl, and —$NR^{10}R^{11}$;

$R^6$, $R^7$, $R^8$, and $R^9$ are each independently selected at each occurrence from the group hereroaryl, heterocyclyl, OH, —$OC_{1-20}$ alkyl, —$OC_{2-20}$ alkenyl, —O-perfluorinated $C_{1-20}$ alkyl, —$OC_{2-20}$ alkynyl, aryl, heteroaryl, heterocyclyl, and —$COOC_{1-20}$ alkyl, —COO perfluorinated $C_{1-20}$ alkyl, —COOaryl, —$CONHC_{1-20}$ alkyl, —$CONHC_{2-20}$ alkenyl, —$CONHC_{2-20}$ alkynyl, —CONH perfluorinated $C_{1-20}$ alkyl, —CONH-aryl, —CONH-heteroaryl, and —CONH-heterocyclyl, wherein each $C_{1-20}$ alkyl, $C_{2-20}$ alkenyl, $C_{2-20}$ alkynyl, perfluorinated $C_{1-20}$ alkyl, aryl, hereroaryl, heterocyclyl, —$OC_{1-20}$ alkyl, —$OC_{2-20}$ alkenyl, —$OC_{2-20}$ alkynyl, —O-perfluorinated $C_{1-20}$ alkyl, —Oaryl, —$COOC_{1-20}$ alkyl, —COO perfluorinated $C_{1-20}$ alkyl, —COOaryl, —$CONHC_{1-20}$ alkyl, —$CONHC_{2-20}$ alkenyl, —$CONHC_{2-20}$ alkynyl, —CONH perfluorinated $C_{1-20}$ alkyl, —CONH-aryl, —CONH-heteroaryl, and —CONH-heterocyclyl can be optionally substituted from 1 to 3 times with a substituent selected from the group consisting of H, halogen, OH, $C_{1-6}$ alkyl, aryl, and arylalkyl;

$R^{10}$ and $R^{11}$ are each independently selected from the group consisting of H, $C_{1-6}$ alkyl, $C_{2-6}$ alkenyl, $C_{2-6}$ alkynyl, aryl, heteroarylalkyl, heterocyclylalkyl, and arylalkyl, wherein each $C_{1-6}$ alkyl, $C_{2-6}$ alkenyl, $C_{2-6}$ alkynyl, aryl, heteroarylalkyl, heterocyclylalkyl, and arylalkyl can be optionally substituted from 1 to 3 times with a substituent selected from the group consisting of H, $C_{1-6}$ alkyl, heteroarylalkyl, heterocyclylalkyl, and arylalkyl;

$X^1$ and $X^2$ are absent or are independently selected from the group consisting of $C_{1-6}$ alkylene, $C_{3-8}$ cycloalkylene, and arylene, wherein $C_{1-6}$ alkylene, $C_{3-8}$ cycloalkylene, and arylene can be optionally substituted from 1 to 3 times with H or $C_{1-6}$ alkyl;

p is 1 to 3;

n is 1 to 10; and m is 1 to 10, said process comprising:

providing one or more compounds of Formula (II) having the structure:

(II)

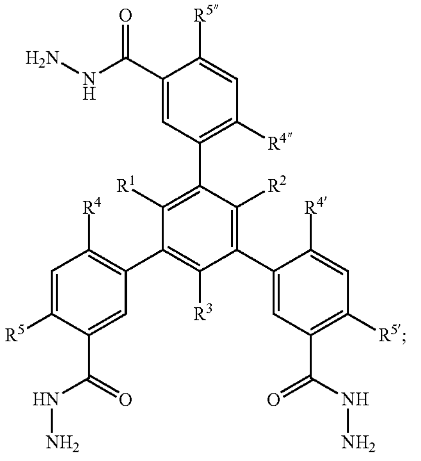

and forming the nanocage of Formula (I) from the one or more compounds of Formula (II).

In accordance with the embodiment, forming the nanocage of Formula (I) may comprise reacting the one or more compounds of Formula (II) with one or more compounds of Formula (III):

(III)

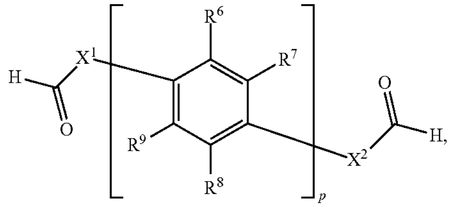

to produce the nanocage of Formula (I).

In one embodiment, the compound of Formula (III) has the following structure:

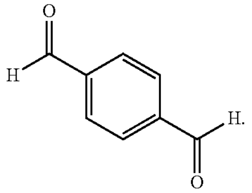

Another embodiment of the present invention comprises providing one or more compounds of Formula (IV) having the structure:

(IV)

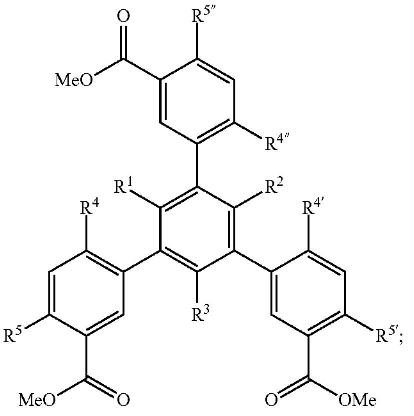

and forming the one or more compounds of Formula (II) from the one or more compounds of Formula (IV).

In accordance with the embodiment, forming the one or more compounds of Formula (II) comprises reacting the one or more compounds of Formula (IV) with a hydrazine source to produce the one or more compounds of Formula (II).

The hydrazine source that can be used according to the present application includes, but is not limited to, hydrazine, hydrazine hydrate, or hydrazine salts (for example hydrazine monohydrochloride).

In one embodiment, the hydrazine source is a compound of Formula (V):

$H_2NNH_2$ (V).

Another embodiment of the present invention further comprises providing one or more compounds of Formula (VI) having the structure:

(VI)

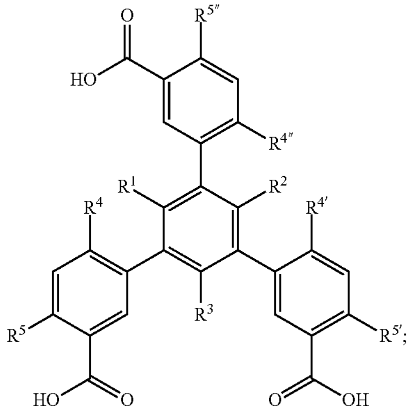

and forming the one or more compounds of Formula (IV) from the one or more compounds of Formula (VI).

In accordance with this embodiment, forming the one or more compounds of Formula (IV) comprises esterifying the one or more compounds of Formula (VI) to produce the one or more compounds of Formula (IV).

In accordance with this embodiment, esterifying the one or more compounds of Formula (VI) comprises reacting the one or more compounds of Formula (VI) with MeOH or MeI to produce the one or more compounds of Formula (IV).

Another embodiment of the present invention further comprises providing one or more compounds of Formula (VII) having the structure:

(VII)

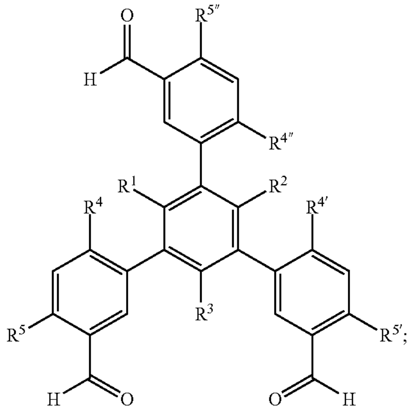

and forming the one or more compounds of Formula (VI) from the one or more compounds of Formula (VII).

In accordance with the embodiment, forming the one or more compounds of Formula (VI) comprises reacting the one or more compounds of Formula (VII) with an oxidizing agent to produce the one or more compounds of Formula (VI). Suitable oxidizing agents include, but are not limited to, $NaClO_2$, oxone (potassium peroxymonosulfate), $H_5IO_6$, $H_2O_2$, $O_2$, sodium perborate, and $KMnO_4$.

Another embodiment of the present invention further comprises providing one or more compounds of Formula (VIII) having the structure:

(VIII)

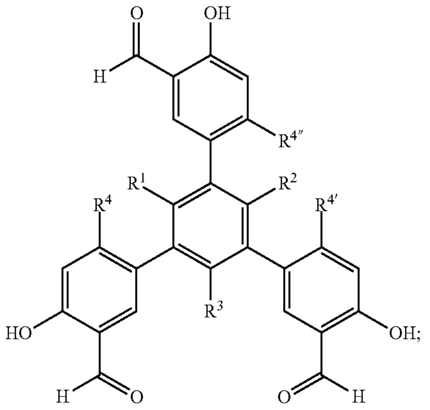

and forming the one or more compounds of Formula (VII) from the one or more compounds of Formula (VIII).

In accordance with the embodiment, forming the one or more compounds of Formula (VII) comprises reacting the one or more compounds of Formula (VIII) with one or more compounds of Formula (IX):

$LG\text{-}(CH_2)_n\text{—}(OCH_2CH_2)_m\text{—}OC_{1\text{-}6}$ alkyl (IX), wherein LG is a suitable leaving group, to produce the one or more compounds of Formula (VII).

Suitable leaving groups that can be used according to the present application include, but not limited to, halogen, mesylate, tosylate, triflate, or nosylate.

In one embodiment, the one or more compounds of Formula (IX) has the formula:

$Hal\text{-}(CH_2)_n\text{—}(OCH_2CH_2)_m\text{—}OC_{1\text{-}6}$ alkyl, wherein Hal is $C_1$ or Br.

Another embodiment of the present invention further comprises providing the one or more compounds of Formula (X) having the structure:

(X)

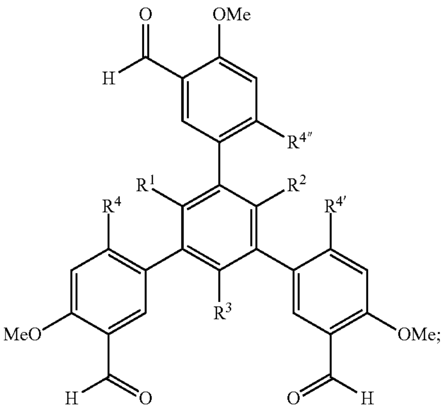

and forming the one or more compounds of Formula (VIII) from the one or more compounds of Formula (X).

In accordance with the embodiment, forming the one or more compounds of Formula (VIII) comprises reacting the one or more compounds of Formula (X) with a compound of Formula (XI):

$BCl_3$ (XI), to produce the one or more compounds of Formula (VIII).

Another embodiment of the present invention further comprises providing one or more compounds of Formula (XII) having the structure:

(XII)

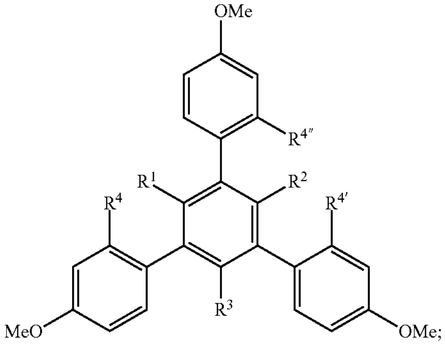

and forming the one or more compounds of Formula (X) from the one or more compounds of Formula (XII).

In accordance with the embodiment, forming the one or more compounds of Formula (X) comprises reacting the one or more compounds of Formula (XII) with a formylating agent to produce the one or more compounds of Formula (X). Suitable formylating agents include, but are not limited to, $DMF/POCl_3$ and paraformaldehyde/$BF_3$.

Another aspect of the present application relates to a method for detecting an analyte in a fluid. This method includes:

providing a sensor comprising a nanocage of Formula (I):

(I)

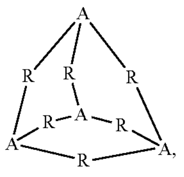

wherein each A is independently selected and has the formula

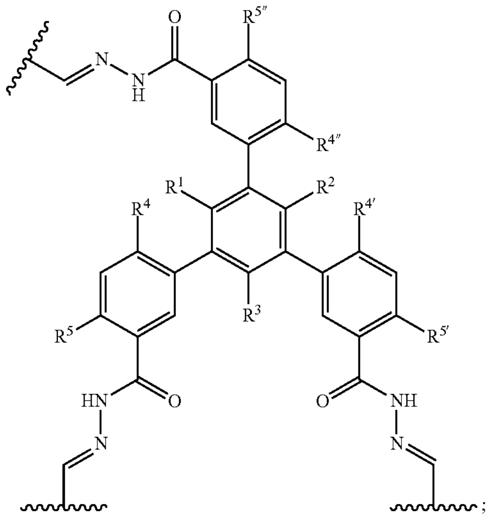

is the point of attachment of A to R;

each R is independently selected and has the formula

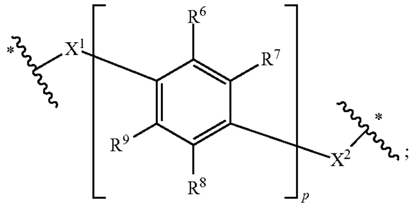

indicates the point of attachment of R to A;

$R^1$, $R^2$, and $R^3$ are each independently selected from the group consisting of H, halogen, OH, $C_{1-20}$ alkyl, $C_{2-20}$ alkenyl, $C_{2-20}$ alkynyl, perfluorinated $C_{1-20}$ alkyl, aryl, hereroaryl, heterocyclyl, —$OC_{1-20}$ alkyl, —$OC_{2-20}$ alkenyl, —$OC_{2-20}$ alkynyl, —O-perfluorinated $C_{1-20}$ alkyl, —Oaryl, —$COOC_{1-20}$ alkyl, —COO perfluorinated $C_{1-20}$ alkyl, —COOaryl, —$CONHC_{1-20}$ alkyl, —$CONHC_{2-20}$ alkenyl, —$CONHC_{2-20}$ alkynyl, —CONH perfluorinated $C_{1-20}$ alkyl, —CONH-aryl, —CONH-heteroaryl, and —CONH-heterocyclyl, wherein each $C_{1-20}$ alkyl, $C_{2-20}$ alkenyl, $C_{2-20}$ alkynyl, perfluorinated $C_{1-20}$ alkyl, aryl, hereroaryl, heterocyclyl, —$OC_{1-20}$ alkyl, —$OC_{2-20}$ alkenyl, —$OC_{2-20}$ alkynyl, —O-perfluorinated $C_{1-20}$ alkyl, —Oaryl, —$COOC_{1-20}$ alkyl, —COO perfluorinated $C_{1-20}$ alkyl, —COOaryl, —$CONHC_{1-20}$ alkyl, —$CONHC_{2-20}$ alkenyl, —$CONHC_{2-20}$ alkynyl, —CONH perfluorinated $C_{1-20}$ alkyl, —CONH-aryl, —CONH-heteroaryl, and —CONH-heterocyclyl can be optionally substituted from 1 to 3 times with a substituent selected from the group consisting of H, halogen, OH, $C_{1-6}$ alkyl, aryl, and arylalkyl;

$R^4$, $R^{4'}$, and $R^{4''}$ are each independently selected from the group consisting of H, halogen, $C_{1-20}$ alkyl, $C_{2-20}$ alkenyl, $C_{2-20}$ alkynyl, perfluorinated $C_{1-20}$ alkyl, aryl, hereroaryl, heterocyclyl, OH, —$OC_{1-20}$ alkyl, —$OC_{2-20}$ alkenyl, —$OC_{2-20}$ alkynyl, —O-perfluorinated $C_{1-20}$ alkyl, —Oaryl, —$COOC_{1-20}$ alkyl, —COO perfluorinated $C_{1-20}$ alkyl, —COOaryl, —$CONHC_{1-20}$ alkyl, —$CONHC_{2-20}$ alkenyl, —$CONHC_{2-20}$ alkynyl, —CONH perfluorinated $C_{1-20}$ alkyl, —CONH-aryl, —CONH-heteroaryl, and —CONH-heterocyclyl, wherein each $C_{1-20}$ alkyl, $C_{2-20}$ alkenyl, alkenyl, —$OC_{2-20}$ alkynyl, —O-perfluorinated $C_{1-20}$ alkyl, —Oaryl, —$COOC_{1-20}$ alkyl, —COO perfluorinated $C_{1-20}$ alkyl, —COOaryl, —$CONHC_{1-20}$ alkyl, —$CONHC_{2-20}$ alkenyl, —$CONHC_{2-20}$ alkynyl, —CONH perfluorinated $C_{1-20}$ alkyl, —CONH-aryl, —CONH-heteroaryl, and —CONH-heterocyclyl can be optionally substituted from 1 to 3 times with a substituent selected from the group consisting of H, halogen, OH, $C_{1-6}$ alkyl, aryl, and arylalkyl;

$R^5$, $R^{5'}$, and $R^{5''}$ are each independently selected from the group consisting of H, halogen, OH, —$O(CH_2)_n$—$(OCH_2CH_2)_m$—$OC_{1-6}$ alkyl, aryl, hereroaryl, heterocyclyl, —$OC_{1-20}$ alkyl, —O-perfluorinated $C_{1-20}$ alkyl, —Oaryl, and —$NR^{10}R^{11}$;

$R^6$, $R^7$, $R^8$, and $R^9$ are each independently selected at each occurrence from the group consisting of H, halogen, $C_{1-20}$ alkyl, $C_{2-20}$ alkenyl, $C_{2-20}$ alkynyl, perfluorinated $C_{1-20}$ alkyl, aryl, hereroaryl, heterocyclyl, OH, —$OC_{1-20}$ alkyl, —$OC_{2-20}$ alkenyl, —O-perfluorinated $C_{1-20}$ alkyl, —$OC_{2-20}$ alkynyl, aryl, heteroaryl, heterocyclyl, and —$COOC_{1-20}$ alkyl, —COO perfluorinated $C_{1-20}$ alkyl, —COOaryl, —$CONHC_{1-20}$ alkyl, —$CONHC_{2-20}$ alkenyl, —$CONHC_{2-20}$ alkynyl, —CONH perfluorinated $C_{1-20}$ alkyl, —CONH-aryl, —CONH-heteroaryl, and —CONH-heterocyclyl, wherein each $C_{1-20}$ alkyl, $C_{2-20}$ alkenyl, $C_{2-20}$ alkynyl, perfluorinated $C_{1-20}$ alkyl, aryl, hereroaryl, heterocyclyl, —$OC_{1-20}$ alkyl, —$OC_{2-20}$ alkenyl, —$OC_{2-20}$ alkynyl, —O-perfluorinated $C_{1-20}$ alkyl, —Oaryl, —$COOC_{1-20}$ alkyl, —COO perfluorinated $C_{1-20}$ alkyl, —COOaryl, —$CONHC_{1-20}$ alkyl, —$CONHC_{2-20}$ alkenyl, —$CONHC_{2-20}$ alkynyl, —CONH perfluorinated $C_{1-20}$ alkyl, —CONH-aryl, —CONH-heteroaryl, and —CONH-heterocyclyl can be optionally substituted from 1 to 3 times with a substituent selected from the group consisting of H, halogen, OH, $C_{1-6}$ alkyl, aryl, and arylalkyl;

$R^{10}$ and $R^{11}$ are each independently selected from the group consisting of H, $C_{1-6}$ alkyl, $C_{2-6}$ alkenyl, $C_{2-6}$ alkynyl, aryl, heteroarylalkyl, heterocyclylalkyl, and arylalkyl, wherein each $C_{1-6}$ alkyl, $C_{2-6}$ alkenyl, $C_{2-6}$ alkynyl, aryl, heteroarylalkyl, heterocyclylalkyl, and arylalkyl can be optionally substituted from 1 to 3 times with a substituent selected from the group consisting of H, $C_{1-6}$ alkyl, heteroarylalkyl, heterocyclylalkyl, and arylalkyl;

$X^1$ and $X^2$ are absent or are independently selected from the group consisting of $C_{1-6}$ alkylene, $C_{3-8}$ cycloalkylene, and arylene, wherein $C_{1-6}$ alkylene, $C_{3-8}$ cycloalkylene, and arylene can be optionally substituted from 1 to 3 times with H or $C_{1-6}$ alkyl;

$X^1$ and $X^2$ are absent or are independently selected from the group consisting of $C_{1-6}$ alkylene, $C_{3-8}$ cycloalkylene, and arylene, wherein $C_{1-6}$ alkylene, $C_{3-8}$ cycloalkylene, and arylene can be optionally substituted from 1 to 3 times with H or $C_{1-6}$ alkyl;

p is 1 to 3;

n is 1 to 10; and m is 1 to 10;

providing a fluid containing an analyte; and contacting a fluid containing the analyte with the sensor to capture the analyte in the nanocage and detect the analyte in the fluid.

In one embodiment, the method further comprises providing a signal generator operatively associated with said sensor, said method further comprising:

producing a signal with the signal generator when said analyte is captured by said sensor.

Suitable analytes that can be detected in accordance with the present application include, but are not limited to, polyvinylpyrrolidone (PVP), poly(isobutylene-alt-n-octyl maleimide) (POI), picrocrocin, curcumin, and components of chinese tea.

According to the present application, the sensor further comprises a substrate having a surface with a layer of the nanocage of Formula (I) covering at least 1% of the surface. Preferably, the layer of the nanocage of Formula (I) covers at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25% of the substrate's surface.

According to the present application, the suitable substrates include paper, plastics (e.g., photoresist materials, acrylic polymers, carbonate polymers, etc.), glass, silicon based materials (e.g., silicon, silicon dioxide, silicon nitride, etc.) and metals.

In one embodiment, the substrate is a paper strip.

In another embodiment, the sensor further comprises a fluorescent polymer.

Suitable fluorescent polymers that can be used according to the present application include, but are not limited to, dye-functionalized glycol polymers (e.g. polyethylene glycol, polypropylene glycol, polybutylene glycol, etc.), polyalkyl-imides (including polyisobutylene-alt-n-octyl imide), and polyacrylates.

In one embodiment, a fluorescent dye is attached to a nanocage of Formula (I). Suitable fluorescent dyes that can be used include, but are not limited to, Cy3-azide, Cy5-azide, Cy3-alkyne, Cy5-alkyne, Azide-fluor 488, Azide-fluor 545, Azide cyanine dye 728, DBCO-Cy3, Azide MegaStokes dye 673.

In another embodiment, a fluorescent dye is attached to an alkylene-containing nanocage of Formula (I) using click chemistry.

In yet another embodiment, the sensor also contains polymers containing fluorescent dies. Suitable polymers that can be used according to the present application include glycol polymers, poly-alkyl-imides, and polyacrylates.

In one embodiment, the method for detecting an analyte in a fluid can provide detection in real time.

In another embodiment, detection of an analyte in a fluid by the sensor will result in a change in color that could be directly observed by a naked eye. Alternatively, the change in color can be observed by applying a light source.

Suitable light sources that can be used in accordance to the present invention include, but are not limited to, light emitting diodes (LED), flash lamps, cold-cathode fluorescent lamps, and electroluminescent lamps. The illumination may be multiplexed and/or collimated. In some cases, the illumination may be pulsed to reduce any background interference. Further, illumination may be continuous or may combine continuous wave (CW) and pulsed illumination where multiple illumination beams are multiplexed (e.g., a pulsed beam is multiplexed with a CW beam), permitting signal discrimination between a signal induced by the CW source and a signal induced by the pulsed source.

In one embodiment, detection of an analyte in a fluid by the sensor will result in a change in color that could be observed by using yellow LED lamp.

According to the present application, qualitative, quantitative, or semi-quantitative determination of the presence or concentration of an analyte may be achieved.

In another embodiment, the color change is concentration-dependent. The higher concentration of the analyte, the bigger is the change in color.

In a further embodiment, the sensor is a nanosensor.

In yet another embodiment, the sensor tests the quality of saffron.

During the manufacture of sensor, a sensor material comprising the nanocage of Formula (I) is placed on the substrate. This sensor material may be deposited, coated, or otherwise applied on the substrate.

Different sensing elements can be deposited in different areas of the substrate to form sensing arrays. Analyte samples of different quality then lead to specific fingerprints of color patterns with the sensing arrays under blue, yellow, green, or red, LED illumination. The color patterns can be recorded with a smartphone camera and analyzed (see, for an example, Kim et al., "Prediction of Key Aroma Development in Coffees Roasted to Different Degrees by Colorimetric Sensor Array," *Food Chem.* 240:808-816 (2018), which is hereby incorporated by reference in its entirety) with standard pattern recognition techniques to determine the sample origin/quality in a semi-quantitative/quantitative manner.

Another aspect of the present application relates to a method of functionalizing a polymer. This method includes:

providing a polymer;

providing a nanocage of Formula (I):

(I)

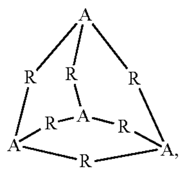

wherein each A is independently selected and has the formula

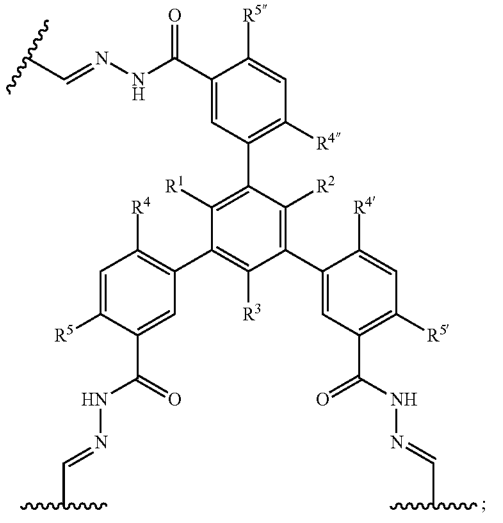

is the point of attachment of A to R;

each R is independently selected and has the formula

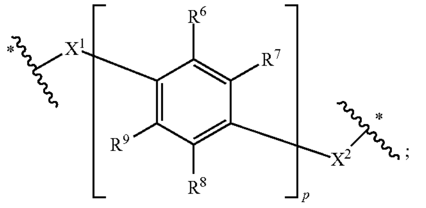

indicates the point of attachment of R to A; $R^1$, $R^2$, and $R^3$ are each independently selected from the group consisting of H, halogen, OH, $C_{1-20}$ alkyl, $C_{2-20}$ alkenyl, $C_{2-20}$ alkynyl, perfluorinated $C_{1-20}$ alkyl, aryl, hereroaryl, heterocyclyl, —$OC_{1-20}$ alkyl, —$OC_{2-20}$ alkenyl, —$OC_{2-20}$ alkynyl, —O-perfluorinated $C_{1-20}$ alkyl, —Oaryl, —$COOC_{1-20}$ alkyl, —COO perfluorinated $C_{1-20}$ alkyl, —COOaryl, —$CONHC_{1-20}$ alkyl, —$CONHC_{2-20}$ alkenyl, —$CONHC_{2-20}$ alkynyl, —CONH perfluorinated $C_{1-20}$ alkyl, —CONH-aryl, —CONH-heteroaryl, and —CONH-heterocyclyl, wherein each $C_{1-20}$ alkyl, $C_{2-20}$ alkenyl, $C_{2-20}$ alkynyl, perfluorinated $C_{1-20}$ alkyl, aryl, hereroaryl, heterocyclyl, —$OC_{1-20}$ alkyl, —$OC_{2-20}$ alkenyl, —$OC_{2-20}$ alkynyl, —O-perfluorinated $C_{1-20}$ alkyl, —Oaryl, —$COOC_{1-20}$ alkyl, —COO perfluorinated $C_{1-20}$ alkyl, —COOaryl, —$CONHC_{1-20}$ alkyl, —$CONHC_{2-20}$ alkenyl, —$CONHC_{2-20}$ alkynyl, —CONH perfluorinated $C_{1-20}$ alkyl, —CONH-aryl, —CONH-heteroaryl, and —CONH-heterocyclyl can be optionally substituted from 1 to 3 times with a substituent selected from the group consisting of H, halogen, OH, $C_{1-6}$ alkyl, aryl, and arylalkyl;

$R^4$, $R^{4'}$, and $R^{4''}$ are each independently selected from the group consisting of H, halogen, $C_{1-20}$ alkyl, $C_{2-20}$ alkenyl, $C_{2-20}$ alkynyl, perfluorinated $C_{1-20}$ alkyl, aryl, hereroaryl, heterocyclyl, OH, —$OC_{1-20}$ alkyl, —$OC_{2-20}$ alkenyl, —$OC_{2-20}$ alkynyl, —O-perfluorinated $C_{1-20}$ alkyl, —Oaryl, —$COOC_{1-20}$ alkyl, —COO perfluorinated $C_{1-20}$ alkyl, —COOaryl, —$CONHC_{1-20}$ alkyl, —$CONHC_{2-20}$ alkenyl, —$CONHC_{2-20}$ alkynyl, —CONH perfluorinated $C_{1-20}$ alkyl, —CONH-aryl, —CONH-heteroaryl, and —CONH-heterocyclyl, wherein each $C_{1-20}$ alkyl, $C_{2-20}$ alkenyl, $C_{2-20}$ alkynyl, perfluorinated $C_{1-20}$ alkyl, aryl, hereroaryl, heterocyclyl, —$OC_{1-20}$ alkyl, —$OC_{2-20}$ alkenyl, —$OC_{2-20}$ alkynyl, —O-perfluorinated $C_{1-20}$ alkyl, —Oaryl, —$COOC_{1-20}$ alkyl, —COO perfluorinated $C_{1-20}$ alkyl, —COOaryl, —$CONHC_{1-20}$ alkyl, —$CONHC_{2-20}$ alkenyl, —$CONHC_{2-20}$ alkynyl, —CONH perfluorinated $C_{1-20}$ alkyl, —CONH-aryl, —CONH-heteroaryl, and —CONH-heterocyclyl can be optionally substituted from 1 to 3 times with a substituent selected from the group consisting of H, halogen, OH, $C_{1-6}$ alkyl, aryl, and arylalkyl;

$R^5$, $R^{5'}$, and $R^{5''}$ are each independently selected from the group consisting of H, halogen, OH, —$O(CH_2)_n$—$(OCH_2CH_2)_m$—$OC_{1-6}$ alkyl, aryl, hereroaryl, heterocyclyl, —$OC_{1-20}$ alkyl, —O-perfluorinated $C_{1-20}$ alkyl, —Oaryl, and —$NR^{10}R^{11}$;

$R^6$, $R^7$, $R^8$, and $R^9$ are each independently selected at each occurrence from the group consisting of H, halogen, $C_{1-20}$ alkyl, $C_{2-20}$ alkenyl, $C_{2-20}$ alkynyl, perfluorinated $C_{1-20}$ alkyl, aryl, hereroaryl, heterocyclyl, OH, —$OC_{1-20}$ alkyl, —$OC_{2-20}$ alkenyl, —O-perfluorinated $C_{1-20}$ alkyl, —$OC_{2-20}$ alkynyl, aryl, heteroaryl, heterocyclyl, and —$COOC_{1-20}$ alkyl, —COO perfluorinated $C_{1-20}$ alkyl, —COOaryl, —$CONHC_{1-20}$ alkyl, —$CONHC_{2-20}$ alkenyl, —$CONHC_{2-20}$ alkynyl, —CONH perfluorinated $C_{1-20}$ alkyl, —CONH-aryl, —CONH-heteroaryl, and —CONH-heterocyclyl, wherein each $C_{1-20}$ alkyl, $C_{2-20}$ alkenyl, $C_{2-20}$ alkynyl, perfluorinated $C_{1-20}$ alkyl, aryl, hereroaryl, heterocyclyl, —$OC_{1-20}$ alkyl, —$OC_{2-20}$ alkenyl, —$OC_{2-20}$ alkynyl, —O-perfluorinated $C_{1-20}$ alkyl, —Oaryl, —$COOC_{1-20}$ alkyl, —COO perfluorinated $C_{1-20}$ alkyl, —COOaryl, —$CONHC_{1-20}$ alkyl, —$CONHC_{2-20}$ alkenyl, —$CONHC_{2-20}$ alkynyl, —CONH perfluorinated $C_{1-20}$ alkyl, —CONH-aryl, —CONH-heteroaryl, and —CONH-heterocyclyl can be optionally substituted from 1 to 3 times with a substituent selected from the group consisting of H, halogen, OH, $C_{1-6}$ alkyl, aryl, and arylalkyl;

$R^{10}$ and $R^{11}$ are each independently selected from the group consisting of H, $C_{1-6}$ alkyl, $C_{2-6}$ alkenyl, $C_{2-6}$ alkynyl, aryl, heteroarylalkyl, heterocyclylalkyl, and arylalkyl, wherein each $C_{1-6}$ alkyl, $C_{2-6}$ alkenyl, $C_{2-6}$ alkynyl, aryl, heteroarylalkyl, heterocyclylalkyl, and arylalkyl can be optionally substituted from 1 to 3 times with a substituent selected from the group consisting of H, $C_{1-6}$ alkyl, heteroarylalkyl, heterocyclylalkyl, and arylalkyl;

$X^1$ and $X^2$ are absent or are independently selected from the group consisting of $C_{1-6}$ alkylene, $C_{3-8}$ cycloalkylene, and arylene, wherein $C_{1-6}$ alkylene, $C_{3-8}$ cycloalkylene, and arylene can be optionally substituted from 1 to 3 times with H or $C_{1-6}$ alkyl;

p is 1 to 3;

n is 1 to 10; and m is 1 to 10;

providing a functionalizing reagent;

reacting the polymer with the functionalizing reagent within the nanocage having a Formula (I) to produce a functionalized polymer.

In one embodiment, one kind of polymer is provided. In another embodiment, a mixture of polydisperse polymers is provided.

Polymers that can be functionalized according to the present invention include, but are not limited to, amine-functionalized polyimides, amine-functionalized glycol polymers, amine-functionalized acrylate polymers, amine-functionalized polyolefins, amine-functionalized polyesters, amine-functionalized polylisocyanates, and amine-functionalized polyamides as well as co-polymers thereof.

In another embodiment, the nanocage of Formula (I) has a void space suitable to receive and functionalize the provided polymer.

According to the present application, functionalization of a polymer can be carried out in any suitable solvent, including, but not limited to deuterated dichloromethane ($CD_2Cl_2$), dichloromethane, deuterated chloroform ($CDCl_3$), chloroform, pentanes, heptanes, octanes, nonanes, acetonitrile, tetrahydrofuran, ethyl acetate, diethyl ether, dipropyl ether, diphenyl ether, tetrachloroethane, carbon tetrachloride, and nitrobenzene, or the mixture thereof.

Functionalization of a polymer can be carried out at room temperature or at an elevated temperature. Preferably, the temperature is below 60° C., below 55° C., below 50° C., below 45° C., below 40° C., below 35° C., below 30° C. More preferably, functionalization of a polymer is carried out at room temperature.

According to the present application, the nanocage of Formula (I) is provided in the amount of 0.01 wt % to 50 wt %. Preferably, the nanocage of Formula (I) is provided in the amount of 0.01 wt % to 50 wt %, 0.1 wt % to 45 wt %, 1 wt % to 40 wt %, 5 wt % to 40 wt %, 10 wt % to 40 wt %, 15 wt % to 40 wt %, 20 wt % to 40 wt %, 25 wt % to 50 wt %, 30 wt % to 40 wt %. More preferably, the nanocage of Formula (I) is provided in the amount of 0.01 wt % to 30 wt %, 0.01 wt % to 20 wt %, 0.01 wt % to 10 wt %, 0.1 wt % to 10 wt %.

In a further embodiment, the functionalizing reagent is selected from the group consisting of nitrophenyl-3,5-dinitrobenzoate and nitrophenyl acetate.

In yet another embodiment, the polymer is acylated.

The above disclosure is general. A more specific description is provided below in the following examples. The examples are described solely for the purpose of illustration and are not intended to limit the scope of the present application. Changes in form and substitution of equivalents are contemplated as circumstances suggest or render expedient. Although specific terms have been employed herein, such terms are intended in a descriptive sense and not for purposes of limitation.

EXAMPLES

The following Examples are presented to illustrate various aspects of the present application, but are not intended to limit the scope of the claimed application.

Example 1—General Methods and Materials

All commercially available starting materials were purchased from Sigma Aldrich, Fisher Scientific, or Oakwood Chemical. Unless notes otherwise, all reagents were used as received without further purification. When needed, tetrahydrofuran (THF), dichloromethane ($CH_2Cl_2$), dimethylformamide (DMF), and toluene were dried using a Glass Contour solvent purification system by SG Water USA, LLC. HPLC grade acetonitrile ($CH_3CN$) and trifluoroacetic acid (TFA) were used as received from Fisher Scientific. Poly(isobutylene-alt-maleic anhydride) was purchased from Sigma Aldrich and Alfa Aesar, respectively. The 5'-(2,4-dimethoxyphenyl)-2,2",4,4"-tetramethoxy-2',4',6'-trimethyl-1,1': 3',1"-terphenyl (Syn-1) was synthesized according to the published (Sharafi et al., "Crystal-Packing-Driven Enrichment of Atropoisomers," Angew. Chem. Int. Ed. 56:7097-7101 (2017), which is hereby incorporated by reference in its entirety) solid-state-amplification protocol. If necessary, air and/or moisture sensitive reactions were carried out under an inert atmosphere of nitrogen. Removal of solvents was accomplished on a Büchi R-210 rotary evaporator and further concentration was attained under a Fisher Scientific Maxima C-Plus vacuum line. Column chromatography was performed manually with Sorbent grade 60 silica with a mesh size between 230-400 using a forced flow of indicated solvents, or automatically with a Teledyne CombiFlash® Rf+ chromatography system. Preparative size exclusion chromatography was performed with columns filled with Bio-Beads™ S—X1 Support (200-400 mesh). DLS measurements were performed on Zetasizer Nano ZPS instrument, using a hellma quartz cuvette (ZEN2112).

All $^1$H-NMR spectra were recorded at 298 K on a Varian Unity Inova 500 (500 MHz) spectrometer or on a Bruker ARX 500 (500 MHz) spectrometer. $^{13}$C-NMR spectra were recorded on a Bruker ARX 500 (125 MHz) spectrometer. Samples for NMR spectroscopy were dissolved in $CDCl_3$, $CD_2Cl_2$, DMSO-d6, or $D_2O$. The spectra were referenced to the residual solvent peak ($CDCl_3$: 7.26 ppm for $^1$H—and 77.16 ppm for $^{13}$C-NMR; $CD_2Cl_2$: 5.32 ppm for $^1$H—and 53.5 ppm for $^{13}$C-NMR), or to tetramethylsilane (TMS, 0.00 ppm for $^1$H—and $^{13}$C-NMR) as the internal standard. Chemical shift values were recorded in parts per million (ppm). Data are reported as follows: chemical shift, multiplicity (s=singlet, d=doublet, t=triplet, q=quartet, m=multiplet, br=broad peak), coupling constants (Hz), and number of protons. FIGS. 42-44 show the 1H and $^{13}$C-NMR spectra of key products and intermediates. FIG. 45 shows the Fourier-transfor infrared (FTIR) spectrum of $NH_2$-POA. FIG. 46 shows the dynamic light scattering (DLS) characterization data for $NH_2$-POA, Short-$NH_2$-POA, and Long-$NH_2$-POA.

Example 2—Synthesis of 15-Bromo-2,5,8,11-tetraoxapentadecane (S2)

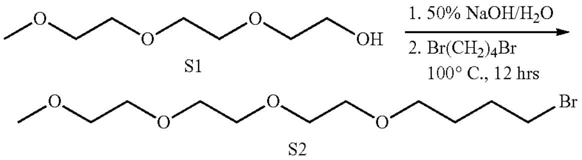

The synthesis of S2 was carried out using conditions reported previously for the synthesis of a similar compound, 18-bromo-2,5,8,11-tetraoxaoctadecane (Chinwangso et al., "Structure, Wettability, and Thermal Stability of Organic Thin-Films on Gold Generated from the Molecular Self- Assembly of Unsymmetrical Oligo (ethylene glycol) Spiroalkanedithiols," *Langmuir* 33:1751-1762 (2017), which is hereby incorporated by reference in its entirety). A mixture of triethylene glycol monomethyl ether ($1, 3.18 g, 19.40 mmol) and an aqueous sodium hydroxide solution (1.6 g in 1.6 mL of water) was stirred at 100° C. under argon for 30 min. The mixture was then added to 1,4-dibromobutane (8.42 g, 39.0 mmol) and the reaction was stirred at 100° C. for 12 hours. Next, the reaction mixture was cooled to room temperature and diluted with 100 ml of water. The resulting solution was extracted with EtOAc (3×75 mL) and the organic phases were combined and washed with water (1×100 mL) and brine (1×100 mL).

The organic layer was dried over anhydrous $MgSO_4$, filtered, and evaporated to dryness. Purification of the crude product was performed by column chromatography over silica gel (eluent: 0 to 50 vol-% EtOAc in hexanes) to afford S2 (3.38 g, 14.750 mmol) as a colorless oil in 58% yield. $^1$H-NMR (500 MHz, $CDCl_3$) δ 3.68-3.61 (m, 8H), 3.56 (ddd, J=14.6, 6.1, 3.0 Hz, 4H), 3.49 (t, J=6.3 Hz, 2H), 3.43 (t, J=6.8 Hz, 2H), 3.37 (s, 3H), 1.98-1.90 (m, 2H), 1.76-1.67 (m, 2H). $^{13}$C-NMR (125 MHz, $CDCl_3$) δ 72.2, 70.8, 70.8, 70.5, 70.4, 59.3, 34.0, 29.9, 28.4. HRMS (ESI) calcd. for $C_{11}H_{24}BrO_4$: m/z=299.0858 $[M+H]^+$; found: 299.0858.

Example 3—Synthesis of Syn-(1'r,3's)-4,4"-bis((2,5,8,11-tetraoxapentadecan-15-yl)oxy)-5'-(4-((2,5,8,11-tetraoxapentadecan-15-yl)oxy)-5-(hydrazinecarbonyl)-2-methoxyphenyl)-6,6"-dimethoxy-2',4',6'-trimethyl-[1,1': 3',1"-terphenyl]-3,3"-dicarbohydrazide (Syn-4,4"-bis((2,5,8,11-tetraoxapentadecan-15-yl)oxy)-5'-(4-((2,5,8,11-tetraoxapentadecan-15-yl)oxy)-5-(hydrazinecarbonyl)-2-methoxyphenyl)-6,6"-dimethoxy-2',4',6'-trimethyl-[1,1': 3',1"-terphenyl]-3,3"-dicarbohydrazide) (Syn-7)

Synthesis of Syn-(1S,3'S)-5'-((R)-5-formyl-2,4-dimethoxyphenyl)-4,4",6,6"-tetramethoxy-2',4',6'-trimethyl-[1,1': 3',1"-terphenyl]-3,3"-dicarbaldehyde (Syn-5'-((R)-5-formyl-2,4-dimethoxyphenyl)-4,4",6,6"-tetramethoxy-2',4',6'-trimethyl-[1,1': 3',1"-terphenyl]-3,3"-dicarbaldehyde) (Syn-2)

Syn-1 (0.71 g, 1.345 mmol) was dissolved in anhydrous DMF (37 mL) followed by the dropwise addition of $POCl_3$ (6.0 mL) at 0° C. The reaction mixture was warmed to room temperature and left stirring. After 20 hours, the reaction was quenched by adding 10 mL of a 1 N aqueous NaOH solution. The precipitated solid was filtered and washed with deionized water to afford syn-2 (0.815 g, 1.330 mmol) as a colorless solid in 98% yield. $^1$H-NMR (500 MHz, $CDCl_3$) δ 10.30 (s, 3H), 7.54 (s, 3H), 6.52 (s, 3H), 3.99 (s, 9H), 3.86 (s, 9H), 1.65 (s, 9H). $^{13}$C-NMR (125 MHz, $CDCl_3$) δ 188.3, 163.2, 162.9, 135.1, 134.5, 132.7, 123.6, 118.7, 94.8, 55.9, 55.8, 18.8. HRMS (ESI) calcd. for $C_{36}H_{37}O_9$: m/z=613.2438 $[M+H]^+$; found: 613.2441.

Synthesis of Syn-(1'r,3's)-5'-(5-formyl-4-hydroxy-2-methoxyphenyl)-4,4"-dihydroxy-6,6"-dimethoxy-2',4',6'-trimethyl-[1,1': 3',1"-terphenyl]-3,3"-dicarbaldehyde (Syn-5'-(5-formyl-4-hydroxy-2-methoxyphenyl)-4,4"-dihydroxy-6,6"-dimethoxy-2',4',6'-trimethyl-[1,1': 3',1"-terphenyl]-3,3"-dicarbaldehyde) (Syn-3)

Syn-2 (0.815 g, 1.330 mmol) was dissolved in 40 mL of anhydrous $CH_2Cl_2$. A 1 M $BCl_3$ solution in $CH_2Cl_2$ (20.0 mL) was then added dropwise to the reaction mixture under an argon atmosphere. After stirring at room temperature for 24 hours, 15 mL of $H_2O$ was added to quench the reaction mixture. The resulting biphasic mixture was extracted with $CH_2Cl_2$, the combined organic layers were dried over anhydrous $MgSO_4$, and concentrated under reduced pressure. The crude product was purified by flash column chromatography over silica gel (eluent: 0 to 30 vol-% EtOAc in $CH_2Cl_2$) to afford syn-3 (0.68 g, 1.190 mmol) as a colorless solid in 89% yield. $^1$H-NMR (500 MHz, $CDCl_3$) δ 11.51 (s, 3H), 9.71 (s, 3H), 7.21 (s, 3H), 6.55 (s, 3H), 3.85 (s, 9H), 1.71 (s, 9H). $^{13}$C-NMR (125 MHz, $CDCl_3$) δ 194.4, 164.4, 163.9, 135.9, 135.5, 134.3, 123.5, 115.0, 99.4, 56.1, 18.8. HRMS (ESI) calcd. for $C_{33}H_{31}O_9$: m/z=571.1968 $[M+H]^+$; found: 571.1970.

Synthesis of Syn-(1'r,3's)-4,4"-bis((2,5,8,11-tetraoxapentadecan-15-yl)oxy)-5'-(4-((2,5,8,11-tetraoxapentadecan-15-yl)oxy)-5-formyl-2-methoxyphenyl)-6,6"-dimethoxy-2',4',6'-trimethyl-[1,1': 3',1"-terphenyl]-3,3"-dicarbaldehyde (Syn-4,4"-bis((2,5,8,11-tetraoxapentadecan-15-yl)oxy)-5'-(4-((2,5,8,11-tetraoxapentadecan-15-yl)oxy)-5-formyl-2-methoxyphenyl)-6,6"-dimethoxy-2',4',6'-trimethyl-[1,1': 3',1"-terphenyl]-3,3"-dicarbaldehyde) (Syn-4)

Syn-3 (0.68 g, 1.190 mmol), 15-bromo-2,5,8,11-tetraoxapentadecane (S2, 2.69 g, 7.140 mmol), and $K_2CO_3$ (1.38 g, 10.0 mmol) were added to a round-bottomed flask containing anhydrous DMF (15 mL) and the reaction mixture was stirred at 40° C. for 72 hours. Then, the reaction mixture was quenched by adding 50 mL of a 1 M aqueous HCl solution. The aqueous layer was extracted with $CH_2Cl_2$ (3×30 mL) and the combined organic layers were washed with brine (4×75 mL), dried over anhydrous $MgSO_4$, filtered, and evaporated under reduced pressure. Excess S2 was removed by column chromatography (eluent: 10 vol-% MeOH in $CH_2Cl_2$) to afford syn-4 (1.24 g, 1.012 mmol) as a yellow oil in 85% yield. $^1$H-NMR (500 MHZ, $CDCl_3$) δ 10.34 (s, 3H), 7.53 (s, 3H), 6.50 (s, 3H), 4.14 (t, J=6.2 Hz, 6H), 3.83 (s, 9H), 3.65-3.52 (m, 42H), 3.36 (s, 9H), 1.96 (m, 6H), 1.81 (m, 6H), 1.63 (s, 9H). $^{13}$C-NMR (125 MHZ, $CDCl_3$) δ 188.0, 163.1, 162.5, 134.9, 134.4, 131.7, 123.5, 118.5, 95.4, 71.9, 70.7, 70.6, 70.5, 70.4, 70.1, 68.4, 58.9, 55.8, 26.2, 26.0, 18.6. HRMS (ESI) calcd. for $C_{66}H_{97}O_{21}$: m/z=1225.6522 $[M+H]^+$; found: 1225.6537.

Synthesis of Syn-(1'r,3's)-4,4"-bis((2,5,8,11-tetraoxapentadecan-15-yl)oxy)-5'-(4-((2,5,8,11-tetraoxapentadecan-15-yl)oxy)-5-carboxy-2-methoxyphenyl)-6,6"-dimethoxy-2',4',6'-trimethyl-[1,1': 3',1"-terphenyl]-3,3"-dicarboxylic acid (Syn-4,4"-bis((2,5,8,11-tetraoxapentadecan-15-yl)oxy)-5'-(4-((2,5,8,11-tetraoxapentadecan-15-yl)oxy)-5-carboxy-2-methoxyphenyl)-6,6"-dimethoxy-2',4',6'-trimethyl-[1,1': 3',1"-terphenyl]-3,3"-dicarboxylic acid) (Syn-5)

Syn-4 (1.24 g, 1.010 mmol) was dissolved in a 1:1 $CH_3CN$/DMSO mixture (56 mL total volume) in a 250 mL round-bottomed flask. Next, a solution of $NaH_2PO_4$ (1.2 g, 10 mmol) and $NaClO_2$ (0.9 g, 10 mmol) in 13 mL deionized water was added to the reaction mixture. After stirring at room temperature for 48 hours, the $CH_3CN$ was evaporated under reduced pressure and the reaction mixture was quenched by adding 30 mL of a 1 N aqueous HCl solution. Next, the water layer was extracted with $CH_2Cl_2$ (4×20 mL)

and the combined organic phases were washed with brine (4×100 mL). After drying over anhydrous $MgSO_4$, the solvent was removed in vacuo and syn-5 (1.03 g, 0.810 mmol) was obtained as a yellow oil in 81% yield. $^1$H-NMR (500 MHZ, $CDCl_3$) δ 7.87 (s, 3H), 6.58 (s, 3H), 4.31 (t, J=6.5 Hz, 6H), 3.83 (s, 9H), 3.67-3.52 (m, 42H), 3.37 (s, 9H), 2.04 (m, J=8.5, 6.6 Hz, 6H), 1.82 (m, J=8.9, 6.2 Hz, 6H), 1.64 (s, 9H). $^{13}$C-NMR (125 MHz, $CDCl_3$) δ 165.2, 161.9, 158.5, 136.7, 135.0, 134.3, 124.7, 110.5, 96.1, 72.0, 70.7, 70.7, 70.6, 70.6, 70.5, 70.2, 70.2, 59.1, 56.0, 26.2, 26.1, 18.8. HRMS (ESI) calcd. for $C_{66}H_{97}O_{24}$: m/z=1273.6370 $[M+H]^+$; found: 1273.6377.

Synthesis of Syn-dimethyl (1's,5'r)-4,4"-bis((2,5,8,11-tetraoxapentadecan-15-yl)oxy)-5'-(4-((2,5,8,11-tetraoxapentadecan-15-yl)oxy)-2-methoxy-5-(methoxycarbonyl)phenyl)-6,6"-dimethoxy-2',4',6'-trimethyl-[1,1': 3',1"-terphenyl]-3,3"-dicarboxylate (Syn-dimethyl-4,4"-bis((2,5,8,11-tetraoxapentadecan-15-yl)oxy)-5'-(4-((2,5,8,11-tetraoxapentadecan-15-yl)oxy)-2-methoxy-5-(methoxycarbonyl)phenyl)-6,6"-dimethoxy-2',4',6'-trimethyl-[1,1': 3',1"-terphenyl]-3,3"-dicarboxylate) (Syn-6)

MeOH (40 mL) was added to syn-5 (1.030 g, 0.810 mmol) in a 100 mL round-bottomed flask, followed by the dropwise addition of concentrated $H_2SO_4$ (1.0 mL). The reaction mixture was stirred under reflux for 24 hours. After evaporation of MeOH under reduced pressure, 1 N aqueous NaOH (10 mL) was added and the product was extracted from the aqueous layer using $CH_2Cl_2$ (2×20 mL). Next, the combined organic layers were dried over anhydrous $MgSO_4$, filtered, and the solvent was removed in vacuo. The resulting brown oil was purified by column chromatography over silica gel (eluent: 15 vol-% MeOH in $CH_2Cl_2$) to afford syn-6 (0.745 g, 0.567 mmol) as a yellow oil in 70% yield. $^1$H-NMR (500 MHZ, $CDCl_3$) δ 7.60 (s, 3H), 6.53 (s, 3H), 4.11 (t, J=6.3 Hz, 6H), 3.83 (s, 9H), 3.80 (s, 9H), 3.67-3.52 (m, 42H), 3.37 (s, 9H), 1.96 (m, 6H), 1.85 (m, 6H), 1.66 (s, 9H). $^{13}$C-NMR (125 MHZ, $CDCl_3$) δ 166.2, 161.2, 160.3, 135.3, 135.2, 134.8, 122.8, 112.0, 97.0, 72.0, 71.0, 70.7, 70.7, 70.6, 70.1, 68.9, 59.1, 55.7, 51.6, 26.3, 26.2, 18.8. HRMS (ESI) calcd. for $C_{69}H_{106}NO_{24}$: m/z=1332.7128 $[M+NH_4]^+$; found: 1332.7105.

Synthesis of Syn-(1'r,3's)-4,4"-bis(2,5,8,11-tetraoxapentadecan-15-yl)oxy)-5'-(4-((2,5,8,11-tetraoxapentadecan-15-yl)oxy)-5-(hydrazinecarbonyl)-2-methoxyphenyl) ~6,6"-dimethoxy-2',4',6'-trimethyl-[1,1': 3',1"-terphenyl]-3,3"-dicarbohydrazide (Syn-4, 4"-bis((2,5,8,11-tetraoxapentadecan-15-yl)oxy)-5'-(4-((2,5,8,11-tetraoxapentadecan-15-yl)oxy)-5-(hydrazinecarbonyl)-2-methoxyphenyl)-6,6"-dimethoxy-2',4',6'-trimethyl-[1,1': 3',1"-terphenyl]-3,3"-dicarbohydrazide) (Syn-7)

Syn-6 (0.745 g, 0.567 mmol) was dissolved in 45 mL of a 1:2 THF/MeOH mixture in a 250 mL sealed heavy-wall glass reaction vessel. Next, the solution was degassed with argon and hydrazine monohydrate (9.0 mL) was added. After heating at 65° C. for 48 hours under argon atmosphere, the solvent was evaporated under reduced pressure (under a nitrogen atmosphere) and the resulting mixture was extracted with $CH_2Cl_2$. The combined organic layers were washed with water (3×60 mL), dried over $MgSO_4$, filtered, concentrated under reduced pressure, and dried in vacuo to afford syn-7 (0.567 g, 0.431 mmol) as a yellow oil in 76% yield. $^1$H-NMR (500 MHZ, $CDCl_3$) δ 8.79 (s, 3H), 7.92 (s, 3H), 6.52 (s, 3H), 4.19 (t, J=6.6 Hz, 6H), 3.77 (s, 9H), 3.68-3.52 (m, 42H), 3.36 (s, 10H), 2.04-1.96 (m, 6H), 1.80 (m, 6H), 1.65 (s, 9H). $^{13}$C-NMR (125 MHz, $CDCl_3$) δ 166.0, 160.0, 157.0, 134.5, 134.2, 123.4, 112.3, 95.8, 71.5, 70.2, 70.2, 70.2, 70.1, 69.8, 68.7, 58.6, 55.5, 25.9, 25.8, 18.4. HRMS (ESI) calcd. for $C_{66}H_{103}N_6O_{21}$: m/z=1315.7176 $[M+H]^+$; found: 1315.7200.

Example 4—Synthesis of Tet-1

Syn-7 (0.274 g, 0.208 mmol) was dissolved in 350 mL of anhydrous $CH_2Cl_2$, and the solution was degassed with argon. Next, terephthalaldehyde (0.0419 g, 0.312 mmol) and HPLC grade TFA (24 μL, 0.313 mmol) were added consecutively, and the reaction mixture was stirred at room temperature under an argon atmosphere. After 48 hours, the acid was neutralized with a saturated aqueous sodium bicarbonate solution (10 mL), the organic layer was separated, and the aqueous phase extracted with additional $CH_2Cl_2$ (30 mL). Finally, the combined organic extracts were washed with brine, dried over anhydrous $Na_2SO_4$, filtered, and concentrated under reduced pressure. The crude product was purified by size exclusion chromatography over polystyrene beads (200-400 mesh) with $CH_2Cl_2$ as the eluent to afford Tet-1 (0.242 g, 0.0416 mmol) as an orange-yellow solid in 80% yield. $^1$H-NMR (500 MHZ, $CD_2Cl_2$) δ 11.08 (s, 12H), 8.26 (s, 12H), 7.99 (s, 12H), 7.84 (s, 24H), 6.64 (s, 12H), 4.33 (t, J=6.6 Hz, 24H), 3.89 (s, 36H), 3.63-3.44 (m, 168H), 3.29 (s, 36H), 2.16-2.08 (m, 24H), 1.88 (m, 24H), 1.67 (s, 36H). $^{13}$C-NMR (125 MHz, $CD_2Cl_2$) δ 162.0, 161.2, 157.9, 146.6, 136.5, 135.7, 135.5, 135.1, 128.3, 124.6, 113.7, 96.4, 72.4, 71.1, 71.0, 71.0, 71.0, 70.9, 70.8, 70.1, 59.1, 56.3, 26.9, 26.9, 19.0. HRMS (ESI) calcd. for $C_{312}H_{425}N_{24}O_{84}Na$: m/z=1170.9964 $[M+5H]^{5+}$; found: 1170.9982.

Example 5—Synthesis of Amine-Functionalized Poly(isobutylene-alt-n-octyl maleamide) ($NH_2$-POA)

Poly(isobutylene-alt-maleic anhydride) ($\overline{M}_w$=6 kDa, 0.500 g, 0.083 mmol of polymer, 3.237 mmol of anhydride units) was dissolved in anhydrous DMF (1.0 mL) while heating at 85° C. In a different vial, n-octylamine (0.378 g, 2.925 mmol) was dissolved in anhydrous DMF (1.0 mL) at the same temperature. Next, the octylamine solution was added to the polymer solution and the reaction mixture was stirred at 89° C. for 24 hours. The temperature was then increased to 125° C. for 2 hours under a stream of dry $N_2$ to remove the water formed in the condensation reaction. Finally, the temperature was increased further to 170° C. and the reaction mixture stirred for another hour at that temperature under a stream of dry $N_2$ to obtain an orange oil. Next, the crude sample (739.85 mg, 0.0706 mmol) was dissolved in anhydrous DMF (2.0 mL), followed by addition of excess 1,6-diaminohexane (75 mg, 0.64 mmol) and the reaction mixture was heated at 71° C. for 45 hours. The temperature was increased to 95° C. and the solvent was evaporated over dry $N_2$ for 2 hours. Finally, the crude reaction mixture was purified by size exclusion chromatography over polystyrene beads (200-400 mesh) with $CH_2Cl_2$ as the eluent to afford $NH_2$-POA as a yellow viscous solid (773 mg, 0.0515 mmol) in 73% yield. Based on elemental analysis, the percentages (defined in Scheme 3) of repeating units a, b, and c were (with 2.2% crystal water): a=57.8%, b=17.8%, and c=22.2%. $^1$H-NMR (500 MHZ, $CD_2Cl_2$) δ 3.70-2.10 (broad m, ~102H), 1.80-0.60 (broad m, ~490H).

Figure 17:
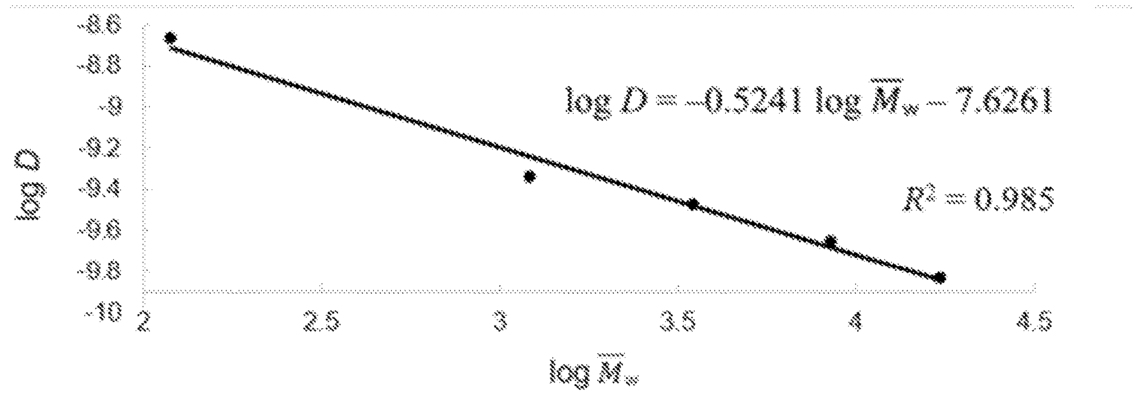
FIG. 17 is a polystyrene calibration curve obtained in $CDCl_3$. The corresponding diffusion constants and molecular weights ($\overline{M}_w$) are listed in Table 1.

IR (KBr) $v_{OH}$ of COOH and $v_{NH}$ of CONH/cm$^{-1}$: broad at 3315.6. DOSY-$^1$H-NMR (500 MHZ, $CDCl_3$, polystyrene standard, see FIG. 17 for the calibration curve): $\overline{M}_w$=6.3 kDa. DLS ($CH_2Cl_2$): PDI=1.5. Anal. calcd. for ($C_{16}H_{29}NO_3$) 12.1 ($C_{22}H_{43}N_3O_2$) 3.7 ($C_{24}H_{46}N_2O_2$)$_{4.7}$·0.5$H_2O$: C, 67.77; H, 10.84; N, 6.39. Found: C, 67.80; H, 11.22; N, 5.99.

Example 6—Isolation of Short and Long Amine-Functionalized Poly(isobutylene-alt-n-octyl Maleamide) (Short-$NH_2$-POA and Long-$NH_2$-POA)

Analytical samples of the shortest (Short-$NH_2$-POA, $\overline{M}_w$ (DOSY)=2.6 kDa) and longest (Long-$NH_2$-POA, $\overline{M}_w$ (DOSY)=9.9 kDa) polymer chains in the $NH_2$-POA sample were obtained by running a second size exclusion column over polystyrene beads (200-400 mesh) with $CH_2Cl_2$ as the eluent. Based on elemental analysis, the percentages (defined in Scheme 3) of repeating units a, b, and c were: a=50.9%, b=12.0%, and c=34.7% (with 2.4% crystal water) for Short-$NH_2$-POA and a=48.7%, b=5.0%, and c=43.6% (with 2.7% crystal water) for Long-$NH_2$-POA.

Characterization data for Short-$NH_2$-POA. $^1$H-NMR (500 MHZ, $CD_2Cl_2$) δ 3.70-2.30 (broad m, ~46H), 2.20-0.50 (broad m, ~220H). DOSY-$^1$H-NMR (500 MHZ, $CDCl_3$, polystyrene standard, see FIG. 17 for the calibration curve): $\overline{M}_w$=2.6 kDa. DLS ($CH_2Cl_2$): PDI=1.3. Anal. calcd. for ($C_{16}H_{29}NO_3$) 4.6 ($C_{22}H_{43}N_3O_2$) 1.1 ($C_{24}H_{46}N_2O_2$)$_{3.1}$·0.2$H_2O$: C, 68.14; H, 10.96; N, 6.30. Found: C, 68.13; H, 11.09; N, 6.33.

Characterization data for Long-$NH_2$-POA. $^1$H-NMR (500 MHZ, $CD_2Cl_2$) δ 3.60-2.20 (broad m, ~162H), 1.70-0.70 (broad m, ~854H). DOSY-$^1$H-NMR (500 MHZ, $CDCl_3$, polystyrene standard, see FIG. 17 for the calibration curve): $\overline{M}_w$=9.9 kDa; DLS ($CH_2Cl_2$): PDI=1.5 Anal. calcd. for ($C_{16}H_{29}NO_3$) 16.1 ($C_{22}H_{43}N_3O_2$) 1.6 ($C_{24}H_{46}N_2O_2$)$_{14.4}$·0.9$H_2O$: C, 68.34; H, 11.01; N, 6.05. Found: C, 68.36; H, 11.34; N, 5.77.

Example 7—Synthesis of N'-Benzylidene-2,4-bis(hexyloxy)benzohydrazide (Control)

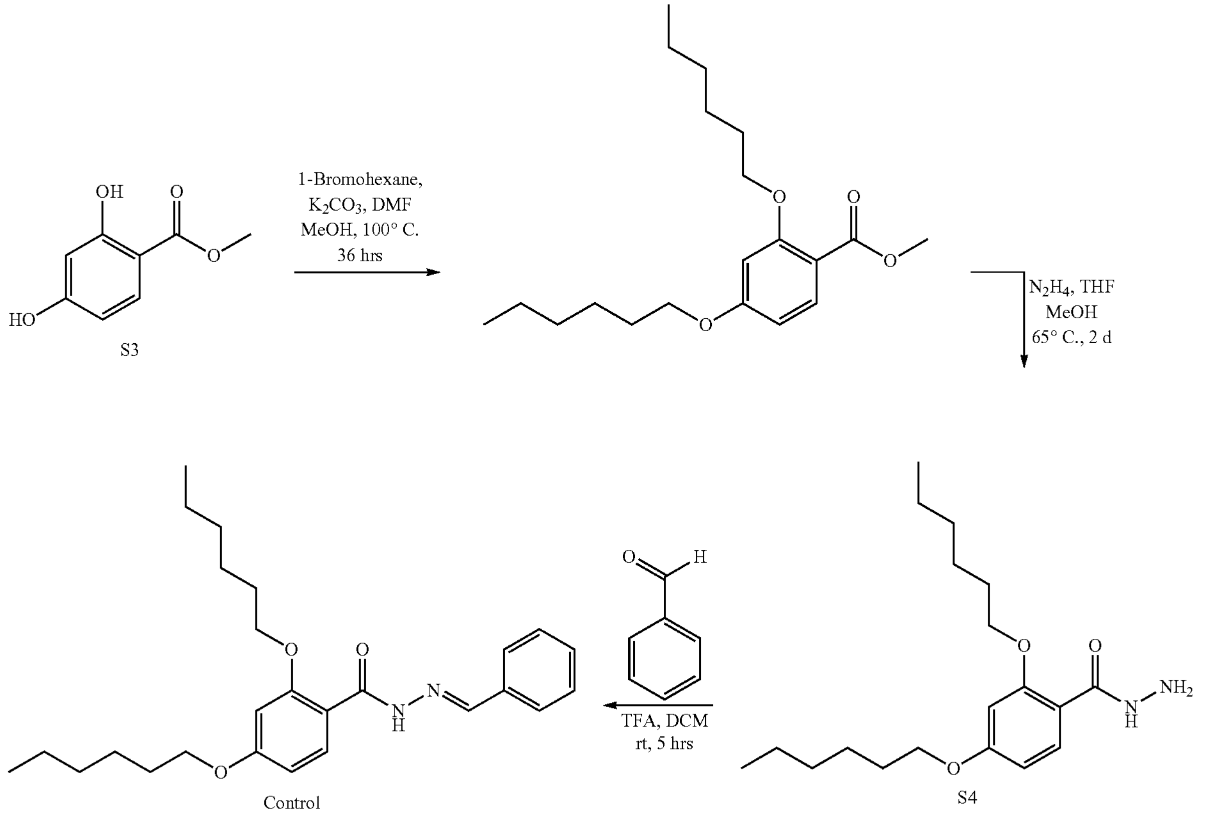

S3

S4

Control

Synthesis of 2,4-Bis(hexyloxy)benzohydrazide (S4)

Methyl 2,4-dihydroxybenzoate (S3, 10.00 g, 59.50 mmol), $K_2CO_3$ (25.00 g, 181.0 mmol), and 25.5 mL bromohexane (30.00 g, 178.0 mmol) were dissolved in a mixture of DMF and MeOH (12:1 volume ratio, 13 mL total volume) in a round-bottomed flask and the resulting solution was heated to 100° C. for 36 hours. Afterwards, the reaction mixture was cooled to room temperature and hexanes (300 mL) as well as a 1 N aqueous NaOH solution (100 mL) were added. The hexane layer was washed with 1 N aqueous NaOH (4x30 mL) and the combined organic fractions were dried over anhydrous $Na_2SO_4$, filtered, and evaporated to dryness under reduced pressure to afford a colorless oil.

The obtained colorless oil (0.20 g, 0.590 mmol) was dissolved in a mixture of THF and MeOH (1:2 volume ratio, 7.5 mL total volume) in a 12 mL sealed reaction vial. The reaction mixture was degassed with argon and hydrazine monohydrate (2 mL) was added. After heating to 63° C. for 48 hours, the solvent was evaporated under reduced pressure under a $N_2$ atmosphere. The resulting solid was purified with preparative TLC over silica gel (eluent: 25 vol-% EtOAc in $CH_2Cl_2$), to afford S4 (68 mg, 0.20 mmol) as a yellow solid in 34% yield over two steps. $^1$H-NMR (500 MHZ, $CDCl_3$) δ 8.87 (s, 1H), 8.14 (d, J=8.7 Hz, 1H), 6.58 (dd, J=8.8, 2.2 Hz, 1H), 6.46 (d, J=2.3 Hz, 1H), 4.08 (t, J=6.7 Hz, 2H), 3.99 (t, J=6.5 Hz, 2H), 1.88 (m, 2H), 1.78 (m, 2H), 1.64-1.31 (m, 12H), 0.91 (td, J=6.9, 3.6 Hz, 6H). $^{13}$C-NMR (125 MHz, $CDCl_3$) δ 167.0, 163.4, 158.6, 133.9, 113.0, 106.2, 100.2, 100.0, 69.4, 68.6, 31.9, 31.7, 29.4, 29.3, 26.1, 26.0, 22.9, 14.3. HRMS (ESI) calcd. for $C_{19}H_{32}N_2O_3$: m/z=337.2491 $[M+H]^+$; found: 337.2495.

Synthesis of Control

S4 (24.3 mg, 0.072 mmol) was dissolved in anhydrous $CH_2Cl_2$ (6 mL) in a 12 mL sealed reaction vial. The solution was degassed with argon and excess benzaldehyde (5.85 mg, 0.144 mmol) was added. Next, HPLC grade TFA (3 μL, 0.015 mmol) was pipetted into the reaction mixture, which was then stirred at room temperature for 5 hours. Afterwards, the acid was neutralized with a saturated sodium bicarbonate solution and the aqueous layer was extracted with $CH_2Cl_2$. The combined organic extracts were washed with brine, dried over anhydrous $Na_2SO_4$, filtered, and concentrated under reduced pressure. The crude product was purified with preparative TLC over silica gel (eluent: 10 vol-% EtOAc in $CH_2Cl_2$) to afford Control (18.37 mg, 0.043 mmol) as a white solid in 60% yield. $^1$H-NMR (500 MHZ, $CDCl_3$) δ 10.97 (s, 1H), 8.27 (d, J=8.8 Hz, 1H), 8.11 (s, 1H), 7.84-7.71 (m, 2H), 7.45-7.35 (m, 3H), 6.62 (dd, J=8.9, 2.2 Hz, 1H), 6.49 (d, J=2.2 Hz, 1H), 4.17 (t, J=6.4 Hz, 2H), 4.01 (t, J=6.5 Hz, 2H), 2.04-1.93 (m, 2H), 1.85-1.73 (m, 2H), 1.65-1.28 (m, 12H), 0.92 (td, J=7.0, 3.6 Hz, 6H). $^{13}$C-NMR (125 MHZ, $CDCl_3$) δ 163.6, 162.2, 158.2, 146.8, 134.6, 134.2, 130.3, 128.7, 127.7, 113.2, 106.4, 99.9, 69.5, 68.5, 31.7, 31.7, 29.4, 29.2, 26.2, 25.8, 22.8, 22.7, 14.2, 14.1. HRMS (ESI) calcd. for $C_{26}H_{36}N_2O_3$: m/z=425.2804 $[M+H]^+$; found: 425.2813.

Example 8—Synthesis of Nitrophenyl-3,5-dinitrobenzoate (NDB)

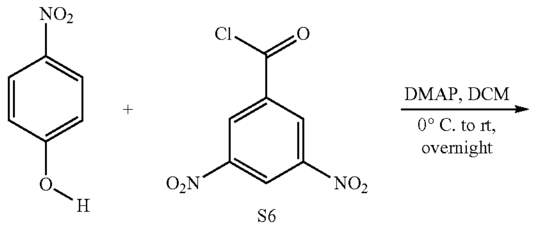

S5 S6

-continued

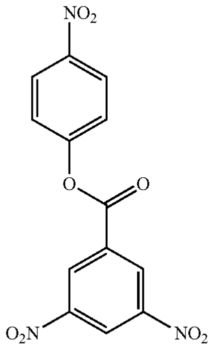

NDB

To a solution of p-nitrophenol (S5, 50 mg, 0.359 mmol) in anhydrous $CH_2Cl_2$ (10 mL) was added 4-(dimethylamino) pyridine (DMAP, 44 mg, 0.359 mmol) and the resulting mixture was stirred under an argon atmosphere at 0° C. for 30 minutes. Next, a solution of 3,5-dinitrobenzoyl chloride (S6, 82.86 mg, 0.359 mmol) in anhydrous $CH_2Cl_2$ (10 mL) was added slowly at 0° C. and the reaction mixture was stirred overnight at room temperature. The reaction mixture was quenched with a 10% aqueous HCl solution, extracted with $CH_2Cl_2$, and the combined organic phases were washed with brine (3×5 mL), dried over anhydrous $Na_2SO_4$, filtered, and evaporated to dryness under reduced pressure to yield NDB. The crude product was purified with flash chromatography over silica gel (eluent: 20 vol-% hexanes in $CH_2Cl_2$) in to afford NDB (145 mg, 0.345 mmol) in 96% yield. $^1$H-NMR (500 MHZ, $CDCl_3$) δ 9.39-9.30 (m, 3H), 8.43-8.31 (m, 2H), 7.52-7.47 (m, 2H). $^{13}$C-NMR (125 MHZ, $CDCl_3$) δ 160.5, 154.577560, 149.1, 146.3, 132.4, 130.1, 125.8, 123.60, 122.4. NDB was unstable in the mass spectrometer. For this reason, NDB was derivatized to obtain a high-resolution mass spectrum, by reacting it with n-octylamine to form 3,5-dinitro-N-octylbenzamide.

Characterization data for 3,5-dinitro-N-octylbenzamide: $^1$H-NMR (500 MHZ, $CDCl_3$) δ 9.18 (t, J=2.1 Hz, 1H), 8.97 (d, J=2.1 Hz, 2H), 3.52 (m, J=7.4, 5.8 Hz, 2H), 1.71-1.61 (m, 2H), 1.42-1.23 (m, 10H), 0.89-0.83 (m, 3H). $^{13}$C-NMR (125 MHZ, $CDCl_3$) δ 162.9, 148.7, 138.3, 127.3, 121.0, 41.02, 31.9, 29.5, 29.36, 29.3, 27.1, 22.7, 14.2. HRMS (ESI) calcd. for $C_{69}H_{73}N_6O_{12}$: m/z=322.1403 $[M-H]^+$; found: 322.1407.

Example 9—Synthesis of Edge-Model

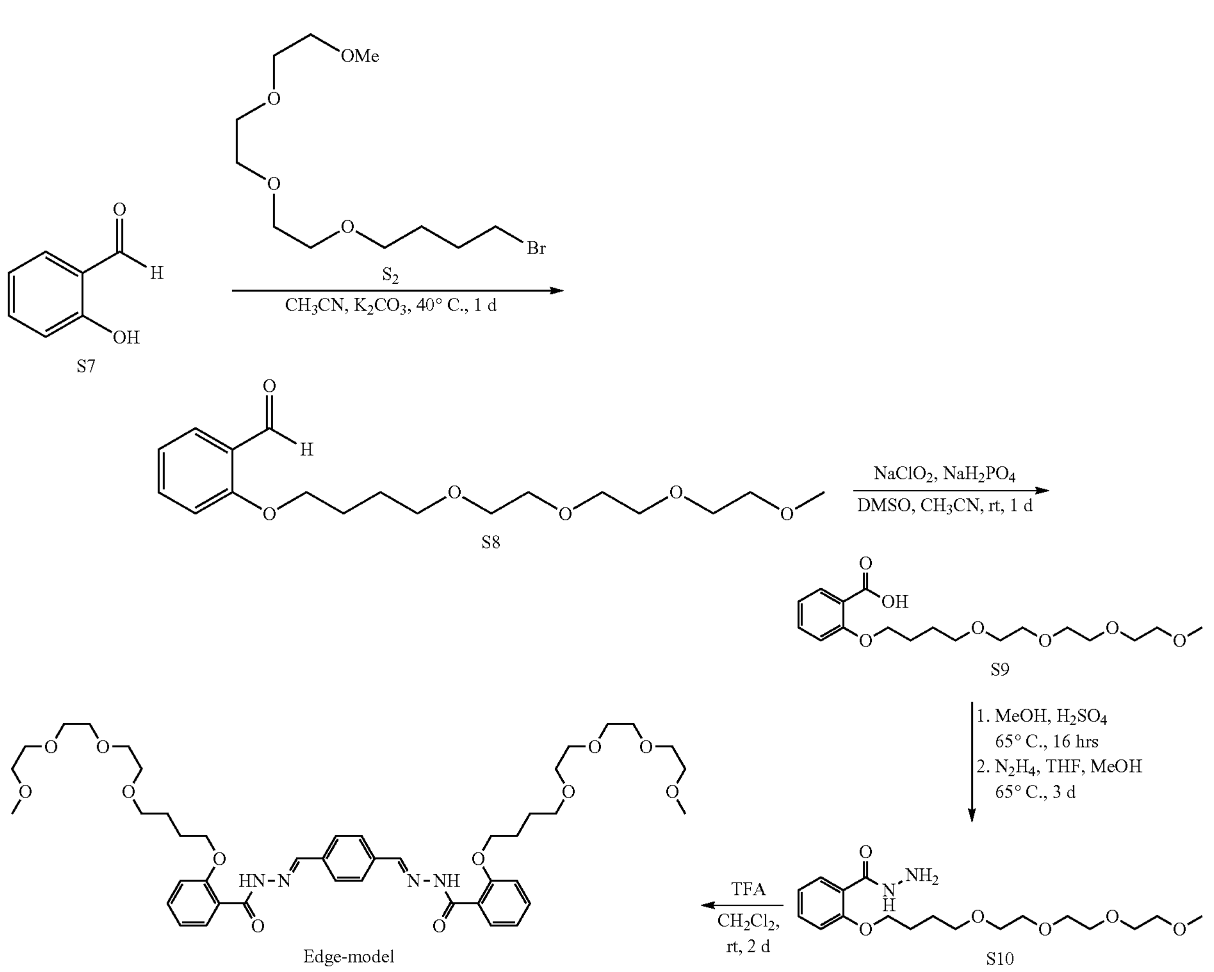

Synthesis of 2-((2,5,8,11-Tetraoxapentadecan-15-yl) oxy)benzaldehyde (S8)

In a round-bottomed flask, 2-hydroxybenzaldehyde (S7, 500 mg, 4.09 mmol), $K_2CO_3$ (1.24 g, 9.01 mmol), and S2 (2.7 g, 9.01 mmol) were dissolved in 25 mL of $CH_3CN$ and the resulting solution was heated to 40° C. for 24 hours. Afterwards, the reaction mixture was cooled to room temperature and the solvent was evaporated under reduced pressure. The concentrated product was dissolved in $CH_2Cl_2$ and washed with water. The combined organic fractions were dried over anhydrous $Na_2SO_4$, filtered, and evaporated to dryness under reduced pressure to afford crude S8 as a colorless oil. The resulting crude product was purified with flash chromatography over silica gel (eluent: 20 vol-% EtOAc in hexanes), to afford S8 (1.39 g, 4.09 mmol) as a yellow oil in 40% yield. $^1$H-NMR (500 MHZ, $CDCl_3$) δ 10.52 (s, 1H), 7.84 (m, 1H), 7.54 (m, 1H), 7.09-6.90 (m, 2H), 4.12 (t, J=6.4 Hz, 2H), 3.69-3.54 (m, 14H), 3.38 (s, 3H), 2.01-1.89 (m, 2H), 1.87-1.75 (m, 2H). $^{13}$C-NMR (126 MHZ, $CDCl_3$) δ 189.9, 161.5, 136.0, 128.4, 125.0, 120.6, 112.6, 72.0, 70.9, 70.7, 70.7, 70.7, 70.3, 68.4, 59.1, 26.3, 26.1. HRMS (ESI) calcd. for $C_{18}H_{28}O_6$: m/z=341.1964 $[M+H]^+$; found: 341.1967.

Synthesis of 2-((2,5,8,11-Tetraoxapentadecan-15-yl)oxy)benzoic Acid (S9)

S8 (540 mg, 1.59 mmol) was dissolved in a 1:1 $CH_3CN$/DMSO mixture (10 mL total volume) in a 250 mL round-bottomed flask. Next, a solution of $NaH_2PO_4$ (729 mg, 5.28 mmol) and $NaClO_2$ (478 mg, 5.28 mmol) in 13 mL of deionized water was added to the reaction mixture. After stirring at room temperature for 24 hours, the $CH_3CN$ was evaporated under reduced pressure and the reaction mixture was quenched by adding 5 mL of a 1 N aqueous HCl solution. Next, the water layer was extracted with $CH_2Cl_2$ (4×20 mL) and the combined organic phases were washed with brine (4×100 mL). After drying over anhydrous $MgSO_4$, the solvent was removed in vacuo and S9 (565 mg, 1.59 mmol) was obtained as a yellow oil in quantitative yield. The crude product was used directly without further purification for the next step. $^1$H-NMR (500 MHz, $CDCl_3$) δ 10.97 (s, 1H), 8.15 (dd, J=7.8, 1.9 Hz, 1H), 7.53 (ddd, J=8.8, 7.3, 1.8 Hz, 1H), 7.10 (td, J=7.6, 1.0 Hz, 1H), 7.04 (dd, J=8.5, 0.9 Hz, 1H), 4.28 (t, J=6.6 Hz, 2H), 3.72-3.44 (m, 14H), 3.36 (s, 3H), 2.11-1.87 (m, 2H), 1.83-1.64 (m, 2H). $^{13}$C-NMR (126 MHz, $CDCl_3$) δ 189.3, 161.2, 135.7, 127.8, 124.6, 120.2, 112.3, 71.7, 71.7, 70.5, 70.3, 70.3, 70.2, 70.2, 69.9, 69.9, 69.9, 68.0, 58.7, 58.7, 33.5, 29.4, 28.0, 26.0, 25.8. HRMS (ESI) calcd. for $C_{13}H_{28}O_7$: m/z=357.1913 [M+H]$^+$; found: 357.1922.

Synthesis of 2-((2,5,8,11-Tetraoxapentadecan-15-yl)oxy)benzohydrazide (S10)

MeOH (20 mL) was added to S9 (577 mg, 1.62 mmol) in a 50 mL round-bottomed flask, followed by the dropwise addition of concentrated $H_2SO_4$ (0.2 mL). Next, the reaction mixture was stirred under reflux for 4 hours. After evaporation of all the MeOH under reduced pressure, a 0.5 M aqueous solution of NaOH (10 mL) was added and the product was extracted from the aqueous layer using $CH_2Cl_2$ (2×20 mL). Next, the combined organic layers were dried over anhydrous $MgSO_4$, filtered, and the solvent was removed in vacuo to afford the crude methyl ester of S9 as a yellow oil. Part of the obtained oil (0.49 g, 1.32 mmol) was dissolved in a mixture of THF and MeOH (1:2 volume ratio, 25 mL total volume) in a 100 ml 3-neck flask. The reaction mixture was degassed with argon and hydrazine monohydrate (2 mL) was added. After heating to 65° C. for 72 hours, the solvent was evaporated under reduced pressure under a $N_2$ atmosphere. The resulting product was dissolved in $CH_2Cl_2$ and washed with brine (3×20 mL), dried over anhydrous $Na_2SO_4$, filtered, and concentrated under reduced pressure to afford S10 (356.9 mg, 0.963 mmol) as a yellow oil in 60% yield over two steps. $^1$H-NMR (500 MHZ, $CDCl_3$) δ 8.96 (s, 1H), 8.14 (dd, J=7.8, 1.8 Hz, 1H), 7.39 (dddd, J=8.2, 7.3, 1.9, 0.6 Hz, 1H), 7.08-6.98 (m, 1H), 6.92 (dd, J=8.3, 0.9 Hz, 1H), 4.12 (t, J=6.6 Hz, 2H), 3.66-3.46 (m, 15H), 3.33 (s, 3H), 2.01-1.86 (m, 2H), 1.82-1.67 (m, 2H). $^{13}$C-NMR (126 MHZ, $CDCl_3$) δ 166.5, 156.9, 133.0, 132.1, 121.3, 120.1, 112.3, 72.0, 70.7, 70.7, 70.7, 70.6, 70.6, 70.3, 69.0, 59.1, 26.2, 26.2. HRMS (ESI) calcd. for $C_{18}H_{30}N_2O_6$: m/z=371.2182 [M+H]$^+$; found: 371.2186.

Synthesis of Edge-Model

S10 (36 mg, 0.0972 mmol) was dissolved in anhydrous $CH_2Cl_2$ (10 mL) in a 12 mL sealed reaction vial. The solution was degassed with argon and terephthalaldehyde (6.36 mg, 0.0474 mmol) was added. Next, HPLC grade TFA (1.45 μL, 0.019 mmol) was pipetted into the reaction mixture, which was then stirred at room temperature for 5 hours. Afterwards, the acid was neutralized with a saturated sodium bicarbonate solution and the aqueous layer was extracted with $CH_2Cl_2$ (2×10 mL). The combined organic extracts were washed with brine, dried over anhydrous $Na_2SO_4$, filtered, and concentrated under reduced pressure. The crude product was purified with preparative TLC over silica gel (eluent: 3.0 vol-% MeOH in $CH_2Cl_2$) to afford Edge-model (32 mg, 0.0380 mmol) as a white solid in 40% yield. $^1$H-NMR (500 MHZ, $CDCl_3$) δ 11.06 (s, 2H), 8.32-8.24 (m, 2H), 8.19 (s, 2H), 7.84 (s, 4H), 7.47 (t, 2H), 7.11 (t, J=7.5 Hz, 2H), 7.00 (d, J=8.3 Hz, 2H), 4.24 (t, J=6.4 Hz, 4H), 3.65-3.49 (m, 28H), 3.35 (s, 6H), 2.07 (m, 4H), 1.95-1.71 (m, 4H). $^{13}$C-NMR (126 MHZ, $CDCl_3$) δ 162.3, 156.7, 146.8, 135.7, 133.4, 132.7, 127.9, 121.6, 120.62, 112.4, 71.9, 70.6, 70.6, 70.5, 70.3, 69.1, 59.0, 26.4, 26.3. HRMS (ESI) calcd. for $C_{44}H_{62}N_4O_{12}$: m/z=839.4442 [M+H]$^+$; found: 839.4464.

Example 10—Synthesis of Syn-(1's,5'r)-4,4"-dibutoxy-5'-(4-butoxy-5-(2-((E)-4-formylbenzylidene)hydrazine-1-carbonyl)-2-methoxyphenyl)-N'3,N""3"-bis((E)-4-formylbenzylidene)-6,6"-dimethoxy-2',4',6'-trimethyl-[1,1': 3',1"-terphenyl]-3,3"-dicarbohydrazide (Syn-4,4"-dibutoxy-5'-(4-butoxy-5-(2-((E)-4-formylbenzylidene)hydrazine-1-carbonyl)-2-methoxyphenyl)-N'3,N""3"-bis((E)-4-formylbenzylidene)-6,6"-dimethoxy-2',4',6'-trimethyl-[1,1': 3',1"-terphenyl]-3,3"-dicarbohydrazide) (Syn-12)

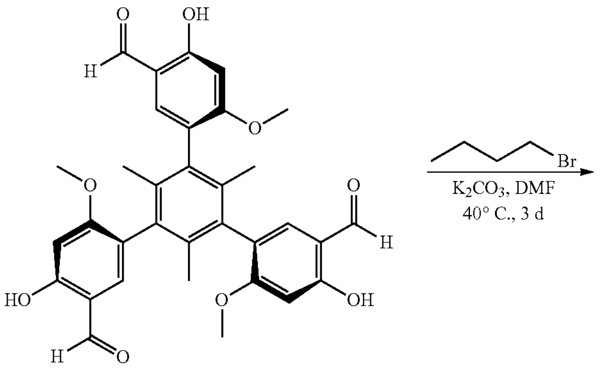

syn-3

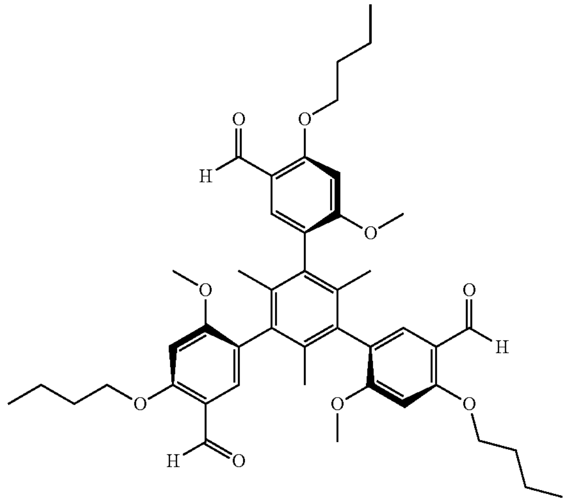

syn-S9

1. $NaClO_2$, $NaH_2PO_4$ DMSO, $CH_3CN$
2. MeOH, $H_2SO_4$, Δ

-continued

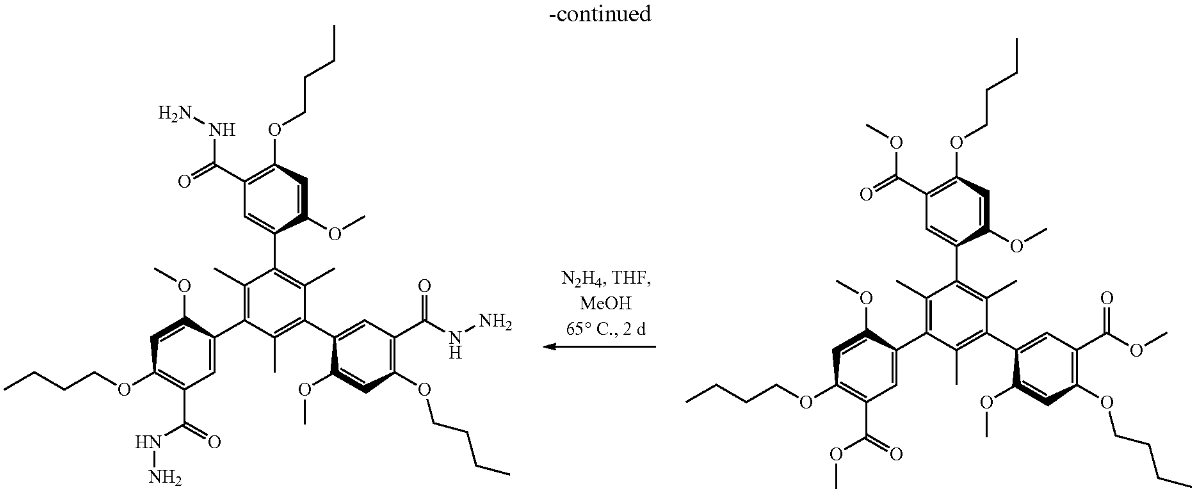

syn-S11 syn-S10

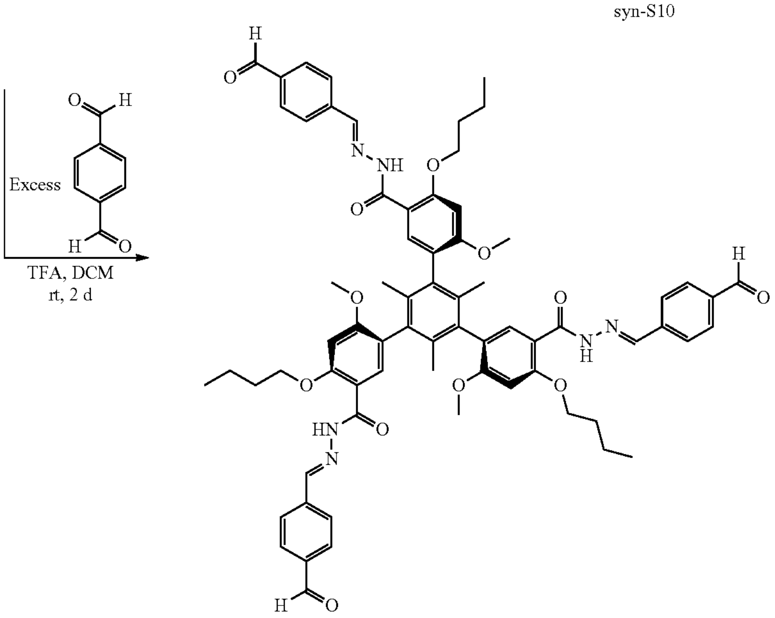

syn-12

Synthesis of Syn-(1'r,3's)-4,4"-dibutoxy-5'-(4-butoxy-5-formyl-2-methoxyphenyl)-6,6"-dimethoxy-2',4',6'-trimethyl-[1,1': 3',1"-terphenyl]-3,3"-dicarbaldehyde (Syn-4,4"-dibutoxy-5'-(4-butoxy-5-formyl-2-methoxyphenyl)-6,6"-dimethoxy-2',4',6'-trimethyl-5 [1,1': 3',1"-terphenyl]-3,3"-dicarbaldehyde) (Syn-S9)

Syn-3 (0.500 g, 0.876 mmol), bromobutane (0.67 ml, 6.3 mmol), and $K_2CO_3$ (1.21 g, 8.76 mmol) were added to a round-bottomed flask containing dry DMF (10 mL) and the reaction mixture was stirred at 60° C. for 48 hours. Afterwards, the solution was added dropwise into 30 mL of a 1 N aqueous HCl solution and the formed precipitate was filtered to afford syn-S9 10 (0.580 g, 0.788 mmol) as a colorless solid in 90% yield. $^{1}$H-NMR (500 MHZ, $CDCl_3$) δ 10.36 (s, 3H), 7.55 (s, 3H), 6.50 (s, 3H), 4.12 (t, J=6.3 Hz, 6H), 3.84 (s, 9H), 1.87 (m, 6H), 1.64 (s, 9H), 1.59-1.53 (m, 9H), 1.01 (t, J=7.4 Hz, 9H). $^{13}$C-NMR (126 MHZ, $CDCl_3$) δ 188.2, 163.2, 162.8, 135.0, 134.5, 131.9, 123.6, 118.8, 95.5, 68.4, 55.9, 31.3, 19.4, 18.8, 13.9. HRMS (ESI) calc. for $C_{45}H_{55}O_9$: m/z=739.3846 $[M+H]^+$; found: 739.3859.

Synthesis of Syn-dimethyl (1's,5'r)-4,4"-dibutoxy-5'-(4-butoxy-2-methoxy-5-(methoxycarbonyl)phenyl)-6,6"-dimethoxy-2',4',6'-trimethyl-[1,1': 3',1"-terphenyl]-3,3"-dicarboxylate (Syn-dimethyl-4,4"-dibutoxy-5'-(4-butoxy-2-methoxy-5-(methoxycarbonyl)phenyl)-6,6"-dimethoxy-2',4',6'-trimethyl-[1,1': 3',1"-terphenyl]-3,3"-dicarboxylate) (Syn-S10)

Syn-S9 (0.580 g, 0.788 mmol) was dissolved in 30 ml of a 2:1 (vol-%) $CH_3CN$/DMSO mixture in a 200 ml round-bottomed flask. Next, a solution of $NaH_2PO_4$ (0.96 g, 8.0 mmol) and $NaClO_2$ (0.870 g, 9.61 mmol) in deionized water (8 ml) was added and the reaction mixture was stirred at room temperature. After 72 hours, the $CH_3CN$ was evaporated under reduced pressure, and 30 ml of a 1 N aqueous HCl solution were added at 0° C. The precipitate which formed was filtered and—to esterify all the acid functional groups-dissolved in MeOH (16 ml) in a 100 ml round-bottomed flask. Concentrated $H_2SO_4$ (1.0 ml) was added dropwise and the reaction was left stirring under reflux for 48 hours. Finally, the MeOH was evaporated under reduced pressure and the acid neutralized with 10 ml of a 1 N aqueous NaOH solution. The product was extracted from the resulting aqueous solution with $CH_2Cl_2$ (2×20 mL) and the combined organic layers were dried over anhydrous $Na_2SO_4$, filtered, and evaporated to dryness under reduced pressure. The resulting crude product was purified with chromatography over silica gel (eluent: 10 vol-% EtOAc in $CH_2Cl_2$) and recrystallized from hexanes to afford syn-S10 (0.320 g, 0.386 mmol) as a colorless solid. $^1$H-NMR (500 MHz, $CDCl_3$) δ 7.60 (s, 3H), 6.54 (s, 3H), 4.09 (t, J=6.5 Hz, 6H), 3.84 (s, 9H), 3.80 (s, 9H), 1.87 (dq, J=8.7, 6.6 Hz, 6H), 1.67 (s, 10H), 1.63-1.53 (m, 6H), 1.00 (t, J=7.4 Hz, 9H). $^{13}$C-NMR (126 MHz, $CDCl_3$) δ 166.3, 161.2, 160.4, 135.3, 135.2, 134.8, 122.7, 112.1, 97.0, 69.0, 55.7, 51.6, 31.5, 19.4, 18.8, 14.0. HRMS (ESI) calcd. for $C_{48}H_{61}O_{12}$: m/z=829.4163 [M+H]$^+$; found: 829.4185.

Synthesis of Syn-(1'r,3's)-4,4"-dibutoxy-5'-(4-butoxy-5-(hydrazinecarbonyl)-2-methoxyphenyl)-6,6"-dimethoxy-2',4',6'-trimethyl-[1,1': 3',1"-terphenyl]-3,3'"-dicarbohydrazide (Syn-4,4"-dibutoxy-5'-(4-butoxy-5-(hydrazinecarbonyl)-2-methoxyphenyl)-6,6"-dimethoxy-2',4',6'-trimethyl-[1,1': 3',1"-terphenyl]-3,3"-dicarbohydrazide) (Syn-S11)

Syn-S10 (0.320 g, 0.386 mmol) was dissolved in 30 ml of a 1:2 vol-% THF/MeOH mixture in a 250 ml sealed heavy-wall glass reaction vessel. The reaction mixture was degassed with argon and hydrazine monohydrate (1.6 ml) was added. After heating to 60° C. for 48 hours, most of the solvent was evaporated under reduced pressure under a $N_2$ atmosphere. The resulting solid was filtered, washed with water (3×10 ml), and dried in vacuo to afford syn-S11 (0.256 g, 0.308 mmol) as a colorless solid in 80% yield. $^1$H-NMR (500 MHZ, $CDCl_3$) δ 8.83 (s, 3H), 7.93 (s, 3H), 6.52 (s, 3H), 4.16 (t, J=6.6 Hz, 6H), 3.77 (s, 9H), 1.90 (dq, J=8.8, 6.6 Hz, 6H), 1.66 (s, 9H), 1.58-1.51 (m, 6H), 1.02 (t, J=7.4 Hz, 9H). $^{13}$C-NMR (126 MHZ, $CDCl_3$) δ 166.7, 160.4, 157.5, 135.1, 135.0, 134.6, 124.0, 112.8, 96.2, 69.1, 55.9, 31.3, 19.5, 18.8, 13.9. HRMS (ESI) calcd. for $C_{45}H_{61}N_6O_9$: m/z=829.4500 [M+H]$^+$; found: 829.4492.

Synthesis of Syn-12

Syn-S11 (0.079 g, 0.096 mmol) was dissolved in dry $CH_2Cl_2$ (10 mL) in a 50 mL round-bottomed flask. The solution was degassed with argon and terephthalaldehyde (1.430 mmol, 0.192 g) was added. Next, HPLC grade TFA (19 μL, 0.096 mmol) was pipetted into the reaction mixture, which was stirred at room temperature for 48 hours. Afterwards, the acid was neutralized with saturated sodium bicarbonate solution and the aqueous layer extracted with $CH_2Cl_2$. The combined organic extracts were washed with brine, dried over anhydrous $Na_2SO_4$, filtered, and concentrated under reduced pressure. The crude product was purified by size exclusion chromatography over polystyrene beads (200-400 mesh) with $CH_2Cl_2$ as the eluent to afford syn-12 (0.096 g, 0.081 mmol) as a light-yellow solid in 85% yield. $^1$H-NMR (500 MHZ, $CD_2Cl_2$) δ 11.14 (s, 3H), 10.02 (s, 3H), 8.23 (s, 3H), 8.00-7.88 (m, 15H), 6.64 (s, 3H), 4.31 (t, J=6.5 Hz, 6H), 3.92 (s, 9H), 2.08-1.96 (m, 6H), 1.71-1.61 (m, 15H), 1.09 (t, J=7.4 Hz, 9H). $^{13}$C-NMR (126 MHZ, $CD_2Cl_2$) δ 192.1, 162.3, 161.5, 158.2, 145.2, 140.6, 137.6, 135.9, 135.5, 135.2, 130.4, 128.3, 124.5, 113.1, 96.2, 70.0, 56.3, 31.9, 20.0, 19.0, 14.1. HRMS (ESI) calcd. for $C_{69}H_{73}N_6O_{12}$: m/z=1177.5286 [M+H]$^+$; found: 1177.5309.

Example 11—Synthesis of Additional Verteces Syn-Dimethyl (1'r,3's)-5'-(2,4-dimethoxy-5-(methoxycarbonyl)phenyl)-4,4",6,6"-tetramethoxy-2',4',6'-trimethyl-[1,1': 3',1"-terphenyl]-3,3"-dicarboxylate (Syn-dimethyl-5'-(2,4-dimethoxy-5-(methoxycarbonyl) phenyl)-4,4",6,6"-tetramethoxy-2',4',6'-trimethyl-[1,1': 3',1"-terphenyl]-3,3"-dicarboxylate) (Syn-S20) and Syn-Dimethyl (1'r,5's)-4,4"-bis((2-ethylhexyl) oxy)-5'-(4-((2-ethylhexyl)oxy)-2-methoxy-5-(methoxycarbonyl)phenyl)-6,6"-dimethoxy-2',4',6'-trimethyl-[1,1': 3',1"-terphenyl]-3,3"-dicarboxylate (Syn-Dimethyl-4,4"-bis((2-ethylhexyl)oxy)-5'-(4-((2-ethylhexyl)oxy)-2-methoxy-5-(methoxycarbonyl)phenyl)-6,6"~dimethoxy-2',4',6'-trimethyl-[1,1': 3',1"-terphenyl]-3,3"-dicarboxylate) (Syn-S21)

Synthesis of Syn-S20

Syn-2 (1.010 mmol) was dissolved in a 1:1 $CH_3CN$/DMSO mixture (56 mL total volume) in a 250 mL round-bottomed flask. Next, a solution of $NaH_2PO_4$ (1.2 g, 10 mmol) and $NaClO_2$ (0.9 g, 10 mmol) in 13 mL deionized water was added to the reaction mixture. After stirring at room temperature for 48 hours, the $CH_3CN$ was evaporated under reduced pressure and the reaction mixture was quenched by adding 30 mL of a 1 N aqueous HCl solution. Next, the water layer was extracted with $CH_2Cl_2$ (4×20 mL) and the combined organic phases were washed with brine (4×100 mL). After drying over anhydrous $MgSO_4$, the solvent was removed in vacuo. Finally, MeOH (40 mL) was added to the resulting oxidized product (0.810 mmol) in a 100 mL round-bottomed flask, followed by the dropwise addition of concentrated $H_2SO_4$ (1.0 mL). The reaction mixture was stirred under reflux for 24 hours. After evaporation of MeOH under reduced pressure, 1 N aqueous NaOH (10 mL) was added and the product was extracted from the aqueous layer using $CH_2Cl_2$ (2×20 mL). Next, the combined organic layers were dried over anhydrous $MgSO_4$, filtered, and the solvent was removed in vacuo. The crude product was purified by recrystallization to afford the methyl ester syn-S20 in 74% yield as a colorless solid. $^1$H-NMR (500 MHZ, $CDCl_3$) δ 7.64 (s, 3H), 6.58 (s, 3H), 4.00 (s, 9H), 3.87 (s, 9H), 3.85 (s, 9H), 1.69 (s, 9H). HRMS characterization data was obtained after derivatization with hydrazine: HRMS (ESI) calcd. for $C_{36}H_{43}N_6O_9$: m/z=703.3092 [M+H]$^+$; found: 703.3086.

Synthesis of Syn-S21

Syn-3 (0.68 g, 1.190 mmol), 7.140 mmol of the corresponding alkylating agent (2-ethylhexyl bromide), as well as $K_2CO_3$ (1.38 g, 10.0 mmol) were added to a round-bottomed flask containing anhydrous DMF (15 mL) and the reaction mixture was stirred at 40° C. for 72 hours. Then, the reaction mixture was quenched by adding 50 mL of a 1 M aqueous HCl solution. The aqueous layer was extracted with $CH_2Cl_2$ (3×30 mL) and the combined organic layers were washed with brine (4×75 mL), dried over anhydrous $MgSO_4$, filtered, and evaporated under reduced pressure. If necessary, excess alkylating agent was removed by column chromatography. The resulting alkylated product (1.010 mmol) was dissolved in a 1:1 $CH_3CN$/DMSO mixture (56 mL total volume) in a 250 mL round-bottomed flask. Next, a solution of $NaH_2PO_4$ (1.2 g, 10 mmol) and $NaClO_2$ (0.9 g, 10 mmol) in 13 mL deionized water was added to the reaction mixture. After stirring at room temperature for 48 hours, the $CH_3CN$ was evaporated under reduced pressure and the reaction mixture was quenched by adding 30 mL of a 1 N aqueous HCl solution. Next, the water layer was extracted with $CH_2Cl_2$ (4×20 mL) and the combined organic phases were washed with brine (4×100 mL). After drying over anhydrous $MgSO_4$, the solvent was removed in vacuo. Finally, MeOH (40 mL) was added to the resulting oxidized product (0.810 mmol) in a 100 mL round-bottomed flask, followed by the dropwise addition of concentrated $H_2SO_4$ (1.0 mL). The reaction mixture was stirred under reflux for 24 hours. After evaporation of MeOH under reduced pressure, 1 N aqueous NaOH (10 mL) was added and the product was extracted from the aqueous layer using $CH_2Cl_2$ (2×20 mL). Next, the combined organic layers were dried over anhydrous $MgSO_4$, filtered, and the solvent was removed in vacuo. The resulting brown oil was purified by column chromatography over silica gel to afford the methyl esters syn-S21 in 60% yield. $^1$H-NMR (500 MHZ, $CDCl_3$) δ 7.62 (s, 3H), 6.55 (s, 3H), 3.99 (dd, J=5.6, 4.5 Hz, 6H), 3.86 (s, 9H), 3.83 (s, 9H), 1.92-1.28 (m, 42H), 0.98 (t, J=7.4 Hz, 9H), 0.96-0.90 (m, 9H). $^{13}$C-NMR (125 MHZ, $CDCl_3$) δ 166.39, 160.98, 160.35, 135.18, 135.16, 134.64, 122.46, 112.09, 96.58, 71.25, 55.67, 51.52, 39.59, 30.49, 29.17, 23.81, 23.06, 18.72, 14.12, 11.20. LC-MS: $MH^+$ at m/z 997.6.

Example 12—Synthesis of Additional Tetrahedra Tet-2, Tet-3, Tet-4, Tet-5, and Tet-6

General Procedure for the Conversion of the Methyl Ester Verteces into Tetrabedra Methyl ester verteces syn-4, syn-S10, syn-S20, or syn-S21 (0.567 mmol) were dissolved in 45 mL of a 1:2 THF/MeOH mixture in a 250 mL sealed heavy-wall glass reaction vessel. Next, the solutions was degassed with argon and hydrazine monohydrate (9.0 mL) was added. After heating at 65° C. for 48 hours under argon atmosphere, the solvents were evaporated under reduced pressure (under a nitrogen atmosphere) and the resulting mixtures were extracted with $CH_2Cl_2$. The combined organic layers were washed with water (3×60 mL), dried over $MgSO_4$, filtered, concentrated under reduced pressure, and dried in vacuo. The resulting crude hydrazides (0.208 mmol) were dissolved in 350 mL of anhydrous $CH_2Cl_2$, and the solutions were degassed with argon. Next, the corresponding dialdehydes (0.312 mmol) and HPLC grade TFA (0.313 mmol) were added consecutively, and the reaction mixtures were stirred at room temperature under an argon atmosphere. After 48 hours, the acid was neutralized with a saturated aqueous sodium bicarbonate solution (10 mL), the organic layers were separated, and the aqueous phases extracted with additional $CH_2Cl_2$ (30 mL). Finally, the combined organic extracts were washed with brine, dried over anhydrous $Na_2SO_4$, filtered, and concentrated under reduced pressure. The crude products were purified by size exclusion chromatography over polystyrene beads (200-400 mesh) with $CH_2Cl_2$ as the eluent to afford the hydrazone-linked organic tetrahedra Tet-2-Tet-6 as orange-yellow solids in 45-72% yield.

Tet-2: $^1$H-NMR (500 MHZ, DMSO-d6) δ 11.30 (s, 3H), 8.28 (s, 3H), 7.67 (d, J=125.0 Hz, 9H), 6.85 (s, 3H), 4.31 (br, 6H), 3.89 (s, 9H), 1.95-1.40 (m, 21H), 1.25 (s, 9H). LC-MS: $MH_2^{2+}$ at m/z 1954.2.

Tet-3: $^1$H-NMR (500 MHz, $CD_2Cl_2$) δ 8.92-8.47 (m, 3H), 8.22-7.64 (m, 9H), 7.12-6.58 (m, 3H), 4.77-3.84 (m, 18H), 1.95-1.65 (m, 9H). LC-MS: $MH_4^{4+}$ at m/z 1701.

Tet-4: $^1$H-NMR (500 MHZ, $CD_2Cl_2$) δ 11.10 (s, 3H), 8.27 (s, 1H), 8.04 (s, 3H), 7.87 (s, 3H), 7.60 (s, 2H), 6.69 (s, 3H), 4.24 (m, 6H), 3.95 (s, 9H), 2.08-1.55 (m, 27H), 1.30 (s, 9H), 1.15-0.85 (m, 18H). LC-MS: $MH_3^{3+}$ at m/z 1527.

Tet-5: $^1$H-NMR (500 MHZ, $CD_2Cl_2$) δ 11.21 (s, 3H), 8.39 (s, 3H), 8.00 (d, J=30.5 Hz, 6H), 6.69 (s, 3H), 4.38 (s, 6H), 4.10-3.83 (m, 18H), 3.80-3.47 (m, 42H), 3.38-3.02 (m, 9H), 2.57-2.06 (m, 6H), 1.95 (m, 6H), 1.79-1.65 (m, 9H). LC-MS: $MH_3^{3+}$ at m/z 2071.6.

Tet-6: $^1$H-NMR (500 MHZ, $CD_2Cl_2$) δ 11.22 (s, 3H), 8.44 (s, 3H), 8.06 (s, 3H), 8.04 (s, 3H), 6.68 (s, 3H), 4.86 (s, 6H), 4.39-4.35 (m, 6H), 3.92 (s, 9H), 3.74-3.41 (m, 42H), 3.33 (s, 9H), 2.28-2.07 (m, 6H), 1.94 (m, 6H), 1.29 (s, 9). $^{13}$C-NMR (125 MHZ, $CD_2Cl_2$) δ 161.1, 160.6, 157.5, 149.6, 134.9, 134.5, 130.9, 124.1, 122.5, 113.1, 78.3, 76.9, 71.9, 70.5, 70.5, 70.4, 70.3, 70.2, 69.5, 61.3, 58.6, 55.8, 31.9, 29.7, 29.3, 26.3, 26.3, 22.7, 18.4, 13.9, 0.7, −0.4. HRMS (ESI) calcd. for $C_{348}H_{448}N_{24}O_{96}$: m/z=1624.7728 $[M+4H]^{4+}$; found: 1624.7725.

Example 13—Sample Preparation and Measurements of Rate Constants

Figure 11:
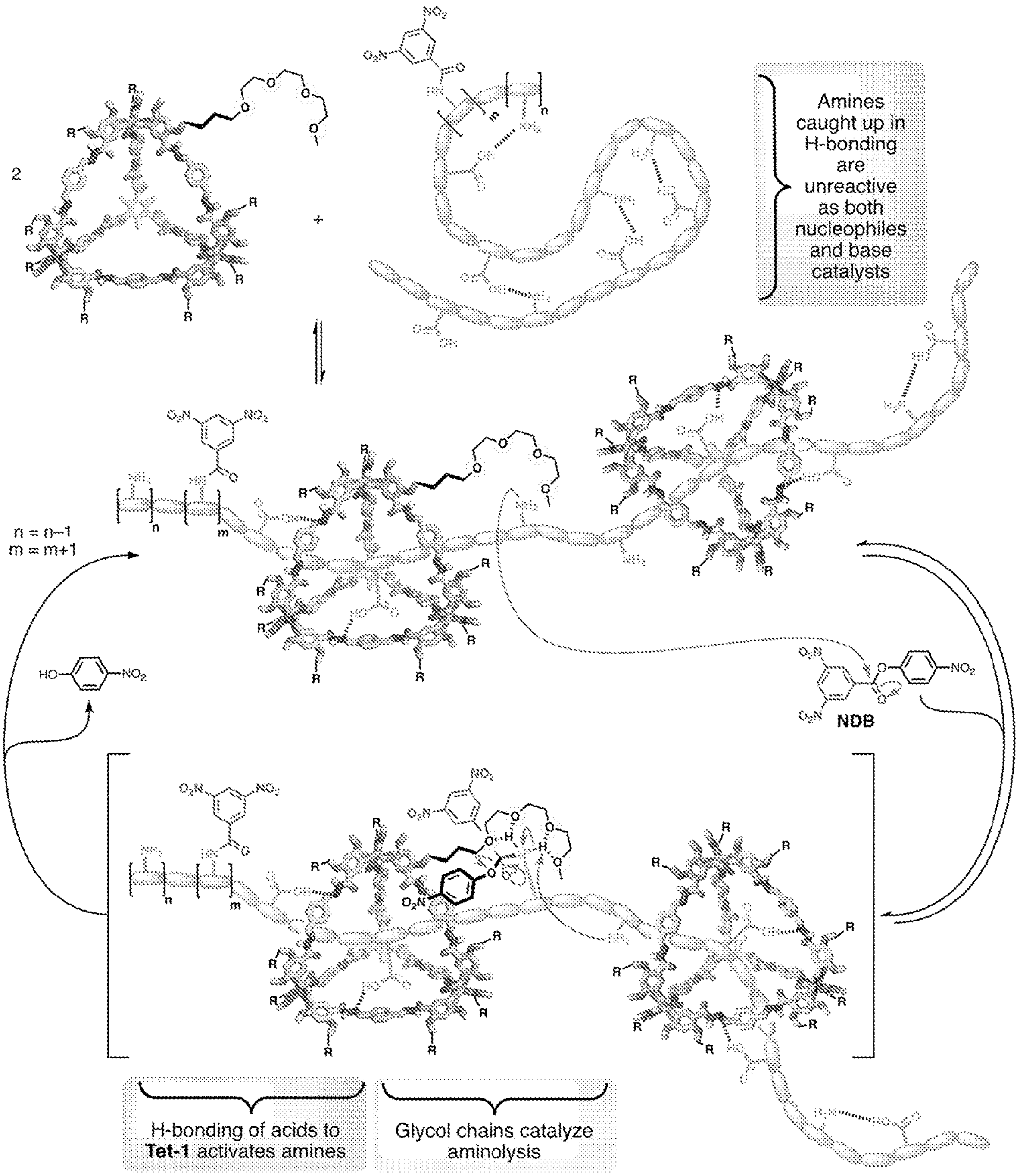
FIG. 11 is a schematic showing the proposed catalytic cycle for Tet-1-catalyzed acylation of $NH_2$-POA polymers. The tetrahedral nanocage catalyst (Tet-1) (i) helps to unfold (see FIGS. 3A-D, 4A-C, and 10 for evidence) the polymeric substrates, which frees up the amino groups on the polymers for acylation and base catalysis. In addition, Tet-1 (ii) utilizes its 12 peripheral triglyme units to stabilize the tetrahedral aminolysis intermediates, while (iii) an internal amino group (freed up by a second equivalent of Tet-1) functions as the base to deprotonate the intermediate. The fact that the amines also act as a base in the mechanism results in the observed second order rate-dependence on the amine-concentration. The two Tet-1 cages bound to the rate-determining transition state lead to the observed (FIG. 39A) second order rate-dependence on the Tet-1 concentration.

For all kinetic measurements, stock solutions of all reagents in $CD_2Cl_2$ were prepared in advance and used promptly. The stock solutions were stored at −10° C. in sealed vials under an argon atmosphere. All volumetric measurements were performed with Rainin Positive Displacement (MR-10, -100, -1000) micropipettes, which are optimized for organic solvents with low vapor pressures like $CD_2Cl_2$. The concentrations of reagents in the stock solutions were calibrated by $^1$H-NMR integration and comparison of the integrals with the integral of 1,2,4,5-tetrabromobenzene as the internal standard. For each time-dependent $^1$H-NMR experiment, the active ester (NDB) was added last to the reaction mixtures and the addition time of NDB is reported as the start time of the experiments. The progress of the aminolysis reactions was monitored by integrating (FIGS. 25-38) the $^1$H-NMR resonance at 6.9 ppm, which corresponds to p-nitrophenol formed (FIG. 11) upon aminolysis of the NDB active ester. Absolute concentrations of the p-nitrophenol in all the samples were obtained by comparing the integrations of the p-nitrophenol resonances to the integrations of the internal 1,2,4,5-tetrabromobenzene standard. Finally, the concentrations of the remaining amino groups ([amine]) on the $NH_2$-POA polymers were calculated for each time point by subtracting the amount of p-nitrophenol formed from the initial amine concentrations ($[amine]_0$). With the 1.8 mg of polymer sample used for each kinetic experiment, the initial amine concentrations were, approximately: 1.8 mM for $NH_2$-POA, 1.2 mM for Short-$NH_2$-POA, and 0.5 mM for Long-$NH_2$-POA.

Example 14—DOSY Size-Selectivity Experiments

For the DOSY $^1$H-NMR size-selectivity experiments, two NMR reaction mixtures were prepared and reaction progress was monitored by following the $^1$H-NMR integrations of the p-nitrophenol resonances at 6.9 ppm. Both reactions were equalized as described in detail in FIG. 7 (caption) at 24% conversion. In order to minimize further reaction progress while recording the DOSY $^1$H-NMR spectra, the DOSY $^1$H-NMR spectra were recorded with 30 increments in 20-25 minutes. The diffusion delay Δ, was set to 60 ms, with the diffusion gradient length δ at 3 ms, which required 32 scans for each gradient-strength measurement.

Example 15—Molecular Dynamics (MD) Simulations of the $NH_2$-POA Polymers on their Own and in Complex with a Prototypical Nanocage (Tet-1)

In order to verify proposed model for the observed kinetic behavior of Tet-1, 800-ns MD simulations with the OPLS3e force field in explicit $CH_2Cl_2$ solvent were employed. The MD simulations (i) explained the outcome of the DOSY $^1$H-NMR spectra shown in FIGS. 3A-D. Specifically, the $NH_2$-POA polymer unfolded upon binding to Tet-1 and it increased (FIGS. 4A-C) in size during that process. (ii) The MD simulations also shed light on the alteration of the supramolecular interactions present within the polymer upon binding to Tet-1. As shown in FIG. 41, the number of intramolecular hydrogen bonds folding up the polymer decreased by binding to Tet-1 as these intra-polymer hydrogen bonds get replaced with hydrogen bonds formed between Tet-1 and the polymer.

Model Preparation

All models were constructed using the Maestro program (Schrödinger Release 2018-2: Maestro, Schrödinger, LLC, New York, NY). Tet-1 and [$NH_2$-POA@Tet-1] (complex formed between POA and Tet-1) (the symbol @ between a two components is used to indicate formation of the complex between the two components) systems were simulated in periodic simulation boxes of ~121×121×121 Å$^3$ and ~67×67×67 Å3, respectively, with $CH_2Cl_2$ molecules as the solvent. Each construct went through minimization, equilibration, and either 100-ns, 250-ns, or 800-ns MD production stages, depending on convergence speed. At least two replicas with differing random seeds were run for all simulations.

Simulation Setup and Analysis

Each model was simulated in the NPT ensemble (300 K, 1 atm, Martyna-Tuckerman-Klein coupling scheme) using the OPLS3 or the OPLS3e force field. All simulations were performed in the Maestro-Desmond program (GPU version 5.4) with a time step of 2 fs. The Ewald technique was used for the electrostatic calculations. The Van der Waals and short-range electrostatics were cut off at 9 Å. Hydrogen atoms were constrained using the SHAKE algorithm. MD trajectories were analyzed using in-house python scripts and the Schrödinger (2018-2 release) API.

Figure 13:
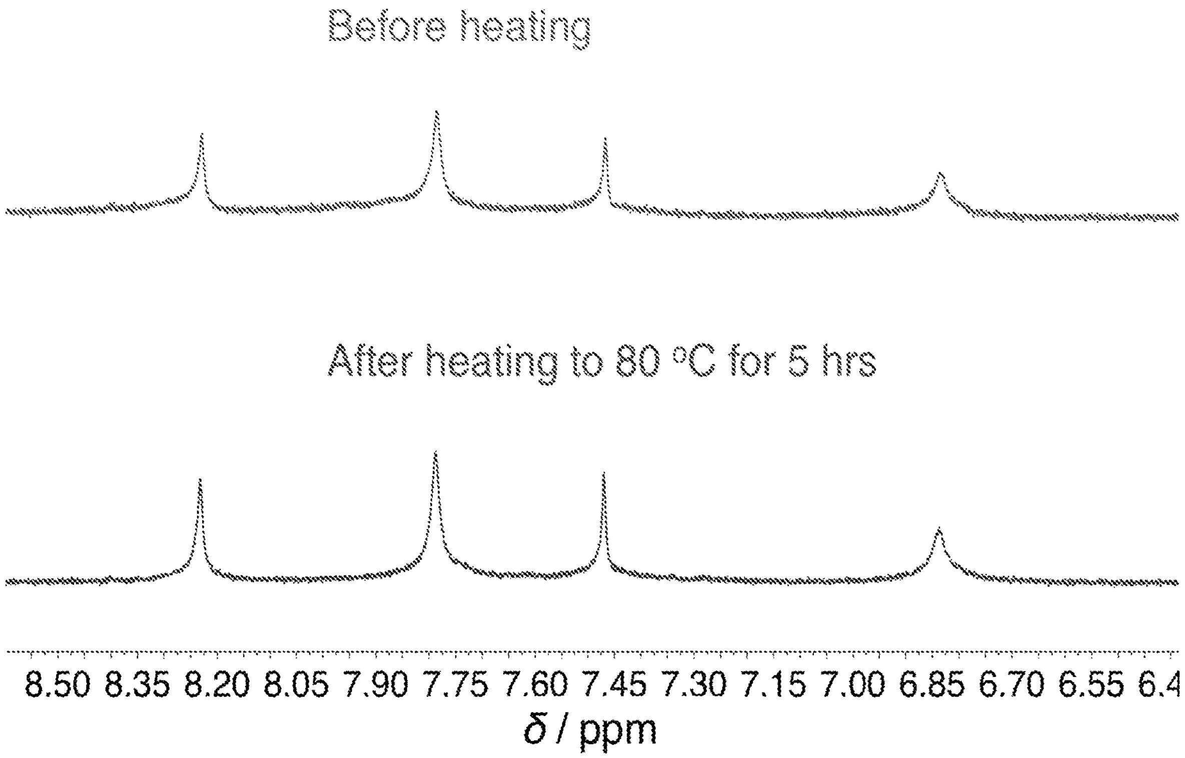
FIG. 13 shows testing the stability of Tet-1 upon heating in water.

Example 16—Testing the Stability of Tet-1 Upon Heating in the Presence of Water To investigate the hydrolytic stability of Tet-1, Tet-1 (2.3 mg, 3.93×10$^{-4}$ mmol) was dissolved in a 90:10 vol-% mixture (440 μL) of DMSO-d6 and $D_2O$. The $^1$H-NMR of the solution was then recorded and the mixture heated at 80° C. for five hours. No changes were observed (FIG. 13) in the $^1$H-NMR spectrum of Tet-1, which indicated that Tet-1 is stable in the presence of water, even at elevated temperatures.

Example 17—Diffusion Ordered Spectroscopy (DOSY)

The NMR samples for DOSY $^1$H-NMR spectroscopy were prepared in $CD_2Cl_2$ at room temperature, with TMS as the internal reference. The DOSY $^1$H-NMR spectra were acquired on a Varian Unity Inova 500 spectrometer, equipped with a HCN probe with Z-axis gradients, and a Highland Technologies L700 gradient amplifier. The standard DOSY Varian pulse program. 'Dbppste' was used, with a stimulated echo sequence and bipolar gradient pulse pairs. All experiments were acquired at 25° C. and DOSY spectra were processed using Agilent's VnmrJ 4.2 software, employing the discrete approach for the inverse Laplace transform in the diffusion dimension.

DOSY $^1$H-NMR Spectrum of Tet-1

Based on the DOSY $^1$H-NMR spectrum (FIG. 14) of Tet-1, the average diffusion constant for the protons attached to Tet-1 equals ca. 5.6×10$^{-10}$ m$^2$s$^{-1}$. By applying the Stokes-Einstein equation, this diffusion constant translates into a solvodynamic radius of ca. 1.1 nm, assuming a viscosity of 0.41 centipoise for the $CD_2Cl_2$ solvent employed.

Full DOSY $^1$H-NMR Spectra of $NH_2$-POA, [$NH_2$-POA@Tet-1], and Tet-1

The full DOSY $^1$H-NMR spectra shown in FIGS. 15A-C demonstrated that the diffusion constant of the $CHDCl_2$ solvent resonance at 5.32 ppm remained constant (32.5×10$^{-10}$ m$^2$ s$^{-1}$ in all cases), indicating that the viscosities of the NMR solutions were not affected significantly by the presence of the polymers. This result confirmed that the decrease of the diffusion constants observed upon mixing of the two binding partners was indeed the result of the complex formation.

Example 18—Molecular Weight Measurements of $NH_2$-POA with DOSY $^1$H-NMR $NH_2$-POA kept getting stuck on GPC columns. Therefore, the molecular weight of the $NH_2$-POA samples was determined with an alternative, well-established (Li et al., "Application of 1H DOSY for Facile Measurement of Polymer Molecular Weights," Macromolecules 45:9595-9603 (2012), which is hereby incorporated by reference in its entirety), DOSY $^1$H-NMR-based technique. Specifically, four dilute (0.4 mg in 0.75 mL of $CDCl_3$) polystyrene (PS) standard samples with different molecular weights ($\overline{M}_w$) were first prepared and the DOSY $^1$H-NMR spectra (see FIG. 16A-D and Table 1) of all the PS standards were record.

TABLE 1

Diffusion Constants (D) Obtained from the DOSY $^1$H-NMR Analysis of the PS Standards

| Standard | D (×10$^{-10}$ m$^2$ s$^{-1}$) | log D | log $\overline{M}_w$ |
|---|---|---|---|
| $CHCl_3$ | 21.4 | −8.669 | 2.077 |
| PS ($\overline{M}_w$ = 1,220 Da) | 4.58 | −9.339 | 3.086 |
| PS ($\overline{M}_w$ = 3,510 Da) | 3.31 | −9.480 | 3.545 |
| PS ($\overline{M}_w$ = 8,560 Da) | 2.21 | −9.655 | 3.932 |
| PS ($\overline{M}_w$ = 17,300 Da) | 1.47 | −9.832 | 4.238 |

Finally, a calibration curve was obtained by plotting log D for the different standards vs. log $\overline{M}_w$. A linear fit (FIG. 17, $R^2$=0.985) to this calibration curve resulted in Equation S4:

$$\log D = -0.5241 \log \overline{M}_w - 7.6261 \quad \text{(Eq. S4)}$$

Figure 18:
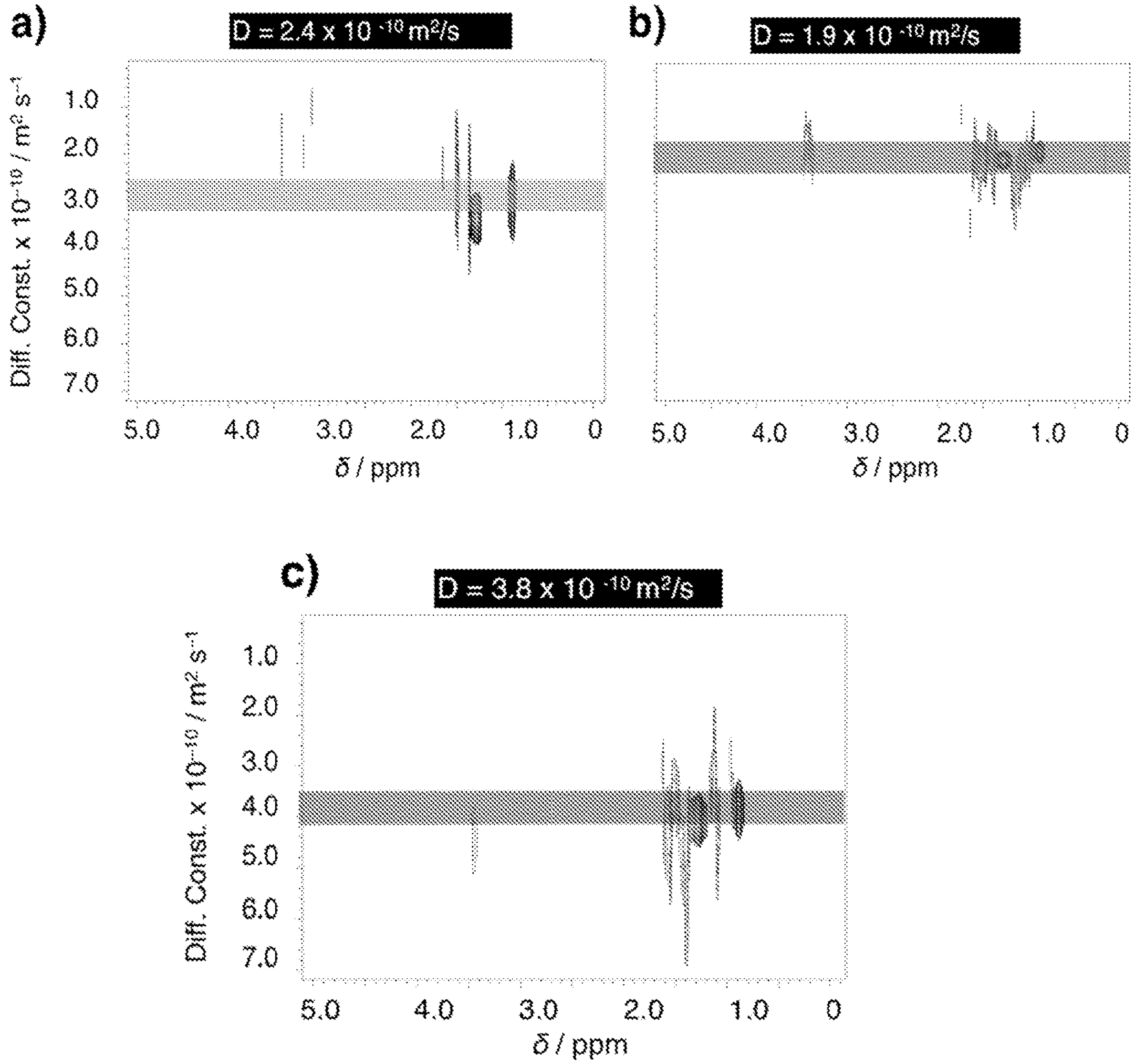
FIGS. 18A-C are DOSY $^1$H-NMR spectra (500 MHZ, $CDCl_3$) of $NH_2$-POA (FIG. 18A), Long-$NH_2$-POA (FIG. 18B), and Short-$NH_2$-POA (FIG. 18C) used to determine the approximate molecular weights of the $NH_2$-POA samples with the calibration equation S4.

Equation S4 was then used to determine the molecular weights ($\overline{M}_w$) of the $NH_2$-POA polymer samples from the measured diffusion constants of the polymers (see Table 2 and FIGS. 18A-C for the results and the corresponding DOSY $^1$H-NMR spectra).

TABLE 2

Diffusion Constants (D) and Corresponding Molecular Weights ($\overline{M}_w$) Obtained from the DOSY $^1$H-NMR Analysis of Short-$NH_2$-POA, $NH_2$-POA, and Long-$NH_2$-POA

| Polymer Sample | D ($\times 10^{-10}$ $m^2$ $s^{-1}$) | $\overline{M}_w$ (kDa) |
|---|---|---|
| Short-$NH_2$-POA | 3.8 | 2.6 |
| $NH_2$-POA | 2.4 | 6.3 |
| Long-$NH_2$-POA | 1.9 | 9.9 |

Next, NMR samples of $NH_2$-POA, Short-$NH_2$-POA, and Long-$NH_2$-POA in $CDCl_3$ were prepared by dissolving 0.4 mg of each polymer in 0.75 mL $CDCl_3$. Finally, the DOSY $^1$H-NMR spectra (FIGS. 18A-C) of the polymer samples were recorded and the approximate molecular weights of the polymers calculated from the calibration equation (Equation S4).

Example 19—$^1$H-$^1$H-NOESY NMR Spectrum of the [Long-$NH_2$-POA@Tet-1] Complex The $^1$H-$^1$H-NOESY NMR spectra for the [Short-$NH_2$-POA@Tet-1] (FIG. 3D) and [Long-$NH_2$-POA@Tet-1] (FIG. 19) complexes were recorded with mixtures of 1.8 mg polymer and 1.0 mg Tet-1 in 600 μL $CD_2Cl_2$. The spectra were acquired on a Varian Unity Inova 500 spectrometer with a NOE mixing time of 600 ms.

Example 20—$^1$H-NMR Titration Experiments

Measurements of the Complex Association Constants and Complex Dissociation Rates for the [Short-$NH_2$-POA@Tet-1] and [Long-$NH_2$-POA@Tet-1] Complexes Tet-1 (1.1 mg, $1.88\times10^{-4}$ mmol) was dissolved in 500 μL of $CD_2Cl_2$ in a scintillation vial and transferred to an NMR tube. In separate vials, Short- and Long-$NH_2$-POA (8.4 mg) were dissolved in 300 μL $CD_2Cl_2$ and the resulting solutions were titrated into the NMR samples containing Tet-1 in up to 10 steps. Upon titration, significant broadening of peaks corresponding to Tet-1 especially with long polymers was observed (FIGS. 20A-B and 21A-B), which was expected to occur for an intermediate-slow host-guest exchange regime on the $^1$H-NMR timescale. The titration curves were fit with a custom python script, which is provided in full in FIG. 47. The script calls the LineshapeKin 4.0 NMR simulation software (Kovrigin, E. L. "NMR Line Shapes and Multi-State Binding Equilibria," *J. Biomol. NMR* 53:257-270 (2012), which is hereby incorporated by reference in its entirety) from the curve-fit algorithm implemented in the SciPy 0.18 package (Virtanen et al. "SciPy 1.0-Fundamental Algorithms for Scientific Computing in Python," *arXiv,* 1907.10121 (2019), which is hereby incorporated by reference in its entirety) with the trust region reflective (TRF) algorithm. Error bars (standard deviations) were calculated from the covariance matrix of the best fit obtained with the SciPy curve-fit algorithm.

To investigate whether hydrogen bonding is important for the binding of $NH_2$-POA with Tet-1, DMSO-d6 (60 μL) was added to an NMR sample containing Short-$NH_2$-POA (1.2 mM) and Tet-1 (0.23 mM) in $CD_2Cl_2$ (740 μL). Immediately after the addition of the DMSO-d6 (which is a well-known hydrogen bond disruptor), the $^1$H-NMR resonances corresponding to Tet-1 sharpened (FIGS. 22A-B) notably, indicating that significant decomplexation is taking place in the presence of DMSO-d6. This finding was consistent with hydrogen bonding between $NH_2$-POA and Tet-1 being primarily responsible for stabilization of the [$NH_2$-POA@Tet-1] complexes.

Titration of Tet-1 With Itself 1 mg of Tet-1 ($1.709\times10^{-4}$ mmol) was dissolved in 600 μL of $CD_2Cl_2$ in a scintillation vial and the solution was transferred into an NMR tube. In a separate scintillation vial, 3 additional equivalents of Tet-1 ($5.1273\times10^{-4}$ mmol) were dissolved in 240 μL $CD_2Cl_2$ and the resulting solution was titrated (FIG. 23) into the NMR tube in 10 steps. No significant shifts of any $^1$H-NMR resonances corresponding to Tet-1 were observed upon increasing the concentration of Tet-1, which indicated that Tet-1 does not oligomerize in solution under the reaction conditions.

Titration of $NH_2$-POA With Itself 1 mg of $NH_2$-POA ($0.166\times10^{-3}$ mmol) was dissolved in 500 μL of $CD_2Cl_2$ in a scintillation vial and the solution was transferred into an NMR tube. In a separate scintillation vial, 4 additional equivalents of $NH_2$-POA ($0.664\times10^{-3}$ mmol) were dissolved in 480 μL $CD_2Cl_2$ and the resulting solution was titrated into the NMR tube in 5 steps. No significant shifts of any $^1$H-NMR resonances corresponding to $NH_2$-POA were observed upon increasing the concentration of $NH_2$-POA.

Example 21—$^1$H-NMR Rate Measurements with $NH_2$-POA $^1$H-NMR rate measurements were performed as described above. All $^1$H-NMR spectra (with integrals of the key p-nitrophenol resonance used to monitor the progress of the reactions) are shown in FIGS. 25-29.

$^1$H-NMR Rate Measurements with Short-$NH_2$-POA are shown in FIGS. 30-32.

$^1$H-NMR Rate Measurements with Long-$NH_2$-POA are shown in FIGS. 33-35.

Example 22—$^1$H-NMR Rate Measurements With $NH_2$-POA in the Presence of DMSO-d6

The $^1$H-NMR rate measurements were performed as described above, except that they were executed in a 90:10 vol % mixture of a $CD_2Cl_2$: DMSO-d6 (instead of in pure $CD_2Cl_2$) with 1.5 mg of $NH_2$-POA polymer, which corresponds to an initial amine concentration ([amine] o) of approximately 1.5 mM. All $^1$H-NMR spectra (with integrals of the key p-nitrophenol resonance used to monitor the progress of the reactions) are shown in FIGS. 36-38.

Example 23—Derivation of Rate Equations

The kinetic data showed that plots of $[amine]^{-1}$ vs. reaction time (FIG. 5B) were approximately linear for all the samples and, therefore, the reactions were all second order in the amine-concentration. The amino groups on the polymer were, therefore, not just acting as the reagent for aminolysis, but also as catalysts to deprotonate (Basilio et al., "A new reaction pathway in the ester aminolysis catalyzed by glymes and crown ethers," J. Org. Chem. 71:4280-4285 (2006), which is hereby incorporated by reference in its entirety) the tetrahedral amine-adducts. Given this information, the Michaelis-Menton equation was written for the glyme-catalyzed aminolysis reactions in the low-substrate limit as:

$$\frac{\partial[\text{amine}]}{\partial t} = \frac{kcat}{K_M}[NDB][\text{cat}]_0^n[\text{amine}]^2 \quad \text{(Eq. S1)}$$

n=1 for cat=Triglyme or Edge-model (see FIGS. 39B-C)

n=2 for cat=Tet-1 (see FIG. 39A)

In Equation S1, [amine] is the total concentration of amino groups on all the polymer chains, $k_{cat}/K_M$ is the catalytic efficiency, $[\text{cat}]_0$ is the initial concentration of the organocatalyst, and [NDB] is the concentration of the active ester. For all the experiments an excess of active ester was used and the same initial amount of active ester was added to all experiments. Therefore, the NDB concentration can be approximated to remain constant during the aminolysis reactions, and, with $[\text{NDB}]_0$ defined as the initial concentration of the active ester, the rate law can be further simplified as:

$$\frac{\partial[\text{amine}]}{\partial t} = \frac{kcat}{K_M}[NDB]_0[\text{cat}]_0^n[\text{amine}]^2 \quad \text{(Eq. S2)}$$

Finally, the observed rate constant $k_{obs}$ was defined as:

$$k_{obs} = \frac{kcat}{K_M}[NDB]_0 \quad \text{(Eq. S3)}$$

Which led to the following simplified rate equation:

$$\frac{\partial[\text{amine}]}{\partial t} = k_{obs}[\text{cat}]_0^n[\text{anime}]^2 \quad \text{(Eq. 1)}$$

For the control reaction without any catalyst added, the rate constant $k_{obs}$ of the reaction was defined in an analogous manner:

$$\frac{\partial[\text{amine}]}{\partial t} = k_{obs}[\text{anime}]^2 \quad \text{(Eq. 2)}$$

Example 24—Custom Python Script Used to Fit the Association Equilibrium Constant and De-Threading Rate Constant for the Complexes Upon addition of the $NH_2$-POA polymers, the Tet-1 $^1$H-NMR resonances likely broadened (FIGS. 20A-B and 21A-B) for a variety of reasons, including (i) slowed host-guest exchange, (ii) desymmetrization of the protons in the cage upon polymer binding, as well as (iii) different polymer-cage binding modes coexisting with the polydisperse polymer sample. For these reasons, a detailed $^1$H-NMR line-shape analysis for the [$NH_2$-POA@Tet-1] systems was impractical. Nevertheless, the sigmoidal characters of the titration curves were accounted for (FIG. 5B) by fitting to the peak maxima with the following custom python script, which runs the software LineshapeKin 4.0 many times, driven by the curve-fit algorithm, implemented in the Scipy software package (FIG. 47).

Example 25—Results of Examples 1-24

Synthesis of a Hydrazone-Linked Molecular Tetrahedron

Figure 12:
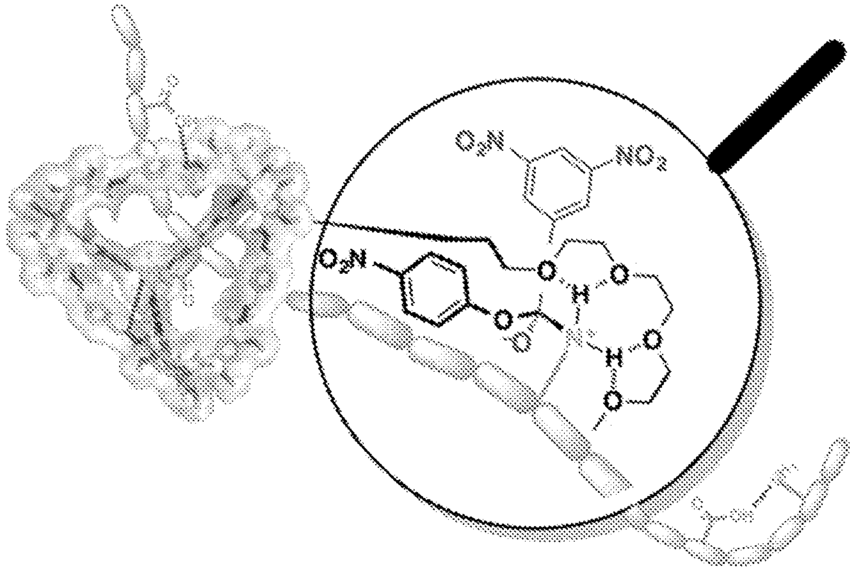
FIG. 12 shows a schematic (simplified) representation of the catalytic mechanism by which a prototypical nanocage functionalizes an amine-functionalized polymer chain.

To achieve activity and selectivity, a PSPM catalyst has to recognize the polymeric substrates to initiate catalysis (FIG. 12). Molecular polyhedra with large opening are well suited to meet this challenge with tetrahedral structures providing the largest openings out of all possible regular polyhedra (Mahata et al., "Giant Electroactive $M_4L_6$ Tetrahedral Host Self-Assembled with Fe(II) Vertices and Perylene Bisimide Dye Edges," *J. Am. Chem. Soc.* 135:15656-15661 (2013), which is hereby incorporated by reference in its entirety). For instance, the surface area per face of a tetrahedron is 1.8 times larger than the corresponding surface area per face for a cube with an identical volume. The present application now shows that—due to their wide openings—tetrahedral cages allow polymers with bulky side chains to thread through, to prepare for further catalytic functionalization. Although molecular polyhedra with $T_d$ symmetry can be synthesized (Liu et al., "Multicomponent Dynamic Covalent Assembly of a Rhombicuboctahedral Nanocapsule," *Chem. Eur. J.* 13:8953-8959 (2007); Holst et al., "Porous Organic Molecules," *Nat. Chem.* 2:915-920 (2010); Mastalerz, M. "Shape-Persistent Organic Cage Compounds by Dynamic Covalent Bond Formation," *Angew. Chem. Int. Ed.* 49:5042-5053 (2010); Beuerle et al., "Covalent Organic Frameworks and Cage Compounds: Design and Applications of Polymeric and Discrete Organic Scaffolds," *Angew. Chem. Int. Ed.* 57:4850-4878 (2018); Hasell et al., "Chirality as a Tool for Function in Porous Organic Cages," *Nanoscale* 9:6783-6790 (2017); Mastalerz, M., "Porous Shape-Persistent Organic Cage Compounds of Different Size, Geometry, and Function," *Acc. Chem. Res* 51:2411-242 (2018), which are hereby incorporated by reference in their entirety) with dynamic covalent chemistry (e.g. with imine linkages) (Liu et al., "Multicomponent Dynamic Covalent Assembly of a Rhombicuboctahedral Nanocapsule," *Chem. Eur. J.* 13:8953-8959 (2007); Hasell et al., "Triply Interlocked Covalent Organic Cages," *Nat. Chem.* 2:750-755 (2010); Chen et al., "Separation of Rare Gases and Chiral Molecules by Selective Binding in Porous Organic Cages," *Nat. Mater.* 13:954-960 (2014); Ding et al., "Controllable Synthesis of Covalent Porphyrinic Cages with Varying Sizes via Template-Directed Imine Condensation Reactions," *J. Org. Chem.* 80:9360-9364 (2015); Kandambeth et al., "Self-Templated Chemically Stable Hollow Spherical Covalent Organic Framework," *Nat. Commun.* 6:6786 (2015); Ronson et al., "Design Principles for the Optimization of Guest Binding in Aromatic-Paneled Fe(II) 4L6 Cages," *J. Am. Chem. Soc.* 139:9698-9707 (2017); Cao et al., "Controllable Self-Assembly of Pills and Cages via Imine Condensation for Silver Cation Detection," *Org. Lett.* 20:7447-7450 (2018); Greenaway et al., "High-Throughput Discovery of Organic Cages and Catenanes using Computational Screening Fused with Robotic Synthesis," *Nat. Commun.* 9:2849 (2018); Mastalerz, M., "Porous Shape-Persistent Organic Cage Compounds of Different Size, Geometry, and Function," *Acc. Chem. Res* 51:2411-242 (2018); Zhang et al., "Porous Organic Cage Embedded C18 Amide Silica Stationary Phase for High Performance Liquid Chromatography," Anal. Sci. 34:445-451 (2018); Hussain et al., "Organic Nanocages: A Promising Testbed for Catalytic $CO_2$ Conversion,"

Sustainable Energy Fuels 3:2567-2571 (2019), which are hereby incorporated by reference in their entirety), the currently reported systems lack sufficient stability (Ciaccia et al., "Fast Transimination in Organic Solvents in the Absence of Proton and Metal Catalysts. A Key to Imine Metathesis Catalyzed by Primary Amines Under Mild Conditions," *Chem. Sci.* 4:2253 (2013); Laha et al., "Implications of Dynamic Imine Chemistry for the Sustainable Synthesis of Nitrogen Heterocycles via Transimination Followed by Intramolecular Cyclisation," *Org. Biomol. Chem.* 14:2473-2479 (2016), which are hereby incorporated by reference in their entirety) for organocatalytic PSPM processes (one possible drawback of imine cages is that the imine bonds of the catalyst would engage in transimination side reactions (Ciaccia et al., "Fast Transimination in Organic Solvents in the Absence of Proton and Metal Catalysts. A Key to Imine Metathesis Catalyzed by Primary Amines Under Mild Conditions," *Chem. Sci.* 4:2253 (2013); Laha et al., "Implications of Dynamic Imine Chemistry for the Sustainable Synthesis of Nitrogen Heterocycles via Transimination Followed by Intramolecular Cyclisation," *Org. Biomol. Chem.* 14:2473-2479 (2016), which are hereby incorporated by reference in their entirety) with the amines of the polymers). While hydrolytic stability can be imparted onto imine-linked cages by reduction of the imines to amines (Zhang et al., "Porous Organic Cage Embedded C18 Amide Silica Stationary Phase for High Performance Liquid Chromatography," Anal. Sci. 34:445-451 (2018); Hussain et al., "Organic Nanocages: A Promising Testbed for Catalytic $CO_2$ Conversion," Sustainable Energy Fuels 3:2567-2571 (2019); Mosquera et al., "Aqueous Anion Receptors Through Reduction of Subcomponent Self-Assembled Structures," *Angew. Chem. Int. Ed.* 53:1556-1559 (2014), which are hereby incorporated by reference in their entirety), the secondary amines formed upon reduction are good nucleophiles, which would engage in side-reactions under the acylation conditions employed here. Thus, rather than using cages with imine/amine linkages, a method to create a porous tetrahedron was first invented (FIGS. 2A-B) with acyl-hydrazone linkages and peripheral glycol chains required for the PSPM catalysis. The primary reasons for utilizing a hydrazone-linked cage (Skene et al., "Dynamers: Polyacylhydrazone Reversible Covalent Polymers, Component Exchange, and Constitutional Diversity,' Proc. *Natl. Acad. Sci.* 101:8270-8275 (2004); Ferguson et al., "One-Pot Formation of Large Macrocycles with Modifiable Peripheries and Internal Cavities," *Angew. Chem. Int. Ed.* 48:3150-3154 (2009); Bhat et al., "Nucleophilic Catalysis of Acylhydrazone Equilibration for Protein-Directed Dynamic Covalent Chemistry," *Nat. Chem.* 2:490-497 (2010); Klein et al., "Dynamic Combinatorial Libraries for the Recognition of Heavy Metal Ions," *Org. Biomol. Chem.* 10:60-66 (2012), which are hereby incorporated by reference in their entirety) as organocatalyst were the following: (i) hydrazone linkages generally display enhanced hydrolytic stability, which renders them excellent candidates for catalysis, (ii) the NH group available in acyl-hydrazones represents a suitable hydrogen bond donor, which can direct the assembly of hydrazone-linked polyhedra, (iii) the hydrogen bonding capabilities of hydrazones can assist PSPM catalysis (FIG. 12) by binding and unfolding polymeric substrates.

For an efficient synthesis of hydrazone-tetrahedra (FIG. 2B) with large openings, a special vertex (syn-7) was designed to encode tetrahedron formation (Scheme 1). Syn-7 combines hindered rotation (Sharafi et al., "Crystal Packing-Driven Enrichment of Atropoisomers," *Angew. Chem. Int. Ed.* 56:7097-7101 (2017), which is hereby incorporated by reference in its entirety) around three Ph-Ph σ-bonds with three intramolecular [NH . . . OR]-hydrogen bonds, which direct (Ferguson et al., "One-Pot Formation of Large Macrocycles with Modifiable Peripheries and Internal Cavities," *Angew. Chem. Int. Ed.* 48:3150-3154 (2009), which is hereby incorporated by reference in its entirety) the growth of the tetrahedron upon hydrazone formation. This strategy allowed to create the first hydrazone-linked $T_d$-symmetric molecular tetrahedron. The tetrahedron was not only bound to side-chain polymers but it also catalyzed the PSPM of amine-functionalized polymers with relatively long side-chains in a size-selective manner.

The synthesis (Scheme 1) of syn-7 started with a trifold formylation of syn-1, which was created on a large scale with a solid state-driven amplification of the syn-atropoisomer of 1 (Sharafi et al., "Crystal Packing-Driven Enrichment of Atropoisomers," *Angew. Chem. Int. Ed.* 56:7097-7101 (2017)), which is hereby incorporated by reference in its entirety).

Scheme 1. Synthesis of the Hydrazone-Linked Molecular Tetrahedron Tet-1
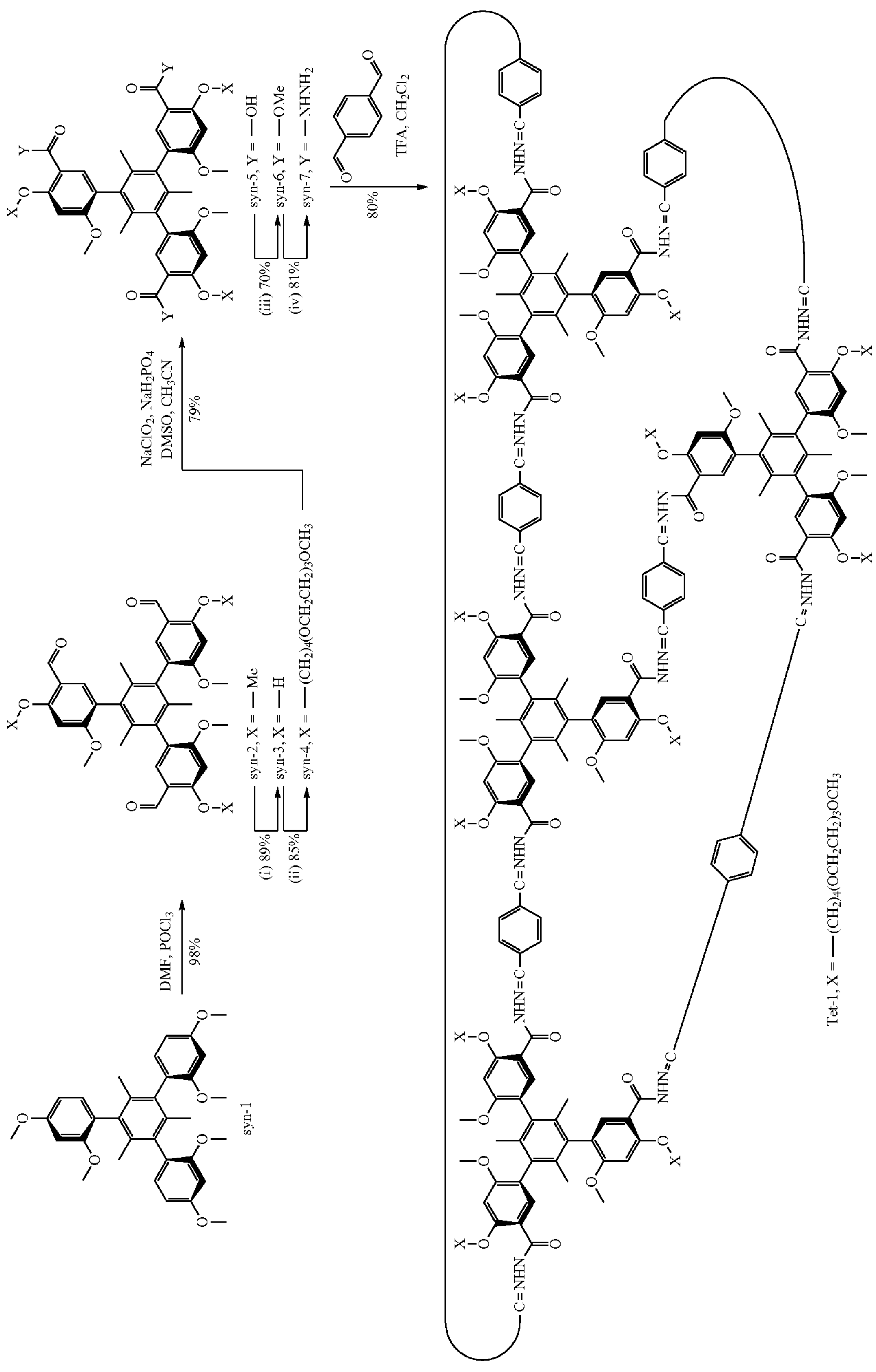
Tet-1, X = —$(CH_2)_4(OCH_2CH_2)_3OCH_3$ Reagents and conditions: (i) $BCl_3$, $CH_2Cl_2$; (ii) Br—$(CH_2)_4(OCH_2CH_2)_3OCH_3$, $K_2CO_3$, DMF, A; (iii) MeOH, $H_2SO_4$, A; (iv) $H_2NNH_2$, MeOH, $H_2O$, A.

The methoxyl groups ortho to the aldehydes of the resulting syn-2 were then removed selectively with $BCl_3$ to afford the tris-phenol syn-3. Finally, syn-3 was converted into the vertex syn-7 through (i) alkylation of the phenolic-OH groups, (ii) Pinnick oxidation (Dalcanale et al., "Selective Oxidation of Aldehydes to Carboxylic Acids with Sodium Chlorite-Hydrogen Peroxide," *J. Org. Chem.* 51:567-569 (1986), which is hereby incorporated by reference in its entirety) of the aldehydes to carboxylic acids, (iii) esterification, and (iv) hydrazinolysis of the resulting methyl esters. To form the tetrahedron Tet-1, two equivalents of the vertex syn-7 were mixed with three equivalents of terephtalaldehyde and trifluoroacetic acid (TFA) as the catalyst in $CH_2Cl_2$. After 48 hours of stirring at room temperature, Tet-1 was formed in 80% yield, as confirmed by high-resolution ESI mass spectrometry as well as $^1$H—, $^{13}$C—and DOSY $^1$H-NMR spectroscopy.

Figure 14:
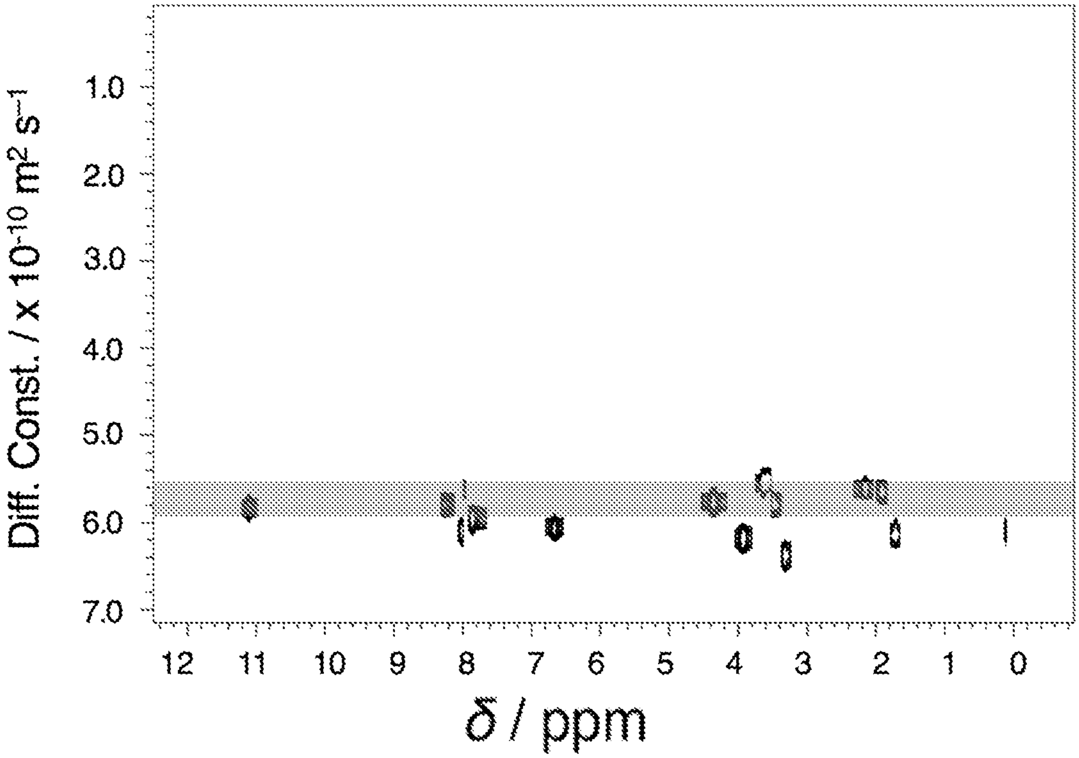
FIG. 14 is a DOSY $^1$H-NMR (500 MHz, $CD_2Cl_2$, 298 K) spectrum of Tet-1.

The $^1$H-NMR spectrum of Tet-1 illustrated its Ta symmetry with only five resonances (all singlets) appearing in the region between 6 and 12 ppm. Based on a minimized molecular model (FIG. 2B), the height of Tet-1 is 22 Å which agrees well with the solvodynamic diameter (21 Å) measured by DOSY $^1$H-NMR spectroscopy (FIG. 14). The cage is not only soluble in organic solvents but also in aqueous mixtures with polar organic solvents. To test its hydrolytic stability, Tet-1 was dissolved in a 90:10 vol-% mixture of DMSO-d6 and $D_{20}$ and the resulting clear solution was heated to 80° C. for 5 hours. No degradation was observed (FIG. 13) under these conditions by $^1$H-NMR spectroscopy, which illustrated the excellent hydrolytic stability of Tet-1, even at elevated temperatures.

Synthesis of Additional Hydrazone-Linked Molecular Tetrahedra

Additional hydrazone-linked tetrahedra Tet-2, Tet-3, Tet-4, Tet-5, and Tet-6 were synthesized analogous to the synthesis of Tet-1 (Scheme 2).

Scheme 2. Synthesis of the Hydrazone-Linked Molecular Tetrahedra Tet-2, Tet-3, Tet-4, Tet-5, and Tet-6
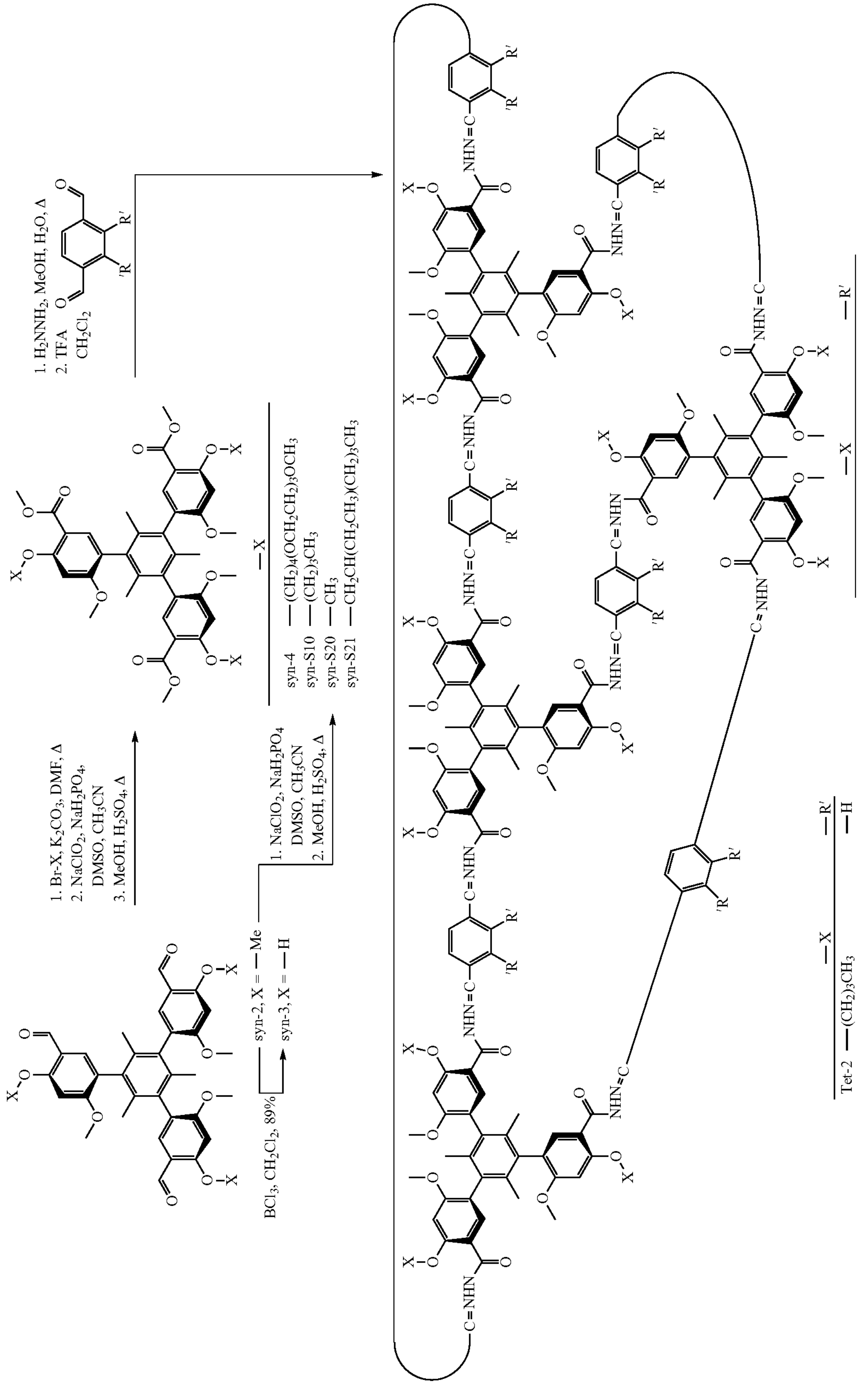
| | —X | —R′ |
|---|---|---|
| Tet-2 | —$(CH_2)_3CH_3$ | —H |
| Tet-3 | —$CH_3$ | —H |
| Tet-4 | —$CH_2CH(CH_2CH_3)(CH_2)_3CH_3$ | —H |
| | —X | —R′ |
|---|---|---|
| Tet-5 | —$(CH_2)_4(OCH_2CH_2)_3OCH_3$ | —$OCH_3$ |
| Tet-6 | —$(CH_2)_4(OCH_2CH_2)_3OCH_3$ | —$OCH_2C\equiv CH$ |

Polymer Recognition with Tet-1

After Tet-1 was isolated, the molecular tetrahedron's ability to recognize amine-functionalized polymers with side chains was investigated, since binding to such macromolecules is a prerequisite for the catalytic polymer functionalization described below. To create amine-functionalized polymers, n-octylamine (90 mol %) was first condensed with commercial poly(isobutylene-alt-maleic) anhydride, and then the remaining anhydride units were reacted with 1,6-diaminohexane (Scheme 3). As shown by (i) elemental analysis, (ii) by Fourier-transform infrared (FTIR) spectroscopy, and (iii) by measuring the percentage of free amino groups through complete acylation at elevated temperature, this procedure led to full and partial amidation of the maleic anhydride units to afford a polydisperse mixture of amine-functionalized poly(isobutylene-alt-n-octyl maleamide) ($NH_2$-POA) polymers with a molecular weight $\overline{M}_w$ of 6.3 kDa. The polymeric mixture is well-soluble in a variety of organic solvents and contains 3.7 repeat units (out of 20.5) with free $NH_2$-containing sidechains on average.

structure of the complex with a long polymer chain) not only with the inside, but also with the outside of the tetrahedron. In turn, the shorter polymers were not long enough to effectively wrap around the tetrahedron, while at the same time threading through Tet-1's cavity, which led to a more active catalytic conformation with the shorter polymer chains.

In the threaded binding geometry, the solvodynamic diameter of $NH_2$-POA increased by ca. 50%, compared to the solvodynamic diameter of the $NH_2$-POA polymer on its own (FIG. 3C). To confirm this finding, MD simulations were run (FIGS. 4A-C) of the polymer with and without Tet-1 for 800 ns. These simulations demonstrated that the observed increase in polymer size (ca. 20% size-increase is predicted by the MD simulations) was indeed caused by unfolding of the polymer, when it threaded through Tet-1. As also indicated by the MD simulations, the polymer-unfolding was driven (FIG. 41) by the cage breaking up the intramolecular hydrogen bonds in the polymer and replacing them with polymer-to-cage hydrogen bonds. Further support Scheme 3. Synthesis of an Amine-Functionalized Polymeric Substrate for Size-Selective Catalysis

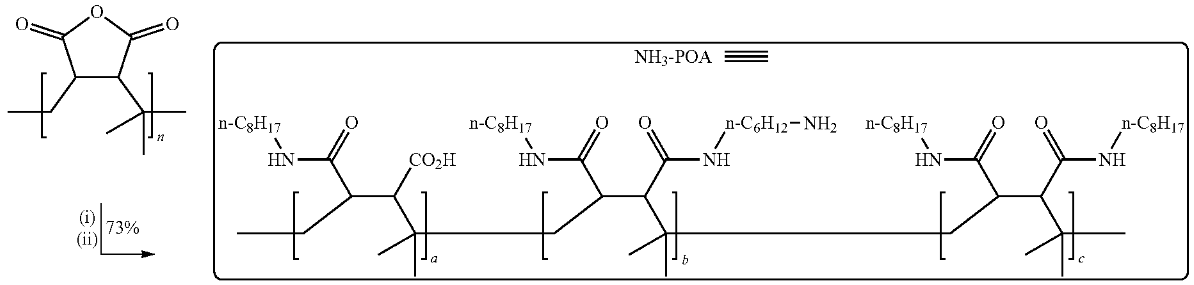

Reagents and conditions: (i) $H_2N$-n-$C_8H_{17}$, DMF, Δ; (ii) $H_2N$-n-$C_6H_{12}$—$NH_2$, DMF, A. Based on elemental analysis and the $\overline{M}_w$ (6.3 kDa), the average number of repeating units a, b, and c were: a=12.1, b=3.7, and c=4.7.

Figure 1A:
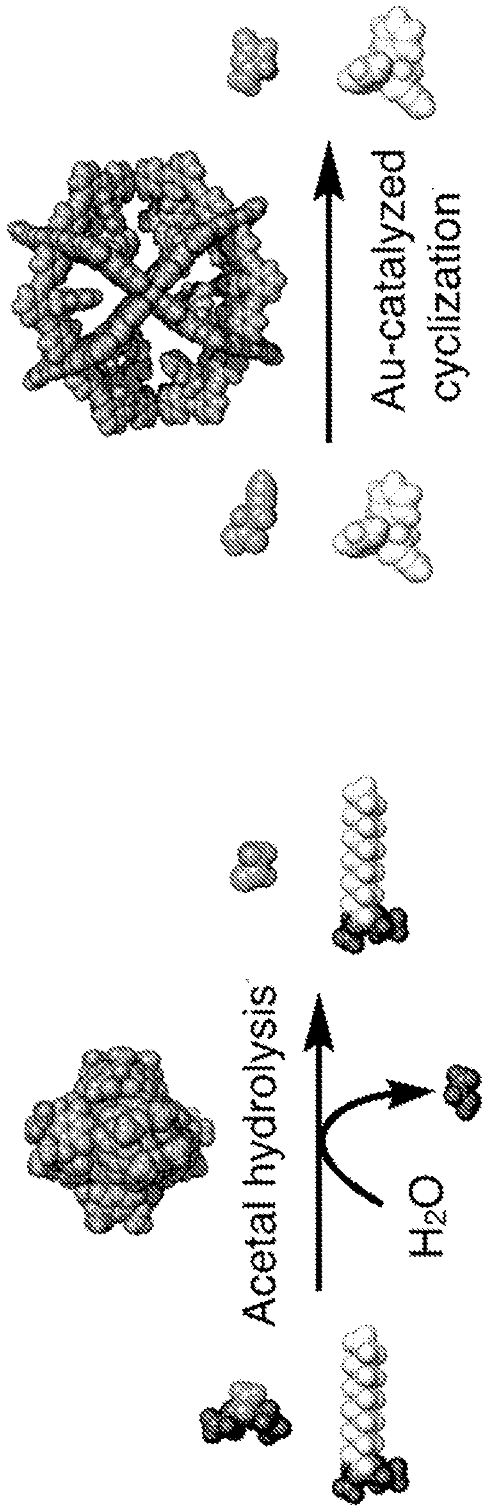
FIGS. 1A-B are schematics showing a substrate-selective catalysis—from small-molecule to polymeric substrates.
Figure 1B:
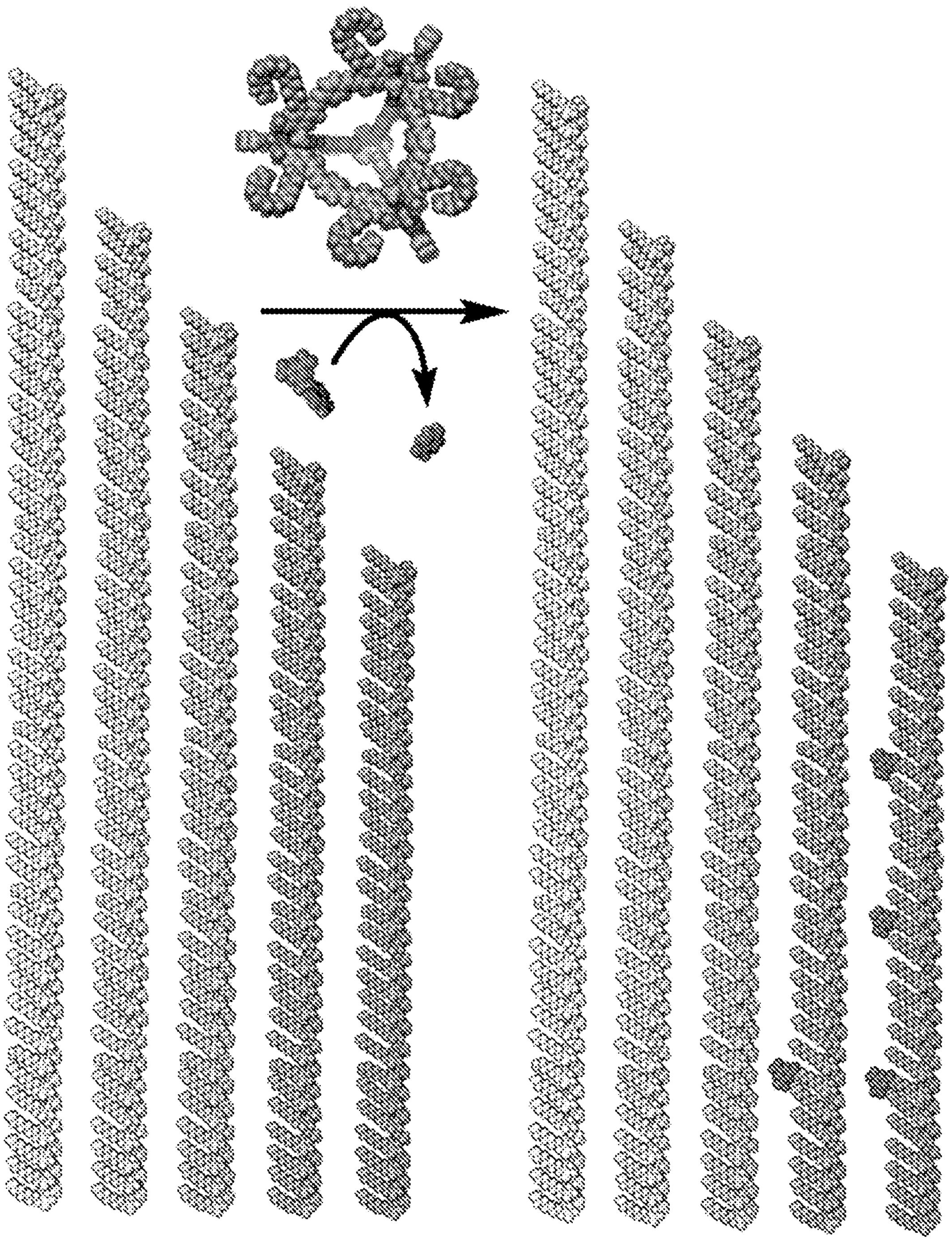
Figure 3D:
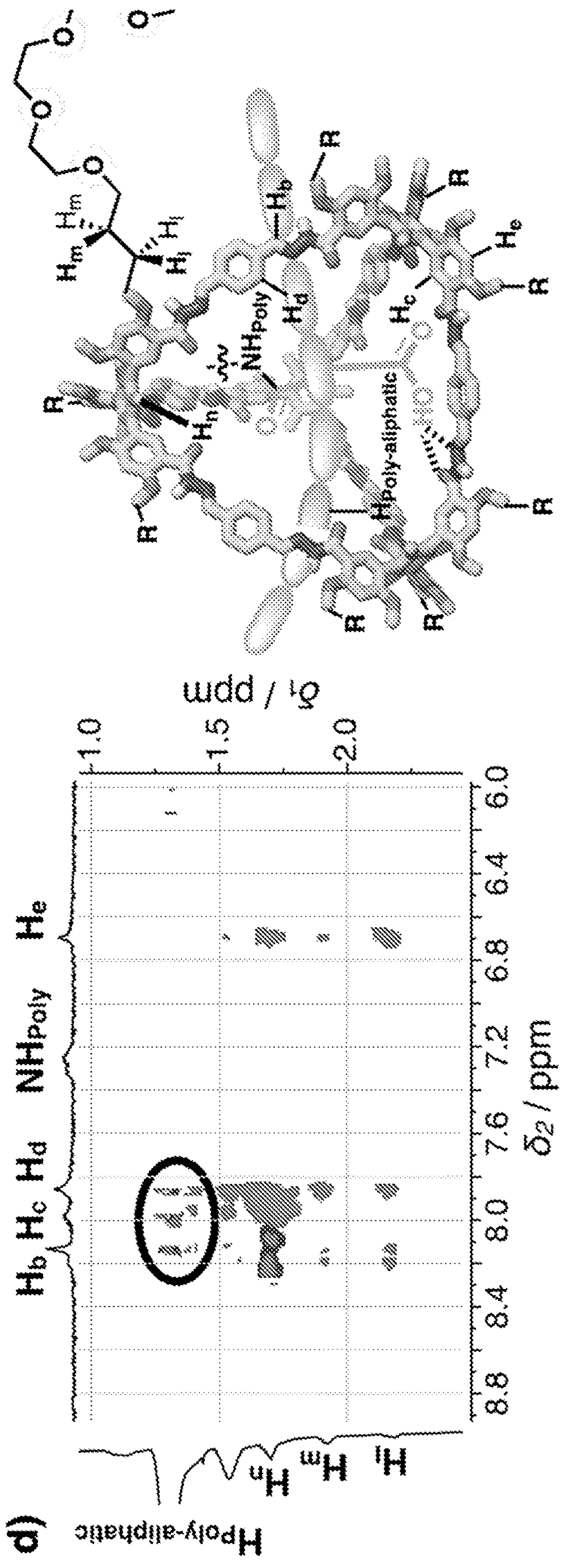
Figure 4C:
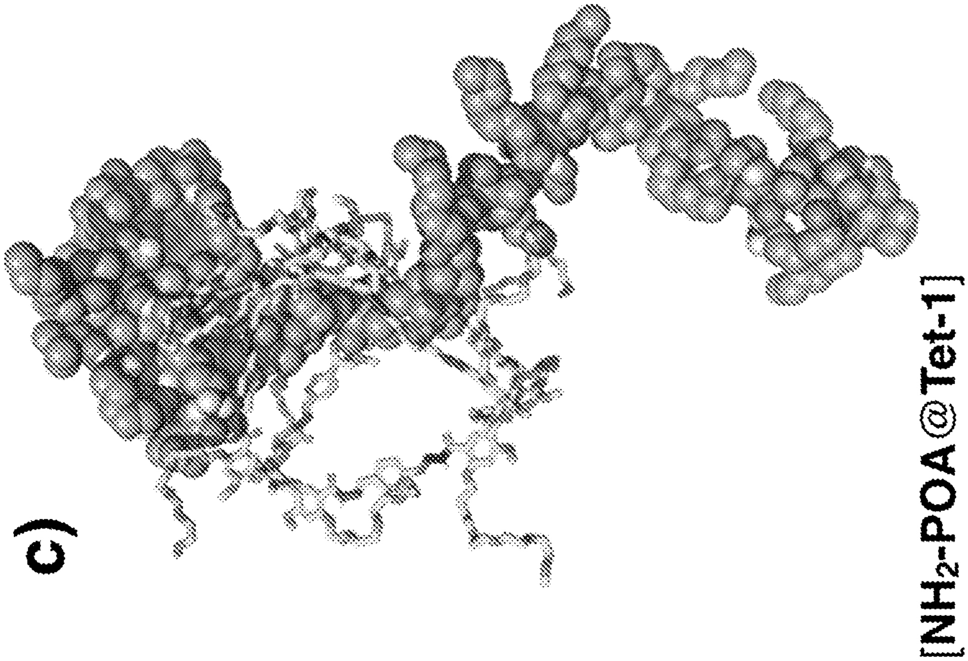

Next, binding between Tet-1 and the polymeric $NH_2$-POA substrate was confirmed with (i) DOSY $^1$H-NMR spectroscopy (FIGS. 3A-C), (ii) $^1$H-$^1$H-NOESY NMR spectroscopy (FIG. 3D), (iii) all-atom molecular dynamics (MD) simulations (FIGS. 4A-C), as well as (iv) $^1$H-NMR-based host-guest titrations (FIGS. 5A-C). The DOSY $^1$H-NMR spectrum of the $NH_2$-POA/Tet-1 mixture showed two diffusion bands for the [$NH_2$-POA@Tet-1] complex at different diffusion coefficient (D) values ($1.7\times10^{-10}$ $m^2$ $s^{-1}$ and $2.5\times10^{-10}$ $m^2$ $s^{-1}$). These two diffusion bands of the complex arise from two different complexation geometries, which interconvert slowly on the NMR timescale. Based on a direct comparison with MD simulations (vide infra), the larger complex, with an average D value of $1.7\times10^{-10}$ $m^2$ $s^{-1}$, is the one where $NH_2$-POA is threaded through the cavity of Tet-1. For this binding geometry, NOE cross peaks were clearly observed (FIGS. 3D and 19) between the $H_e$ protons of Tet-1 (which point straight into the cavity of the molecular tetrahedron) and the aliphatic protons ($H_{Poly\text{-}aliphatic}$) of the polymer chains. This finding strongly supported threading of the polymer chains through the cavity of Tet-1. In general, the NOE cross-peaks between the protons of the polymers and Tet-1 (especially with $H_a$) were stronger (FIGS. 3D and 19) with the shorter polymers (Short-$NH_2$-POA). Thus, since the longer polymers binded the strongest (FIG. 5B) to Tet-1, they very likely interact (FIG. 4C showed a simulated for this finding was provided by (i) FIGS. 22A-B, which shows that when DMSO-d6 (a well-known hydrogen-bond disruptor) was added to a solution of the [$NH_2$-POA@Tet-1] complex in $CD_2Cl_2$, rapid decomplexation occurred as well as (ii) by FIG. 40, which demonstrates that Tet-1 no longer served as an effective catalyst in a polar solvent like DMSO-d6. In the second diffusion band, the diffusion coefficient (D) of the polymer decreased only slightly, compared to the D of the polymer by itself, from $2.8\times10^{-10}$ $m^2$ $s^{-1}$ (unbound polymer, FIG. 3C) to $2.5\times10^{-10}$ $m^2$ $s^{-1}$ (bound polymer, FIG. 3B). Thus, it was concluded that in the second binding conformation, the polymer got unfolded to a lesser extent then when it was threaded through the cage, likely because the polymer and Tet-1 interacted with side-on coordination modes in the second binding conformation.

To gain further insight into the nature of the polymer recognition abilities of Tet-1, the shortest (Short-$NH_2$-POA, $\overline{M}_w$=2.6 kDa) and longest (Long-$NH_2$-POA, $\overline{M}_w$=9.9 kDa) fractions contained in the original $NH_2$-POA sample were separated and isolated with an additional size-exclusion chromatography run. Both the short and long polymer samples were then titrated into 0.28 mM solutions of Tet-1 in $CD_2Cl_2$ while recording the $^1$H-NMR spectra of the mixtures at each titration point. The titration curves obtained (FIG. 5A) showed that the polymer resonances shifted downfield. The percentage of polymer chains complexed to Tet-1 is highest at the titration point with [Short-$NH_2$-POA]=0.26 mM and [Tet-1]=0.28 mM. A smaller percentage of the polymers are complexed to the Tet-1 receptor at the titration point with [Short-$NH_2$-POA]=0.50 mM. Thus, based on the data shown in FIG. 5A, the resonances of $NH_2$-POA clearly shift downfield upon complexation to Tet-1) when the polymer threaded through the cavity of Tet-1. This finding can be explained (FIG. 5C) by the detailed structure and associated aromatic ring-current effects (Wannere et al., "How do Ring Currents Affect 1H NMR Chemical Shifts?," *Org. Lett.* 5:605-608 (2003), which is hereby incorporated by reference in its entirety) of the threaded binding geometry, wherein the polymer chain passes by the side (and not the face as in most small-molecule pseudo-rotaxanes/rotaxanes (Liu et al., "Surveying Macrocyclic Chemistry: From Flexible Crown Ethers to Rigid Cyclophanes," *Chem. Soc. Rev.* 46:2459-2478 (2017); Stoddart, J. F., "Mechanically Interlocked Molecules (MIMs)-Molecular Shuttles, Switches, and Machines (Nobel Lecture)," *Angew. Chem. Int. Ed.* 56:11094-11125 (2017), which are hereby incorporated by reference in their entirety)) of the aromatic linkers in Tet-1.

Analysis of the NMR titration data (FIG. 5B) with the LineshapeKin 4.0 software (Kovrigin, E. L., "NMR Line Shapes and Multi-State Binding Equilibria," *J. Biomol. NMR* 53:257-270 (2012), which is hereby incorporated by reference in its entirety) (fit to a simple 1:1 binding model) provided further information regarding the complexation thermodynamics and kinetics between the $NH_2$-POA polymer substrates of different lengths and the Tet-1 catalyst. First, it was discovered that the shorter polymer chains ($\overline{M}_w$=2.6 kDa) de-complex nearly three times as fast as the longer ($\overline{M}_w$=9.9 kDa) ones (FIG. 5B shows the de-complexation rate-constants, $k_{off}$, measured for Short- and Long-$NH_2$-POA). This result represented further evidence for pseudorotaxane formation between Tet-1 and the $NH_2$-POA polymers, as de-threading from a pseudorotaxane-like conformation was expected (Wang et al., "Orchestrating Directional Molecular Motions: Kinetically Controlled Supramolecular Pathways of a Helical Host on Rodlike Guests," *J. Am. Chem. Soc.* 139:9350-9358 (2017), which is hereby incorporated by reference in its entirety) to slow down with increasing polymer length, since it takes longer on average for Tet-1 to slide to the end of a longer polymer chain. Second, the complex association constants ($K_a$) determined (FIGS. 5A-C) by the $^1$H-NMR titration experiments demonstrated that the longer $NH_2$-POA polymer chains bind stronger to Tet-1 than the shorter ones. Interestingly, for enzymes, it is well-known (Albery et al., "Evolution of Enzyme Function and the Development of Catalytic Efficiency," *Biochemistry* 15:5631-5640 (1976), which is hereby incorporated by reference in its entirety) that if an enzyme binds too strongly (i.e. too "tight") to its substrate (but not as strongly to the transition state), the enzymatic reaction will slow-down with increasing substrate-binding strength. Here, a similar phenomenon was observed (FIG. 9D) for a fully synthetic system. Specifically, it was discovered (vide infra) that the shorter $NH_2$-POA polymers (which bind the weakest to the Tet-1 catalyst) nevertheless reacted the fastest with Tet-1. Overall, these results provided evidence that Tet-1 was able to thread-over and partially unfold/stretch out the $NH_2$-POA polymers in $CD_2Cl_2$ (which is an ideal solvent for glyme-catalyzed aminolysis), laying the foundation to use Tet-1 as a size-selective organocatalyst as described below.

Organocatalytic Polymer Functionalization with Tet-1

Triglyme functional groups act (Basilio et al., "A New Reaction Pathway in the Ester Aminolysis Catalyzed by Glymes and Crown Ethers," *J. Org. Chem.* 71:4280-4285 (2006), which is hereby incorporated by reference in its entirety) as organocatalysts to accelerate aminolysis reactions. Since Tet-1 possesses 12 peripheral triglyme chains and binds to amine-functionalized $NH_2$-POA polymers, Tet-1 can engage in size-selective catalytic (FIGS. 6A-B) functionalization of these polymeric substrates. The catalytic performance of Tet-1 was evaluated by monitoring the kinetics of the aminolysis reaction with $^1$H-NMR in the presence of an internal standard (1,2,4,5-tetrabromobenzene). Five reaction mixtures were prepared in $CD_2Cl_2$ as the solvent. Each of the reaction mixtures contained (i) nitrophenyl-3,5-dinitrobenzoate (NDB) active ester, (ii) $NH_2$-POA polymer as the substrate, as well as (iii) one of the following catalysts/controls: a) Tet-1, b) Edge-Model (a model for an edge of Tet-1), c) Triglyme+a simple control hydrazone (Control) in equimolar amounts, d) Triglyme by itself, and d) no additives. NDB was selected as the active ester, since it attaches dinitrobenzoate groups onto the polymers, which are readily observed in the aromatic region of the spectrum in DOSY $^1$H-NMR. This fact enabled determination the size-selectivity of the polymer-functionalization reactions.

The progress of the reactions was followed by integrating (FIGS. 24-28) the distinct $^1$H-NMR resonance at 6.9 ppm, which corresponded to p-nitrophenol formed upon aminolysis of the NDB active ester. From the p-nitrophenol concentration and the initial amine concentration ($[amine]_0$=1.8 mM), the concentrations of the remaining amino groups ([amine]) on the $NH_2$-POA polymers were calculated for each time point. Kinetic data showed that plots of $[amine]^{-1}$ vs. reaction time (FIG. 6A) are linear for all the samples and therefore the reactions are all second order in the amine-concentration. The amino groups on the polymers are therefore not just acting as the reagent for aminolysis, but also as catalysts to deprotonate (Basilio et al., "A New Reaction Pathway in the Ester Aminolysis Catalyzed by Glymes and Crown Ethers," *J. Org. Chem.* 71:4280-4285 (2006), which is hereby incorporated by reference in its entirety) the tetrahedral amine-adducts. Furthermore, it was found that by changing the catalyst concentrations (FIGS. 39B-C show the corresponding rate-plots) that the reactions are approximately first order in the catalyst concentration for the simple Triglyme+Control as well as for the Edge-Model catalysts. This result is in line with the prior literature for glyme-catalyzed aminolysis reactions (Basilio et al., "A New Reaction Pathway in the Ester Aminolysis Catalyzed by Glymes and Crown Ethers," *J. Org. Chem.* 71:4280-4285 (2006), which is hereby incorporated by reference in its entirety). However, with Tet-1 as the catalyst, it was discovered (FIG. 39A), that the reaction is not just second order in the amine concentration, but also second order in the Tet-1 concentration. Given this information, the rate-laws for the PSPM reactions can (Maude et al., "Complexation Catalysis: Effective Charge Development in the Aminolysis of Phenyl Esters in Chlorobenzene Catalysed by Crown Ether," *J. Chem. Soc. Perkin Trans.* 2:691 (1995); Basilio et al., "Molecular Recognition-Based Catalysis in Nucleophilic Aromatic Substitution: A Mechanistic Study," *New J. Chem.* 36:1519 (2012), which are hereby incorporated by reference in their entirety) be written with cat=Edge-Model or Triglyme as:

$$\frac{\partial[\text{amine}]}{\partial t} = k_{obs}[\text{cat}]_0^n[\text{anime}]^2 \quad \text{(Eq. 1)}$$

On the other hand, with cat=Tet-1, the rate law can be written as:

$$\frac{\partial[\text{amine}]}{\partial t} = k_{obs}[\text{cat}]_0^2[\text{anime}]^2 \quad \text{(Eq. 2)}$$

Finally, for the control reaction without any catalyst added, the rate constant $k_{obs}$ of the reaction was defined in an analogous manner:

$$\frac{\partial[\text{amine}]}{\partial t} = k_{obs}[\text{amine}]^2 \quad \text{(Eq. 3)}$$

$k_{obs}$ in equations 1-3 are observed rate constant (defined in equation S3), [amine] is the total concentration of amino groups on all the polymer chains, and $[\text{cat}]_0$ is the initial concentration of the organocatalyst.

The rate constants $k_{obs}$ (FIG. 6B) and slopes obtained from the second-order rate-plots (FIG. 6B) demonstrated that acylation of the amines on the polymers with Tet-1 as the catalyst was significantly faster than with any of the other control reactions. Thus, Tet-1 was a more effective catalyst than either simple Triglyme or the Edge-Model, both of which lack the large cavity of the hydrazone cage.

Size-Selectivity of the Organocatalytic Polymer Functionalization Process

The present application demonstrates that the Tet-1 catalyst can distinguish between different chain-lengths of the $NH_2$-POA substrates directly in the complex mixture of all the polymer chains and partially reverse the intrinsic size selectivity for the catalytic polymer functionalization process. Evidence for the size selectivity includes:

(i) A distinct difference (FIG. 7) in the average solvodynamic diameter for the polymers functionalized with Tet-1, compared to the polymers functionalized with the control catalysts.

(ii) DOSY $^1$H-NMR spectra (FIGS. 8A-B), which confirm directly that-when the reaction is executed with the real polymer mixture—the functionalized polymers display a smaller solvodynamic diameter than the unfunctionalized ones when Tet-1 is used as the catalyst.

(iii) Explicit measurements (FIGS. 9A-D) of all the catalytic rate constants, $k_{obs}$, for the short and long polymer chains with all catalysts (Tet-1, Edge-Model, and Triglyme).

(i) Evidence of Size-Selectivity Based on Solvodynamic Diameters

To investigate the size selectivity in the presence of all polymer chains, PSPM reactions were first ran with different catalysts and NDB as the acylation reagent to the same conversion (24%). For the first catalytic system, Tet-1 (0.28 mM) was used as the catalyst, while a combination of Triglyme+Control (3.4 mM each) was used as the control. To be able to directly compare the different reaction systems, they were equalized before analysis with the following protocol: (i) for the functionalization reaction catalyzed by Tet-1 (0.28 mM), Triglyme (3.4 mM) and Control (3.4 mM) were added just before analysis. (ii) For the control reaction catalyzed by Triglyme (3.4 mM equivalents)+Control (3.4 mM), Tet-1 (0.28 mM) was added again just before analysis. All measurements were executed with volumetric additions from identical stock solutions. In this manner it was ensured that, besides the differently-functionalized polymers, all other components and amounts thereof were exactly the same for all the samples in the end. As a result, different properties of the equalized reaction mixtures were expected to directly correlate with differences in the functionalization patterns of the polydisperse $NH_2$-POA substrates.

DOSY $^1$H-NMR spectra of all reaction mixtures were recorded immediately after equalization. From these spectra, the average solvodynamic diameters of the polymers were determined. Significant differences in the solvodynamic diameters of the polymers were observed between the control reaction and the Tet-1-catalyzed variant. These differences indicate (FIG. 7) a change in size-selectivity for polymer functionalization with Tet-1: with the control reaction, the longer polymer chains get acylated the fastest, which resulted in a significant reduction of the number-averaged solvodynamic diameter of the polymer (from 4.9 to 2.8 nm) upon acylation of the amines. This reduction in polymer size can be explained with less aggregation occurring after acylation (since fewer strong [—$NH_2$ . . . . HOOC-]-hydrogen bonds are present after acylation) and the fact that longer polymers have a higher tendency to aggregate, because they contain more $NH_2$ and COOH groups on average than shorter ones. A much smaller reduction in the solvodynamic polymer diameter upon acylation (from 4.9 to 4.5 nm) was observed for functionalization with Tet-1 as the catalyst. This finding indicated that, with Tet-1 as the catalyst, shorter polymer chains (which have a weaker tendency to aggregate) get acylated the fastest.

The $NH_2$-POA polymers contain (Scheme 3) both $NH_2$ and COOH functional groups. In the non-polar $CD_2Cl_2$ solvent used for the acylation reactions, these functionalities formed strong hydrogen bonds, that are required (FIG. 5C) in order for Tet-1 to bind to the polymeric substrates. In addition, the hydrogen-bonding capabilities of the polymers also induced some aggregation of the polymers. Overall, longer polymer chains have a statistically higher chance to form aggregated structures, since they contain a larger number of $NH_2$ and COOH functional groups on average. When the $NH_2$ groups on the polymers were acylated with NDB, some of the [—$NH_2$ . . . HOOC-]-hydrogen bonds disappeared, which reduced aggregation of the polymers. Now, if longer polymers get acylated the most, the observed reduction in aggregation will be stronger than if shorter polymer chains get acylated the most. From the measured solvodynamic diameters a smaller reduction in average size (from 4.9 to 4.5 nm) was observed for the reaction executed with Tet-1 as the catalyst than for the control reaction (4.9 nm to 2.8 nm). This data therefore indicated that shorter polymer chains got acylated the fastest with Tet-1 as the catalyst, while longer polymer chains got acylated preferentially in the control reaction.

(ii) Comparing the Diffusion Constants of the Functionalized to the Unfunctionalized Polymers Provides Direct Evidence for Size Selectivity in the Polydisperse Mixture To obtain additional evidence for the size-selectivity in the polymer mixture, the average size of the functionalized polymer chains was compared (FIGS. 8A-B) to the average size of all the polymer chains (both functionalized and unfunctionalized) with DOSY $^1$H-NMR spectroscopy. Acylation with NDB-which attaches 3,5-dinitrobenzamide units with distinct aromatic $^1$H-NMR resonances to the polymers. Thus, the average diffusion constant of the functionalized polymers were determined from the DOSY $^1$H-NMR resonances of the 3,5-dinitrobenzamide units. The results obtained clearly showed (FIGS. 8A-B) that the aromatic resonance corresponding to the acylated $NH_2$-POA substrates was lined up with the shorter polymer chains of the sample when Tet-1 was used as the catalyst. In contrast, when Triglyme+Control were used as the catalysts instead, the medium/longer polymer chains reacted faster in the PSPM reaction.

Figure 6A:
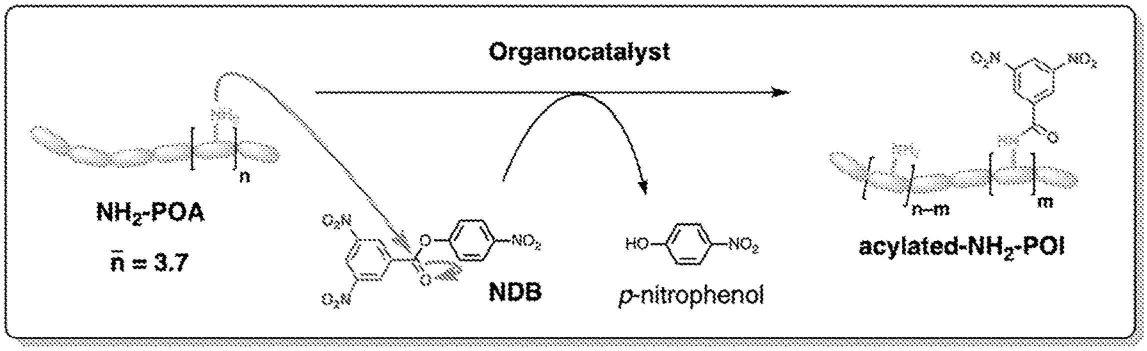
Figure 6B:
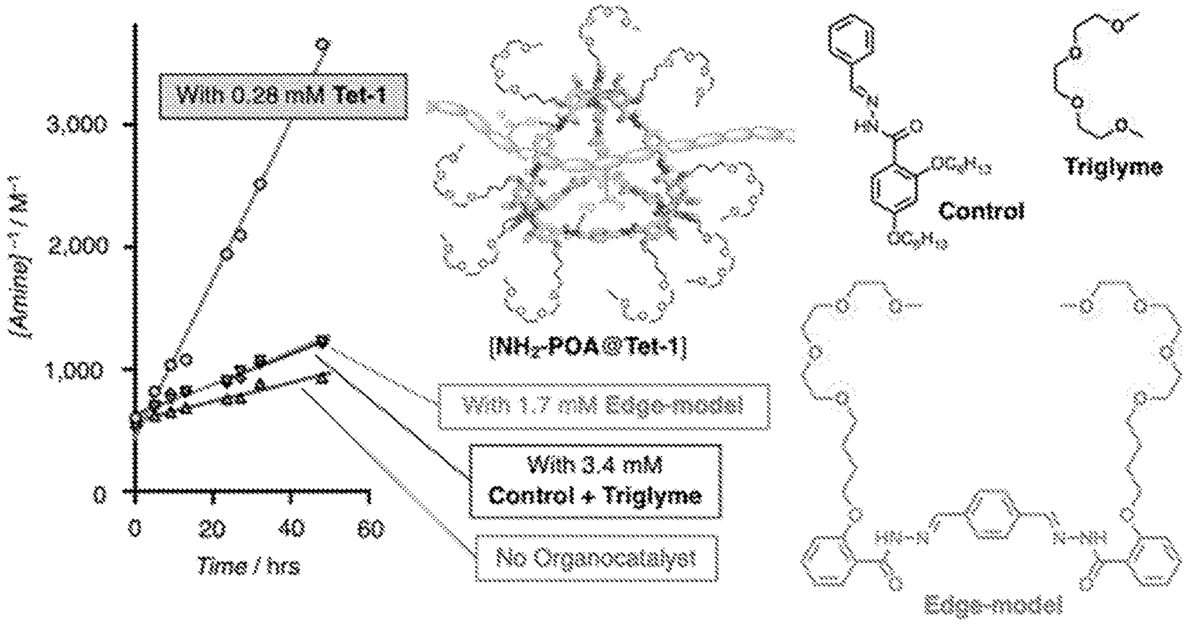

(iii) Measurements of the Relative Rate Constants for the Acylation of Short and Long Polymers Separately Confirm the Selectivity of the Tet-1 Catalyst for Shorter Polymers Some of the shortest (Short-$NH_2$-POA; $\overline{M}_w$=2.6 kDa) and longest (Long-$NH_2$-POA; $\overline{M}_w$=9.9 kDa) polymer chains contained within the original $NH_2$-POA sample were isolated (FIGS. 5A-C). Thus, the acylation rate constants of the short and long polymer samples were measured separately (FIGS. 9A-D), analogous to how the rate constants ($k_{obs}$) with the mixed $NH_2$-POA sample were determined (FIG. 6A-B).

Figure 7:
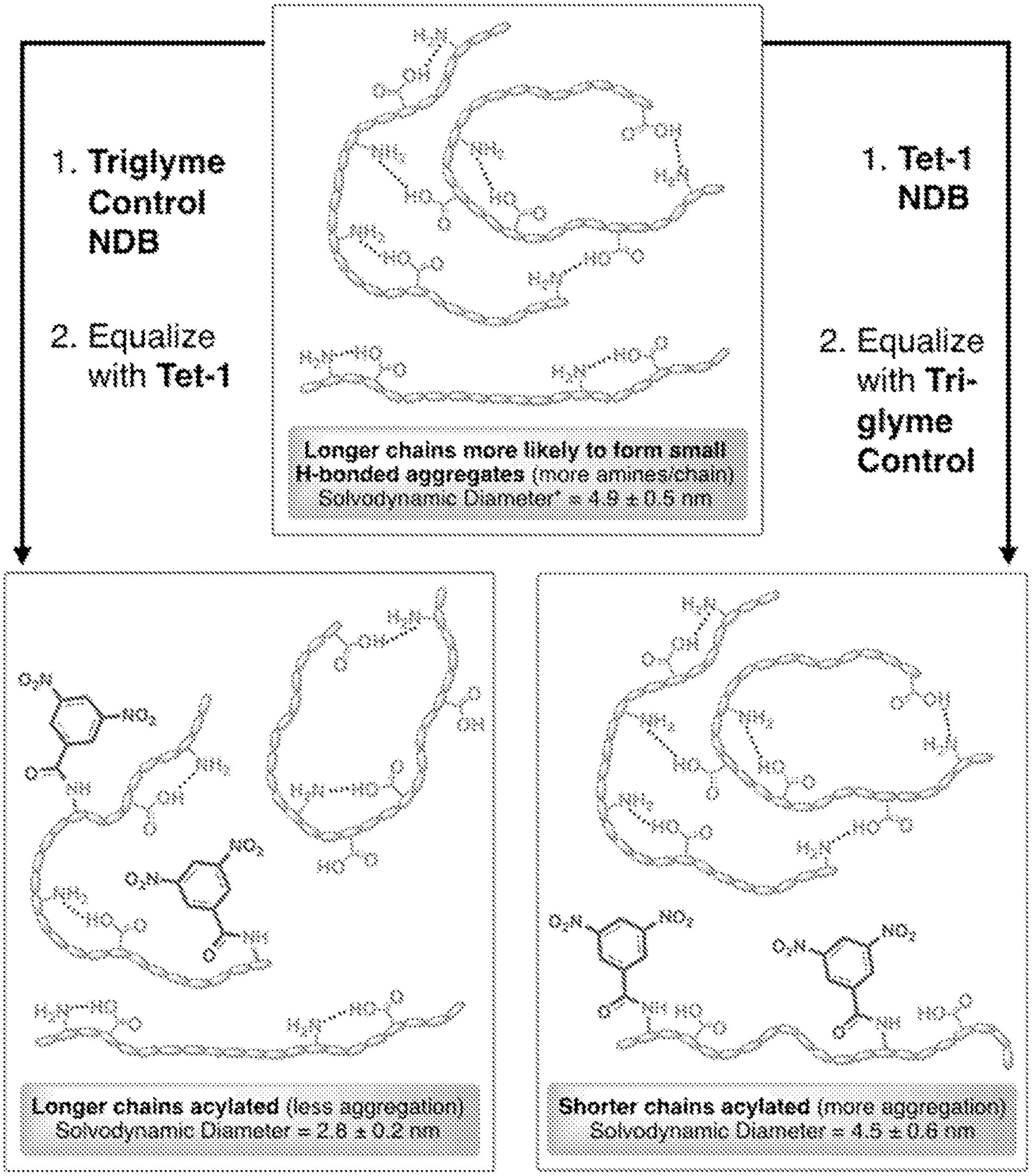
FIG. 7 is a schematic showing that solvodynamic diameters of the $NH_2$-POA polymers provide evidence for size selectivity in the polymer mixture. The $NH_2$-POA polymers contain (Scheme 3) both $NH_2$ and COOH functional groups. In the non-polar $CD_2Cl_2$ solvent used for the acylation reactions, these functionalities form strong hydrogen bonds, that are required (FIG. 5C) in order for Tet-1 to bind to the polymeric substrates. In addition, the hydrogen-bonding capabilities of the polymers also induce some aggregation of the polymers. Overall, longer polymer chains have a statistically higher chance to form aggregated structures, since they contain a larger number of $NH_2$ and COOH functional groups on average. When the $NH_2$ groups on the polymers are acylated with NDB, some of the [—$NH_2$·HOOC-]-hydrogen bonds disappear, which reduces aggregation of the polymers. Now, if longer polymers get acylated the most, the observed reduction in aggregation will be stronger than if shorter polymer chains get acylated the most. From the measured solvodynamic diameters a smaller reduction in average size (from 4.9 to 4.5 nm) was observed for the reaction executed with Tet-1 as the catalyst than for the control reaction (4.9 nm to 2.8 nm). This data therefore indicated that shorter polymer chains got acylated the fastest with Tet-1 as the catalyst, while longer polymer chains got acylated preferentially in the control reaction.
Figure 10:
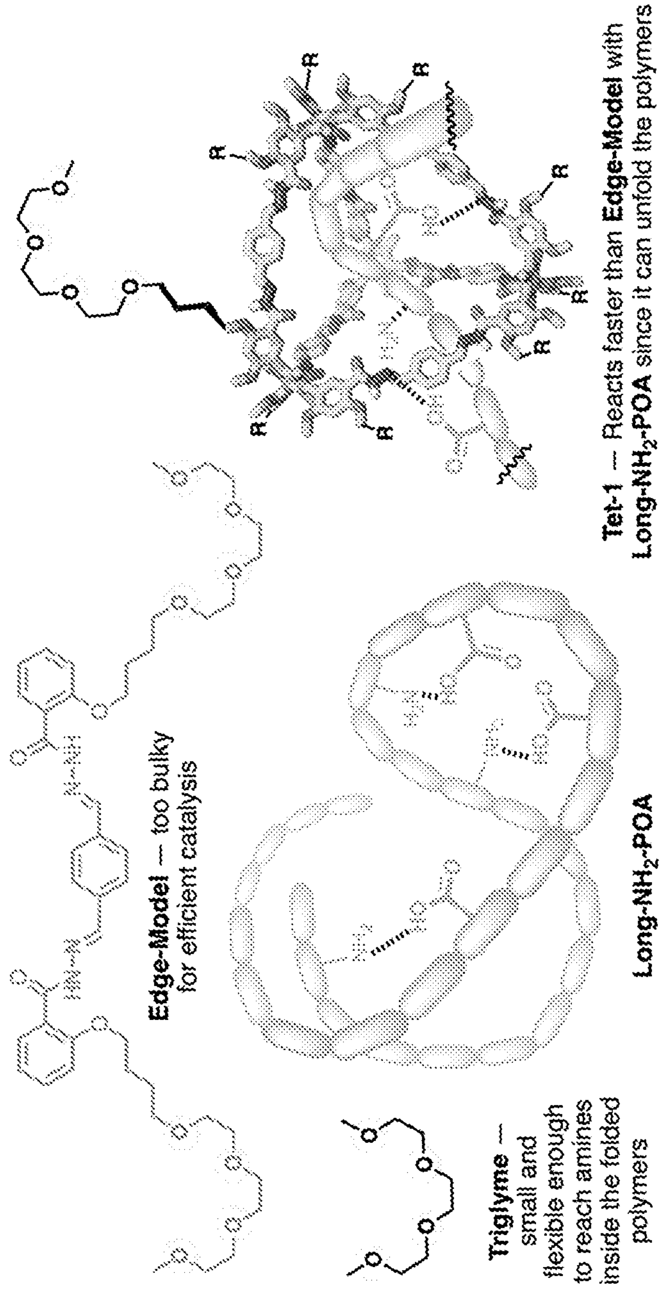
FIG. 10 shows Tet-1's ability to unfold the polymer chains, explaining the relative acylation rates observed with Long-$NH_2$-POA with the three different catalysts. Triglyme (3.4 mM) acts (FIG. 9B) as a more effective catalyst than Edge-Model (1.7 mM) for the Long-$NH_2$-POA substrates, while for the Short-$NH_2$-POA substrates both of these catalytic systems perform (FIG. 9A) at approximately equal rates. This reactivity trend is explained by polymer folding/aggregation (FIG. 7) which occurs preferentially for the longer polymers, which contain more amino groups per chain on average. Remarkably, with the even larger Tet-1 as the catalyst, the acylation reaction speeds up again for the long polymers. This finding indicated that the large cavity of Tet-1 can unfold (see FIGS. 3A-D and 4A-C for additional evidence) the polymeric substrates to free up the amines on the polymeric substrates.

The results shown in FIGS. 9A-D demonstrated that the short polymers (Short-$NH_2$-POA; $k_{obs}$=2.9±0.4×$10^9$ $M^{-3}$ $hr^{-1}$) indeed reacted faster with the Tet-1 catalyst than the longer ones (Long-$NH_2$-POA; $k_{obs}$=1.9±0.3×$10^9$ $M^{-3}$ $hr^{-1}$), which confirmed the size-selectivity determined directly (FIGS. 7 and 8A-B) in the polymer mixture. The results shown in FIGS. 9A-D also demonstrated that the longer chains intrinsically react faster than the shorter ones, if the reactivity with the small Triglyme catalyst was taken as a measure for the intrinsic reactivity of the polymer chains. This finding once again agreed with the conclusions from the DOSY $^1$H-NMR measurements (FIGS. 7 and 8A-B). It was assumed that the longer polymer chains intrinsically react faster than the shorter ones, since they contain more amino-groups per polymer chain on average, which are needed (FIG. 11) for intramolecular base-catalysis. Overall, the rate constants determined for the short and long polymer chains by themselves were faster with all the catalysts than with the mixed polymer sample. Therefore, the mixture does not behave exactly like its individual components, which is expected for a complex system with many interacting parts. For example, the longer polymer chains bind (FIG. 5B) stronger to the Tet-1 catalyst than the shorter ones. Nevertheless, the shorter chains reacted faster with the catalyst, as weaker binding to the substrate helped to further lower (Albery et al., "Evolution of Enzyme Function and the Development of Catalytic Efficiency," *Biochemistry* 15:5631-5640 (1976), which is hereby incorporated by reference in its entirety) (FIG. 9D) the activation Gibbs free energy of the reaction. Thus, from the measured binding and rate constants, it was concluded that the longer polymers must inhibit the reaction with the shorter polymers, which is likely why the rate constant for the shorter polymers alone with Tet-1 ($k_{obs}$=2.9±0.4×$10^9$ $M^{-3}$ $hr^{-1}$) is indeed larger than the rate constant of the mixture ($k_{obs}$=8.3±0.8×$10^8$ $M^{-3}$ $hr^{-1}$) with Tet-1. The relative rate-plot-slopes obtained with the three different catalysts also provide (FIGS. 3A-D and 4A-C provide additional evidence) direct evidence for polymer unfolding by Tet-1 during acylation catalysis as detailed in FIG. 11.

Overall, based on the evidence shown in FIGS. 7, 8A-B and 9A-D, Triglyme catalyzed the reaction with the long polymer chains faster than with the short ones. In turn, with Tet-1 as the catalyst, the shorter polymer chains reacted faster than the longer ones, which demonstrated that the Tet-1 catalyst was able to switch the intrinsic reactivity of acylation toward selective functionalization of the shorter chains via size-selective acceleration of the reaction with the shorter chains.

Example 26—Discussion of Examples 1-25

Mechanism of the Size-Selective Catalytic Polymer Functionalization

The control reactions executed with simple Triglyme and the Edge-model demonstrated that not only the triglyme functions of Tet-1, but also the cavity of the tetrahedron are important for catalysis. For instance, the slope (=$k_{obs}$ [cat] o) of the rate plot with the $NH_2$-POA substrate increased (FIG. 6A) from 7.9±0.9 $M^{-1}$ $hr^{-1}$ ($R^2$=0.96) without any additives to 13.0±0.9 $M^{-1}$ $hr^{-1}$ ($R^2$=0.97) with simple Triglyme (3.4 mM) as the catalyst, demonstrating glyme-catalysis (Basilio et al., "A New Reaction Pathway in the Ester Aminolysis Catalyzed by Glymes and Crown Ethers," *J. Org. Chem.* 71:4280-4285 (2006), which is hereby incorporated by reference in its entirety) in the system. Next, with Edge-model (1.7 mM) as the catalyst, the slope of the rate plot-13.3±0.7 $M^{-1}$ $hr^{-1}$ ($R^2$=0.98)—turned out to be almost identical to the value obtained with Triglyme. However, a very significant jump in the rate plot slope (=$k_{obs}$ [cat] 02) was observed to 64.9±3.0 $M^{-1}$ $hr^{-1}$ ($R^2$=0.99) by utilizing the whole tetrahedron (Tet-1, 0.28 mM) as the catalyst. This data was consistent with a mechanism (FIG. 11), where both the glyme functionalities as well as the voluminous cavity of the molecular tetrahedron Tet-1 actively participate in the size-selective polymer-functionalization mechanism.

Furthermore, from the measured second-order rate dependence on the Tet-1 concentration, it was concluded that two tetrahedra must be interacting (Yamashina et al., "Cramming Versus Threading of Long Amphiphilic Oligomers into a Polyaromatic Capsule," *Nat. Commun.* 9:4227 (2018), which is hereby incorporated by reference in its entirety) with the polymeric substrate in the rate-determining transition state of the reaction. Thus, based on (i) the kinetic data and (ii) the fact that the solvodynamic diameter of the polymers increased very significantly upon binding to Tet-1 (FIGS. 3A-D, 4A-C, and 10), the mechanism shown in FIG. 11 for the observed catalytic polymer functionalization was proposed. In the proposed mechanism, the hydrazone functionalities hydrogen bond (FIG. 5C) with functional groups on the polymers and thereby help unfold (FIGS. 4A-C shows an MD simulation of this process) the polymer chains to render the amines more reactive: the first Tet-1 molecule involved in the transition state freed up the amine nucleophile, while the second Tet-1 freed up the amine-base. At the same time, the triglyme functional groups of Tet-1 engaged in catalysis by stabilizing the tetrahedral intermediates arising during aminolysis. Finally, another amino-group on the polymer acted as a base (freed up by the second equivalent of Tet-1 bound to the transition state) to deprotonate and break apart the tetrahedral intermediate, which is clearly shown by the observed (FIGS. 6A, 9A, and 9B) second order rate-dependence on the amine concentration.

the Role of Tet-1's Cavity During Catalysis

FIGS. 9A-D provided additional evidence for polymer unfolding taking place thanks to the cavity of the Tet-1 catalyst. Specifically, it was observed that an edge of Tet-1 (Edge-Model) leads to an overall slower acylation rate than the much smaller Triglyme catalyst only for the longer polymeric substrates (Long-$NH_2$-POA) (FIG. 9B). At the same time these two control catalytic systems performed (FIG. 9A) at approximately identical rates with the shorter polymer chains (Short-$NH_2$-POA). This difference in catalytic activity is explained (FIG. 10) by polymer folding and the formation of relatively small aggregates (FIG. 7). Since the longer polymers contain, on average, more amino groups per chain than the shorter ones, polymer folding and aggregate formation occurs to a larger extent with the longer chains. Thus, the bulky Edge-Model as the catalyst performs worse as a catalyst for the longer polymer chains only, since the amino-groups occluded inside of the folded/aggregated long polymers can't be approached (FIG. 10) effectively by the bulky Edge-Model catalyst. While, these results were in line with what has been observed (Riess et al., "Dissipative Assemblies that Inhibit their Deactivation," *Soft Matter* 14:4852-4859 (2018), which is hereby incorporated by reference in its entirety) previously for non-catalytic reactions—for which aggregation has been shown to reduce reaction rates—the present application demonstrates that folding/aggregation-dependent reactivity can be directly influenced by changing the nature of an organocatalyst. Remarkably, with the even bulkier Tet-1 as the catalyst, the reaction speeds up again (FIG. 9B) with the longer polymer chains (Long-$NH_2$-POA) as the substrates. This result is a clear indication that Tet-1 was able to unfold the polymeric substrates. It further highlights the importance of Tet-1's large cavity, which is lacking in Edge-Model and seems to be required for efficient unfolding and catalytic functionalization of the polymeric substrates.

Origin of the Observed Size Selectivity

It is likely that a nanosized catalyst like Tet-1 can distinguish polymeric substrates of different sizes due to complex, large-section contacts, resembling interactions between biological macromolecules. Such non-local supramolecular recognition is difficult to achieve with small-molecule catalysts like Triglyme, since a small molecule catalyst interacts with reactive groups on the polymers (e.g. amines in this case) mostly in a local fashion. Although a small-molecule catalyst can also form multivalent contacts with its polymeric substrates, it will, in most instances, simply not be able to reach far away sections of a polymeric substrate to enable size-selective functionalization of such large substrates.

As suggested by MD simulations (FIGS. 4A-C), Tet-1 interacted with the polymeric substrates in a non-local fashion. Specifically, other amines and carboxylic acids—far away from a reactive amino group on the same polymer—can still influence the interactions between the polymeric substrate and Tet-1 through hydrogen-bonding networks (FIG. 5C). Therefore, it was expected for Tet-1 catalyst to distinguish different, non-local aspects of a polymer's structure, including (i) polymer length, (ii) the number and types of functional groups present on the polymer, as well as (iii) the positioning of these functional groups. Present application provides evidence (FIGS. 7, 8A-B, and 9A-D) for the effect of polymer length on the catalytic rates with Tet-1 and with small-molecule catalysts. From the kinetic evidence (i.e. the observed second order dependence of the reaction rates on the amine concentration), it is clear that longer polymer chains intrinsically reacted faster with a small-molecule catalyst like Triglyme. However, by switching to Tet-1 as the catalyst, this intrinsic reactivity can be partially reversed. Key factors for size selectivity with polymeric substrates include:

(i) The thermodynamic stability of the [polymer@Tet-1] complex. As has been established for classical enzyme kinetics, where the binding strength of the substrate with the enzyme has to be (Albery et al., "Evolution of Enzyme Function and the Development of Catalytic Efficiency," *Biochemistry* 15:5631-5640 (1976), which is hereby incorporated by reference in its entirety) "just right" and neither "too tight" nor "too loose" for efficient catalysis, it was found (FIG. 5B) that weaker binding of the substrate can indeed enhance the catalytic activity of the PSPM catalyst.

(ii) The availability of a large cavity in the catalyst, which is able to unfold the polymeric substrates. Notably, a simple edge of the tetrahedron (Edge-model) does not perform nearly as efficiently as the full tetrahedron.

(iii) A reactive complexation geometry, in which the polymers are not only partially unfolded (and threaded through the cavity of the catalyst), but also placed in close proximity to the catalytic triglyme units on the tetrahedron.

(iv) The ability of the catalyst to free up at least two amino groups on a polymer, the first one acing as the nucleophilic substrate for acylation, and the second one as the amine base needed for efficient deprotonation of the tetrahedral acylation intermediates.

(v) Aggregation (FIG. 7) of the polymer chains. While prior work has shown (Riess et al., "Dissipative Assemblies that Inhibit their Deactivation," *Soft Matter* 14:4852-4859 (2018); Qian et al., "Controlling the Isomerization Rate of an Azo-$BF_2$ Switch Using Aggregation," *J. Am. Chem. Soc.* 139:1037-1040 (2017), which are hereby incorporated by reference in their entirety) that aggregation reduces the reaction rates for non-catalytic reactions, it was discovered that for the present system aggregation and folding effects are strongly catalyst dependent. For example, folding/aggregation of the longer polymer chains significantly reduced (FIG. 9B) the reactivity of the long chains with the Edge-model catalyst. At the same time, aggregation effects were not strong enough (FIG. 9B) to slow down the Tet-1-catalyzed reaction with the long polymers in comparison with the small Triglyme catalyst. Rather, the results shown in FIGS. 9A-D clearly indicated that the observed size selectivity is caused by selective acceleration of Tet-1's reaction with the short polymers. Overall, the findings (especially the relative rates shown in FIGS. 9A-D) clearly demonstrated (FIG. 10) that aggregation/folding effects can mostly be overcome by threading polymers through the cavity of a porous catalytic tetrahedron, which lead to partial unfolding (FIGS. 4A-C) of the polymer chains.

CONCLUSIONS

In conclusion, the concept of post-synthetic selective polymer modification operating in complex mixtures of polymeric substrates was demonstrated. The reaction proceeds with size selectivity in the presence of a hydrazone-linked tetrahedron with wide openings as the catalyst, in sharp contrast to the results observed with small-molecule catalysts. This conclusion is supported by (i) distinct differences in the overall solvodynamic radii of the of the polymeric products, (ii) by a significant alteration in the relative diffusion constants for the functionalized polymers compared to the unfunctionalized ones, as well as (iii) by rate constants measured separately for the shorter and longer polymer chains. These findings extend the scope of catalyst-controlled size selectivity to large substrates for post-synthetic polymer-functionalization reactions, applied to polydisperse polymer mixtures. This size-selective, catalytic approach represents a promising avenue to create new polymers.

Example 27—Synthesis of Poly(isobutylene-alt-n-octyl maleimide) (POI)

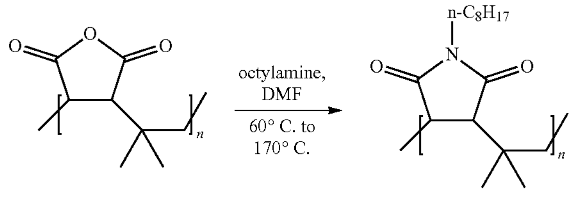

POI

Poly(isobutylene-alt-maleic anhydride) ($\overline{M}_w$ ~6,000 Da, 0.100 g, ~0.0166 mmol) was dissolved in anhydrous DMF (1.0 ml) while heating at 60° C. In a different vial, n-octylamine (0.252 g, 1.94 mmol) was dissolved in anhydrous DMF (1.0 ml) at the same temperature. Next, the octylamine solution was added to the polymer solution at 60° C. and the reaction mixture was stirred at 60° C. for 2 hours. The temperature was then increased to 120° C. for 2 hours under a stream of dry $N_2$ to remove the water formed in the condensation reaction. Finally, to assure that ring closure of all amide groups was complete, the temperature was increased further to 170° C. and reaction mixture stirred for another hour at that temperature under a stream of dry $N_2$ to obtain an orange oil. The crude product was washed twice with 5 ml of a 1 N aqueous NaOH solution. It was purified further by size exclusion chromatography over polystyrene beads (200-400 mesh) with $CH_2Cl_2$ as the eluent to afford POI as a yellow oil (0.151 g, 0.0146 mmol) in 88% yield. $^1H$ NMR (500 MHz, $CDCl_3$) δ 3.58-2.69 (broad m, 4H), 2.58-1.86 (broad m, 2H), 1.59 (broad m, 2H), 1.34-1.06 (broad m, 13H), 0.87 (broad m, 6H). IR: Vmax/$cm^{-1}$ (KBr): 1687.7; GPC: $\overline{M}_w$=9,076 Da, PDI=1.105.

Example 28—Binding Studies

Materials and Instruments

Deuterated solvents were purchased from Cambridge Isotope Laboratory and used without further purification. Tetramethylsilane (TMS), which was applied as the internal standard in all $^1H$-NMR binding studies, was purchased from Sigma Aldrich and used as received. All volumetric measurements were performed with Rainin Positive Displacement (MR-10, -100, -1000) micropipettes. The picrocrocin for the binding studies was isolated from the dry stigma of *Crocus sativus* (Persian Saffron), which was received from the Skinner Laboratory at the University of Vermont's Department of Agricultural Sciences. For extraction and purification of the picrocrocin, dehydrated stigma of *Crocus sativus* was grinded with mortar and pestle in $CH_3CN$. Next, the solution was filtered and the solvent evaporated under reduced pressure. The crude picrocrocin was purified with preparative thin-layer chromatography (TLC) over silica gel (eluent: $CH_3CN$, $R_f$=0.15). The $^1H$-NMR (500 MHZ, $CD_3OD$) spectrum of the picrocrocin obtained with applicants' purification method matched the characterization data reported (Sobolev et al., "Saffron Samples of Different Origin: An NMR Study of Microwave-Assisted Extracts," *Foods* 3:403-419 (2014), which is hereby incorporated by reference in its entirety) previously in the literature.

Sample Preparation and Measurements of Host-Guest Binding Constants

For all titration experiments with Tet-1, solutions of Tet-1 in $CD_2Cl_2$ were prepared first. The guests were then dissolved in the same solvent separately and titrated into the host solutions. For each titration, a series with approximately 10 $^1H$-NMR spectra was recorded. For the fitting of the association constants, the concentrations of both the host and guest were listed (i.e. the dilution effect for each experiment was considered) together with the corresponding $^1H$-NMR chemical shifts of representative protons. Next, those listings were entered into DynaFit (Kuzmic, P. "Program DYNAFIT for the Analysis of Enzyme Kinetic Data: Application to HIV Proteinase," *Anal. Biochem.* 237:260-273 (1996), which is hereby incorporated by reference in its entirety), which was used to obtain association constants and corresponding standard errors by fitting to all representative $^1H$-NMR resonances at the same time. To ensure that the fitted binding models are not distorted by the host and/or guests binding with themselves, a series of $^1H$-NMR spectra ($CD_2Cl_2$, 298 K) was also recorded for varying concentrations of just Tet-1 as well as all the guests alone. No significant self-binding was observed (vide infra) for Tet-1 or any of the guest.

Measurement of the Complex Association Constant for [PVP@Tet-1] (Complex Formed Between PVP and Tet-1)

Tet-1 (1.1 mg, $1.88\times10^{-4}$ mmol) was dissolved in 500 μL of $CD_2Cl_2$ in a scintillation vial and then transferred to an NMR tube. In a separate vial, 5.0 equivalents of the guest polymer polyvinylpyrrolidone (PVP, $9.47\times10^{-4}$ mmol) were dissolved in 340 μL of $CD_2Cl_2$ and the resulting solution was titrated into the NMR tube in 11 steps. The best fit (FIG. 48A) to the titration data was obtained with a 1:1 binding model with an association constant for [PVP@Tet-1] of (2.0±0.2)x10-3 $M^{-1}$.

Measurement of the Complex Association Constants for [POI@Tet-1] (Complex Formed Between POI and Tet-1)

Tet-1 (1.1 mg, $1.88\times10^{-4}$ mmol) was dissolved in 500 μL of $CD_2Cl_2$ in a scintillation vial and transferred to an NMR tube. In a separate vial, 5.0 equivalents of the guest polymer polyvinylpyrrolidone (POI, $9.47\times10^{-4}$ mmol) were dissolved in 340 μL $CD_2Cl_2$ and the resulting solution was titrated into the NMR tube in 11 steps. Upon titration, very significant broadening of peaks corresponding to Tet-1 was observed (FIG. 50), which is expected to occur for an intermediate-slow host-guest exchange/rearrangement regime on the $^1H$-NMR timescale. Consistent (Kovrigin, E. L., "NMR Line Shapes and Multi-State Binding Equilibria," *J. Biomol. NMR* 53:257-270 (2012), which is hereby incorporated by reference in its entirety) with this notion is also the fact that the titration curve with POI looks sigmoidal, although it does not fit a higher order (i.e. 2:1 or 3:1) binding model. The sigmoidal character of the titration curve (FIG. 48B) was accounted for with LineShapeKin (Kovrigin, E. L., "NMR Line Shapes and Multi-State Binding Equilibria," *J. Biomol. NMR* 53:257-270 (2012), which is hereby incorporated by reference in its entirety). A 1:1 binding model (dashed line in FIG. 48B) with an effective [POI@Tet-1]-dissociation rate constant of 40 $s^{-1}$ and a $K_a$ of (6.9±1.0)× $10^3$ $M^{-1}$ accurately reproduces the titration data.

To investigate whether hydrogen bonding is important for the binding of POI with Tet-1, DMSO-d6 (10 μL) was added to an NMR sample containing POI (1.13 mM) and Tet-1 (0.22 mM) in $CD_2Cl_2$. Immediately after the addition of the DMSO-d6 (which is a well-known hydrogen bond disruptor), the $^1$H-NMR resonances corresponding to Tet-1 sharpened (FIG. 51) notably. This finding was consistent with hydrogen bonding between POI and Tet-1 slowing down the dissociation rate of the [POI@Tet-1] complex. In doing so, the hydrogen bonding between the host and the guest likely also stabilizes the complex thermodynamically.

Measurement of the Complex Association Constant for [PS@Tet-1] (Complex Formed Between PS and Tet-1)

In a vial, Tet-1 (2.83 mg, $4.83\times10^{-4}$ mmol) was dissolved in 600 μL of $CD_2Cl_2$ and the solution was transferred to an NMR tube. In a separate vial, 5.0 equivalents of polystyrene (PS, $\overline{M}_w$=3,510 Da, 8.48 mg) were dissolved in 240 μL of $CD_2Cl_2$ and titrated into the NMR tube containing the solution of Tet-1. No shifts of any $^1$H-NMR resonances corresponding to Tet-1 were observed (FIG. 52) during the titration with PS and it was concluded that PS does not bind to Tet-1 due to absence of hydrogen bonding interactions between PS and Tet-1.

Measurement of the Complex Association Constant for [$Picrocrocin_3$@Tet-1] (Complex Formed Between 3 molecules of Picrocrocin and Tet-1)

Tet-1 (1.1 mg, $1.88\times10^{-4}$ mmol) was dissolved in 500 μL of $CD_2Cl_2$ in a scintillation vial and transferred to an NMR tube. In a separate vial, picrocrocin (6.0 mg, $6.16\times10^{-3}$ mmol) was dissolved in 640 μL $CD_2Cl_2$ and the resulting solution was titrated into the NMR tube in 20 steps. Additional points for the titration were obtained by (i) evaporating all the NMR solvent and (ii) redissolving the picrocrocin/Tet-1 mixture in 500 μL of $CD_2Cl_2$. The resulting more concentrated sample was then diluted back to a total volume of 900 μL in four titration steps. The exact concentration of the picrocrocin in the titration samples was determined by integration of its $^1$H-NMR (500 MHZ, $CD_2Cl_2$) resonance at 10.06 ppm, with Tet-1's $^1$H-NMR (500 MHZ, $CD_2Cl_2$) resonance at 6.64 ppm serving as the internal standard. The best fit (FIG. 48C) to the titration data was obtained with a 3:1 binding model with an association constant for [$Picrocrocin_3$@Tet-1] of $(5.4\pm0.4)\times10^7$ $M^{-3}$.

Titration of Tet-1 with Itself 1 mg of Tet-1 ($1.709\times10^{-4}$ mmol) was dissolved in 600 μL of $CD_2Cl_2$ in a scintillation vial and the solution was transferred into an NMR tube. In a separate scintillation vial, 3 additional equivalents of Tet-1 ($5.1273\times10^{-4}$ mmol) were dissolved in 240 μL $CD_2Cl_2$ and the resulting solution was titrated (FIG. 53) into the NMR tube in 10 steps. No significant shifts of any $^1$H-NMR resonances corresponding to Tet-1 were observed upon increasing the concentration of Tet-1.

Titration of PVP with Itself 7.5 mg of PVP ($9.375\times10^{-4}$ mmol) were dissolved in 200 μL $CD_2Cl_2$ in a scintillation vial. Next, 20 μL of the solution were added to an NMR tube and diluted by adding 500 μL of $CD_2Cl_2$. The 180 μL of solution remaining in the vial were then titrated (FIG. 54) into the NMR tube in a series of 6 steps. No significant shifts of any $^1$H-NMR resonances corresponding to PVP were observed upon increasing the concentration of PVP.

Titration of POI with Itself 7.1 mg of POI ($6.867\times10^{-4}$ mmol) were dissolved in 500 μL of $CD_2Cl_2$ in a scintillation vial and the resulting solution was transferred into an NMR tube. An additional 5.0 equivalents (35.5 mg) of POI was dissolved in 340 μL of $CD_2Cl_2$ in a separate scintillation vial and the solution was titrated (FIG. 55) into the NMR tube in a series of 6 steps. No significant shifts of any $^1$H-NMR resonances corresponding to POI were observed upon increasing the concentration of POI.

Titration of Picrocrocin with Itself 2.5 mg of picrocrocin (3.32 mmol) were dissolved in 200 μL of $CD_2Cl_2$ in a scintillation vial. Next, 20 μL of the solution were transferred to an NMR tube and diluted by adding 500 μL of $CD_2Cl_2$. The 180 μL of solution remaining in the vial were then titrated (FIG. 56) into the NMR tube in a series of 6 steps. No significant shifts of any $^1$H-NMR resonances corresponding to picrocrocin were observed during this titration.

Example 29—Molecular Dynamics (MD) Simulations of Picrocrocin and/or Polyvinylpyrrolidone (PVP) in Complex with a Prototypical Nanocage (Tet-1)

Model Preparation

All models were constructed using the program Maestro (Maestro, Schrödinger, LLC, New York, NY, 2018). The tetrahedron cage Tet-1 and picrocrocin models were built according to Scheme 1 and FIG. 48A-C, respectively. The PVP model was built with 72 vinylpyrrolidone repeat units and the POI model was built with 24 PVP repeat units. [PVP@Tet-1]-, [POI@Tet-1]-, and [picrocrocinn@Tet-1] (Complex Formed Between n molecules of Picrocrocin and Tet-1)-models were simulated in periodic simulation boxes of ~113×113×113 Å$^3$,~122×122×122 Å$^3$, and ~67×67×67 Å$^3$, respectively, with $CH_2Cl_2$ molecules as the solvent. Each construct went through minimization, equilibration, and 100-ns MD production stages. Two replicas were run for all simulations.

Simulation Setup

Each model was simulated in the NPT ensemble (300 K, 1 atm, Martyna-Tuckerman-Klein coupling scheme) using the OPLS3 (Harder et al., "OPLS3: A Force Field Providing Broad Coverage of Drug-like Small Molecules and Proteins," *J. Chem. Theory Comput.* 12:281-296 (2016), which is hereby incorporated by reference in its entirety) force field. All simulations were performed in the Maestro-Desmond program (Desmond Molecular Dynamics System, D. E. Shaw Research, New York, NY, 2018) (GPU version) with a time step of 2 fs, except for the tetrahedron/picrocrocin system which was simulated with a time step of 1 fs. The Ewald technique was used for the electrostatic calculations. The Van der Waals and short-range electrostatics were cut off at 9 Å. Hydrogen atoms were constrained using the SHAKE algorithm.

Visualization and Analysis

Using in-house Tcl and Python scripts, the distance between the center of mass (COM) of Tet-1 and the COM of each picrocrocin molecule was measured. A picrocrocin molecule was considered inside the cage when the picrocrocin—Tet-1 COM distance was within a 10 Å cutoff, the approximate radius of the cage. The snapshots of the last frame of each simulation as well as the three trajectory movies (displayed as web enhanced objects) were made using Pymol (The PyMOL Molecular Graphics System, Version 2.0 Schrödinger, LLC) and Maestro, respectively.

Example 30—Results and Discussion of Examples 27-29

Polymer recognition with the cage was performed. First, a $^1$H-NMR (500 MHZ, $CD_2Cl_2$, 298 K) titration of Tet-1 with commercial polyvinylpyrrolidone (PVP, $\overline{M}_w$=8,000

Da) carried out. The $^{1}$H-NMR titration curve (FIG. 48A) clearly indicated 1:1 binding between PVP and Tet-1, with an association constant $K_a$ of $(2.0\pm0.2)\times10^3$ $M^{-1}$. With PVP, complex association and dissociation was fast on the NMR timescale, which lead to a standard hyperbolic binding curve (FIG. 48A). A molecular dynamics (MD) simulation (FIG. 49) of the [PVP@Tet-1] complex, explains this finding. It showed that a PVP polymer chain is small enough to freely thread through the large faces of Tet-1. The molecular model of the complex—with 72 pyrrolidone repeat units—was equilibrated with a 100 ns-long MD simulation, starting from a model of the bound state. The simulations were carried out with the OPLS3 (Harder et al., "OPLS3: A Force Field Providing Broad Coverage of Drug-like Small Molecules and Proteins," *J. Chem. Theory Comput.* 12:281-296 (2016), which is hereby incorporated by reference in its entirety) force field in explicit $CH_2Cl_2$ solvent.

If the side chains attached to the polymer are elongated further, however, host-guest exchange was expected to slow down. To test this hypothesis, poly(isobutylene-alt-n-octyl maleimide) (POI, $\overline{M}_w$=9,076 Da) was synthesized by condensing n-octylamine with commercial poly(isobutylene-alt-maleic anhydride). A $^{1}$H-NMR (500 MH, $CD_2Cl_2$, 298 K) titration (FIG. 48B) of Tet-1 with POI still lead to averaged resonances. However, the singlets resonances of Tet-1 broaden (FIG. 50) significantly upon addition of POI. Furthermore, the $^{1}$H-NMR titration curves with POI all looked sigmoidal, even though they do not fit to a higher order 2:1 or 3:1 binding model. Rather, the sigmoidal nature of the POI titration curves was very likely caused (Kovrigin E. L., "NMR Line Shapes and Multi-State Binding Equilibria.," *J. Biomol. NMR* 53:257-270 (2012), which is hereby incorporated by reference in its entirety) by further slowed host-guest exchange, which is triggered by the n-octyl side chains of POI.

Upon addition of POI, the Tet-1 $^{1}$H-NMR resonances likely broaden for a variety of reasons, including (i) slowed host-guest exchange, (ii) desymmetrization of the protons in the cage upon POI binding, as well as (iii) different polymer-cage binding modes coexisting with the polydisperse polymer sample. For these reasons, a detailed $^{1}$H-NMR line-shape analysis for the [POI@Tet-1] system was impractical. Nevertheless, the sigmoidal character of the titration curve shown in FIG. 48B was accounted for with LineShapeKin (Kovrigin E. L., "NMR Line Shapes and Multi-State Binding Equilibria.," *J. Biomol. NMR* 53:257-270 (2012), which is hereby incorporated by reference in its entirety). A simple 1:1 binding model (dashed line in FIG. 48B) with an effective [POI@Tet-1]-dissociation rate constant of 40 $s^{-1}$ and a $K_a$ of $(6.9\pm1.0)\times10^3$ $M^{-1}$ accurately reproduced the titration data. Furthermore, a molecular model (FIG. 49) of the [POI@Tet-1] complex shows that the n-octyl side chains of POI are indeed long enough to significantly slow down sliding of Tet-1 along the polymer chain. Again, the model of the complex—with 24 isobutylene-alt-n-octylmaleimide repeat units threaded through the openings of Tet-1—was simulated for 100 ns in explicit $CH_2Cl_2$ solvent. Snapshots of the MD simulation also show (FIG. 49, inset) the presence of multiple [hydrazone-NH . . . O-maleimide] hydrogen bonds, which stabilized the [POI@Tet-1] complex. This finding was verified experimentally by adding a drop of DMSO-d6 (a known hydrogen bond disruptor) (Zhang et al., "Molecular Recognition in Different Environments: β-Cyclodextrin Dimer Formation in Organic Solvents," *J. Phys. Chem. B* 116:12684-12693 (2012); Frish et al., "Complexation of a Peptidocalix [4] arene, a Vancomycin Mimic, with Alanine-Containing Guests by NMR Diffusion Measurements," *J. Org. Chem.* 65:5026-5030 (2000), which are hereby incorporated by reference in their entirety) to a solution of the complex in $CH_2Cl_2$, which instantaneously lead to sharper (FIG. 51) $^{1}$H-NMR resonances. Last, polystyrene-which cannot form strong hydrogen bonds-does not bind (FIG. 52) to Tet-1.

The hydrazone-linked tetrahedron also displayed utility in binding to glycoside natural products. For instance, while working toward selective sensors to gage the quality of saffron, it was discovered with a $^{1}$H-NMR titration (500 MHZ, $CD_2Cl_2$, 298 K, FIG. 48C) that Tet-1 binds to picrocrocin in saffron extracts. Picrocrocin—the main component in saffron (Melnyk et al., "Chemical and Biological Properties of the World's Most Expensive Spice: Saffron," *Food Res. Int.* 43:1981-1989 (2010), which is hereby incorporated by reference in its entirety) responsible for its flavor—enters and exits readily through the large triangular openings of Tet-1. Nonetheless, a sigmoidal titration curve (FIG. 48C) was observed, which fits a strongly cooperative 3:1 binding model with a Hill coefficient $n_h$ of ~3.0.

100 ns-long MD simulations of Tet-1 in a 5 mol % solution of picrocrocin in $CH_2Cl_2$ qualitatively reproduced the observed cooperativity. At ~8 ns of simulation time, three of the picrocrocins start to bind cooperatively to Tet-1 in a stable binding conformation with a fourth one more loosely associated with the side of the cage. Overall, a statistical analysis of the trajectory revealed (see the histogram displayed in FIG. 49) that [picrocrocin$_3$@Tet-1] complexes were formed more frequently than [picrocrocin@Tet-1] (Complex Formed Between Picrocrocin and Tet-1) complexes with other stoichiometries. Furthermore, snapshots of the trajectory clearly indicate that in the most stable binding conformations (FIG. 49), three picrocrocins clinch to three vertices of Tet-1.

In summary, the hydrazone-linked molecular tetrahedron binds not only to polymers with side-chains, but also to the natural product picrocrocin—a key component of saffron. Experimental and computational evidence both manifested that picrocrocin binding is cooperative, providing a rare (Yoshizawa et al., "Discrete Stacking of Large Aromatic Molecules Within Organic-Pillared Coordination Cages," *Angew. Chem., Int. Ed.* 44:1810-1813 (2005), which is hereby incorporated by reference in its entirety) example of cooperativity with a 3:1 binding stoichiometry inside a synthetic molecular host.

Example 31—Measurement of the Complex Association Constant for [Curcumin$_2$@Tet-1] (Complex Formed Between 2 Molecules of Curcumin and Tet-1)

Other spices were also extracted in an analogous manner and the resulting extracts titrated into solutions of a prototypical nanocage (Tet-1) to determine the recognition abilities of Tet-1. In one example, turmeric was extracted and when the extract was mixed with a $CD_2Cl_2$ solution of Tet-1, significant shifts of prominent Tet-1 $^{1}$H NMR resonances were observed. Careful analysis of the $^{1}$H NMR shifts observed during the addition of the turmeric extract indicated that it is likely the curcumin component in turmeric, which binds selectively to the nanocage Tet-1. Molecular docking studies (FIG. 57) indicated that the curcumin selectively binds to the corners of the nanocage Tet-1, driven by favorable π-π-stacking interactions. The molecular docking was performed in cartesian coordinates with the AutoDock Vina (version 1.1.2) software (Trott et al., "AutoDock Vina: Improving the Speed and Accuracy of Docking with a new Scoring Function, Efficient Optimization and Multithreading," *J. Comput. Chem.* 31:455-461 (2010)) using a 40 Å-sized box centered at the centroid of the nanocage Tet-1. The most favorable docking pose shown in FIG. 57 corresponds to a binding affinity of 5.8 kcal/mol. Like picrocrocin, curcumin (1,7-bis(4-hydroxy-3-methoxyphenyl)-1,6-heptadiene-3,5-dione) is a powerful natural compound, which has been associated with a multitude of potential beneficial properties, including but not limited to anti-inflammatory action, anti-cancer action, anti-oxidant action, anti-viral action, and cytoprotective action. For a review of curcumin's beneficial properties, see: Hewlings et al., "Curcumin: A Review of Its' Effects on Human Health," *Foods* 6:92 (2017).

Next, to confirm recognition of curcumin by Tet-1, a commercial sample of purified curcumin was obtained from Sigma Aldrich and the purified curcumin was titrated into a solution of Tet-1. Specifically, Tet-1 (2.0 mg, $3.41\times10^{-4}$ mmol) was first dissolved in 500 AL of $CD_2Cl_2$ in a scintillation vial and then transferred the Tet-1 solution to an NMR tube. In a separate vial, curcumin (1.0 mg, $2.7\times10^{-3}$ mmol) was dissolved in 450 µL of $CD_2Cl_2$ and the resulting solution was titrated into the NMR tube containing the Tet-1 solution in 8 steps. The $^1H$ NMR ($CD_2Cl_2$, 500 MHz, 298 K) spectrum was then recorded for each titration point, and the chemical shifts plotted (FIG. 48D) against the concentration of the curcumin present in the NMR tube. The best fit (FIG. 48D, dotted line) to the titration data (which was obtained like in the case of picrocrocin with the software DynaFit (Kuzmic, P., "Program DYNAFIT for the Analysis of Enzyme Kinetic Data: Application to HIV Proteinase," *Anal. Biochem.* 237:260-273 (1996), which is hereby incorporated by reference in its entirety) was obtained with a 2:1 binding model with the product of the two association constants $K_a1$ and $K_a2$ for [Curcumin$_2$@Tet-1] equal to $(2.6\pm0.5)\times10^5$ $M^{-2}$.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A nanocage of Formula (I):

(I)

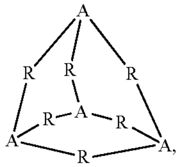

wherein each A is independently selected and has the formula

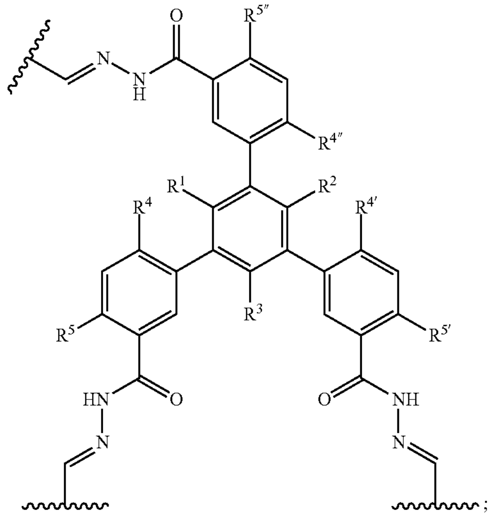

is the point of attachment of A to R;

each R is independently selected and has the formula

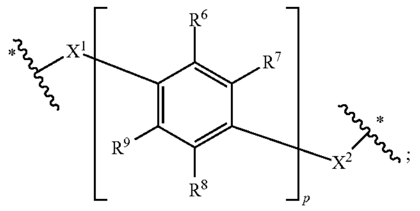

indicates the point of attachment of R to A;

$R^1$, $R^2$, and $R^3$ are each independently selected from the group consisting of H, halogen, OH, $C_{1-20}$ alkyl, $C_{2-20}$ alkenyl, $C_{2-20}$ alkynyl, perfluorinated $C_{1-20}$ alkyl, aryl, hereroaryl, heterocyclyl, —$OC_{1-20}$ alkyl, —$OC_{2-20}$ alkenyl, —$OC_{2-20}$ alkynyl, —O-perfluorinated $C_{1-20}$ alkyl, —Oaryl, —$COOC_{1-20}$ alkyl, —COO perfluorinated $C_{1-20}$ alkyl, —COOaryl, —$CONHC_{1-20}$ alkyl, —$CONHC_{2-20}$ alkenyl, —$CONHC_{2-20}$ alkynyl, —CONH perfluorinated $C_{1-20}$ alkyl, —CONH-aryl, —CONH-heteroaryl, and —CONH-heterocyclyl, wherein each $C_{1-20}$ alkyl, $C_{2-20}$ alkenyl, $C_{2-20}$ alkynyl, perfluorinated $C_{1-20}$ alkyl, aryl, hereroaryl, heterocyclyl, —$OC_{1-20}$ alkyl, —$OC_{2-20}$ alkenyl, —$OC_{2-20}$ alkynyl, —O-perfluorinated $C_{1-20}$ alkyl, —Oaryl, —$COOC_{1-20}$ alkyl, —COO perfluorinated $C_{1-20}$ alkyl, —COOaryl, —$CONHC_{1-20}$ alkyl, —$CONHC_{2-20}$ alkenyl, —$CONHC_{2-20}$ alkynyl, —CONH perfluorinated $C_{1-20}$ alkyl, —CONH-aryl, —CONH-heteroaryl, and —CONH-heterocyclyl can be optionally substituted from 1 to 3 times with a substituent selected from the group consisting of H, halogen, OH, $C_{1-6}$ alkyl, aryl, and arylalkyl;

$R^4$, $R^{4'}$, and $R^{4''}$ are each independently selected from the group consisting of H, halogen, $C_{1-20}$ alkyl, $C_{2-20}$ alkenyl, $C_{2-20}$ alkynyl, perfluorinated $C_{1-20}$ alkyl, aryl, hereroaryl, heterocyclyl, OH, —$OC_{1-20}$ alkyl, —$OC_{2-20}$ alkenyl, —$OC_{2-20}$ alkynyl, —O-perfluorinated $C_{1-20}$ alkyl, —Oaryl, —$COOC_{1-20}$ alkyl, —COO perfluorinated $C_{1-20}$ alkyl, —COOaryl, —$CONHC_{1-20}$ alkyl, —$CONHC_{2-20}$ alkenyl, —$CONHC_{2-20}$ alkynyl, —CONH perfluorinated $C_{1-20}$ alkyl, —CONH-aryl, —CONH-heteroaryl, and —CONH-heterocyclyl, wherein each $C_{1-20}$ alkyl, $C_{2-20}$ alkenyl, $C_{2-20}$ alkynyl, perfluorinated $C_{1-20}$ alkyl, aryl, hereroaryl, heterocyclyl, —$OC_{1-20}$ alkyl, —$OC_{2-20}$ alkenyl, —$OC_{2-20}$ alkynyl, —O-perfluorinated $C_{1-20}$ alkyl, —Oaryl, —$COOC_{1-20}$ alkyl, —COO perfluorinated $C_{1-20}$ alkyl, —COOaryl, —$CONHC_{1-20}$ alkyl, —$CONHC_{2-20}$ alkenyl, —$CONHC_{2-20}$ alkynyl, —CONH perfluorinated $C_{1-20}$ alkyl, —CONH-aryl, —CONH-heteroaryl, and —CONH-heterocyclyl can be optionally substituted from 1 to 3 times with a substituent selected from the group consisting of H, halogen, OH, $C_{1-6}$ alkyl, aryl, and arylalkyl;

$R^5$, $R^{5'}$, and $R^{5''}$ are each independently selected from the group consisting of H, halogen, OH, $O(CH_2)_n$—$(OCH_2CH_2)_m$—$OC_{1-6}$ alkyl, aryl, hereroaryl, heterocyclyl, —$OC_{2-20}$ alkyl, —O-perfluorinated $C_{1-20}$ alkyl, —Oaryl, and —$NR^{10}R^{11}$;

$R^6$, $R^7$, $R^8$, and $R^9$ are each independently selected at each occurrence from the group consisting of H, halogen, $C_{1-20}$ alkyl, $C_{2-20}$ alkenyl, $C_{2-20}$ alkynyl, perfluorinated $C_{1-20}$ alkyl, aryl, hereroaryl, heterocyclyl, OH, —$OC_{1-20}$ alkyl, —$OC_{2-20}$ alkenyl, —O-perfluorinated $C_{1-20}$ alkyl, —$OC_{2-20}$ alkynyl, aryl, heteroaryl, heterocyclyl, and —$COOC_{1-20}$ alkyl, —COO perfluorinated $C_{1-20}$ alkyl, —COOaryl, —$CONHC_{1-20}$ alkyl, —$CONHC_{2-20}$ alkenyl, —$CONHC_{2-20}$ alkynyl, —CONH perfluorinated $C_{1-20}$ alkyl, —CONH-aryl, —CONH-heteroaryl, and —CONH-heterocyclyl, wherein each $C_{1-20}$ alkyl, $C_{2-20}$ alkenyl, $C_{2-20}$ alkynyl, perfluorinated $C_{1-20}$ alkyl, aryl, hereroaryl, heterocyclyl, —$OC_{1-20}$ alkyl, —$OC_{2-20}$ alkenyl, —$OC_{2-20}$ alkynyl, —O-perfluorinated $C_{1-20}$ alkyl, —Oaryl, —$COOC_{1-20}$ alkyl, —COO perfluorinated $C_{1-20}$ alkyl, —COOaryl, —$CONHC_{1-20}$ alkyl, —$CONHC_{2-20}$ alkenyl, —$CONHC_{2-20}$ alkynyl, —CONH perfluorinated $C_{1-20}$ alkyl, —CONH-aryl, —CONH-heteroaryl, and —CONH-heterocyclyl can be optionally substituted from 1 to 3 times with a substituent selected from the group consisting of H, halogen, OH, $C_{1-6}$ alkyl, aryl, and arylalkyl;

$R^{10}$ and $R^{11}$ are each independently selected from the group consisting of H, $C_{1-6}$ alkyl, $C_{2-6}$ alkenyl, $C_{2-6}$ alkynyl, aryl, heteroarylalkyl, heterocyclylalkyl, and arylalkyl, wherein each $C_{1-6}$ alkyl, $C_{2-6}$ alkenyl, $C_{2-6}$ alkynyl, aryl, heteroarylalkyl, heterocyclylalkyl, and arylalkyl can be optionally substituted from 1 to 3 times with a substituent selected from the group consisting of H, $C_{1-6}$ alkyl, heteroarylalkyl, heterocyclylalkyl, and arylalkyl;

$X^1$ and $X^2$ are absent or are independently selected from the group consisting of $C_{1-6}$ alkylene, $C_{3-8}$ cycloalkylene, and arylene, wherein $C_{1-6}$ alkylene, $C_{3-8}$ cycloalkylene, and arylene can be optionally substituted from 1 to 3 times with H or $C_{1-6}$ alkyl;

p is 1 to 3;

n is 1 to 10; and m is 1 to 10.

2. The nanocage of claim 1, wherein the nanocage is $T_d$-symmetric.

3. The nanocage of claim 1, wherein the nanocage has a height from 15 Å to 40 Å.

4. The nanocage of claim 1, wherein the nanocage has a height from 20 Å to 25 Å.

5. The nanocage of claim 1, wherein $R^1$, $R^2$, and $R^3$ are Me, $R^4$ is —OMe, $R^5$ is —$O(CH_2)_4$—$(OCH_2CH_2)_3$—OMe.

6. A process for preparation of a nanocage of Formula (I):

(I)

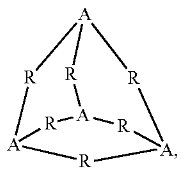

wherein each A is independently selected and has the formula

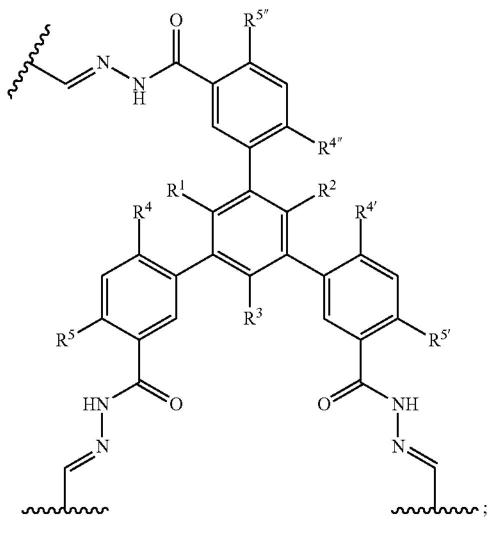

is the point of attachment of A to R;

each R is independently selected and has the formula

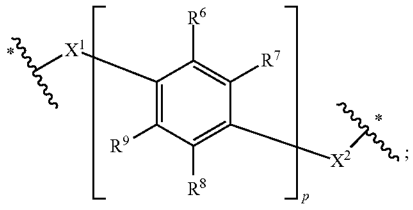

indicates the point of attachment of R to A;

$R^1$, $R^2$, and $R^3$ are each independently selected from the group consisting of H, halogen, OH, $C_{1-20}$ alkyl, $C_{2-20}$ alkenyl, $C_{2-20}$ alkynyl, perfluorinated $C_{1-20}$ alkyl, aryl, hereroaryl, heterocyclyl, —$OC_{1-20}$ alkyl, —$OC_{2-20}$ alkenyl, —$OC_{2-20}$ alkynyl, —O-perfluorinated $C_{1-20}$ alkyl, —Oaryl, —$COOC_{1-20}$ alkyl, —COO perfluorinated $C_{1-20}$ alkyl, —COOaryl, —$CONHC_{1-20}$ alkyl, —$CONHC_{2-20}$ alkenyl, —$CONHC_{2-20}$ alkynyl, —CONH perfluorinated $C_{1-20}$ alkyl, —CONH-aryl, —CONH-heteroaryl, and —CONH-heterocyclyl, wherein each $C_{1-20}$ alkyl, $C_{2-20}$ alkenyl, alkenyl, —$OC_{2-20}$ alkynyl, —O-perfluorinated $C_{1-20}$ alkyl, —Oaryl, —$COOC_{1-20}$ alkyl, —COO perfluorinated $C_{1-20}$ alkyl, —COOaryl, —$CONHC_{1-20}$ alkyl, —$CONHC_{2-20}$ alkenyl, —$CONHC_{2-20}$ alkynyl, —CONH perfluorinated $C_{1-20}$ alkyl, —CONH-aryl, —CONH-heteroaryl, and —CONH-heterocyclyl can be optionally substituted from 1 to 3 times with a substituent selected from the group consisting of H, halogen, OH, $C_{1-6}$ alkyl, aryl, and arylalkyl;

$R^4$, $R^{4'}$, and $R^{4''}$ are each independently selected from the group consisting of H, halogen, $C_{1-20}$ alkyl, $C_{2-20}$ alkenyl, $C_{2-20}$ alkynyl, perfluorinated $C_{1-20}$ alkyl, aryl, hereroaryl, heterocyclyl, OH, —$OC_{1-20}$ alkyl, —$OC_{2-20}$ alkenyl, —$OC_{2-20}$ alkynyl, —O-perfluorinated $C_{1-20}$ alkyl, —Oaryl, —$COOC_{1-20}$ alkyl, —COO perfluorinated $C_{1-20}$ alkyl, —COOaryl, —$CONHC_{1-20}$ alkyl, —$CONHC_{2-20}$ alkenyl, —$CONHC_{2-20}$ alkynyl, —CONH perfluorinated $C_{1-20}$ alkyl, —CONH-aryl, —CONH-heteroaryl, and —CONH-heterocyclyl, wherein each $C_{1-20}$ alkyl, $C_{2-20}$ alkenyl, $C_{2-20}$ alkynyl, perfluorinated $C_{1-20}$ alkyl, aryl, hereroaryl, heterocyclyl, —$OC_{1-20}$ alkyl, —$OC_{2-20}$ alkenyl, —$OC_{2-20}$ alkynyl, —O-perfluorinated $C_{1-20}$ alkyl, —Oaryl, —$COOC_{1-20}$ alkyl, —COO perfluorinated $C_{1-20}$ alkyl, —COOaryl, —$CONHC_{1-20}$ alkyl, —$CONHC_{2-20}$ alkenyl, —$CONHC_{2-20}$ alkynyl, —CONH perfluorinated $C_{1-20}$ alkyl, —CONH-aryl, —CONH-heteroaryl, and —CONH-heterocyclyl can be optionally substituted from 1 to 3 times with a substituent selected from the group consisting of H, halogen, OH, $C_{1-6}$ alkyl, aryl, and arylalkyl;

$R^5$, $R^{5'}$, and $R^{5''}$ are each independently selected from the group consisting of H, halogen, OH, —$O(CH_2)_n$—$(OCH_2CH_2)_m$—$OC_{1-6}$ alkyl, aryl, hereroaryl, heterocyclyl, —$OC_{2-20}$ alkyl, —O-perfluorinated $C_{1-20}$ alkyl, —Oaryl, and —$NR^{10}R^{11}$;

$R^6$, $R^7$, $R^8$, and $R^9$ are each independently selected at each occurrence from the group consisting of H, halogen, $C_{1-20}$ alkyl, $C_{2-20}$ alkenyl, $C_{2-20}$ alkynyl, perfluorinated $C_{1-20}$ alkyl, aryl, hereroaryl, heterocyclyl, OH, —$OC_{1-20}$ alkyl, —$OC_{2-20}$ alkenyl, —O-perfluorinated $C_{1-20}$ alkyl, —$OC_{2-20}$ alkynyl, aryl, heteroaryl, heterocyclyl, and —$COOC_{1-20}$ alkyl, —COO perfluorinated $C_{1-20}$ alkyl, —COOaryl, —$CONHC_{1-20}$ alkyl, —$CONHC_{2-20}$ alkenyl, —$CONHC_{2-20}$ alkynyl, —CONH perfluorinated $C_{1-20}$ alkyl, —CONH-aryl, —CONH-heteroaryl, and —CONH-heterocyclyl, wherein each $C_{1-20}$ alkyl, $C_{2-20}$ alkenyl, $C_{2-20}$ alkynyl, perfluorinated $C_{1-20}$ alkyl, aryl, hereroaryl, heterocyclyl, —$OC_{1-20}$ alkyl, —$OC_{2-20}$ alkenyl, —$OC_{2-20}$ alkynyl, —O-perfluorinated $C_{1-20}$ alkyl, —Oaryl, —$COOC_{1-20}$ alkyl, —COO perfluorinated $C_{1-20}$ alkyl, —COOaryl, —$CONHC_{1-20}$ alkyl, —$CONHC_{2-20}$ alkenyl, —$CONHC_{2-20}$ alkynyl, —CONH perfluorinated $C_{1-20}$ alkyl, —CONH-aryl, —CONH-heteroaryl, and —CONH-heterocyclyl can be optionally substituted from 1 to 3 times with a substituent selected from the group consisting of H, halogen, OH, $C_{1-6}$ alkyl, aryl, and arylalkyl;

$R^{10}$ and $R^{11}$ are each independently selected from the group consisting of H, $C_{1-6}$ alkyl, $C_{2-6}$ alkenyl, $C_{2-6}$ alkynyl, aryl, heteroarylalkyl, heterocyclylalkyl, and arylalkyl, wherein each $C_{1-6}$ alkyl, $C_{2-6}$ alkenyl, $C_{2-6}$ alkynyl, aryl, heteroarylalkyl, heterocyclylalkyl, and arylalkyl can be optionally substituted from 1 to 3 times with a substituent selected from the group consisting of H, $C_{1-6}$ alkyl, heteroarylalkyl, heterocyclylalkyl, and arylalkyl;

$X^1$ and $X^2$ are absent or are independently selected from the group consisting of $C_{1-6}$ alkylene, $C_{3-8}$ cycloalkylene, and arylene, wherein $C_{1-6}$ alkylene, $C_{3-8}$ cycloalkylene, and arylene can be optionally substituted from 1 to 3 times with H or $C_{1-6}$ alkyl;

p is 1 to 3;

n is 1 to 10; and m is 1 to 10, said process comprising:

providing one or more compounds of Formula (II) having the structure:

(II)

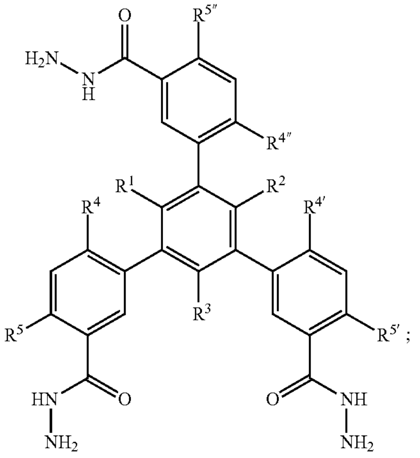

;

and forming the nanocage of Formula (I) from the one or more compounds of Formula (II).

7. The process according to claim 6, wherein said forming the nanocage of Formula (I) comprises:

reacting the one or more compounds of Formula (II) with one or more compounds of Formula (III):

(III)

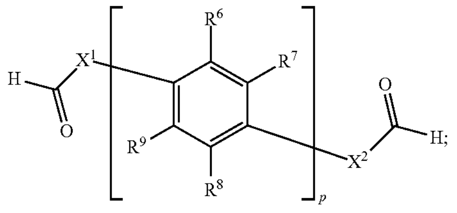

to produce the nanocage of Formula (I).

8. The process according to claim 6 further comprising:

providing one or more compounds of Formula (IV) having the structure:

(IV)

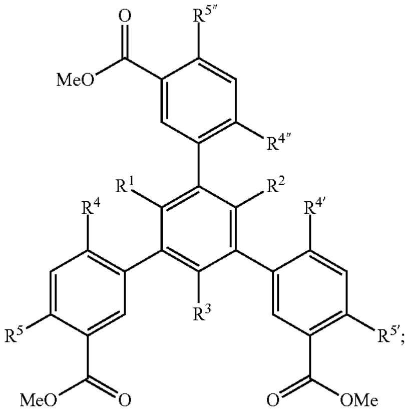

and forming the one or more compounds of Formula (II) from the one or more compounds of Formula (IV).

9. The process according to claim 8 further comprising:

providing one or more compounds of Formula (VI) having the structure:

(VI)

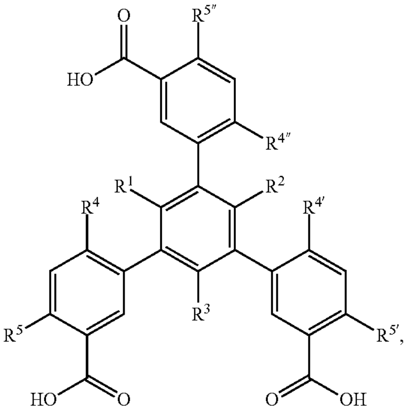

and forming the one or more compounds of Formula (IV) from the one or more compounds of Formula (VI).

10. The process according to claim 9 further comprising:

providing one or more compounds of Formula (VII) having the structure:

(VII)

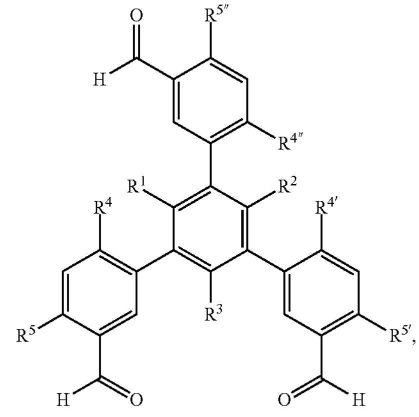

and forming the one or more compounds of Formula (VI) from the one or more compounds of Formula (VII).

11. The process according to claim 10, wherein said forming the one or more compounds of Formula (VI) comprises:

reacting the compound of Formula (VII) with an oxidizing agent to produce the one or more compounds of Formula (VI).

12. The process according to claim 6 further comprising:

providing one or more compounds of Formula (VIII) having the structure:

(VIII)

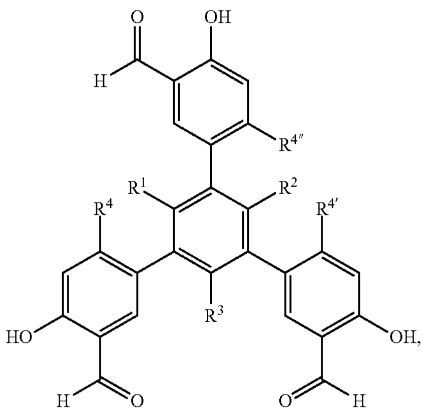

and forming the one or more compounds of Formula (VII) from the one or more compounds of Formula (VIII).

13. The process according to claim 12 further comprising:

providing one or more compounds of Formula (X) having the structure:

(X)

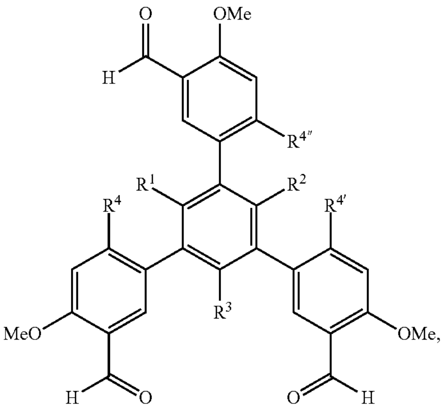

and forming the one or more compounds of Formula (VIII) from the one or more compounds of Formula (X).

14. The process according to claim 13 further comprising:

providing one or more compounds of Formula (XII) having the structure:

(XII)

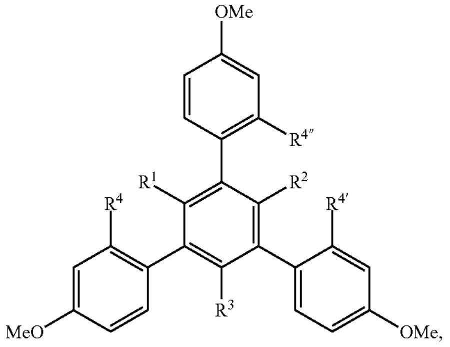

and forming the one or more compounds of Formula (X) from the one or more compounds of Formula (XII).

15. A method for detecting an analyte in a fluid comprising:

providing a sensor comprising a nanocage of Formula (I):

(I)

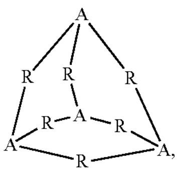

wherein each A is independently selected and has the formula

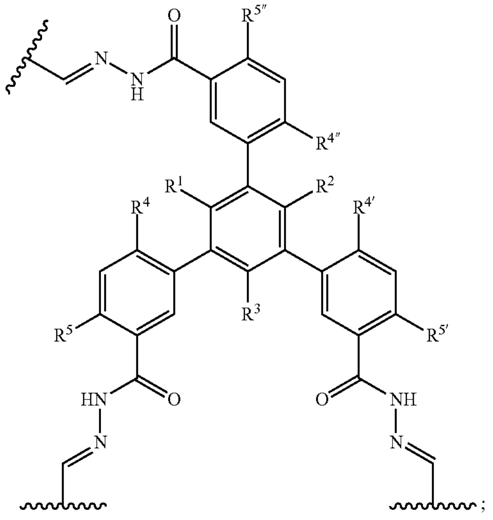

is the point of attachment of A to R;

each R is independently selected and has the formula

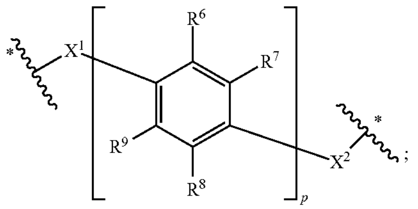

indicates the point of attachment of R to A;

$R^1$, $R^2$, and $R^3$ are each independently selected from the group consisting of H, halogen, OH, $C_{1-20}$ alkyl, $C_{2-20}$ alkenyl, $C_{2-20}$ alkynyl, perfluorinated $C_{1-20}$ alkyl, aryl, hereroaryl, heterocyclyl, —$OC_{1-20}$ alkyl, —$OC_{2-20}$ alkenyl, —$OC_{2-20}$ alkynyl, —O-perfluorinated $C_{1-20}$ alkyl, —Oaryl, —$COOC_{1-20}$ alkyl, —COO perfluorinated $C_{1-20}$ alkyl, —COOaryl, —$CONHC_{1-20}$ alkyl, —$CONHC_{2-20}$ alkenyl, —$CONHC_{2-20}$ alkynyl, —CONH perfluorinated $C_{1-20}$ alkyl, —CONH-aryl, —CONH-heteroaryl, and —CONH-heterocyclyl, wherein each $C_{1-20}$ alkyl, $C_{2-20}$ alkenyl, alkenyl, —$OC_{2-20}$ alkynyl, —O-perfluorinated $C_{1-20}$ alkyl, —Oaryl, —$COOC_{1-20}$ alkyl, —COO perfluorinated $C_{1-20}$ alkyl, —COOaryl, —$CONHC_{1-20}$ alkyl, —$CONHC_{2-20}$ alkenyl, —$CONHC_{2-20}$ alkynyl, —CONH perfluorinated $C_{1-20}$ alkyl, —CONH-aryl, —CONH-heteroaryl, and —CONH-heterocyclyl can be optionally substituted from 1 to 3 times with a substituent selected from the group consisting of H, halogen, OH, $C_{1-6}$ alkyl, aryl, and arylalkyl;

$R^4$, $R^{4'}$, and $R^{4''}$ are each independently selected from the group consisting of H, halogen, $C_{1-20}$ alkyl, $C_{2-20}$ alkenyl, $C_{2-20}$ alkynyl, perfluorinated $C_{1-20}$ alkyl, aryl, hereroaryl, heterocyclyl, OH, —$OC_{1-20}$ alkyl, —$OC_{2-20}$ alkenyl, —$OC_{2-20}$ alkynyl, —O-perfluorinated $C_{1-20}$ alkyl, —Oaryl, —$COOC_{1-20}$ alkyl, —COO perfluorinated $C_{1-20}$ alkyl, —COOaryl, —$CONHC_{1-20}$ alkyl, —$CONHC_{2-20}$ alkenyl, —$CONHC_{2-20}$ alkynyl, —CONH perfluorinated $C_{1-20}$ alkyl, —CONH-aryl, —CONH-heteroaryl, and —CONH-heterocyclyl, wherein each $C_{1-20}$ alkyl, $C_{2-20}$ alkenyl, $C_{2-20}$ alkynyl, perfluorinated $C_{1-20}$ alkyl, aryl, hereroaryl, heterocyclyl, —$OC_{1-20}$ alkyl, —$OC_{2-20}$ alkenyl, —$OC_{2-20}$ alkynyl, —O-perfluorinated $C_{1-20}$ alkyl, —Oaryl, —$COOC_{1-20}$ alkyl, —COO perfluorinated $C_{1-20}$ alkyl, —COOaryl, —$CONHC_{1-20}$ alkyl, —$CONHC_{2-20}$ alkenyl, —$CONHC_{2-20}$ alkynyl, —CONH perfluorinated $C_{1-20}$ alkyl, —CONH-aryl, —CONH-heteroaryl, and —CONH-heterocyclyl can be optionally substituted from 1 to 3 times with a substituent selected from the group consisting of H, halogen, OH, $C_{1-6}$ alkyl, aryl, and arylalkyl;

$R^5$, $R^{5'}$, and $R^{5''}$ are each independently selected from the group consisting of H, halogen, OH, —$O(CH_2)_n$—$(OCH_2CH_2)_m$—$OC_{1-6}$ alkyl, aryl, hereroaryl, heterocyclyl, —$OC_{1-20}$ alkyl, —O-perfluorinated $C_{1-20}$ alkyl, —Oaryl, and —$NR^{10}R^{11}$;

$R^6$, $R^7$, $R^8$, and $R^9$ are each independently selected at each occurrence from the group consisting of H, halogen, $C_{1-20}$ alkyl, $C_{2-20}$ alkenyl, $C_{2-20}$ alkynyl, perfluorinated $C_{1-20}$ alkyl, aryl, hereroaryl, heterocyclyl, OH, —$OC_{1-20}$ alkyl, —$OC_{2-20}$ alkenyl, —O-perfluorinated $C_{1-20}$ alkyl, —$OC_{2-20}$ alkynyl, aryl, heteroaryl, heterocyclyl, and —$COOC_{1-20}$ alkyl, —COO perfluorinated $C_{1-20}$ alkyl, —COOaryl, —$CONHC_{1-20}$ alkyl, —$CONHC_{2-20}$ alkenyl, —$CONHC_{2-20}$ alkynyl, —CONH perfluorinated $C_{1-20}$ alkyl, —CONH-aryl, —CONH-heteroaryl, and —CONH-heterocyclyl, wherein each $C_{1-20}$ alkyl, $C_{2-20}$ alkenyl, $C_{2-20}$ alkynyl, perfluorinated $C_{1-20}$ alkyl, aryl, hereroaryl, heterocyclyl, —$OC_{1-20}$ alkyl, —$OC_{2-20}$ alkenyl, —$OC_{2-20}$ alkynyl, —O-perfluorinated $C_{1-20}$ alkyl, —Oaryl, —$COOC_{1-20}$ alkyl, —COO perfluorinated $C_{1-20}$ alkyl, —COOaryl, —$CONHC_{1-20}$ alkyl, —$CONHC_{2-20}$ alkenyl, —$CONHC_{2-20}$ alkynyl, —CONH perfluorinated $C_{1-20}$ alkyl, —CONH-aryl, —CONH-heteroaryl, and —CONH-heterocyclyl can be optionally substituted from 1 to 3 times with a substituent selected from the group consisting of H, halogen, OH, $C_{1-6}$ alkyl, aryl, and arylalkyl;

$R^{10}$ and $R^{11}$ are each independently selected from the group consisting of H, $C_{1-6}$ alkyl, $C_{2-6}$ alkenyl, $C_{2-6}$ alkynyl, aryl, heteroarylalkyl, heterocyclylalkyl, and arylalkyl, wherein each $C_{1-6}$ alkyl, $C_{2-6}$ alkenyl, $C_{2-6}$ alkynyl, aryl, heteroarylalkyl, heterocyclylalkyl, and arylalkyl can be optionally substituted from 1 to 3 times with a substituent selected from the group consisting of H, $C_{1-6}$ alkyl, heteroarylalkyl, heterocyclylalkyl, and arylalkyl;

$X^1$ and $X^2$ are absent or are independently selected from the group consisting of $C_{1-6}$ alkylene, $C_{3-8}$ cycloalkylene, and arylene, wherein $C_{1-6}$ alkylene, $C_{3-8}$ cycloalkylene, and arylene can be optionally substituted from 1 to 3 times with H or $C_{1-6}$ alkyl;

p is 1 to 3;

n is 1 to 10; and m is 1 to 10;

providing a fluid containing an analyte; and contacting a fluid containing the analyte with the sensor to capture the analyte in the nanocage and detect the analyte in the fluid.

16. The method according to claim 15, wherein the sensor further comprises:

a substrate having a surface with a layer of the nanocage of Formula (I) covering at least 5% of the surface.

17. The method according to claim 15 further comprising:

providing a signal generator operatively associated with said sensor, said method further comprising:

producing a signal with the signal generator when said analyte is captured by said sensor.

18. The method according to claim 15, wherein the analyte is selected from the group consisting of polyvinylpyrrolidone (PVP), poly(isobutylene-alt-n-octyl maleimide) (POI), picrocrocin, curcumin, and components of chinese tea.

* * * * *